US012595415B2

(12) United States Patent
Brocke et al.

(10) Patent No.: US 12,595,415 B2
(45) **Date of Patent: *Apr. 7, 2026**

(54) AROMATIC ISOTHIOCYANATES

(71) Applicant: MERCK PATENT GMBH, Darmstadt (DE)

(72) Inventors: Constanze Brocke, Darmstadt (DE); Dagmar Klass, Darmstadt (DE); Carsten Fritzsch, Darmstadt (DE)

(73) Assignee: MERCK PATENT GMBH, Darmstadt (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/034,483

(22) PCT Filed: Oct. 25, 2021

(86) PCT No.: PCT/EP2021/079440

§ 371 (c)(1),
(2) Date: Apr. 28, 2023

(87) PCT Pub. No.: WO2022/090099

PCT Pub. Date: May 5, 2022

(65) Prior Publication Data

US 2023/0392076 A1 Dec. 7, 2023

(30) Foreign Application Priority Data

Oct. 28, 2020 (EP) .................................... 20204316

(51) Int. Cl.

*C09K 19/30* (2006.01)
*C07C 331/28* (2006.01)
*C09K 19/04* (2006.01)
*H01Q 1/36* (2006.01)

(52) U.S. Cl.

CPC ........ *C09K 19/3059* (2013.01); *C07C 331/28* (2013.01); *C09K 19/3001* (2013.01); *C07C 2601/02* (2017.05); *C07C 2601/04* (2017.05); *C07C 2601/08* (2017.05); *C07C 2601/10* (2017.05); *C07C 2601/14* (2017.05); *C09K 2019/0448* (2013.01); *C09K 2019/3063* (2013.01); *H01Q 1/36* (2013.01)

(58) Field of Classification Search

CPC ...................................................... C09K 19/30
See application file for complete search history.

(56) References Cited

U.S. PATENT DOCUMENTS

| | | | |
|---|---|---|---|
| 4,826,620 | A | 5/1989 | Heppke et al. |
| 4,988,458 | A | 1/1991 | Heppke et al. |
| 5,043,095 | A | 8/1991 | Bahr et al. |
| 5,788,880 | A | 8/1998 | Schierlinger et al. |
| 5,886,242 | A | 3/1999 | Etzbach et al. |
| 6,217,792 | B1 | 4/2001 | Parri et al. |
| 6,468,444 | B1 | 10/2002 | Meyer et al. |
| 6,511,719 | B2 | 1/2003 | Farrand |
| 7,041,345 | B2 | 5/2006 | Kirsch et al. |
| 7,060,331 | B2 | 6/2006 | Kirsch et al. |
| 7,318,950 | B2 | 1/2008 | Kirsch et al. |
| 7,361,288 | B2 | 4/2008 | Lüssem et al. |
| 7,385,067 | B2 | 6/2008 | Kirsch et al. |
| 7,425,356 | B2 | 9/2008 | Taugerbeck et al. |
| 9,693,997 | B2 | 7/2017 | Bilotta et al. |
| 10,711,197 | B2 | 7/2020 | Wittek et al. |
| 11,268,026 | B2 | 3/2022 | Klass et al. |
| 2016/0000760 | A1 | 1/2016 | Bilotta et al. |
| 2016/0040066 | A1 | 2/2016 | Wittek et al. |
| 2017/0081312 | A1 | 3/2017 | Berthel et al. |
| 2018/0155625 | A1 | 6/2018 | Wittek et al. |
| 2019/0292458 | A1 | 9/2019 | Klass et al. |
| 2020/0255737 | A1 | 8/2020 | Wittek et al. |
| 2022/0306938 | A1* | 9/2022 | Brocke .............. C09K 19/0403 |
| 2023/0025385 | A1 | 1/2023 | Brocke et al. |

FOREIGN PATENT DOCUMENTS

| | | | | | |
|---|---|---|---|---|---|
| CN | 110499163 | A | | 11/2019 | |
| EP | 1054001 | A1 | * | 11/2000 | ........... C07C 331/28 |
| EP | 2982730 | A1 | * | 2/2016 | ............. C09K 19/10 |
| EP | 3543313 | A1 | | 9/2019 | |

(Continued)

OTHER PUBLICATIONS

International Search report PCT/EP2021/079440 dated Jan. 31, 2022 (pp. 1-4).

*Primary Examiner* — Chanceity N Robinson

(74) *Attorney, Agent, or Firm* — Csaba Henter; Millen, White, Zelano & Branigan, P.C.

(57) ABSTRACT

A compound of formula UI

UI

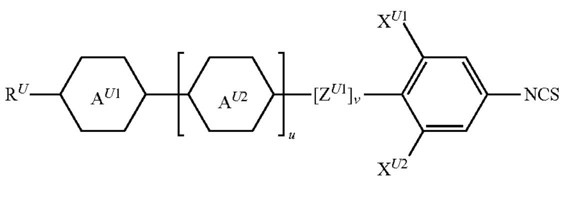

and a liquid crystal medium containing the compound of formula UI and high-frequency components containing such media, especially microwave components for high-frequency devices, such as devices for shifting the phase of microwaves, tunable filters, tunable metamaterial structures, and electronic beam steering antennas, for example, phased array antennas.

20 Claims, No Drawings

(56) References Cited

FOREIGN PATENT DOCUMENTS

| | | | | | |
|---|---|---|---|---|---|
| JP | 2002012868 | A | | 1/2002 | |
| JP | 2016513620 | A | | 5/2016 | |
| JP | 2018523006 | A | | 8/2018 | |
| JP | 2019512023 | A | | 5/2019 | |
| WO | WO-2014135495 | A1 | * | 9/2014 | ......... A61K 31/4196 |
| WO | WO-2021037962 | A1 | * | 3/2021 | ........... C07C 331/28 |
| WO | WO-2021069535 | A1 | * | 4/2021 | ........... C07C 331/28 |

* cited by examiner

AROMATIC ISOTHIOCYANATES

The present invention relates to aromatic isothiocyanates, liquid-crystalline media comprising same, and to high-frequency components comprising these media, especially microwave components for high-frequency devices, such as devices for shifting the phase of microwaves, tunable filters, tunable metamaterial structures, and electronic beam steering antennas (e.g. phased array antennas), and to devices comprising said components.

Liquid-crystalline media have been used for many years in electro-optical displays (liquid crystal displays: LCDs) in order to display information. More recently, however, liquid-crystalline media have also been proposed for use in components for microwave technology, such as, for example, in DE 10 2004 029 429.1 A and in JP 2005-120208 (A).

A. Gaebler, F. Goelden, S. Müller, A. Penirschke and R. Jakoby "Direct Simulation of Material Permittivites using an Eigen-Susceptibility Formulation of the Vector Variational Approach", 12MTC 2009—International Instrumentation and Measurement Technology Conference, Singapore, 2009 (IEEE), pp. 463-467, describe the corresponding properties of the known liquid-crystal mixture E7 (Merck KGaA, Germany).

DE 10 2004 029 429 A describes the use of liquid-crystal media in microwave technology, inter alia in phase shifters. Therein, liquid-crystalline media with respect to their properties in the corresponding frequency range have been discussed and liquid-crystalline media based on mixtures of mostly aromatic nitriles and isothiocyanates have been shown.

Fluorine atoms are commonly used in mesogenic compounds to introduce polarity. Especially in combination with a terminal NCS group high dielectric anisotropy values can be achieved in particular when an NCS group in the 1-position has two fluorine atoms in its ortho positions as the overall molecular dipole is the sum of all individual dipoles of a molecule's partial structures. On the other hand, a well balanced compromise with respect to the number of fluorine atoms has to be found as fluorine substitution often has a negative influence in the nematic phase properties of a compound.

In EP 2 982 730 A1, mixtures are described that completely consist of isothiocyanate compounds.

However, compositions available for the use in microwave applications are still afflicted with several disadvantages. It is required to improve these media with respect to their general physical properties, the shelf life and the stability under operation in a device. In view of the multitude of different parameters which have to be considered and improved for the development of liquid crystalline media for microwave application it is desirable to have a broader range of possible mixture components for the development of such liquid-crystalline media.

An object of the present invention is to provide a compound for the use in liquid crystalline media with improved properties relevant for the application in the microwave range of the electromagnetic spectrum.

To solve the problem, a compound of formula UI defined below is provided and a liquid crystalline medium comprising the compound.

The present invention relates to a compound of formula UI

UI

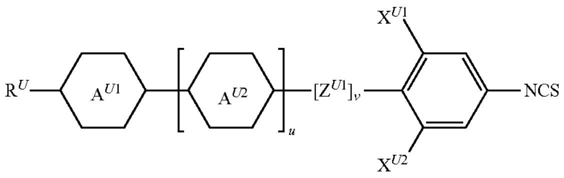

in which $R^U$ denotes H, straight-chain or branched non-fluorinated alkyl having 1 to 12 C atoms or non-fluorinated alkenyl having 2 to 12 C atoms, in which one or more $CH_2$-groups may be replaced by

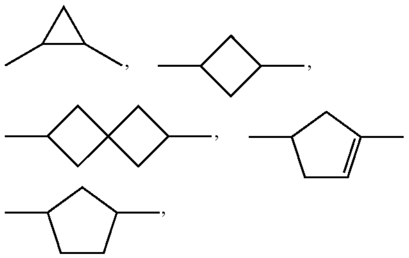

or where one or more non-adjacent $CH_2$-groups may be replaced by O, or denotes a group $R^P$, $R^P$ denotes halogen, CN, NCS, fluorinated alkyl, $R^F$—O— or $R^F$—S—, wherein $R^F$ denotes fluorinated alkyl or fluorinated alkenyl having up to 9 C atoms, $Z^{U1}$ denotes —CH═CH—, —CF═CF—, —CH═CF—, —CF═CH—, —C≡C— or —C≡C—C≡C—, preferably —CF═CF— or —C≡C—, $X^{U1}$, $X^{U2}$, identically or differently, denote Cl or F, preferably F.

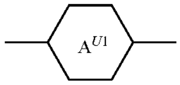 and 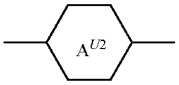

denote a radical selected from the following groups:

a) the group consisting of 1,4-phenylene, 1,4-naphthylene, and 2,6-naphthylene, in which one or two CH groups may be replaced by N and in which one or more H atoms may be replaced by L, b) the group consisting of trans-1,4-cyclohexylene, 1,4-cyclohexenylene, tetralin-2,6-diyl, tetralin-5,8-diyl, decalin-2,6-diyl, bicyclo[1.1.1]pentane-1,3-diyl, 4,4'-bicyclohexylene, bicyclo[2.2.2]octane-1,4-diyl, and spiro[3.3]heptane-2,6-diyl, in which one or two CH groups may be replaced by N, one or more non-adjacent $CH_2$ groups may be replaced by —O— and/or —S— and in which one or more H atoms may be replaced by L, c) the group consisting of thiophene-2,5-diyl, thieno[3,2-b]thiophene-2,5-diyl, selenophene-2,5-diyl, each of which may also be mono- or polysubstituted by L, L on each occurrence, identically or differently, denotes F, Cl, CN, SCN, $SF_5$ or straight-chain or branched, in each case optionally fluorinated, alkyl, alkoxy, alkylcarbonyl, alkoxycarbonyl, alkylcarbonyloxy or alkoxycarbonyloxy each having 1 to 12 C atoms, u is 0 or 1, v is 0 or 1, with the proviso that

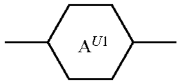
and
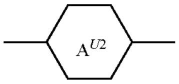

do not both denote optionally fluorinated 1,4-phenylene.

According to another aspect of the present invention there is provided a liquid crystal medium comprising one or more compounds of formula UI.

Preferred embodiments of the present invention are subject-matter of the dependent claims or can also be taken from the description.

Surprisingly, it has been found that it is possible to achieve liquid-crystalline media having excellent stability and at the same time a high dielectric anisotropy, suitably fast switching times, a suitable, nematic phase range, high tunability and low dielectric loss in the microwave range of the electromagnetic spectrum by using compounds of formula UI in liquid-crystalline media.

In particular, the media according to the invention comprising the compound according to the invention are distinguished by an improved figure-of-merit $\eta$ due to a higher tunability $\tau$ and lower dielectric loss.

The media according to the present invention are further distinguished by a high clearing temperature, a broad nematic phase range and excellent low-temperature stability (LTS). As a result, devices containing the media are operable under extreme temperature conditions.

The media are further distinguished by high values of the dielectric anisotropy and low rotational viscosities. As a result, the threshold voltage, i.e. the minimum voltage at which a device is switchable, is very low. A low operating voltage and low threshold voltage is desired in order to enable a device having improved switching characteristics and high energy efficiency. Low rotational viscosities enable fast switching of the devices according to the invention.

These properties as a whole make the media particularly suitable for use in components and devices for high-frequency technology and applications in the microwave range, in particular devices for shifting the phase of microwaves, tunable filters, tunable metamaterial structures, and electronic beam steering antennas (e.g. phased array antennas).

According to another aspect of the present invention there is thus provided a component and a device comprising said component, both operable in the microwave region of the electromagnetic spectrum. Preferred components are phase shifters, varactors, wireless and radio wave antenna arrays, matching circuits and adaptive filters.

Herein, "high-frequency technology" means applications of electromagnetic radiation having frequencies in the range of from 1 MHz to 1 THz, preferably from 1 GHz to 500 GHz, more preferably 2 GHz to 300 GHz, particularly preferably from about 5 GHz to 150 GHz.

As used herein, halogen is F, Cl, Br or I, preferably F or Cl, particularly preferably F.

Herein, alkyl is straight-chain or branched or cyclic and has 1 to 15 C atoms, is preferably straight-chain and has, unless indicated otherwise, 1, 2, 3, 4, 5, 6 or 7 C atoms and is accordingly preferably methyl, ethyl, n-propyl, n-butyl, n-pentyl, n-hexyl or n-heptyl.

Herein, branched alkyl is preferably isopropyl, s-butyl, isobutyl, isopentyl, 2-methylbutyl, 2-methylhexyl or 2-ethylhexyl.

As used herein, cyclic alkyl is taken to mean straight-chain or branched alkyl or alkenyl having up to 12 C atoms, preferably alkyl having 1 to 7 C atoms, in which a group $CH_2$ is replaced with a carbocyclic ring having 3 to 5 C atoms, very preferably selected from the group consisting of cyclopropylalkyl, cyclobutylalkyl, cyclopentylalkyl and cyclopentenylalkyl.

Herein, an alkoxy radical is straight-chain or branched and contains 1 to 15 C atoms. It is preferably straight-chain and has, unless indicated otherwise, 1, 2, 3, 4, 5, 6 or 7 C atoms and is accordingly preferably methoxy, ethoxy, n-propoxy, n-butoxy, n-pentoxy, n-hexoxy or n-heptoxy.

Herein, an alkenyl radical is preferably an alkenyl radical having 2 to 15 C atoms, which is straight-chain or branched and contains at least one C—C double bond. It is preferably straight-chain and has 2 to 7 C atoms. Accordingly, it is preferably vinyl, prop-1- or -2-enyl, but-1-, -2- or -3-enyl, pent-1-, -2-, -3- or -4-enyl, hex-1-, -2-, -3-, -4- or -5-enyl, hept-1-, -2-, -3-, -4-, -5- or -6-enyl. If the two C atoms of the C—C double bond are substituted, the alkenyl radical can be in the form of E and/or Z isomer (trans/cis). In general, the respective E isomers are preferred. Of the alkenyl radicals, prop-2-enyl, but-2- and -3-enyl, and pent-3- and -4-enyl are particularly preferred.

Herein, alkynyl is taken to mean an alkynyl radical having 2 to 15 C atoms, which is straight-chain or branched and contains at least one C—C triple bond. 1- and 2-propynyl and 1-, 2- and 3-butynyl are preferred.

In case $R^F$ denotes a halogenated alkyl-, alkoxy-, alkenyl or alkenyloxy it can be branched or unbranched. Preferably it is unbranched, mono-poly or perfluorinated, preferably perfluorinated and has 1, 2, 3, 4, 5, 6 or 7 C atoms, in case of alkenyl 2, 3, 4, 5, 6 or 7 C atoms.

$R^F$ preferably denotes CN, NCS, Cl, F, $-(CH_2)_n-CH=CF_2$, $-(CH_2)_n-CH=CHF$, $-(CH_2)_n-CH=Cl_2$, $-C_nF_{2n+1}$, $-(CF_2)_n-CF_2H$, $-(CH_2)_n-CF_3$, $-(CH_2)_n-CHF_2$, $-(CH_2)_nCH_2F$, $-CH=CF_2$, $-O(CH_2)_n-CH=CF_2$, $-O(CH_2)_nCHCl_2$, $-OC_nF_{2n+1}$, $-O(CF_2)_n-CF_2H$, $-O(CH_2)_nCF_3$, $-O(CH_2)_n-CHF_2$, $-O(CF)_nCH_2F$, $-OCF=CF_2$, $-SC_nF_{2n+1}$, $-S(CF)_n-CF_3$, wherein n is an integer from 0 to 7.

A structurally related compound with a trifluorvinyl substituent is shown in CN 105294526 A for use as a co-component in a medium for a display device.

The compounds of the general formula UI are prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and are suitable for said reactions. Use can be made here of variants which are known per se, but are not mentioned here in greater detail.

If desired, the starting materials can also be formed in situ by not isolating them from the reaction mixture, but instead by immediately reacting them further into the compounds of the general formula UI.

Preferred synthetic pathways towards compounds according to the invention are exemplified in scheme 1 below in which the occurring groups and parameters have the meanings given for formula UI. It is further illustrated by means of the working examples and can be adapted to the particular desired compounds of the general formula UI by choice of suitable starting materials.

Preferred building blocks 2 (scheme 1) are 4-bromo-3,5-difluoroaniline, 4-bromo-3,5-dichloroaniline and 4-bromo-3-chloro-5-fluoroaniline, all described in the literature, which can be reacted with suitable intermediates 1 to give compounds of the formula UI for example by cross coupling reactions commonly known as Sonogashira reactions (scheme 1, wherein $Z^{U1}$ is —C≡C— and G is H), Suzuki coupling (wherein $Z^{U1}$ is —CH═CH—, —CF═CF—, —CH═CF— or —CF═CH— and G is a boronic acid or alkyl boronic ester group) and the like. The compounds of formula N are reacted with a thiocarbonic acid derivative

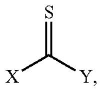

in which X and Y are leaving groups, or with $CS_2$ to give the compounds of formula UI.

Scheme 1

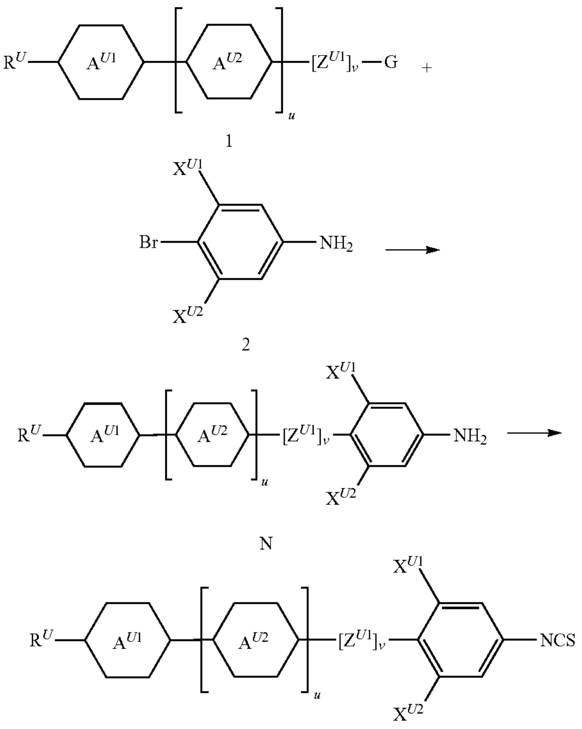

1

2

N

UI

A similar synthesis towards structurally related compounds with a trifluorovinyl substituent is shown in CN 105294526 A in which compounds for use as a co-component in a medium for a display device are disclosed. The compounds of the formula UII shown below are prepared analogously, or as described in EP 1 054 001 A1. Preferred reagents for the process according to the invention for the transformation of compounds of the formula N into compounds of the formula UI are carbon disulfide, thiophosgene, thiocarbonyl diimidazole, di-2-pyridyl thionocarbonate, bis (dimethylthiocarbamoyl) disulfide, dimethylthiocarbamoyl chloride and phenyl chlorothionoformate, very preferably thiophosgene.

The described reactions should only be regarded as illustrative. The person skilled in the art can carry out corresponding variations of the syntheses described and also follow other suitable synthetic routes in order to obtain compounds of the formula UI.

The compounds of formula UI are preferably selected from the group of compounds consisting of the formulae UI-1, UI-2 and UI-3:

UI-1

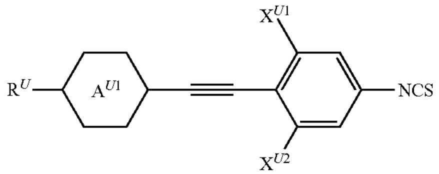

UI-2

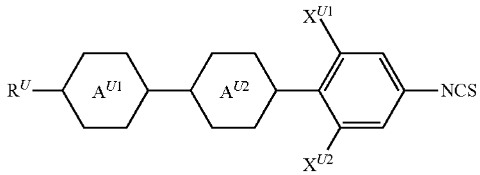

UI-3

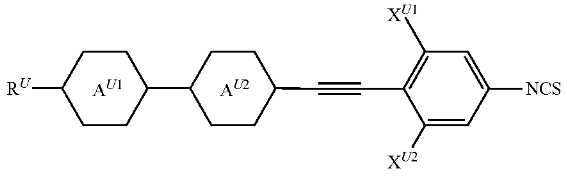

in which $R^U$,

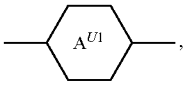

,

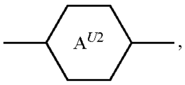

, $X^{U1}$ and $X^{U2}$ have the meanings given above for formula UI, and where in formula UI-3 at least one of and

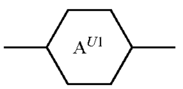

and

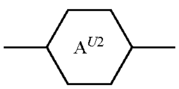

denotes trans-1,4-cyclohexylene, 1,4-cyclohexenylene, tetralin-2,6-diyl, tetralin-5,8-diyl, decalin-2,6-diyl, bicyclo [1.1.1]pentane-1,3-diyl, 4,4'-bicyclohexylene, bicyclo [2.2.2]octane-1,4-diyl, or spiro[3.3]heptane-2,6-diyl, in which one or two CH groups may be replaced by N, one or more non-adjacent $CH_2$ groups may be replaced by —O— and/or —S— and in which one or more H atoms may be replaced by L, wherein L, on each occurrence, identically or differently, denotes F, Cl, CN, SCN, $SF_5$ or straight-chain or branched, in each case optionally fluorinated, alkyl, alkoxy, alkylcarbonyl, alkoxycarbonyl, alkylcarbonyloxy or alkoxycarbonyloxy each having 1 to 12 C atoms, and preferably $X^{U1}$ and $X^{U2}$ denote F, $R^U$ preferably denotes straight chain or branched or cyclic alkyl or alkenyl having 1 to 7 C atoms, or fluorinated alkyl or fluorinated alkoxy having 1 to 7 C atoms, and

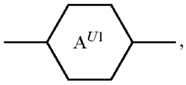, 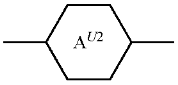

identically or differently, preferably denote

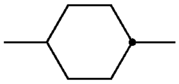, 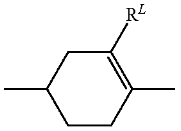,

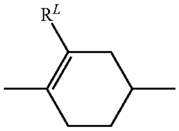, 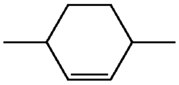,

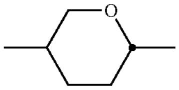, 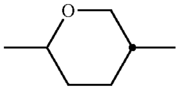,

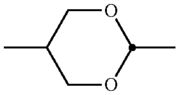, 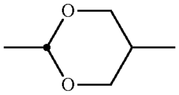,

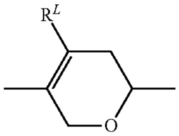, 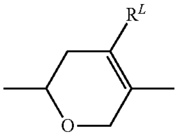,

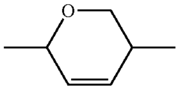, 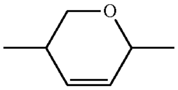,

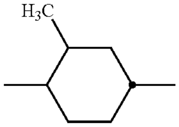, 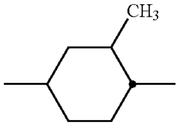,

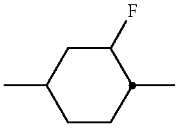 or 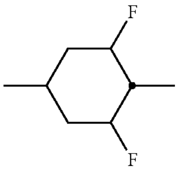,

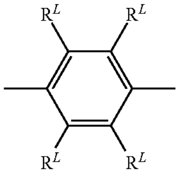, 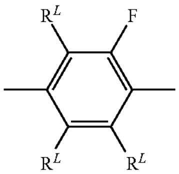,

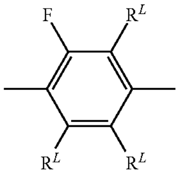, 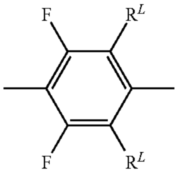,

-continued

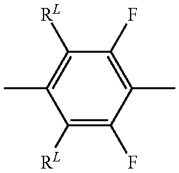, 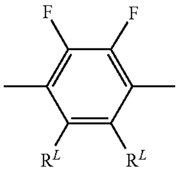,

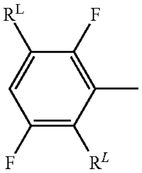, 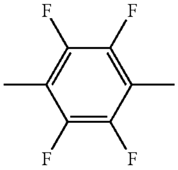,

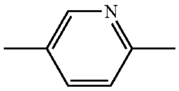, 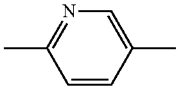,

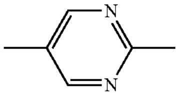, 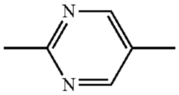

in which $R^L$, on each occurrence, identically or differently, denotes H or alkyl having 1 to 6 C atoms, or denote

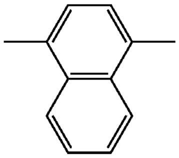 or 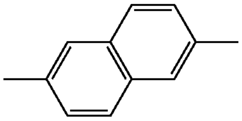

in which one or more H atoms may be replaced by alkyl having 1 to 6 C atoms or F.

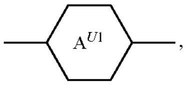, 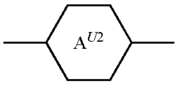

very preferably denote,

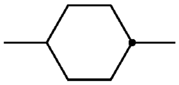, 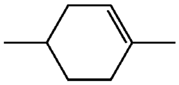,

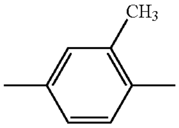, 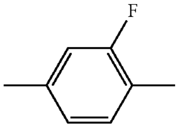 or

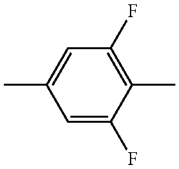. 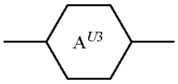

preferably denotes
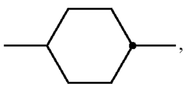, 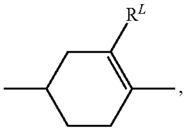,
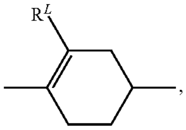, 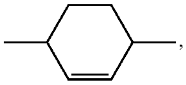,
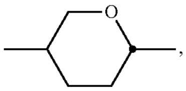, 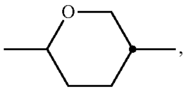,
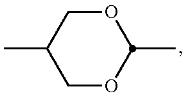, 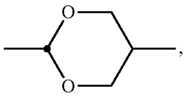,
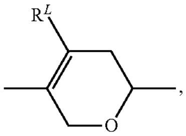, 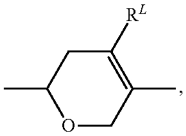,
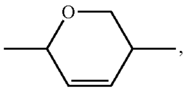, 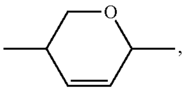,
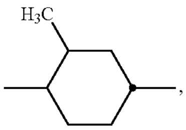, 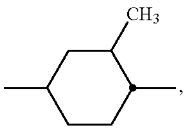,
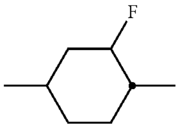 or 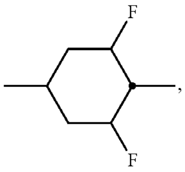,
more preferably
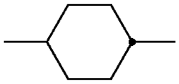 or 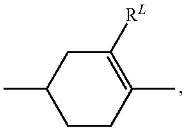,
very preferably
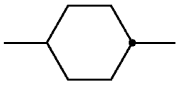,
in which
$R^L$ denotes H or alkyl having 1 to 6 C atoms.
Preferred compounds of formula UI are selected from the following sub-formulae:
UI-1-1
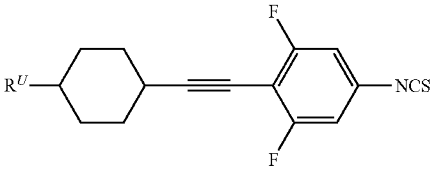
UI-1-2
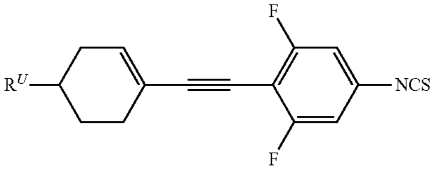
UI-1-3
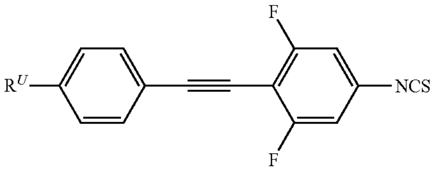
UI-2-1
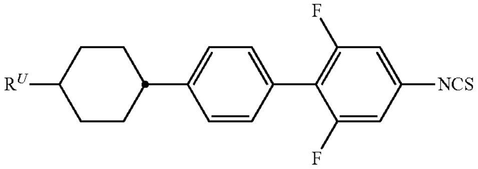
UI-2-2
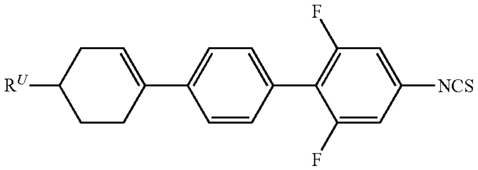
UI-2-3
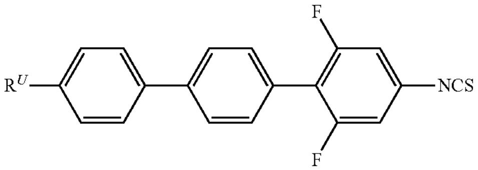
UI-3-1
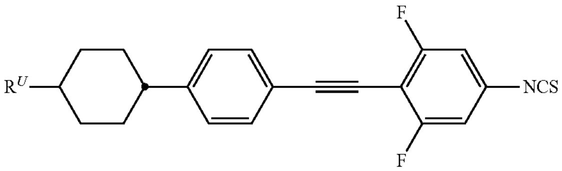

-continued

UI-3-2

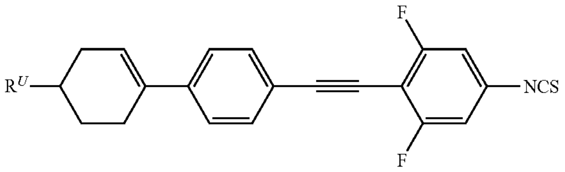

in which $R^U$ has the meanings given above and preferably denotes straight chain or branched alkyl having 1 to 7 C atoms, in particular methyl, ethyl, n-propyl, n-butyl, n-pentyl, n-hexyl or n-heptyl.

The liquid crystal medium according to the invention preferably comprises one or more compounds of formula UI and additionally one or more compounds of the formula UII

UII

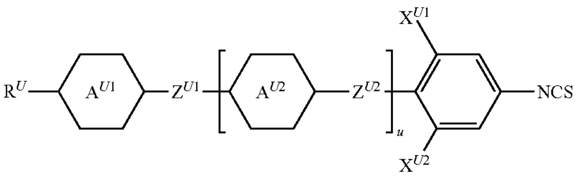

in which $R^U$ denotes H, straight-chain or branched alkyl having 1 to 12 C atoms or alkenyl having 2 to 12 C atoms, in which one or more $CH_2$-groups may be replaced by

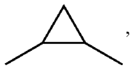,
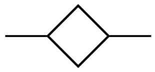,
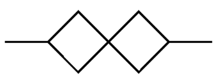,
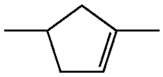 or
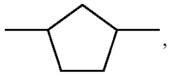, where one or more non-adjacent $CH_2$-groups may be replaced by O, or a group $R^P$, $R^P$ denotes halogen, CN, NCS, $R^F$—, $R^F$—O— or $R^F$—S—, wherein $R^F$ denotes fluorinated alkyl or fluorinated alkenyl having up to 9 C atoms, $Z^{U1}$, $Z^{U2}$ identically or differently, denote —CH═CH—, —CF═CF—, —CH═CF—, —CF═CH—, —C≡C—, —C—C—C—C— or a single bond, preferably —CF═CF—, —C≡C— or a single bond, very preferably —C≡C— or a single bond, $X^{U1}$, $X^{U2}$, identically or differently, denote Cl or F, preferably F,

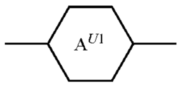 and 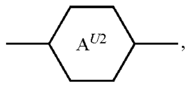, denote a radical selected from the following groups:

a) the group consisting of 1,4-phenylene, 1,4-naphthylene, and 2,6-naphthylene, in which one or two CH groups may be replaced by N and in which one or more H atoms may be replaced by L, b) the group consisting of trans-1,4-cyclohexylene, 1,4-cyclohexenylene, tetralin-2,6-diyl, tetralin-5,8-diyl, decalin-2,6-diyl, bicyclo[1.1.1]pentane-1,3-diyl, 4,4'-bicyclohexylene, bicyclo[2.2.2]octane-1,4-diyl, and spiro[3.3]heptane-2,6-diyl, in which one or two CH groups may be replaced by N, one or more non-adjacent $CH_2$ groups may be replaced by —O— and/or —S— and in which one or more H atoms may be replaced by L, c) the group consisting of thiophene-2,5-diyl, thieno[3,2-b]thiophene-2,5-diyl, selenophene-2,5-diyl, each of which may also be mono- or polysubstituted by L, L on each occurrence, identically or differently, denotes F, Cl, CN, SCN, $SF_5$ or straight-chain or branched, in each case optionally fluorinated, alkyl, alkoxy, alkylcarbonyl, alkoxycarbonyl, alkylcarbonyloxy or alkoxycarbonyloxy each having 1 to 12 C atoms, and u is 0, 1 or 2, preferably 1, where the compounds of formula UI are excluded from the compounds of formula UII.

Preferably, the compounds of the formula UII are selected from the compounds of the formulae UII-1, UII-2 and UII-3, preferably UII-1 and UII-2, in particular UII-1:

UII-1

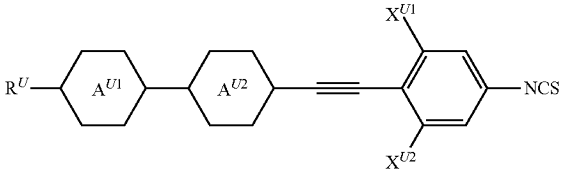

UII-2

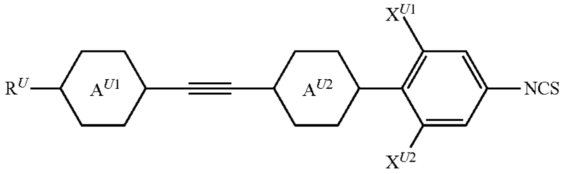

UII-3

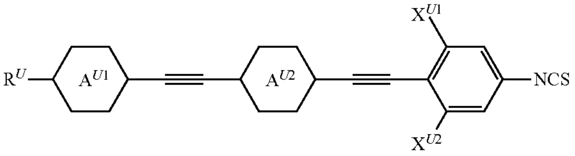

in which the occurring groups have the meanings given above for formula UII and preferably

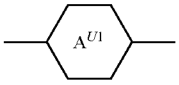 and 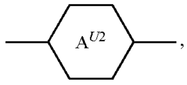, identically or differently, denote

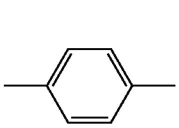 , 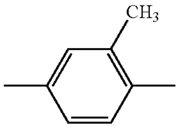 ,

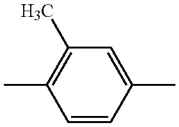 , 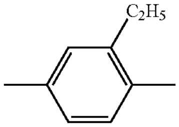 ,

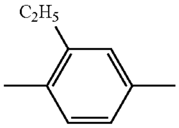 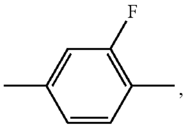 ,

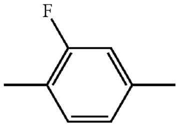 , 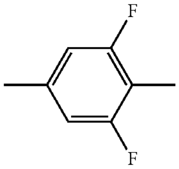 ,

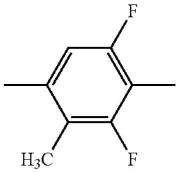 or 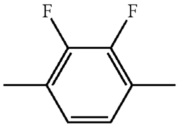 , $X^{U1}$ and $X^{U2}$ denote F, and $R^U$ preferably denotes straight chain or branched or cyclic alkyl or alkenyl having 1 to 7 C atoms, or fluorinated alkyl or fluorinated alkoxy having 1 to 7 C atoms.

Very preferred compounds of formula UII are selected from the following sub-formulae:

UII-1-1

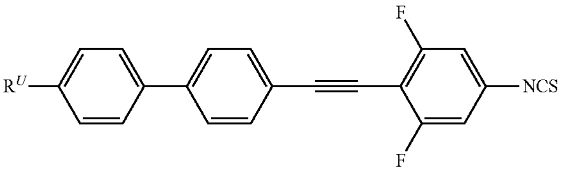

UII-1-2

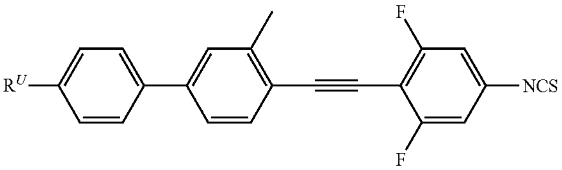

UII-1-3

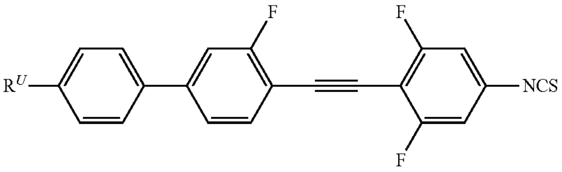

-continued

UII-2-1

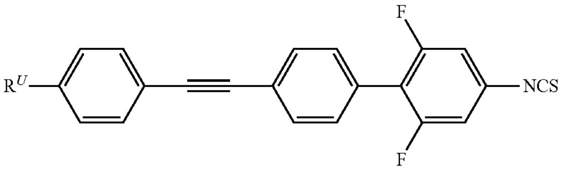

UII-2-2

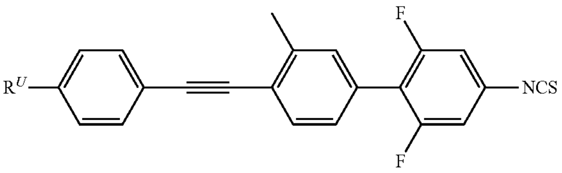

UII-2-3

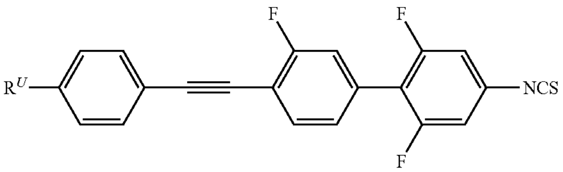

in which $R^U$ has the meanings given above and preferably denotes straight chain or branched alkyl having 1 to 7 C atoms, in particular methyl, ethyl, n-propyl, n-butyl, n-pentyl, n-hexyl or n-heptyl.

In a preferred embodiment the medium according to the invention comprises one or more compounds selected from the group of the formulae I, II and III:

I

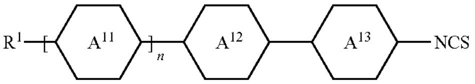

II

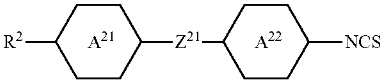

III

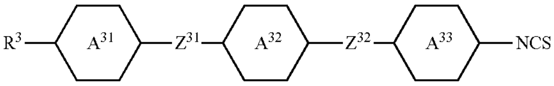

in which $R^1$ denotes H, unfluorinated alkyl or unfluorinated alkoxy having 1 to 17, preferably 2 to 10 C atoms, or unfluorinated alkenyl, unfluorinated alkenyloxy or unfluorinated alkoxyalkyl having 2 to 15, preferably 3 to 10, C atoms, in which one or more $CH_2$-groups may be replaced by

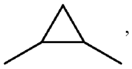 , 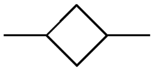 ,

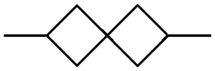 , 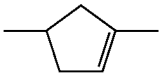 or

-continued

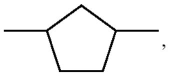, preferably unfluorinated alkyl or unfluorinated alkenyl, n is 0, 1 or 2,

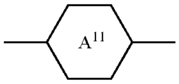 to 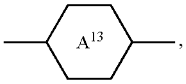, on each occurrence, independently of one another, denote

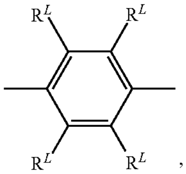, 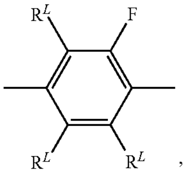,

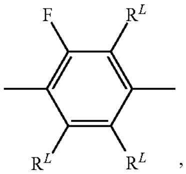, 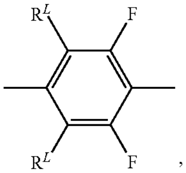,

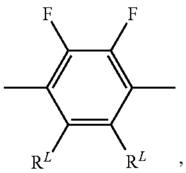, 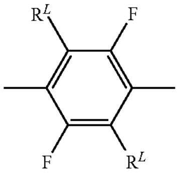 or

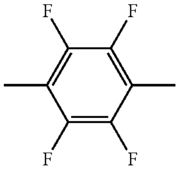

in which $R^L$, on each occurrence, identically or differently, denotes H or alkyl having 1 to 6 C atoms, preferably H, methyl or ethyl, particularly preferably H, or

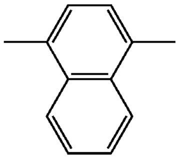 or 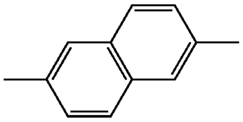

in which one or more H atoms may be replaced by alkyl having 1 to 6 C atoms or F, and wherein

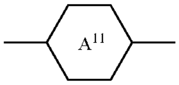

alternatively denotes

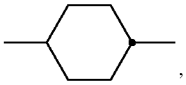, 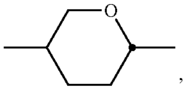,

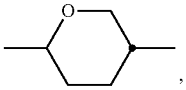, 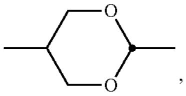,

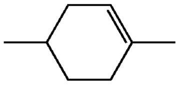 or 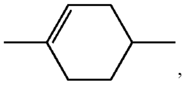, preferably

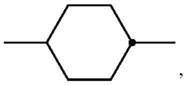, and in case n=2, one of

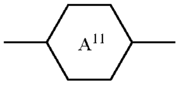

preferably denotes

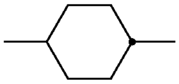

and the other preferably denotes

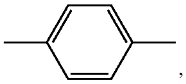, 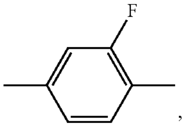,

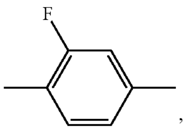, 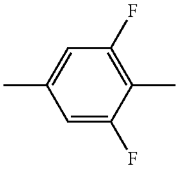 or

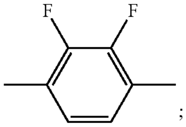;

preferably

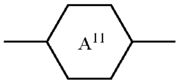 to 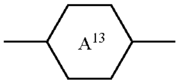, independently of one another, denote

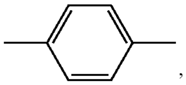, 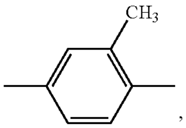, 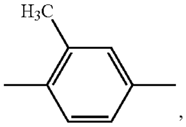, 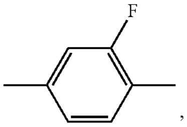, 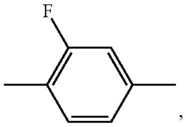, 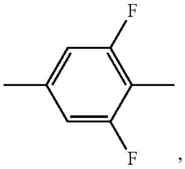, 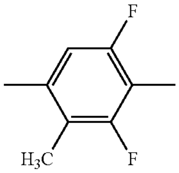 or 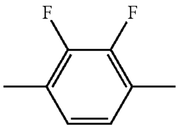, more preferably

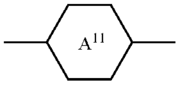

denotes

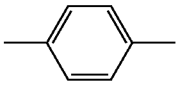 or 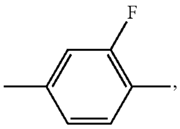,

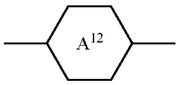

denotes

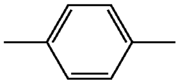, 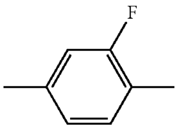 or

-continued

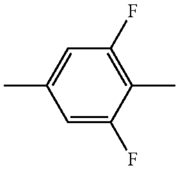,

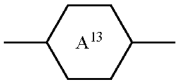

denotes

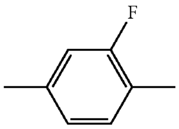 or 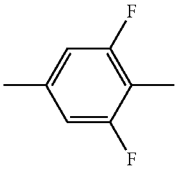;

$R^2$ denotes H, unfluorinated alkyl or unfluorinated alkoxy having 1 to 17, preferably 2 to 10 C atoms, or unfluorinated alkenyl, unfluorinated alkenyloxy or unfluorinated alkoxyalkyl having 2 to 15, preferably 3 to 10, C atoms, in which one or more $CH_2$-groups may be replaced by

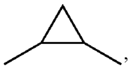, 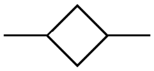, 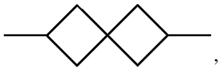, 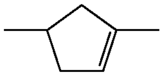 or 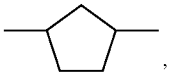, preferably unfluorinated alkyl or unfluorinated alkenyl, $Z^{21}$ denotes trans-CH═CH—, trans-CF═CF— or —C≡C—, preferably —C≡C— or trans-CH═CH—, and

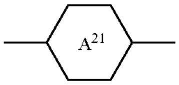 and 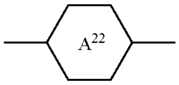, independently of one another, denote

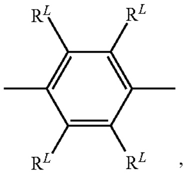, 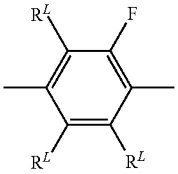,

-continued

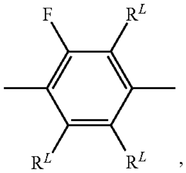,
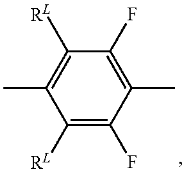,
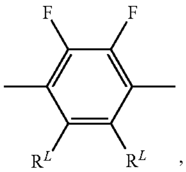,
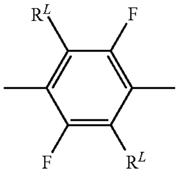
or
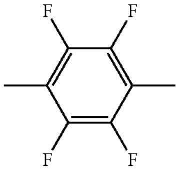

in which $R^L$, on each occurrence, identically or differently, denotes H or alkyl having 1 to 6 C atoms, preferably H, methyl or ethyl, particularly preferably H, or

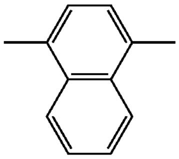
or
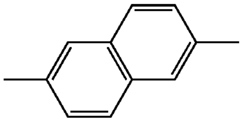

in which one or more H atoms may be replaced by alkyl having 1 to 6 C atoms or F, preferably

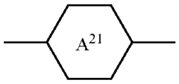
and
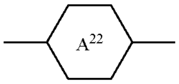, independently of one another, denote

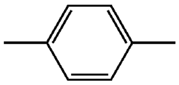,
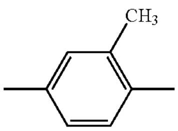,
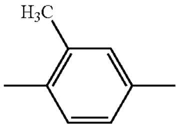,
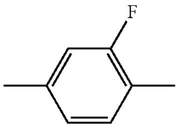,
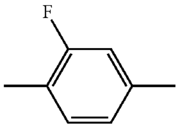,
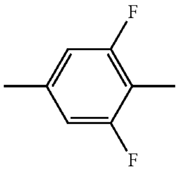,

-continued

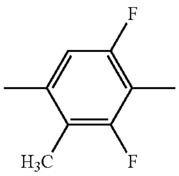
or
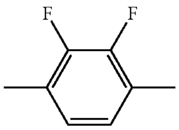,
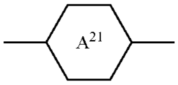

preferably denotes

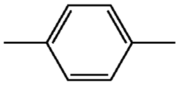
or
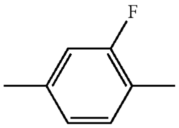, and

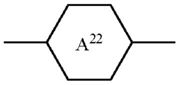

preferably denotes

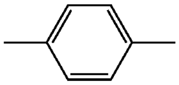,
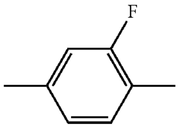
or
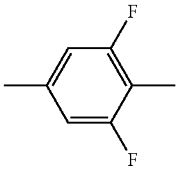, more preferably

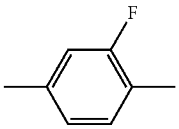
or
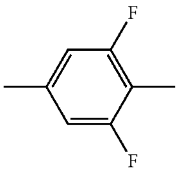;

$R^3$ denotes H, unfluorinated alkyl or unfluorinated alkoxy having 1 to 17, preferably 2 to 10 C atoms, or unfluorinated alkenyl, unfluorinated alkenyloxy or unfluorinated alkoxyalkyl having 2 to 15, preferably 3 to 10, C atoms, in which one or more $CH_2$-groups may be replaced by

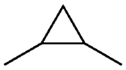, 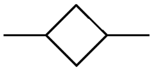,

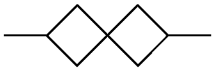, 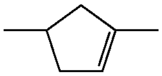 or

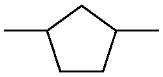, preferably unfluorinated alkyl or unfluorinated alkenyl, one of $Z^{31}$ and $Z^{32}$, preferably $Z^{32}$, denotes trans-CH═CH—, trans-CF═CF— or —C≡C— and the other one, independently thereof, denotes —C═C—, trans-CH═CH—, trans-CF═CF— or a single bond, preferably one of them, preferably $Z^{32}$ denotes —C═C— or trans-CH═CH— and the other denotes a single bond, and

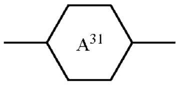 to 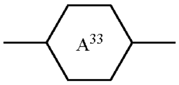, independently of one another, denote

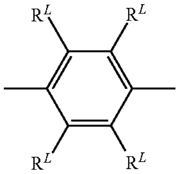, 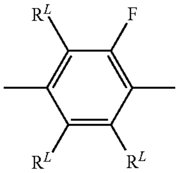,

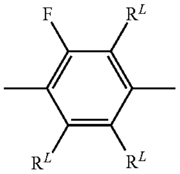, 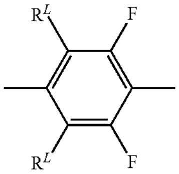,

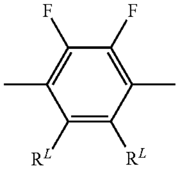, 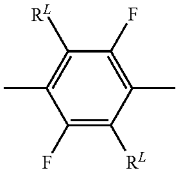 or

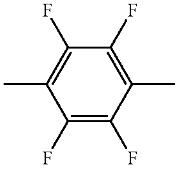, in which $R^L$, on each occurrence, identically or differently, denotes H or alkyl having 1 to 6 C atoms, preferably H, methyl or ethyl, particularly preferably H, or

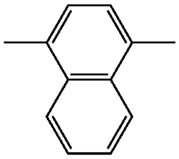 or 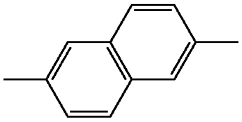

in which one or more H atoms may be replaced by alkyl having 1 to 6 C atoms or F, and wherein

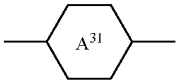

alternatively denotes, or

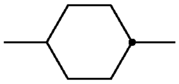, 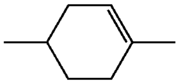 or

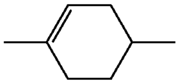, preferably

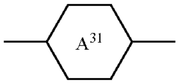 to 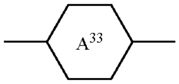, independently of one another, denote

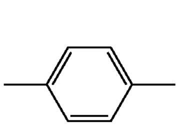, 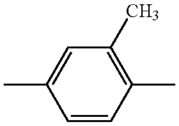,

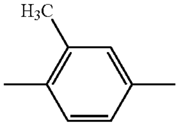, 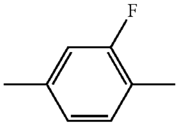,

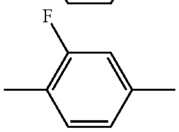, 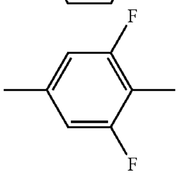,

-continued

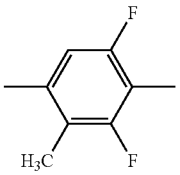

, or

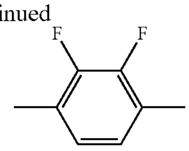

, more preferably

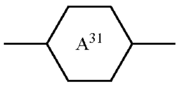

denotes

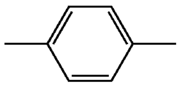

or

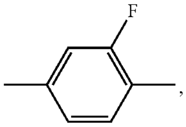

,

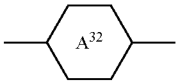

denotes

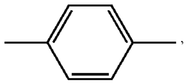

,

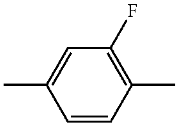

or

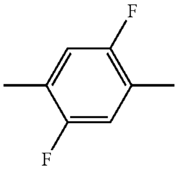

in particular

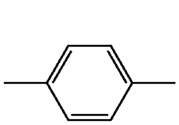

or

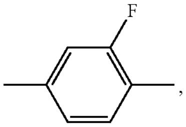

,

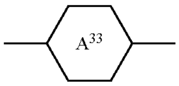

denotes

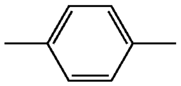

,

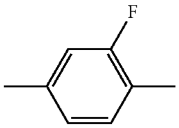

or

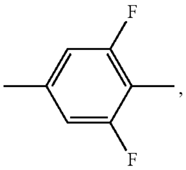

, in particular

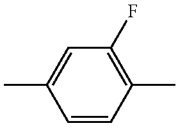

or

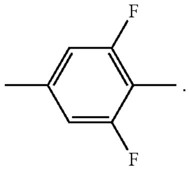

.

In the compounds of the formulae I, II and III, $R^L$ preferably denotes H. In another preferred embodiment, in the compounds of formulae I, II and III, one or two groups $R^L$, preferably one group $R^L$ is different from H.

In a preferred embodiment of the present invention, the compounds of formula I are selected from the group of compounds of the formulae I-1 to 1-5:

I-1

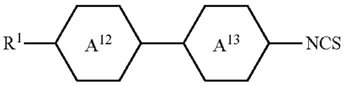

I-2

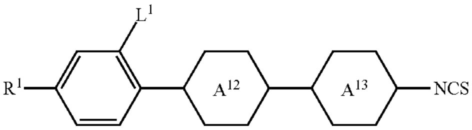

I-3

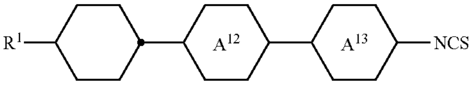

I-4

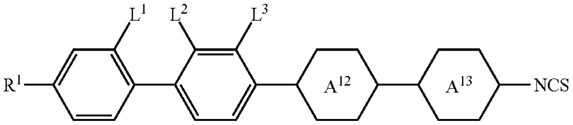

I-5

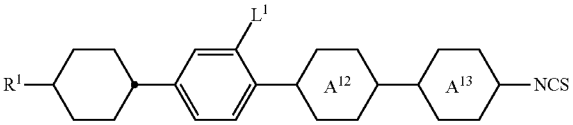

in which $L^1$, $L^2$ and $L^3$ on each occurrence, identically or differently, denote H or F, and the other groups have the respective meanings indicated above for formula I and preferably $R^1$ denotes unfluorinated alkyl having 1 to 7 C atoms or unfluorinated alkenyl having 2 to 7 C atoms.

Preferably, the medium comprises one or more compounds selected from the compounds of the formula 1-1 and optionally one or more compounds selected from the compounds of the formula Cy-1

I-1

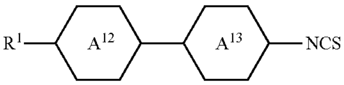

Cy-I

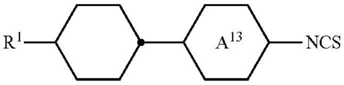

in which the occurring groups have the meanings given above for formula 1-1. The total amount of compounds of the formula 1-1 and/or Cy-I in the medium according to the invention is less than 10%, more preferably less than 5%, and in particular less than 2%. Particularly preferably, the medium contains no compound of formula Cy-1.

The media preferably comprise one or more compounds of formula 1-1, which are preferably selected from the group of the compounds of the formulae I-1a to I-1d, preferably of formula 1-1b:

I-1a

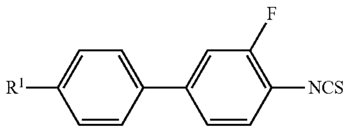

I-1b

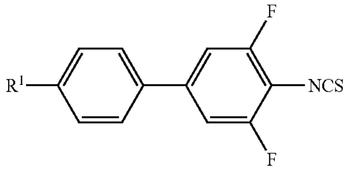

I-1c

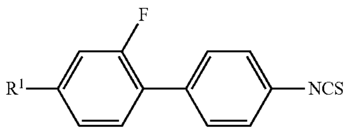

I-1d

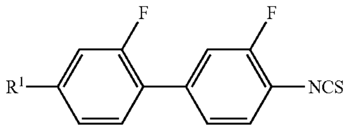

in which $R^1$ has the meaning indicated above for formula I and preferably denotes unfluorinated alkyl having 1 to 7 C atoms or unfluorinated alkenyl having 2 to 7 C atoms.

The media preferably comprise one or more compounds of formula 1-2, which are preferably selected from the group of the compounds of the formulae 1-2a to 1-2e, preferably of formula 1-2c:

I-2a

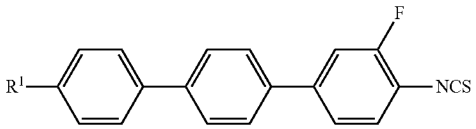

I-2b

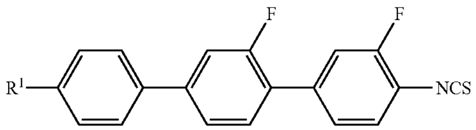

I-2c

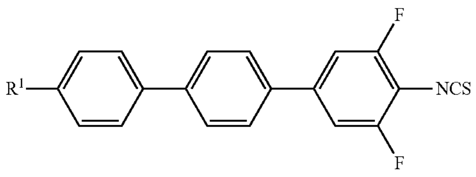

I-2d

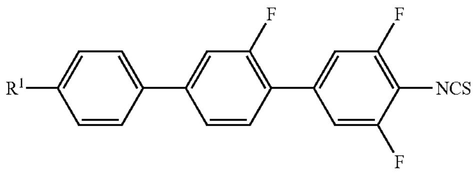

-continued

I-2e

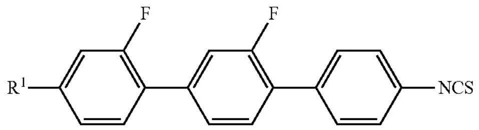

in which $R^1$ has the meaning indicated above for formula I and preferably denotes unfluorinated alkyl having 1 to 7 C atoms or unfluorinated alkenyl having 2 to 7 C atoms.

The media preferably comprise one or more compounds of formula 1-3, which are preferably selected from the group of the compounds of the formulae 1-3a to I-3d, particularly preferably of formula 1-3b:

I-3a

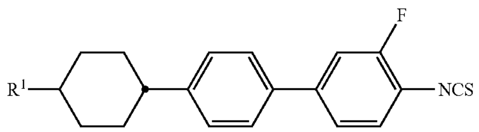

I-3b

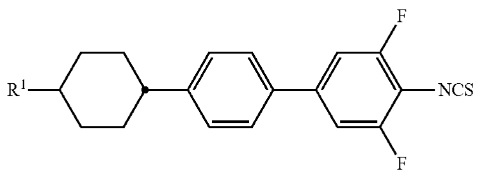

I-3c

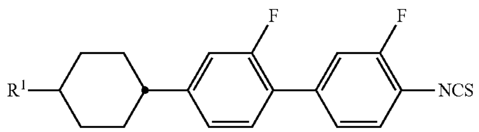

I-3d

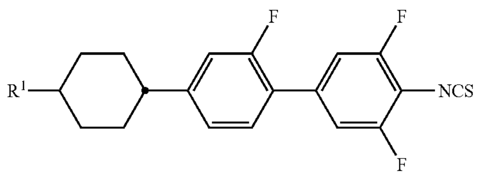

in which $R^1$ has the meaning indicated above for formula I and preferably denotes unfluorinated alkyl having 1 to 7 C atoms or unfluorinated alkenyl having 2 to 7 C atoms.

The media preferably comprise one or more compounds of formula 1-4, which are preferably selected from the group of the compounds of the formulae 1-4a to 1-4e, particularly preferably of formula 1-4b:

I-4a

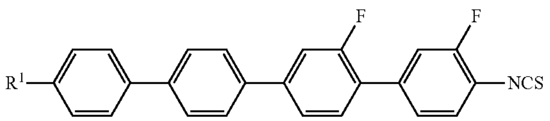

I-4b

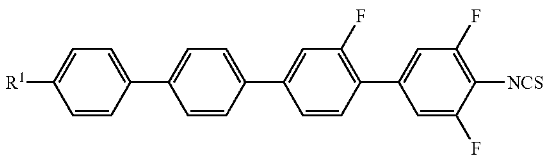

-continued

I-4c

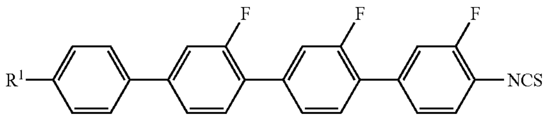

I-4d

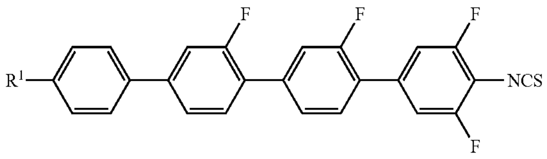

I-4e

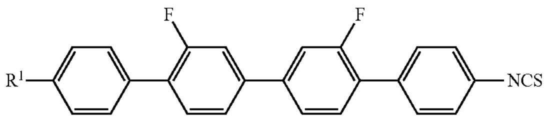

in which $R^1$ has the meaning indicated above for formula I and preferably denotes unfluorinated alkyl having 1 to 7 C atoms or unfluorinated alkenyl having 2 to 7 C atoms.

The media preferably comprise one or more compounds of formula 1-5, which are preferably selected from the group of the compounds of the formulae 1-5a to 1-5d, particularly preferably of formula 1-5b:

I-5a

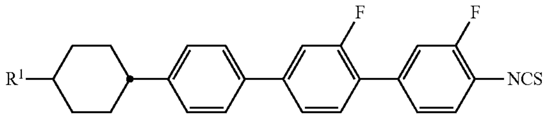

I-5b

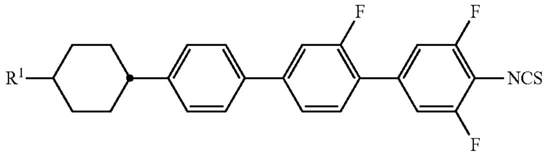

I-5c

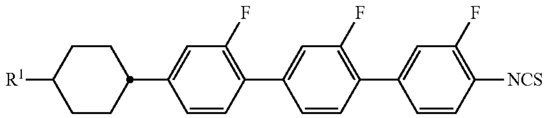

I-5d

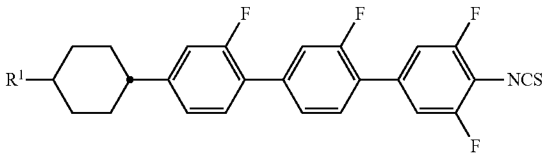

in which $R^1$ has the meaning indicated above for formula I and preferably denotes unfluorinated alkyl having 1 to 7 C atoms or unfluorinated alkenyl having 2 to 7 C atoms.

The media preferably comprise one or more compounds of formula II, which are preferably selected from the group of the compounds of the formulae II-1 to II-3, preferably selected from the group of the compounds of the formulae II-1 and II-2:

II-1

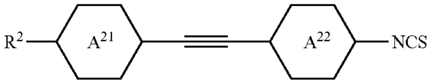

II-2

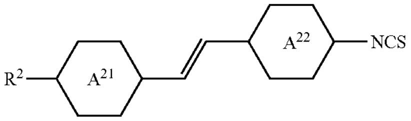

II-3

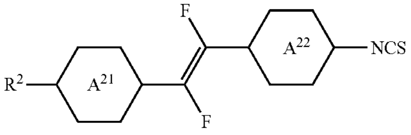

in which the occurring groups have the meanings given under formula II above and preferably $R^2$ denotes unfluorinated alkyl or alkoxy having 1 to 7 C atoms or unfluorinated alkenyl having 2 to 7 C atoms, and one of

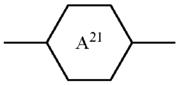 and 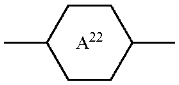

denotes

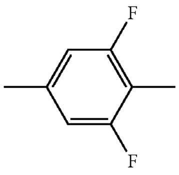 or 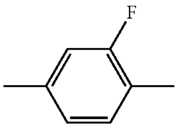, and the other, independently denotes

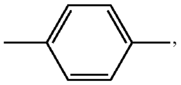, 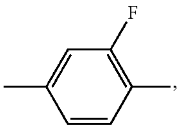,

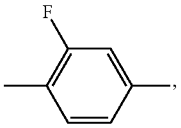, 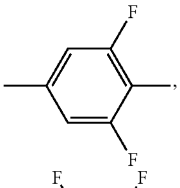,

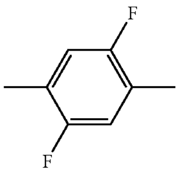 or 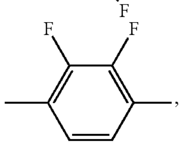, preferably

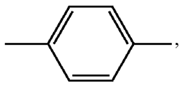,
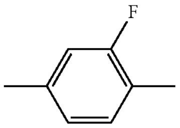 or
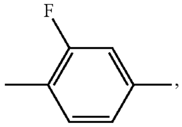, most preferably

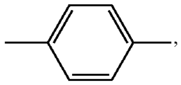, and preferably $R^2$ denotes $C_nH_{2n+1}$ or $CH_2{=}CH{-}(CH_2)_z$, and n denotes an integer in the range from 1 to 7, preferably in the range from 2 to 6 and particularly preferably 3 to 5, and z denotes 0, 1, 2, 3 or 4, preferably 0 or 2.

The compounds of formula II-1 are preferably selected from the group of the compounds of the formulae II-1a to II-1e:

II-1a

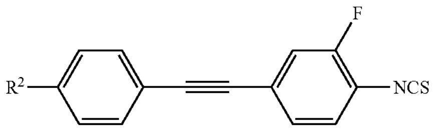

II-1b

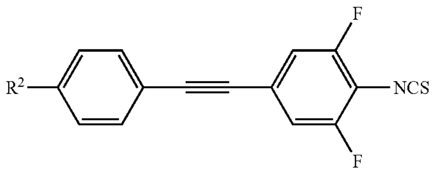

II-1c

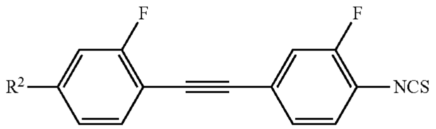

II-1d

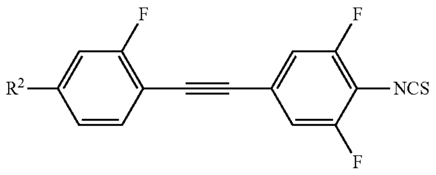

II-1e

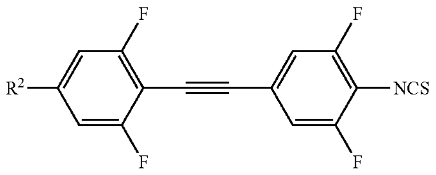

$R^2$ has the meaning indicated above and preferably denotes $C_nH_{2n+1}$ or $CH_2{=}CH{-}(CH_2)_z$, and n denotes an integer in the range from 1 to 7, preferably in the range from 2 to 6 and particularly preferably 3 to 5, and z denotes 0, 1, 2, 3 or 4, preferably 0 or 2.

The compounds of formula II-2 are preferably selected from the group of the compounds of the formulae II-2a and II-2b:

II-2a

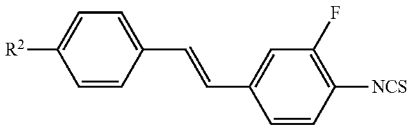

II-2b

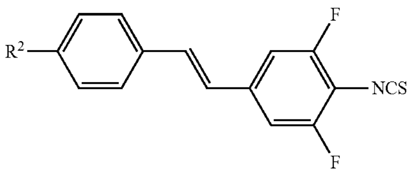

in which $R^2$ has the meaning indicated above and preferably denotes $C_nH_{2n+1}$ or $CH_2{=}CH{-}(CH_2)_z$, n denotes an integer in the range from 1 to 7, preferably in the range from 2 to 6 and particularly preferably 3 to 5, and z denotes 0, 1, 2, 3 or 4, preferably 0 or 2.

The compounds of formula II-3 are preferably selected from the group of the compounds of the of formulae II-3a to II-3d:

II-3a

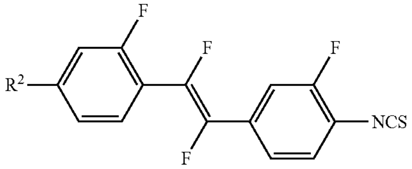

II-3b

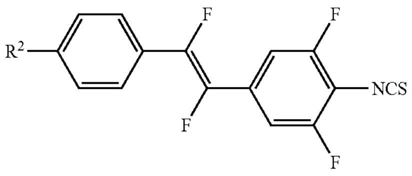

II-3c

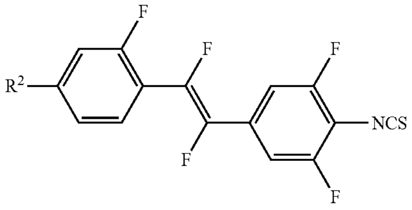

-continued

II-3d

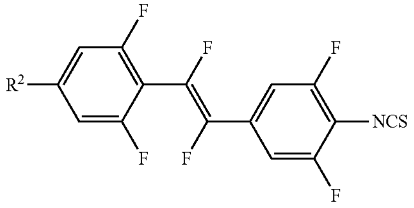

in which $R^2$ has the meaning indicated above and preferably denotes $C_nH_{2n+1}$ or $CH_2$═CH—$(CH_2)_z$, n denotes an integer in the range from 1 to 7, preferably in the range from 2 to 6 and particularly preferably 3 to 5, and z denotes 0, 1, 2, 3 or 4, preferably 0 or 2.

The compounds of formula III are preferably selected from the group of the compounds of the formulae III-1 to III-6, more preferably of the formulae selected from the group of the compounds of the formulae III-1, III-2, III-3 and III-4, and particularly preferably of formula III-1:

III-1

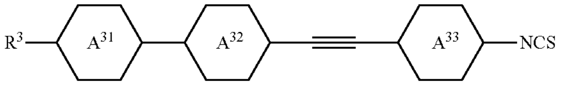

III-2

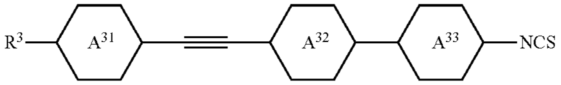

III-3

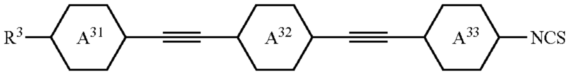

III-4

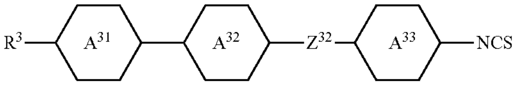

III-5

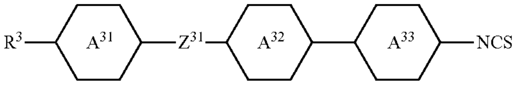

III-6

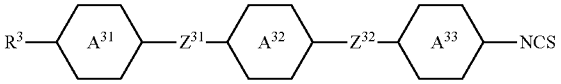

in which $Z^{31}$ and $Z^{32}$ independently of one another denote trans-CH═CH— or trans-CF═CF—, preferably trans-CH═CH—, and in formula III-6 alternatively one of $Z^{31}$ and $Z^{32}$ may denote —C≡C— and the other groups have the meaning given above under formula III, and preferably $R^3$ denotes unfluorinated alkyl or alkoxy having 1 to 7 C atoms or unfluorinated alkenyl having 2 to 7 C atoms, and one of

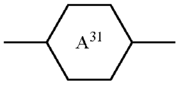

to

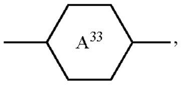

, preferably

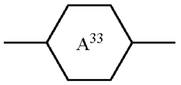

, denotes

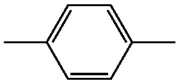

,

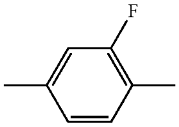

,

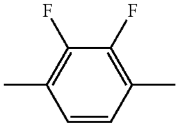

,

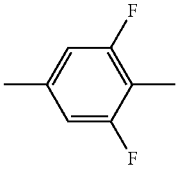

or

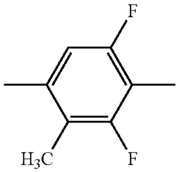

, very preferably

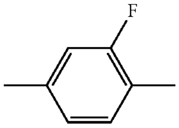

or

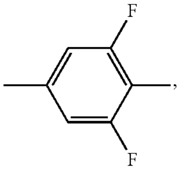

, and the others, independently of one another, denote

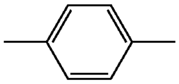

,

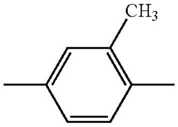

,

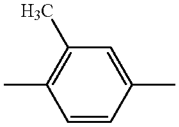

,

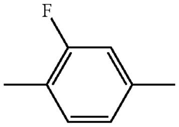

,

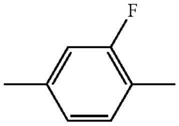

,

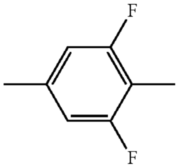

,

-continued

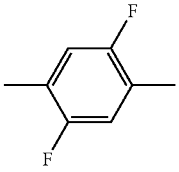

or

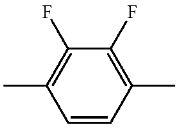

, preferably

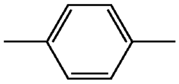

,

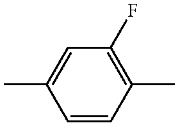

,

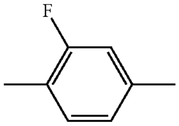

, or

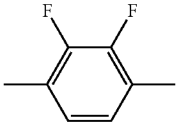

, more preferably

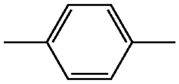

or,

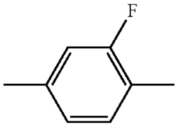

, where

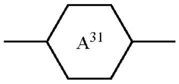

alternatively denotes

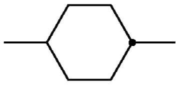

and preferably $R^3$ denotes $C_nH_{2n+1}$ or $CH_2{=}CH{-}(CH_2)_z$, n denotes an integer in the range from 1 to 7, preferably in the range from 2 to 6 and particularly preferably 3 to 5, and z denotes 0, 1, 2, 3 or 4, preferably 0 or 2.

The compounds of formula III-1 are preferably selected from the group of the compounds of the formulae III-1a to III-1j, more preferably selected from the group of the compounds of the formulae III-1a, III-1 b, III-1g and III-1 h, particularly preferably of formula III-1b and/or III-1h:

III-1a

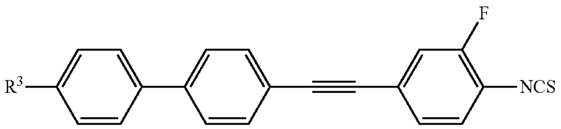

-continued

III-1b

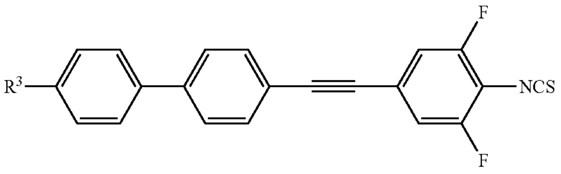

III-1c

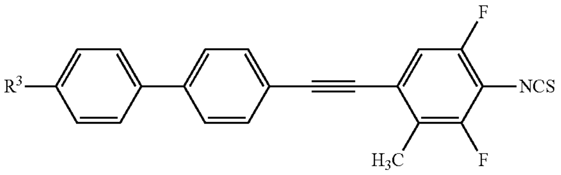

III-1d

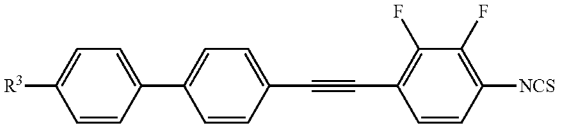

III-1e

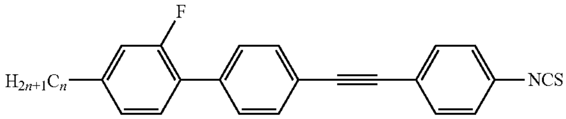

III-1f

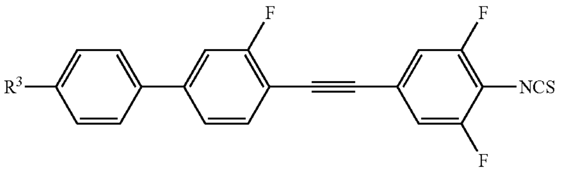

III-1g

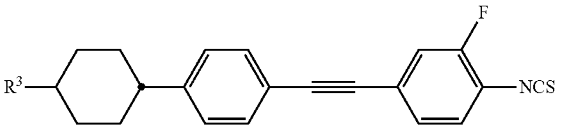

III-1h

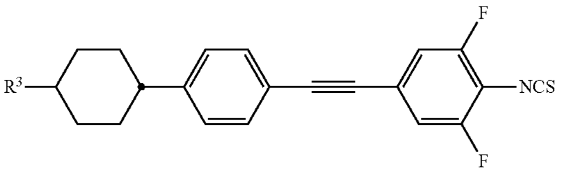

III-1i

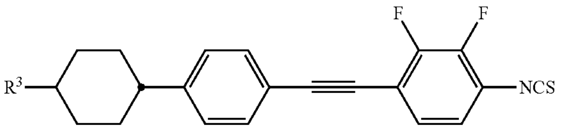

-continued

III-1j

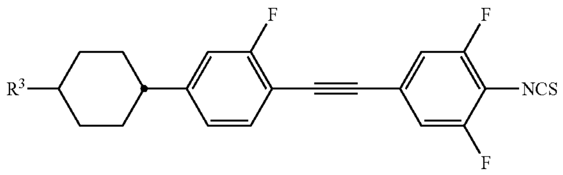

in which $R^3$ has the meaning indicated above and preferably denotes $C_nH_{2n+1}$ or $CH_2{=}CH{-}(CH_2)_z$, n denotes an integer in the range from 1 to 7, preferably in the range from 2 to 6 and particularly preferably 3 to 5, and z denotes 0, 1, 2, 3 or 4, preferably 0 or 2.

The compounds of formula III-2 are preferably compounds of formula III-2a to III-21, very preferably III-2b and/or III-2j:

III-2a

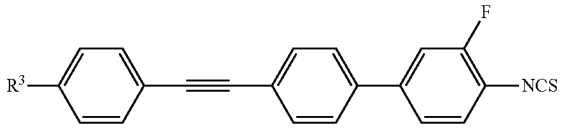

III-2b

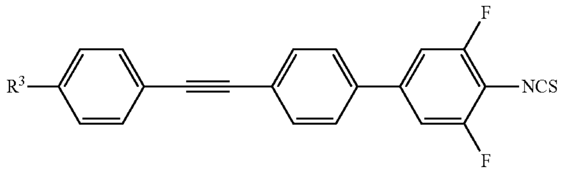

III-2c

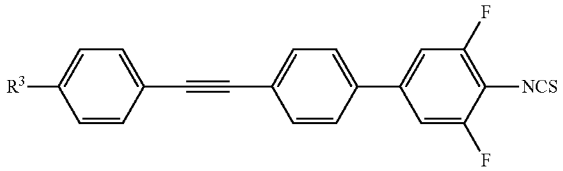

III-2d

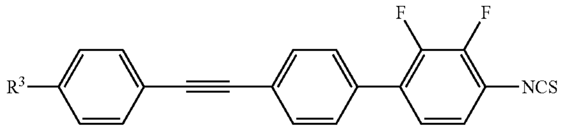

III-2e

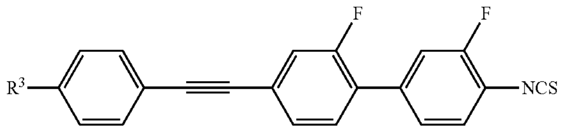

III-2f

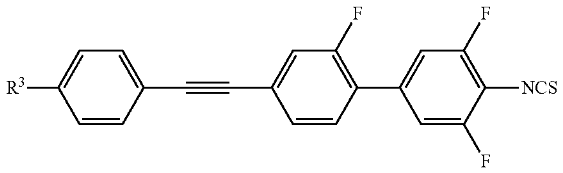

-continued

III-2g

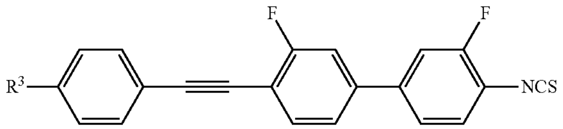

III-2h

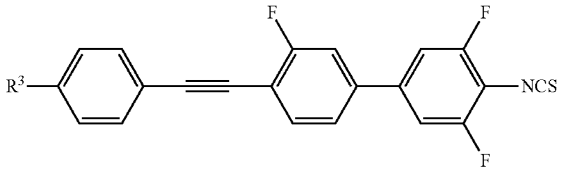

III-2i

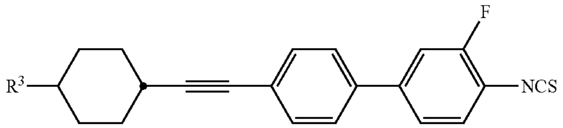

III-2j

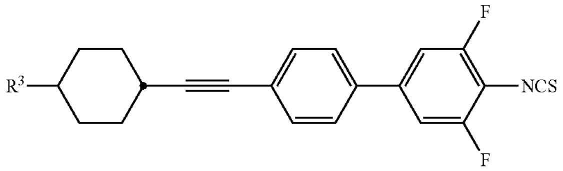

III-2k

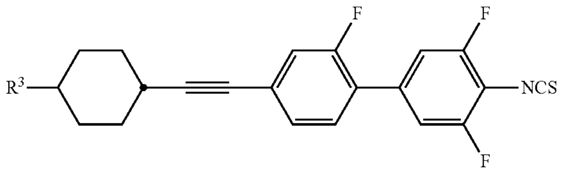

III-2l

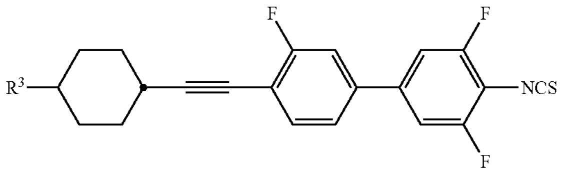

in which $R^3$ has the meaning indicated above and preferably denotes $C_nH_{2n+1}$ or $CH_2{=}CH{-}(CH_2)_z$, n denotes an integer in the range from 1 to 7, preferably in the range from 2 to 6 and particularly preferably 3 to 5, and z denotes 0, 1, 2, 3 or 4, preferably 0 or 2.

The compounds of formula III-5 are preferably selected from the compounds of formula III-5a:

III-5a

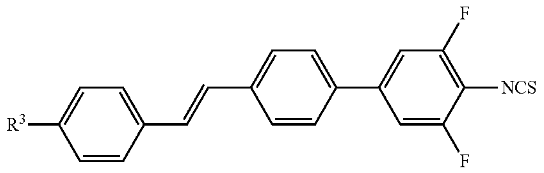

$R^3$ has the meaning indicated above for formula III-5 and preferably denotes $C_nH_{2n+1}$, in which n denotes an integer in the range from 1 to 7, preferably in the range from 2 to 6.

In a preferred embodiment, the media according to the invention comprise one or more compounds selected from the group of compounds of the formulae IIA-1-1 to IIA-1-12, very preferably IIA-1-1 or IIA-1-2:

IIA-1-1

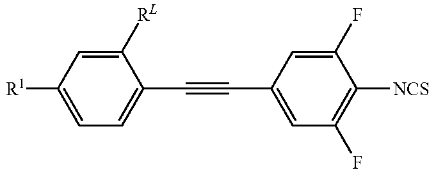

IIA-1-2

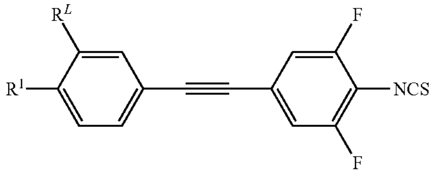

IIA-1-3

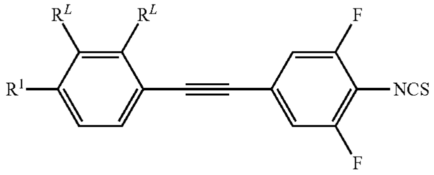

IIA-1-4

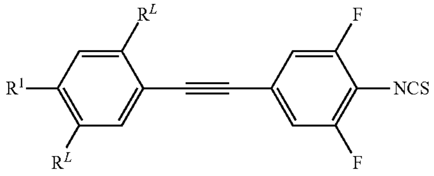

IIA-1-5

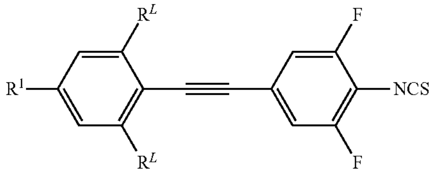

IIA-1-6

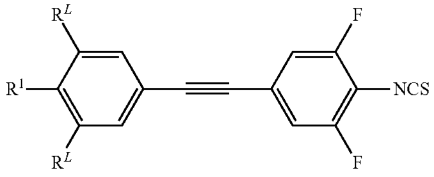

IIA-1-7

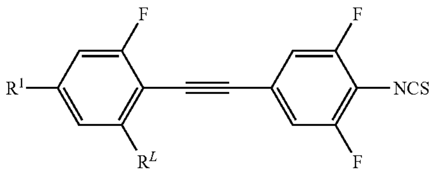

-continued

IIA-1-8

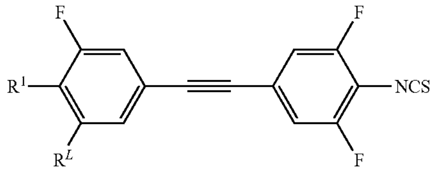

IIA-1-9

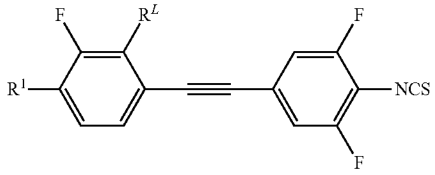

IIA-1-10

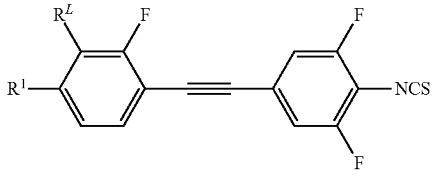

IIA-1-11

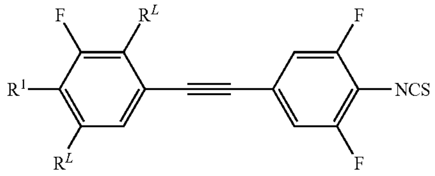

IIA-1-12

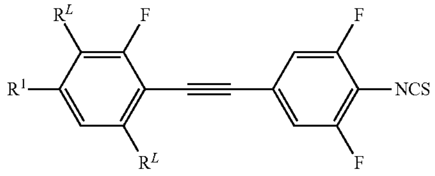

in which $R^1$ denotes alkyl or alkenyl having up to 7 C atoms, preferably ethyl, n-propyl, n-butyl or n-pentyl, n-hexyl, $R^L$ on each occurrence, the same or differently, denotes alkyl or alkenyl having 1 to 5 C atoms, or cycloalkyl or cycloalkenyl each having 3 to 6 C atoms, preferably methyl, ethyl, n-propyl, n-butyl, isopropyl, cyclopropyl, cyclobutyl, cyclopentyl or cyclopent-1-enyl, very preferably ethyl, and from which the compounds of formula II-1 are excluded.

Additionally, the liquid-crystalline media according to the present invention in a certain embodiment, which may be the same or different from the previous preferred embodiments preferably comprise one or more compounds of formula IV,

IV

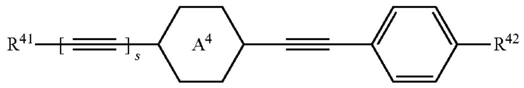

in which

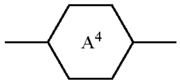

denotes

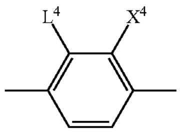,
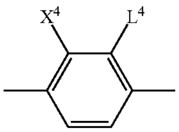,
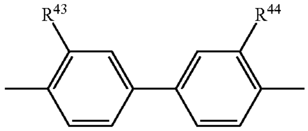,
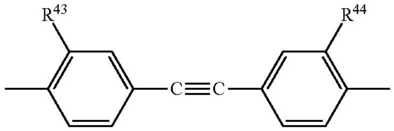 or
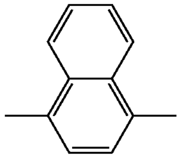, is is 0 or 1, preferably 1, and preferably

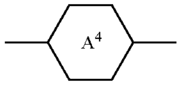

denotes

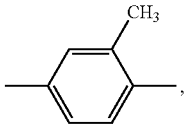,
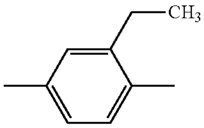,
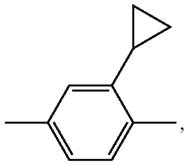,
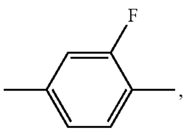,
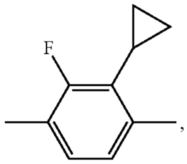,
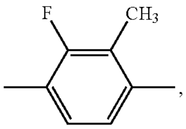,
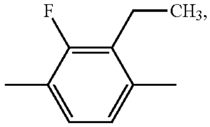

-continued

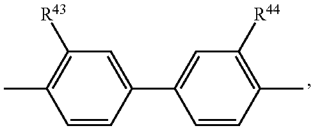,
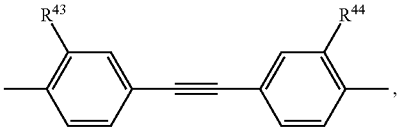, or
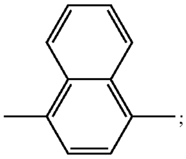;

particularly preferably

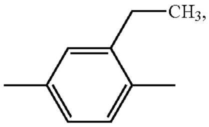
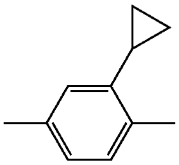,
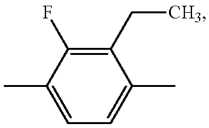
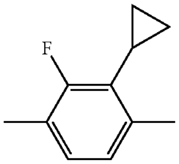 or
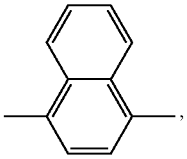, $L^4$ denotes H or alkyl having 1 to 6 C atoms, cycloalkyl having 3 to 6 C atoms or cycloalkenyl having 4 to 6 C atoms, preferably $CH_3$, $C_2H_5$, n-$C_3H_7$, i-$C_3H_7$, cyclopropyl, cyclobutyl, cyclohexyl, cyclopent-1-enyl or cyclohex-1-enyl, and particularly preferably $CH_3$, $C_2H_5$, cyclopropyl or cyclobutyl, $X^4$ denotes H, alkyl having 1 to 3 C atoms or halogen, preferably H, F or Cl, more preferably H or F and very particularly preferably F, $R^{41}$ to $R^{44}$, independently of one another, denote unfluorinated alkyl or unfluorinated alkoxy, each having 1 to 15 C atoms, unfluorinated alkenyl, unfluorinated alkenyloxy or unfluorinated alkoxyalkyl, each having 2 to 15 C atoms, or cycloalkyl, alkylcycloalkyl, cycloalkenyl, alkylcycloalkenyl, alkylcycloalkyl-alkyl or alkylcycloalkenylalkyl, each having up to 15 C atoms, and alternatively one of $R^{43}$ and $R^{44}$ or both also denote H, preferably $R^{41}$ and $R^{42}$, independently of one another, denote unfluorinated alkyl or unfluorinated alkoxy, each having 1 to 7 C atoms, or unfluorinated alkenyl, unfluorinated alkenyloxy or unfluorinated alkoxyalkyl, each having 2 to 6 C atoms, particularly preferably $R^{41}$ denotes unfluorinated alkyl having 1 to 7 C atoms or unfluorinated alkenyl, unfluorinated alkenyloxy or unfluorinated alkoxyalkyl, each having 2 to 6 C atoms, and particularly preferably $R^{42}$ denotes unfluorinated alkyl or unfluorinated alkoxy, each having 1 to 7 C atoms, and preferably $R^{43}$ and $R^{44}$ denote H, unfluorinated alkyl having 1 to 5 C atoms, unfluorinated cycloalkyl or cycloalkenyl having 3 to 7 C atoms, unfluorinated alkylcyclohexyl or unfluorinated cyclohexylalkyl, each having 4 to 12 C atoms, or unfluorinated alkylcyclohexylalkyl having 5 to 15 C atoms, particularly preferably cyclopropyl, cyclobutyl or cyclohexyl, and very particularly preferably at least one of $R^{43}$ and $R^{44}$ denotes n-alkyl, particularly preferably methyl, ethyl or n-propyl, and the other denotes H or n-alkyl, particularly preferably H, methyl, ethyl or n-propyl.

Very preferably, the compounds of formula IV are selected from the compounds of the formula IV-1

IV-1

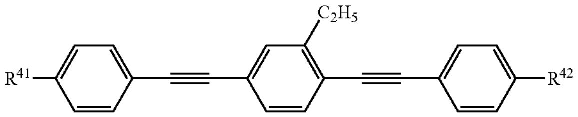

in which $R^{41}$ and $R^{42}$, identically or differently, denote alkyl having 2, 3, 4, 5 or 6 C atoms.

In a preferred embodiment of the present invention, the liquid-crystal medium additionally comprises one or more compounds selected from the group of compounds of the formulae V, VI, VII, VIII and IX:

V

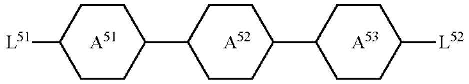

VI

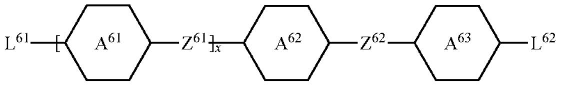

VII

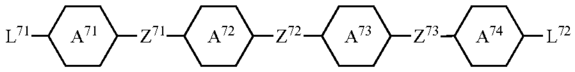

VIII

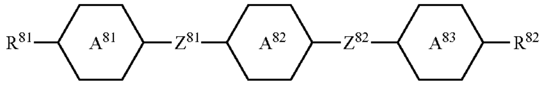

IX

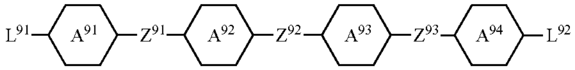

in which $L^{51}$ denotes $R^{51}$ or $X^{51}$, $L^{52}$ denotes $R^{52}$ or $X^{52}$, $R^{51}$ and $R^{52}$, independently of one another, denote H, unfluorinated alkyl or unfluorinated alkoxy having 1 to 17, preferably 2 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, $X^{51}$ and $X^{52}$, independently of one another, denote H, F, Cl, —CN, $SF_5$, fluorinated alkyl or fluorinated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F or Cl, and

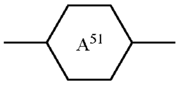 to 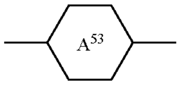, independently of one another, denote

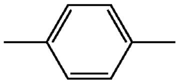, 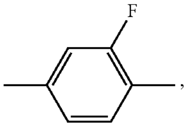,

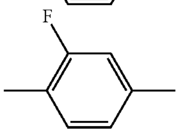, 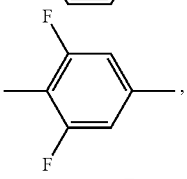,

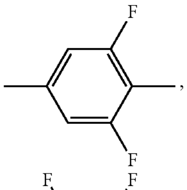, 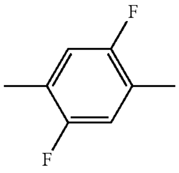 or

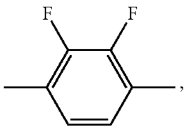, preferably

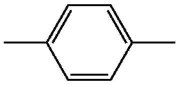, 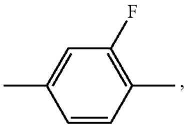,

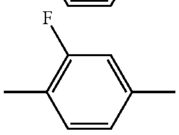, or 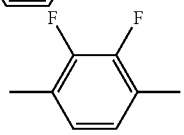, $L^{61}$ denotes $R^{61}$ and, in the case where $Z^{61}$ and/or $Z^{62}$ denote trans-CH═CH— or trans-CF═CF—, alternatively also denotes $X^{61}$, $L^{6}$2 denotes $R^{62}$ and, in the case where $Z^{61}$ and/or $Z^{62}$ denote trans-CH═CH— or trans-CF═CF—, alternatively also denotes $X^{62}$, $R^{61}$ and $R^{62}$, independently of one another, denote H, unfluorinated alkyl or unfluorinated alkoxy having 1 to 17, preferably 2 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, $X^{61}$ and $X^{62}$, independently of one another, denote F or Cl, —CN, $SF_5$, fluorinated alkyl or alkoxy having 1 to 7 C atoms or fluorinated alkenyl, alkenyloxy or alkoxyalkyl having 2 to 7 C atoms, one of $Z^{61}$ and $Z^{62}$ denotes trans-CH═CH—, trans-CF═CF— or —C≡C— and the other, independently thereof, denotes trans-CH═CH—, trans-CF═CF— or a single bond, preferably one of them denotes —C≡C— or trans-CH═CH— and the other denotes a single bond, and

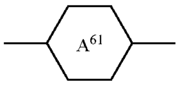

to

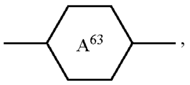

, independently of one another, denote

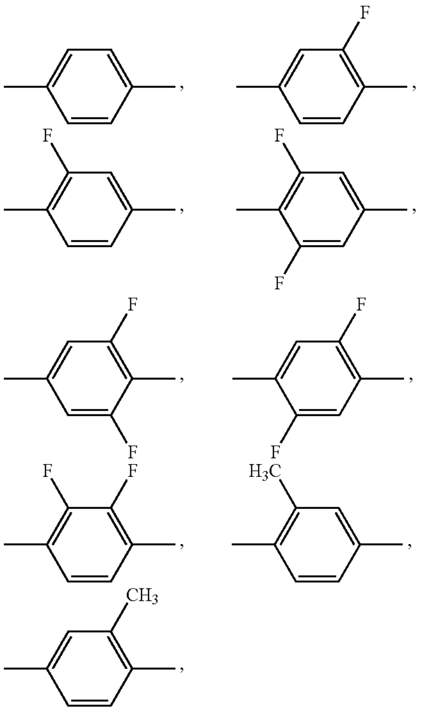

or preferably

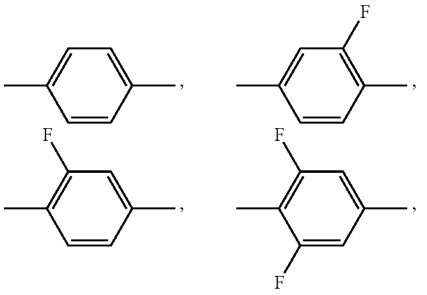

-continued

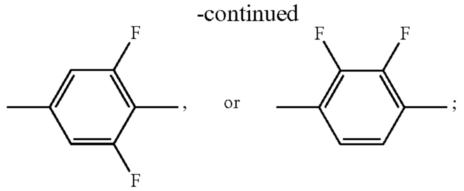

;

and x denotes 0 or 1;

$L^{71}$ denotes $R^{71}$ or $X^{71}$, $L^{72}$ denotes $R^{72}$ or $X^{72}$, $R^{71}$ and $R^{72}$, independently of one another, denote H, unfluorinated alkyl or unfluorinated alkoxy having 1 to 17, preferably 2 to 10, C atoms or unfluorinated alkenyl, unfluorinated alkenyloxy or unfluorinated alkoxyalkyl having 2 to 15, preferably 3 to 10, C atoms, preferably alkyl or unfluorinated alkenyl, $X^{71}$ and $X^{72}$, independently of one another, denote H, F, Cl, —CN, —NCS, —$SF_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and $Z^{71}$ to $Z^{73}$, independently of one another, denote trans-CH═CH—, trans-CF═CF—, —C≡C— or a single bond, preferably one or more of them denote a single bond, particularly preferably all denote a single bond and

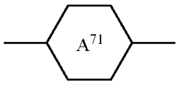

to

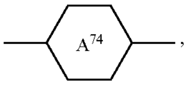

, independently of one another, denote

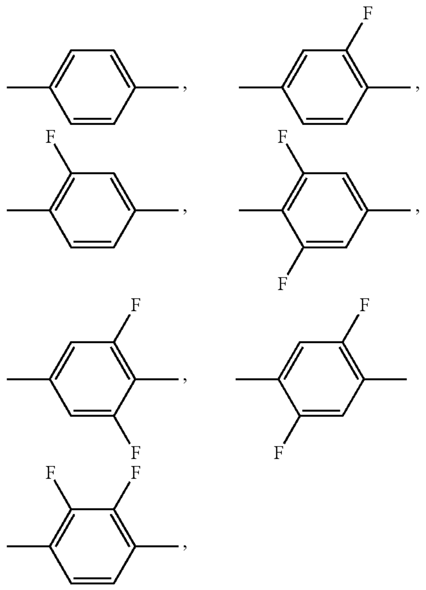

or preferably

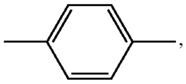, 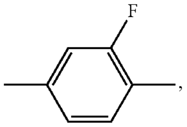,

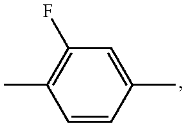, or 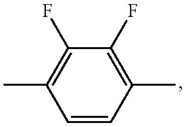, $R^{81}$ and $R^{82}$, independently of one another, denote H, unfluorinated alkyl or alkoxy having 1 to 15, preferably 2 to 10, C atoms or unfluorinated alkenyl, alkenyloxy or alkoxyalkyl having 2 to 15, preferably 3 to 10, C atoms, preferably unfluorinated alkyl or alkenyl, one of $Z^{81}$ and $Z^{82}$ denotes trans-CH═CH—, trans-CF═CF— or —C≡C— and the other, independently thereof, denotes trans-CH═CH—, trans-CF═CF— or a single bond, preferably one of them denotes —C≡C— or trans-CH═CH— and the other denotes a single bond, and

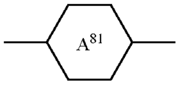

denotes

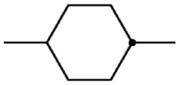, 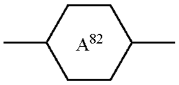 and

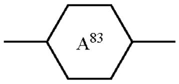, independently of one another, denote

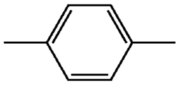, 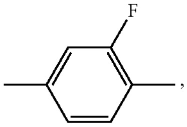,

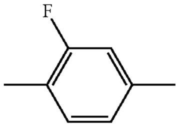, 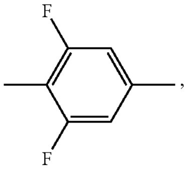,

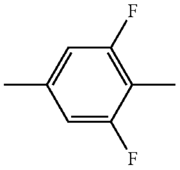, 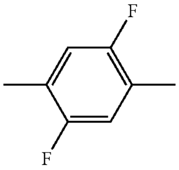 or

-continued

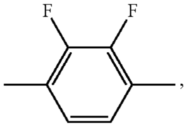, $L^{91}$ denotes $R^{91}$ or $X^{91}$, $L^{92}$ denotes $R^{92}$ or $X^{92}$, $R^{91}$ and $R^{92}$, independently of one another, denote H, unfluorinated alkyl or alkoxy having 1 to 15, preferably 2 to 10, C atoms or unfluorinated alkenyl, alkenyloxy or alkoxyalkyl having 2 to 15, preferably 3 to 10, C atoms, preferably unfluorinated alkyl or alkenyl, $X^{91}$ and $X^{92}$, independently of one another, denote H, F, Cl, —CN, —NCS, —$SF_5$, fluorinated alkyl or fluorinated alkoxy having 1 to 7 C atoms or fluorinated alkenyl, unfluorinated or fluorinated alkenyloxy or unfluorinated or fluorinated alkoxyalkyl having 2 to 7 C atoms, preferably fluorinated alkoxy, fluorinated alkenyloxy, F or Cl, and $Z^{91}$ to $Z^{93}$, independently of one another, denote trans-CH═CH—, trans-CF═CF—, —C—C—or a single bond, preferably one or more of them denotes a single bond, and particularly preferably all denote a single bond,

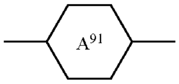

denotes

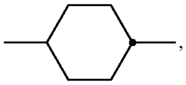, 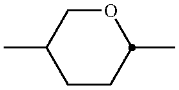 or

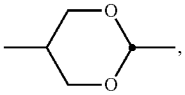, 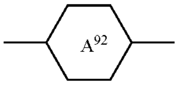 to

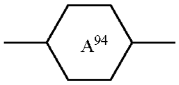

independently of one another, denote

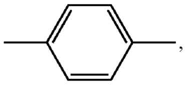, 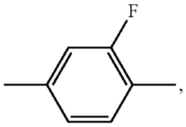,

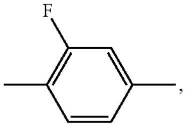, 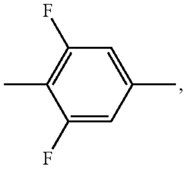,

-continued

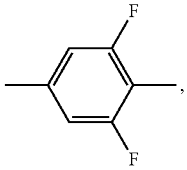
,
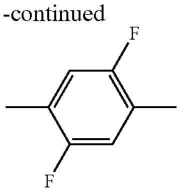
or
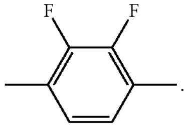
.

In a preferred embodiment of the present invention, the liquid-crystal medium comprises one or more compounds of the formula V, preferably selected from the group of the compounds of the formulae V-1 to V-3, preferably of the formulae V-1 and/or V-2 and/or V-3, preferably of the formulae V-1 and V-2:

V-1

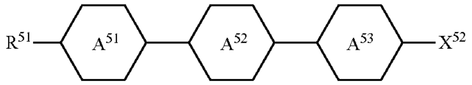

V-2

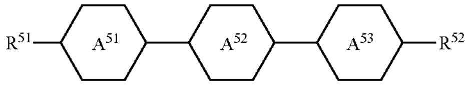

V-3

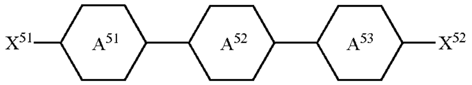

in which the occurring groups have the respective meanings indicated above for formula V and preferably $R^{51}$ denotes unfluorinated alkyl having 1 to 7 C atoms or unfluorinated alkenyl having 2 to 7 C atoms, $R^{52}$ denotes unfluorinated alkyl having 1 to 7 C atoms or unfluorinated alkenyl having 2 to 7 C atoms or unfluorinated alkoxy having 1 to 7 C atoms, $X^{51}$ and $X^{52}$, independently of one another, denote F, Cl, —$OCF_3$, —$CF_3$, —CN or —$SF_5$, preferably F, Cl, —$OCF_3$ or —CN.

The compounds of the formula V-1 are preferably selected from the group of the compounds of the formulae V-1a to V-1d, preferably V-1c and V-1d V-1a

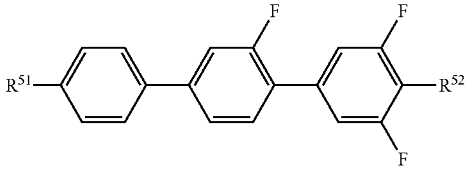

V-1b

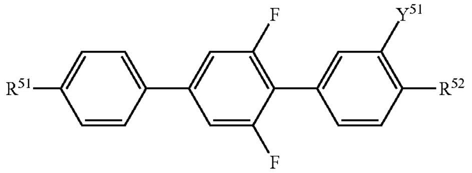

-continued

V-1c

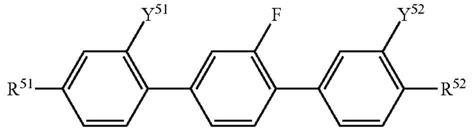

V-1d

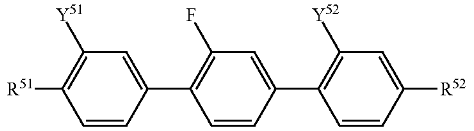

in which the parameters have the respective meanings indicated above for formula V-1 and in which $Y^{51}$ and $Y^{52}$, in each case independently of one another, denote H or F, and preferably $R^{51}$ denotes alkyl or alkenyl, and $X^{51}$ denotes F, Cl or —$OCF_3$.

The compounds of the formula V-2 are preferably selected from the group of the compounds of the formulae V-2a to V-2e and/or from the group of the compounds of the formulae V-2f and V-2g:

V-2a

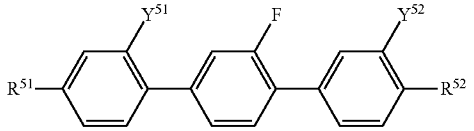

V-2b

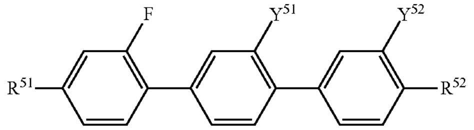

V-2c

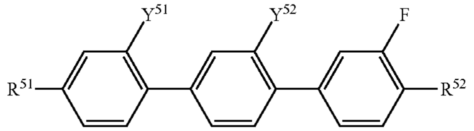

V-2d

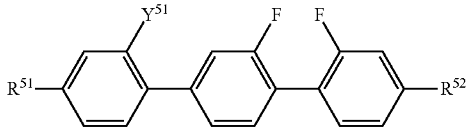

V-2e

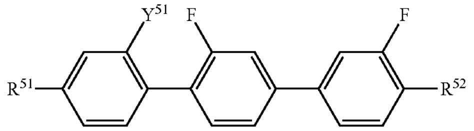

V-2f

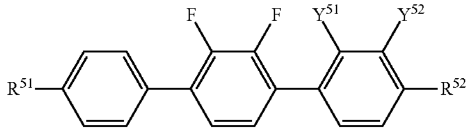

-continued

V-2g

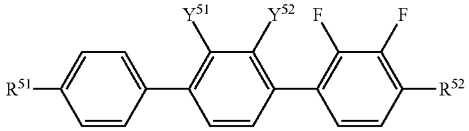

where in each case the compounds of the formula V-2a are excluded from the compounds of the formulae V-2b and V-2c, the compounds of the formula V-2b are excluded from the compounds of the formula V-2c and the compounds of the formula V-2f are excluded from the compounds of the formula V-2g, and in which the parameters have the respective meanings indicated above for formula V-1 and in which $Y^{51}$ and $Y^{52}$, in each case independently of one another, denote H or F, and preferably $Y^{51}$ and $Y^{52}$ denotes H and the other denotes H or F, preferably likewise denotes H.

The compounds of the formula V-3 are preferably compounds of the formula V-3a:

V-3a

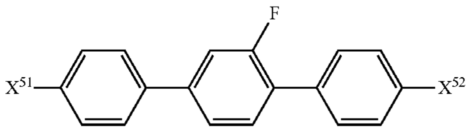

in which the parameters have the respective meanings indicated above for formula V-1 and in which preferably $X^{51}$ denotes F, Cl, preferably F, $X^{52}$ denotes F, Cl or —$OCF_3$, preferably —$OCF_3$.

The compounds of the formula V-1a are preferably selected from the group of the compounds of the formulae V-1a-1 and V-1a-2:

V-1a-1

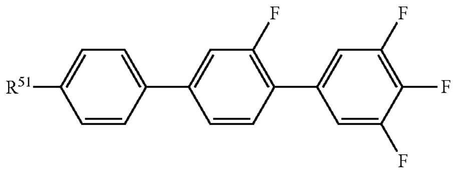

V-1a-2

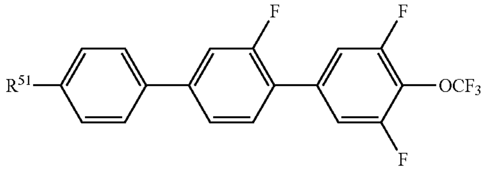

in which $R^{51}$ has the meaning indicated above and preferably denotes $C_nH_{2n+1}$, in which n denotes an integer in the range from 1 to 7, preferably in the range from 1 to 6 and particularly preferably 3 to 5.

The compounds of the formula V-1b are preferably compounds of the formula V-1b-1:

V-1b-1

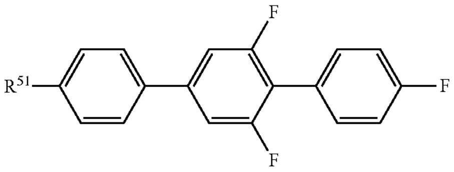

in which $R^{51}$ has the meaning indicated above and preferably denotes $C_nH_{2n+1}$, in which n denotes an integer in the range from 1 to 7, preferably in the range from 1 to 6 and particularly preferably 3 to 5.

The compounds of the formula V-1c are preferably selected from the group of the compounds of the formulae V-1c-1 to V-1c-4, particularly preferably selected from the group of the compounds of the formulae V-1c-1 and V-1c-2:

V-1c-1

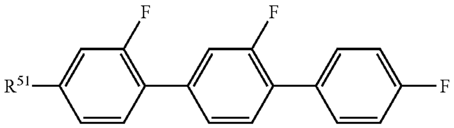

V-1c-2

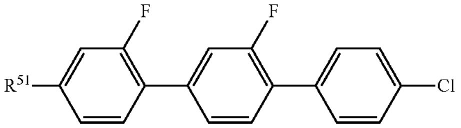

V-1c-3

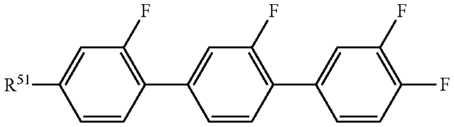

V-1c-4

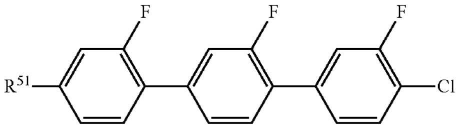

in which $R^{51}$ has the meaning indicated above and preferably denotes $C_nH_{2n+1}$, in which n denotes an integer in the range from 1 to 7, preferably in the range from 1 to 6 and particularly preferably 3 to 5.

The compounds of the formula V-1d are preferably selected from the group of the compounds of the formulae V-1d-1 and V-1d-2, particularly preferably the compound of the formula V-d-2:

V-1d-1

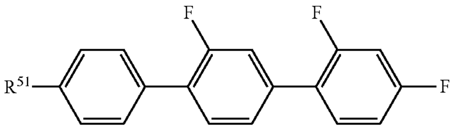

-continued

V-1d-2

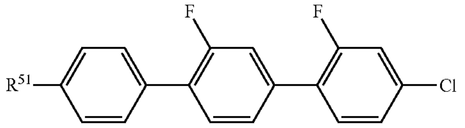

in which $R^{51}$ has the meaning indicated above and preferably denotes $C_nH_{2n+1}$, in which n denotes an integer in the range from 1 to 7, preferably in the range from 1 to 6 and particularly preferably 3 to 5.

The compounds of the formula V-2a are preferably selected from the group of the compounds of the formulae V-2a-1 and V-2a-2, particularly preferably the compounds of the formula V-2a-1:

V-2a-1

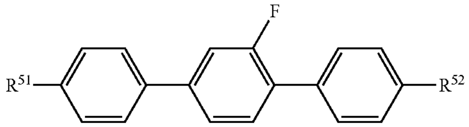

V-2a-2

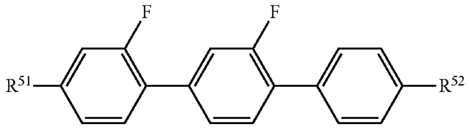

in which $R^{51}$ has the meaning indicated above and preferably denotes $C_nH_{2n+1}$ or $CH_2{=}CH{-}(CH_2)_z$, and $R^{52}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 1 to 6 and particularly preferably 3 to 5, and z denotes 0, 1, 2, 3 or 4, preferably 0 or 2.

Preferred combinations of $R^{51}$ with $R^{52}$, in particular in the case of formula V-2a-1, are ($C_nH_{2n+1}$ and $C_mH_{2m+1}$), ($C_nH_{2n+1}$ and $O{-}C_mH_{2m+1}$), ($CH_2{=}CH{-}(CH_2)_z$ and $C_mH_{2m+1}$), ($CH_2{=}CH{-}(CH_2)_z$ and $O{-}C_mH_{2m+1}$) and ($C_nH_{2n+1}$ and $(CH_2)_z{-}CH{=}CH_2$).

Preferred compounds of the formula V-2b are the compounds of the formula V-2b-1:

V-2b-1

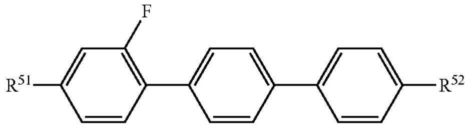

in which $R^{51}$ has the meaning indicated above and preferably denotes $C_nH_{2n+1}$ or $CH_2{=}CH{-}(CH_2)_z$, and $R^{52}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 1 to 6 and particularly preferably 3 to 5, and z denotes 0, 1, 2, 3 or 4, preferably 0 or 2.

The preferred combination of $R^{51}$ with $R^{52}$ here is, in particular, $C_nH_{2n+1}$ and $C_mH_{2m+1}$. Preferred compounds of the formula V-2c are the compounds of the formula V-2c-1:

V-2c-1

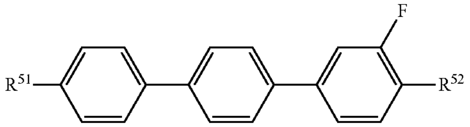

in which $R^{51}$ has the meaning indicated above and preferably denotes $C_nH_{2n+1}$ or $CH_2{=}CH{-}(CH_2)_z$, and $R^{52}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 1 to 6 and particularly preferably 3 to 5, and z denotes 0, 1, 2, 3 or 4, preferably 0 or 2.

The preferred combination of ($R^{51}$ and $R^{52}$) here is, in particular, ($C_nH_{2n+1}$ and $C_mH_{2m+1}$).

Preferred compounds of the formula V-2d are the compounds of the formula V-2d-1:

V-2d-1

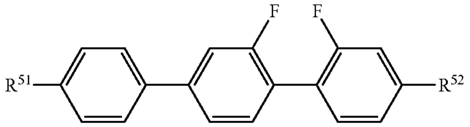

in which $R^{51}$ has the meaning indicated above and preferably denotes $C_nH_{2n+1}$ or $CH_2{=}CH{-}(CH_2)_z$, and $R^{52}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 1 to 6 and particularly preferably 3 to 5, and z denotes 0, 1, 2, 3 or 4, preferably 0 or 2.

The preferred combination of ($R^{51}$ and $R^{52}$) here is, in particular, ($C_nH_{2n+1}$ and $C_mH_{2m+1}$). Preferred compounds of the formula V-2e are the compounds of the formula V-2e-1:

V-2e-1

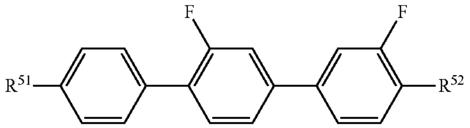

in which $R^{51}$ has the meaning indicated above and preferably denotes $C_nH_{2n+1}$ or $CH_2{=}CH{-}(CH_2)_z$, and $R^{52}$ has the meaning indicated above and preferably denotes $C_mH_{2m+1}$ or O—$C_mH_{2m+1}$ or $(CH_2)_z$—CH═$CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combination of ($R^{51}$ and $R^{52}$) here is, in particular, ($C_nH_{2n+1}$ and O—$C_mH_{2m+1}$).

Preferred compounds of the formula V-2f are the compounds of the formula V-2f-1:

V-2f-1

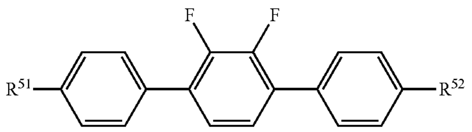

in which $R^{51}$ has the meaning indicated above and preferably denotes $C_nH_{2n+1}$ or $CH_2$═CH—$(CH_2)_z$, and $R^{52}$ has the meaning indicated above and preferably denotes $C_mH_{2m+1}$ or O—$C_mH_{2m+1}$ or $(CH_2)_z$—CH═$CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{51}$ and $R^{52}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and $C_mH_{2m+1}$).

Preferred compounds of the formula V-2g are the compounds of the formula V-2g-1:

V-2g-1

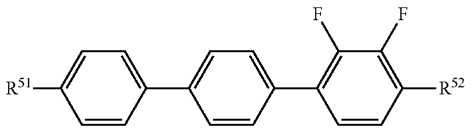

in which $R^{51}$ has the meaning indicated above and preferably denotes $C_nH_{2n+1}$ or $CH_2$═CH—$(CH_2)_z$, and $R^{52}$ has the meaning indicated above and preferably denotes $C_mH_{2m+1}$ or O—$C_mH_{2m+1}$ or $(CH_2)_z$—CH═$CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{51}$ and $R^{52}$) here are, in particular, ($C_nH_{2n+1}$ and $C_mH_{2m+1}$) and ($C_nH_{2n+1}$ and O—$C_mH_{2m+1}$), particularly preferably ($C_nH_{2n+1}$ and O—$C_mH_{2m+1}$).

The compounds of the formula VI are preferably selected from the group of the compounds of the formulae VI-1 to VI-5:

VI-1

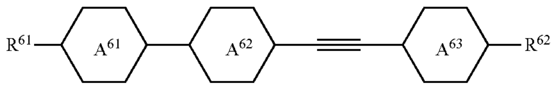

VI-2

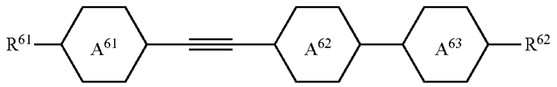

VI-3

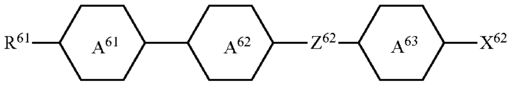

VI-4

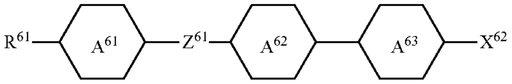

VI-5

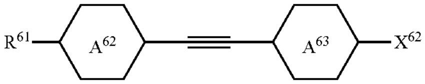

in which $Z^{61}$ and $Z^{62}$ denote —C≡C—, trans-CH═CH— or trans-CF═CF—, preferably —C≡C— or trans-CH═CH—, and the other occurring groups and parameters have the meaning given above under formula VI, and preferably $R^{61}$ and $R^{62}$, independently of one another, denote H, unfluorinated alkyl or alkoxy having 1 to 7 C atoms or unfluorinated alkenyl having 2 to 7 C atoms, $X^{62}$ denotes F, Cl, —$OCF_3$ or —CN, The compounds of the formula VI-1 are preferably selected from the group of the compounds of the formulae VI-1a and VI-1b, more preferably selected from compounds of the formula VI-1a:

VI-1a

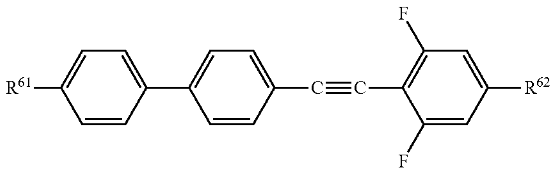

VI-1b

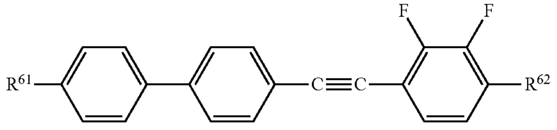

in which $R^{61}$ has the meaning indicated above and preferably denotes $C_nH_{2n+1}$ or $CH_2$═CH—$(CH_2)_z$, and $R^{62}$ has the meaning indicated above and preferably denotes $C_mH_{2m+1}$ or O—$C_mH_{2m+1}$ or $(CH_2)_z$—CH═$CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{61}$ and $R^{62}$) here are, in particular, ($C_nH_{2n+1}$ and $C_mH_{2m+1}$) and ($C_nH_{2n+1}$ and $O—C_mH_{2m+1}$), in the case of formula VI-1a particularly preferably ($C_nH_{2n+1}$ and $C_mH_{2m+1}$) and in the case of formula VI-1b particularly preferably ($C_nH_{2n+1}$ and $O—C_mH_{2m+1}$).

The compounds of the formula VI-3 are preferably selected from the compounds of the formula VI-3a to VI-3e:

VI-3a

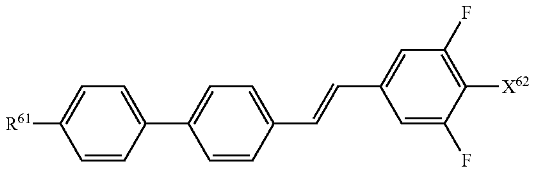

VI-3b

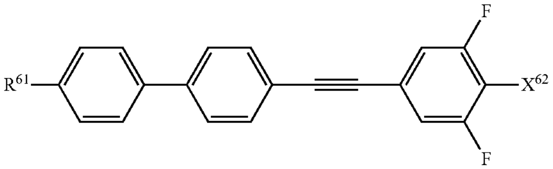

VI-3c

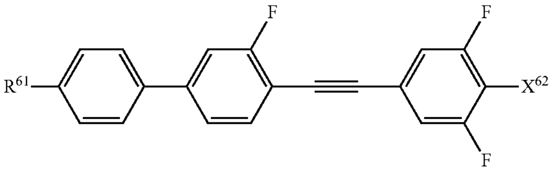

VI-3d

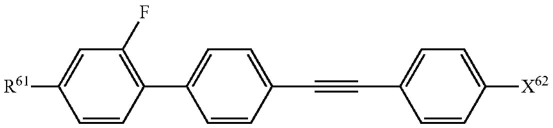

VI-3e

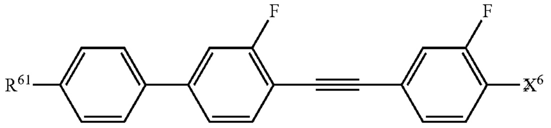

in which the parameters have the meaning given above under formula VI-3 and preferably $R^{61}$ has the meaning indicated above and preferably denotes $C_nH_{2n+1}$, in which n denotes an integer in the range from 1 to 7, preferably in the range from 1 to 5, and $X^{62}$ denotes —F, —Cl, —$OCF_3$, or —CN.

The compounds of the formula VI-4 are preferably selected from compounds of the formulae VI-4a to VI-4e:

VI-4a

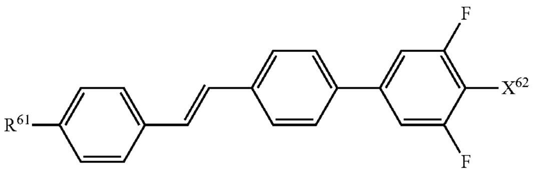

VI-4b

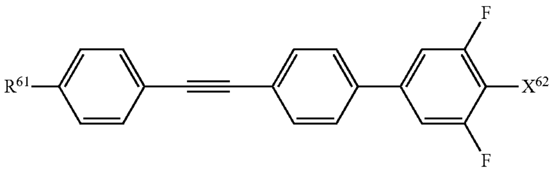

VI-4c

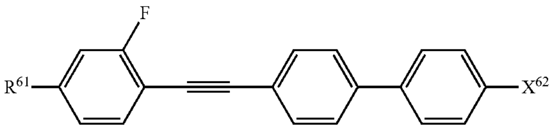

VI-4d

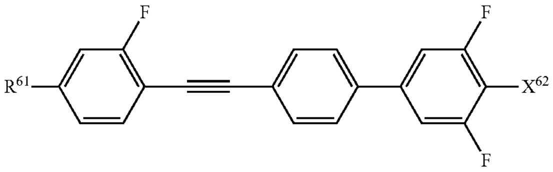

VI-4e

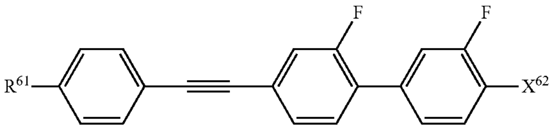

in which the parameters have the meaning given above under formula VI-4 and preferably $R^{61}$ has the meaning indicated above and preferably denotes $C_nH_{2n+1}$, in which n denotes an integer in the range from 1 to 7, preferably in the range from 1 to 5, and $X^{62}$ denotes F, Cl, $OCF_3$, or —CN.

The compounds of the formula VI-5 are preferably selected from the compounds of the formulae VI-5a to VI-5d, preferably VI-5b:

VI-5a

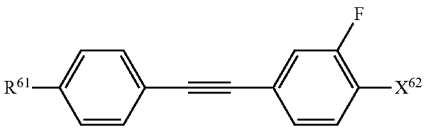

VI-5b

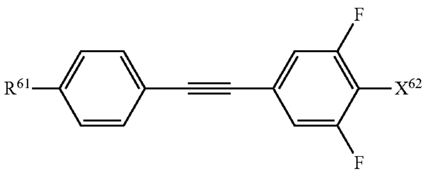

-continued

VI-5c

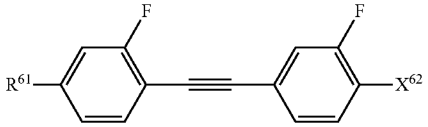

VI-5d

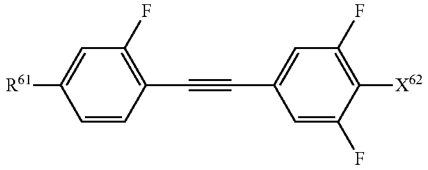

in which the parameters have the meaning given above under formula VI-5 and preferably $R^{61}$ has the meaning indicated above and preferably denotes $C_nH_{2n+1}$, in which n denotes an integer in the range from 1 to 7, preferably in the range from 1 to 5, and $X^{62}$ denotes —F, —Cl, —$OCF_3$, or —CN, particularly preferably —$OCF_3$.

The compounds of the formula VII are preferably selected from the group of the compounds of the formulae VII-1 to VII-6:

VII-1

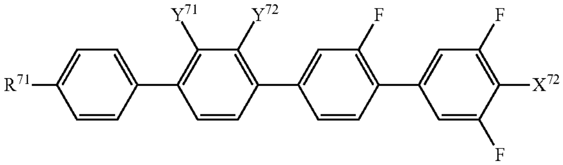

VII-2

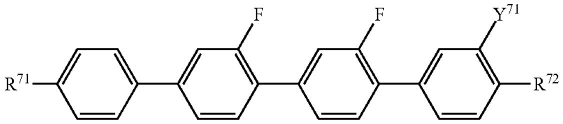

VII-3

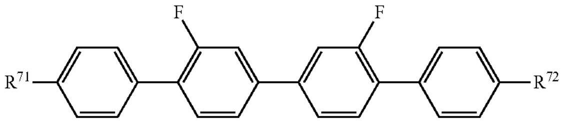

VII-4

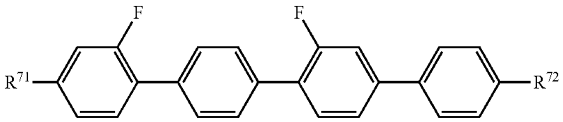

VII-5

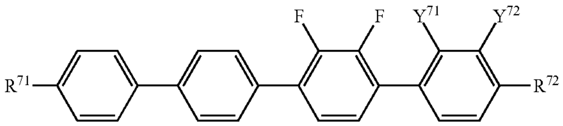

VII-6

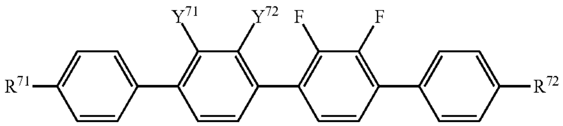

-continued

VII-7

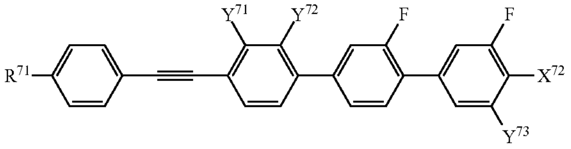

where the compounds of the formula VII-5 are excluded from the compounds of the formula VII-6, and in which the parameters have the respective meanings indicated above for formula VII, $Y^{71}$, $Y^{72}$, $Y^{73}$ independently from one another, denote H or F, and preferably $R^{71}$ denotes unfluorinated alkyl or alkoxy, each having 1 to 7 C atoms, or unfluorinated alkenyl having 2 to 7 C atoms, $R^{72}$ denotes unfluorinated alkyl or alkoxy, each having 1 to 7 C atoms, or unfluorinated alkenyl having 2 to 7 C atoms, $X^{72}$ denotes F, Cl; NCS or —$OCF_3$, preferably F or NCS, and particularly preferably $R^{71}$ has the meaning indicated above and preferably denotes $C_nH_{2n+1}$ or $CH_2$═CH—$(CH_2)_z$, and $R^{72}$ has the meaning indicated above and preferably denotes $C_mH_{2m+1}$ or O—$C_mH_{2m+1}$ or $(CH_2)_z$—CH═$CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The compounds of the formula VII-1 are preferably selected from the group of the compounds of the formulae VII-1a to VII-1d:

VII-1a

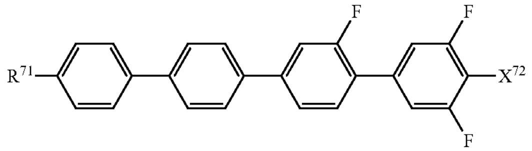

VII-1b

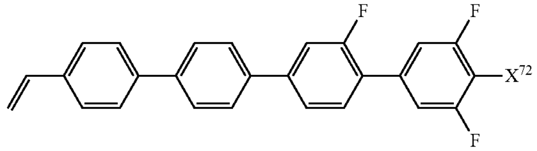

VII-1c

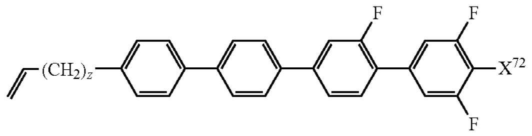

-continued

VII-1d

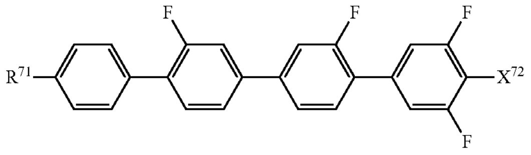

in which $X^{72}$ has the meaning given above for formula VII-2 and $R^{71}$ has the meaning indicated above and preferably denotes $C_nH_{2n+1}$, in which n denotes an integer in the range from 1 to 7, preferably in the range from 2 to 6 and particularly preferably 3 to 5, and z denotes 0, 1, 2, 3 or 4, preferably 0 or 2, and $X^{72}$ preferably denotes F.

The compounds of the formula VII-2 are preferably selected from the group of the compounds of the formulae VII-2a and VII-2b, particularly preferably of the formula VII-2a:

VII-2a

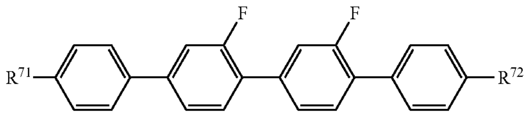

VII-2b

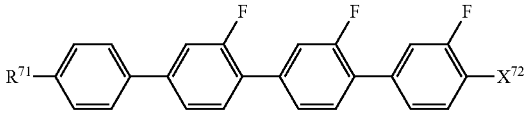

in which $R^{71}$ has the meaning indicated above and preferably denotes $C_nH_{2n+1}$ or $CH_2{=}CH{-}(CH_2)_z$, and $R^{72}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O{-}C_mH_{2m+1}$), particularly preferably ($C_nH_{2n+1}$ and $C_mH_{2m+1}$).

The compounds of the formula VII-3 are preferably compounds of the formula VII-3a:

VII-3a

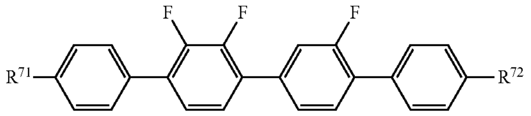

in which $R^{71}$ has the meaning indicated above and preferably denotes $C_nH_{2n+1}$ or $CH_2{=}CH{-}(CH_2)_z$, and $R^{72}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O{-}C_mH_{2m+1}$), particularly preferably ($C_nH_{2n+1}$ and $C_mH_{2m+1}$).

The compounds of the formula VII-4 are preferably compounds of the formula VII-4a:

VII-4a

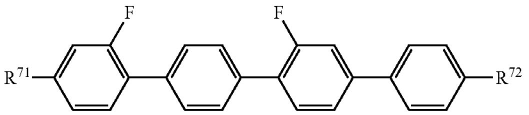

in which $R^{71}$ has the meaning indicated above and preferably denotes $C_nH_2n+_1$ or $CH_2{=}CH{-}(CH_2)_z$, and $R^{72}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O{-}C_mH_{2m+1}$), particularly preferably ($C_nH_{2n+1}$ and $C_mH_{2m+1}$).

The compounds of the formula VII-5 are preferably selected from the group of the compounds of the formulae VII-5a and VII-5b, more preferably of the formula VII-5a:

VII-5a

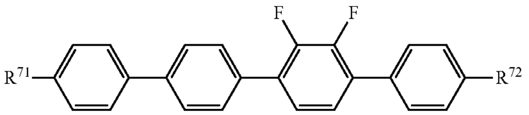

VII-5b

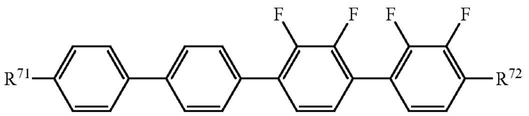

in which $R^{71}$ has the meaning indicated above and preferably denotes $C_nH_{2n+1}$ or $CH_2{=}CH{-}(CH_2)_z$, and $R^{72}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O{-}C_mH_{2m+1}$), particularly preferably ($C_nH_{2n+1}$ and $C_mH_{2m+1}$).

The compounds of the formula VII-6 are preferably selected from the group of the compounds of the formulae VII-6a and VII-6b:

VII-6a

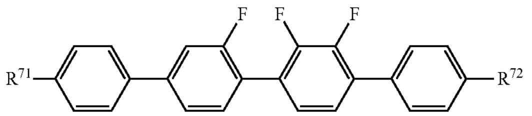

VII-6b

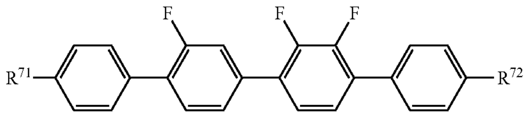

in which $R^{71}$ has the meaning indicated above and preferably denotes $C_nH_{2n+1}$ or $CH_2{=}CH{-}(CH_2)_z$, and $R^{72}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{71}$ and $R^{72}$) here are, in particular, ($C_nH_{2n+1}$ and $C_mH_{2m+1}$) and ($C_nH_{2n+1}$ and $O{-}C_mH_{2m+1}$), particularly preferably ($C_nH_{2n+1}$ and $C_mH_{2m+1}$).

The compounds of the formula VII-7 are preferably selected from the group of the compounds of the formulae VII-7a to VII-7d:

VII-7a

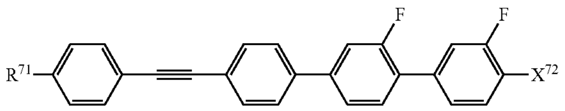

VII-7b

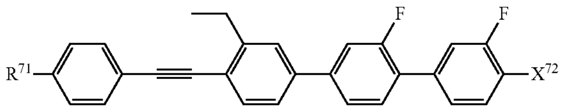

VII-7c

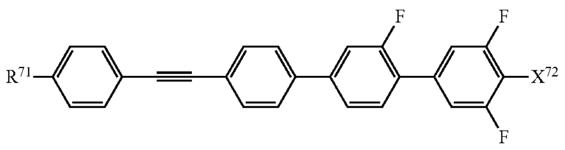

VII-7s

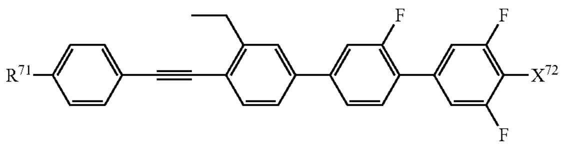

in which $R^{71}$ has the meaning indicated above and preferably denotes $C_nH_{2n+1}$ or $CH_2{=}CH{-}(CH_2)_z$, $X^{72}$ denotes F, $-OCF_3$ or $-NCS$, n denotes an integer in the range from 1 to 7, preferably in the range from 2 to 6 and particularly preferably 3 to 5, and z denotes 0, 1, 2, 3 or 4, preferably 0 or 2.

The compounds of the formula VIII are preferably selected from the group of the compounds of the formulae VIII-1 to VIII-3, more preferably these compounds of the formula VIII predominantly consist, even more preferably essentially consist and very particularly preferably completely consist thereof:

VIII-1

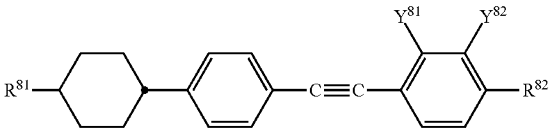

VIII-2

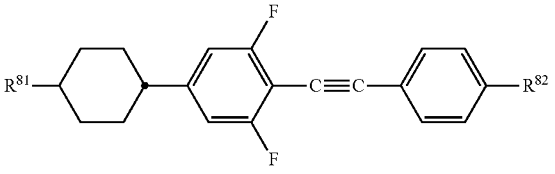

VIII-3

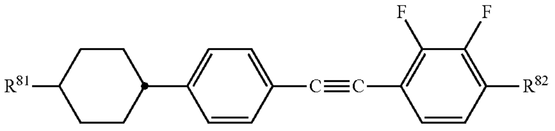

in which one of $Y^{81}$ and $Y^{82}$ denotes H and the other denotes H or F, and $R^{81}$ has the meaning indicated above and preferably denotes $C_nH_{2n+1}$ or $CH_2{=}CH{-}(CH_2)_z$, and $R^{82}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and $O{-}C_mH_{2m+1}$), particularly preferably ($C_nH_{2n+1}$ and $C_mH_{2m+1}$).

The compounds of the formula VIII-1 are preferably selected from the group of the compounds of the formulae VIII-1a to VIII-1c:

VIII-1a

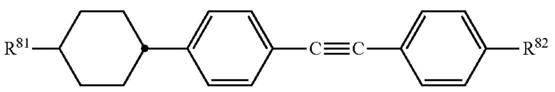

VIII-1b

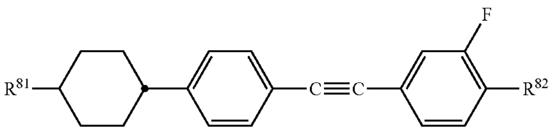

-continued

VIII-1c

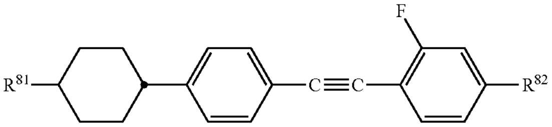

in which $R^{81}$ has the meaning indicated above and preferably denotes $C_nH_{2n+1}$ or $CH_2{=}CH-(CH_2)_z$, and $R^{82}$ has the meaning indicated above and preferably denotes $C_mH_{2m+1}$ or $O-C_mH_{2m+1}$ or $(CH_2)_z-CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and $O-C_mH_{2m+1}$), particularly preferably ($C_nH_{2n+1}$ and $C_mH_{2m+1}$).

The compounds of the formula VIII-2 are preferably compounds of the formula VIII-2a:

VIII-2a

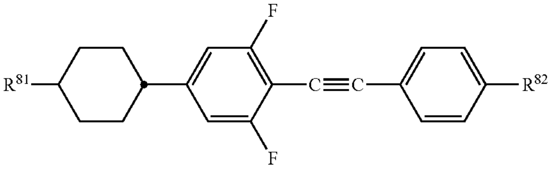

in which $R^{81}$ has the meaning indicated above and preferably denotes $C_nH_{2n+1}$ or $CH_2{=}CH-(CH_2)_z$, and $R^{82}$ has the meaning indicated above and preferably denotes $C_mH_{2m+1}$ or $O-C_mH_{2m+1}$ or $(CH_2)_z-CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$), ($C_nH_{2n+1}$ and $O-C_mH_{2m+1}$) and ($CH_2{=}CH-(CH_2)_z$ and $C_mH_{2m+1}$), particularly preferably ($C_nH_{2n+1}$ and $C_mH_{2m+1}$).

The compounds of the formula VIII-3 are preferably compounds of the formula VIII-3a:

VIII-3a

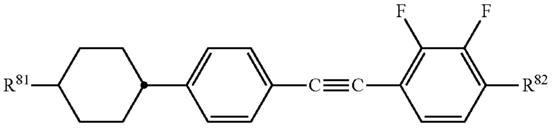

in which $R^{81}$ has the meaning indicated above and preferably denotes $C_nH_{2n+1}$ or $CH_2{=}CH-(CH_2)_z$, and $R^{82}$ has the meaning indicated above and preferably denotes $C_mH_{2m+1}$ or $O-C_mH_{2m+1}$ or $(CH_2)_z-CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{81}$ and $R^{82}$) here are, in particular, ($C_nH_{2n+1}$ and $C_mH_{2m+1}$) and ($C_nH_{2n+1}$ and $O-C_mH_{2m+1}$).

The compounds of the formula IX are preferably selected from the group of the compounds of the formulae IX-1 to IX-3:

IX-1

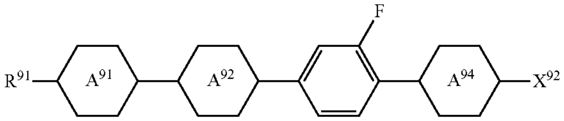

IX-2

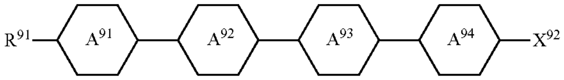

IX-3

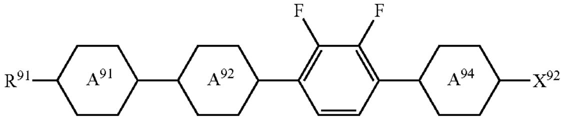

in which the parameters have the respective meaning indicated above under formula IX and preferably one of

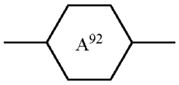

to

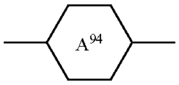

denotes

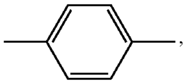

,

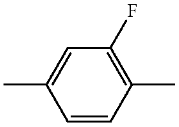

or

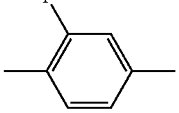

, and in which $R^{91}$ has the meaning indicated above and preferably denotes $C_nH_{2n+1}$ or $CH_2{=}CH-(CH_2)_z$, and $R^{92}$ has the meaning indicated above and preferably denotes $C_mH_{2m+1}$ or $O-C_mH_{2m+1}$ or $(CH_2)_z-CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{91}$ and $R^{92}$) here are, in particular, ($C_nH_{2n+1}$ and $C_mH_{2m+1}$) and ($C_nH_{2n+1}$ and $O-C_mH_{2m+1}$).

The compounds of the formula IX-1 are preferably selected from the group of the compounds of the formulae IX-1a to IX-1e:

IX-1a

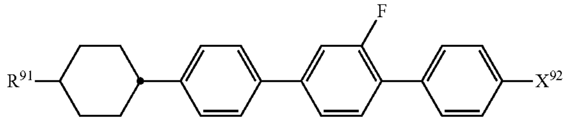

IX-1b

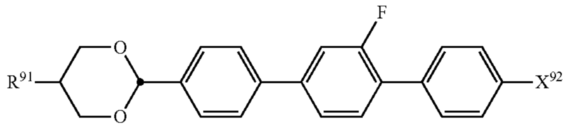

IX-1c

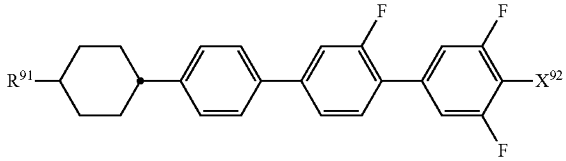

IX-1d

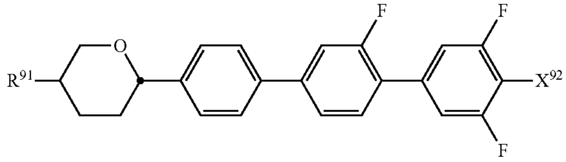

IX-1e

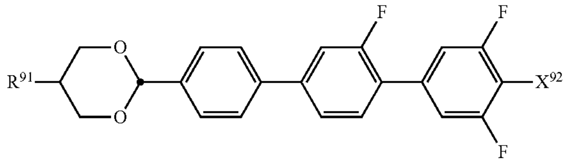

in which the parameters have the meaning given above and preferably $R^{91}$ has the meaning indicated above and preferably denotes $C_nH_{2n+1}$, and n denotes an integer in the range from 0 to 15, preferably in the range from 1 to 7 and particularly preferably 1 to 5, and $X^{92}$ preferably denotes F or Cl.

The compounds of the formula IX-2 are preferably selected from the group of the compounds of the formulae IX-2a and IX-2b:

IX-2a

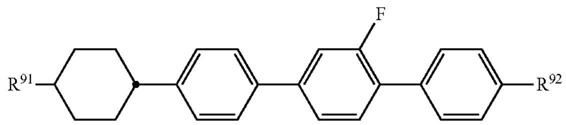

-continued

IX-2b

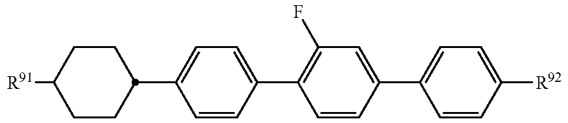

in which $R^{91}$ has the meaning indicated above and preferably denotes $C_nH_{2n+1}$ or $CH_2{=}CH{-}(CH_2)_z$, and $R^{92}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combination of ($R^{91}$ and $R^{92}$) here is, in particular, ($C_nH_{2n+1}$ and $C_mH_{2m+1}$).

The compounds of the formula IX-3 are preferably compounds of the formulae IX-3a and IX-3b:

IX-3a

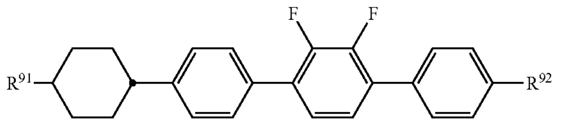

IX-3b

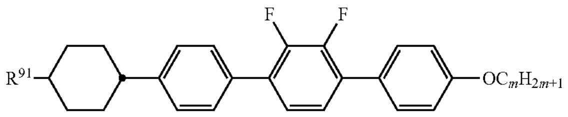

in which $R^{91}$ has the meaning indicated above and preferably denotes $C_nH_{2n+1}$ or $CH_2{=}CH{-}(CH_2)_z$, and $R^{92}$ has the meaning indicated above and preferably denotes $C_mH_{2m+1}$ or $O{-}C_mH_{2m+1}$ or $(CH_2)_z{-}CH{=}CH_2$, and in which n and m, independently of one another, denote an integer in the range from 1 to 7, preferably in the range from 2 to 6 and particularly preferably 3 to 5, and z denotes 0, 1, 2, 3 or 4, preferably 0 or 2.

The preferred combinations of ($R^{91}$ and $R^{92}$) here are, in particular, ($C_nH_{2n+1}$ and $C_mH_{2m+1}$) and ($C_nH_{2n+1}$ and $O{-}C_mH_{2m+1}$), particularly preferably ($C_nH_{2n+1}$ and $O{-}C_mH_{2m+1}$).

In a preferred embodiment of the present invention the medium comprises one or more compounds of formula X

X

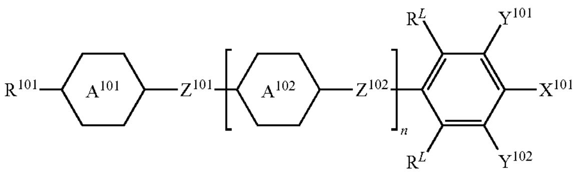

in which $R^{10}1$ denotes H, alkyl or alkoxy having 1 to 15, preferably 2 to 10, C atoms or unfluorinated alkenyl, unfluorinated alkenyloxy or unfluorinated alkoxyalkyl having 2 to 15, preferably 3 to 10, C atoms, preferably alkyl or alkenyl, $X^{101}$ denotes H, F, Cl, —CN, $SF_5$, NCS, fluorinated alkyl or fluorinated alkoxy having 1 to 7 C atoms or fluorinated alkenyl, fluorinated alkenyloxy or fluorinated alkoxyalkyl having 2 to 7 C atoms, preferably fluorinated alkoxy, fluorinated alkenyloxy, F, Cl or NCS, particularly preferably NCS, $Y^{101}$ denotes methyl, ethyl or Cl, $Y^{102}$ denotes H, methyl, ethyl, F or Cl, preferably H or F, $Z^{101}$, $Z^{102}$ identically or differently, denote a single bond, —CH═CH—, —CF═CF— or —C≡C—,

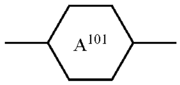 and 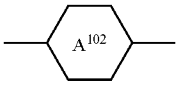

independently of one another, denote

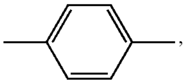, 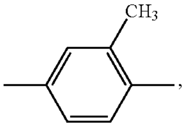, 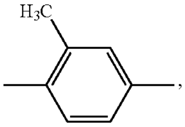,

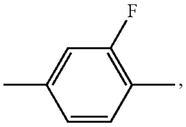, 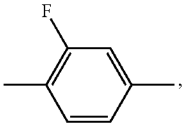, 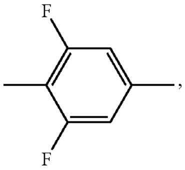,

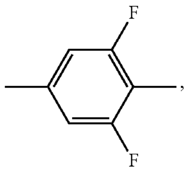, 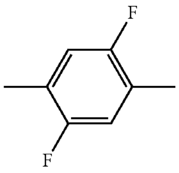 or

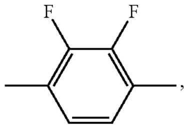, preferably

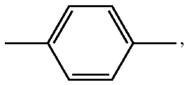, 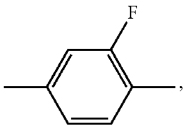,

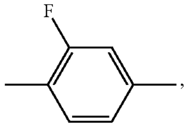, or 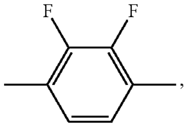, and where

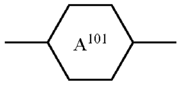

alternatively denotes

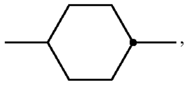, and n is 0 or 1.

Preferably, the compounds of formula X are selected from the sub-formulae X-1 and X-2

X-1

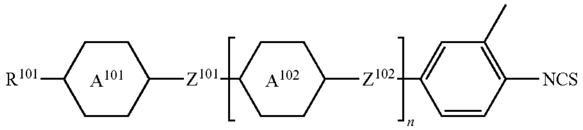

X-2

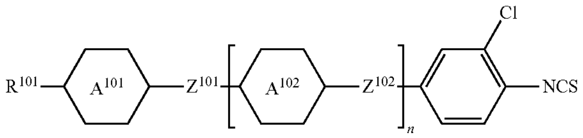

in which the occurring groups and parameters have the meanings given above for formula X.

Particularly preferably, the media according to the invention comprise one or more compounds selected from the group of compounds of the formulae X-1-1 to X-1-9

X-1-1

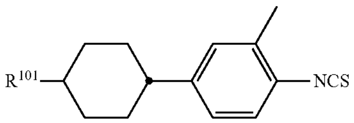

X-1-2

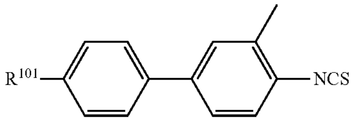

X-1-3

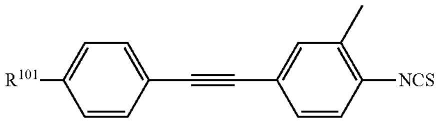

X-1-4

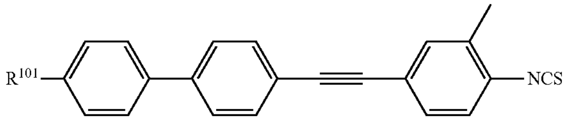

-continued

X-1-5

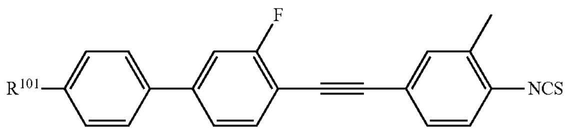

X-1-6

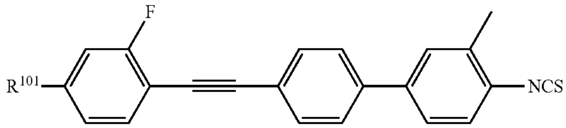

X-1-7

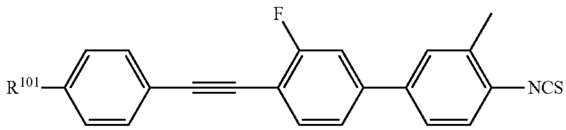

X-1-8

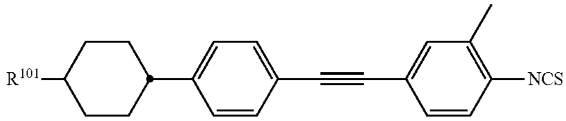

X-1-9

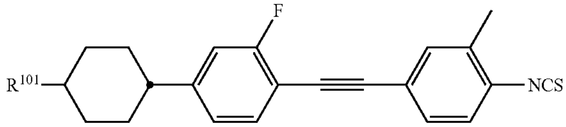

In which $R^{101}$ denotes alkyl having 1 to 7 C atoms.

In a preferred embodiment, the medium according to the invention comprises one or more compounds of formula XI

XI

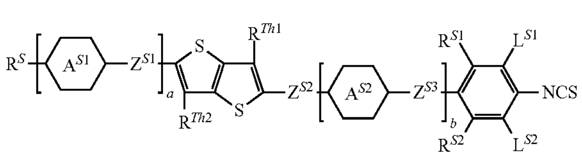

in which $R^S$ denotes H, alkyl or alkoxy having 1 to 12 C atoms, or alkenyl, alkenyloxy or alkoxyalkyl having 2 to 12 C atoms, in which one or more $CH_2$-groups may be replaced by

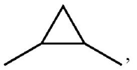, 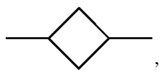,

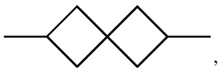, 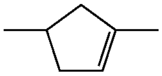 or

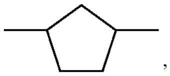, and in which one or more H atoms may be replaced by F,

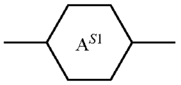 and 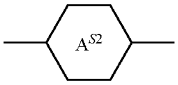

on each occurrence, independently of one another, denote

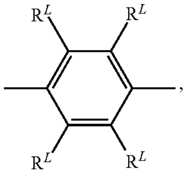, 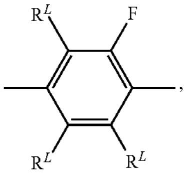, 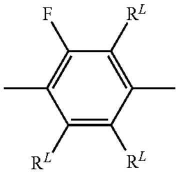,

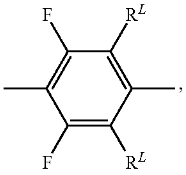, 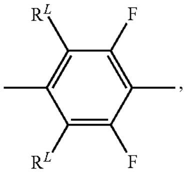,

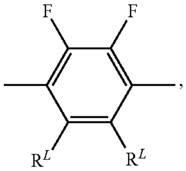, or 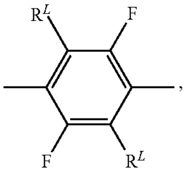, in which $R^L$, on each occurrence identically or differently, denotes H, Cl or straight-chain, branched or cyclic alkyl having 1 to 6 C atoms, $L^{S1}$, $L^{S2}$ identically or differently, denote H, Cl or F, $R^{S1}$, $R^{S2}$, identically or differently, denote H, alkyl or alkenyl, having up to 6 C atoms, or cyclopropyl, cyclobutyl, cyclopentenyl, or cyclopentyl, $R^{Th1}$, $R^{Th2}$ identically or differently, denote H, alkyl or alkenyl or alkoxy, having up to 6 C atoms, or cyclopropyl, cyclobutyl, cyclopentenyl or cyclopentyl, $Z^1$, $Z^{S}2$, $Z^{S3}$ identically or differently, denote —CH═CH—, —CH═CF—, —CF═CH—, —CF═CF—, —C≡C—, or a single bond, a, b identically or differently, are 0 or 1.

Preferably, the compounds of formula XI are selected from the group of compounds of the formulae XI-1 to XI-24:

XI-1

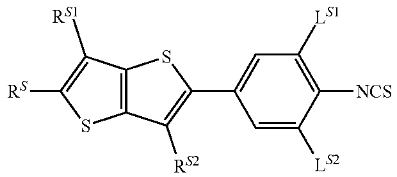

XI-2

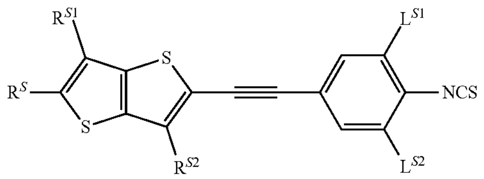

-continued
XI-3
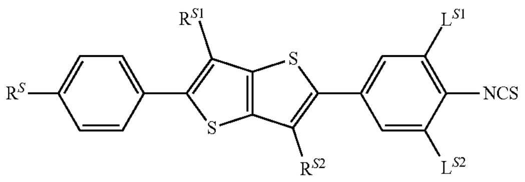
XI-4
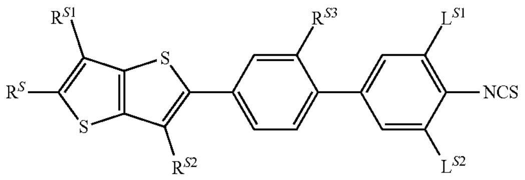
XI-5
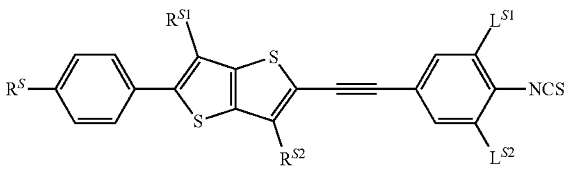
XI-6
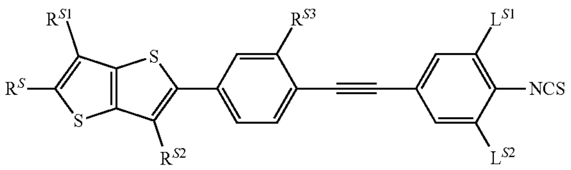
XI-7
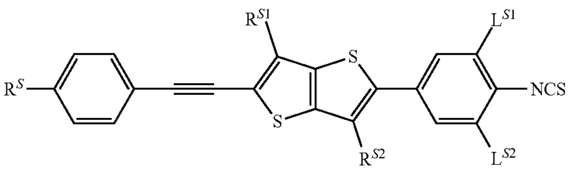
XI-8
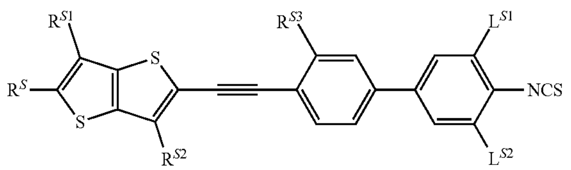
XI-9
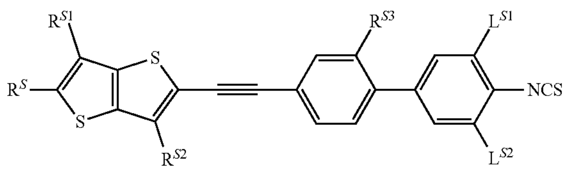
XI-10
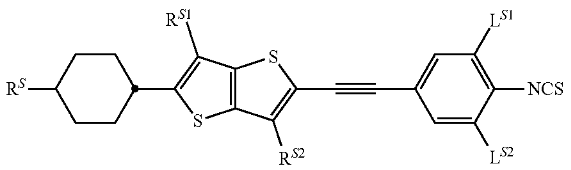
-continued
XI-11
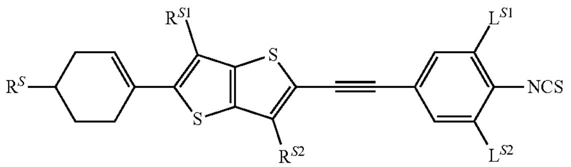
XI-12
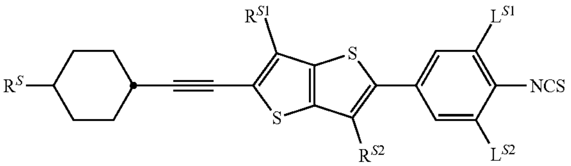
XI-13
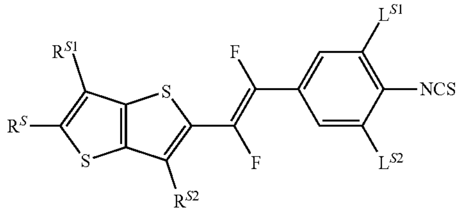
XI-14
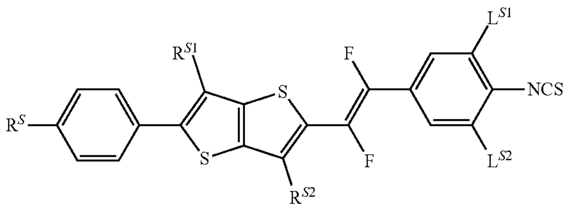
XI-15
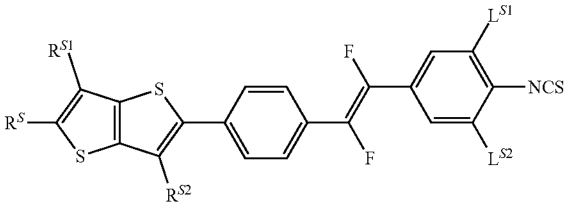
XI-16
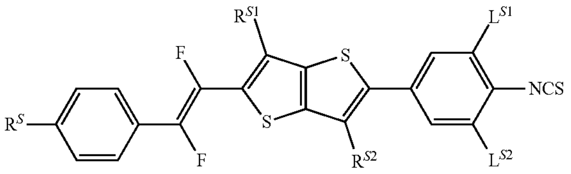
XI-17
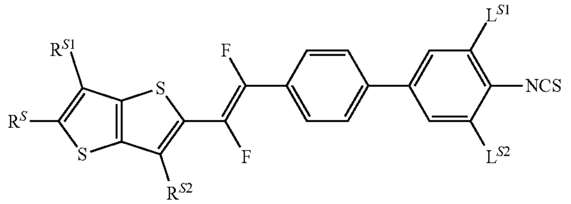

-continued

XI-18

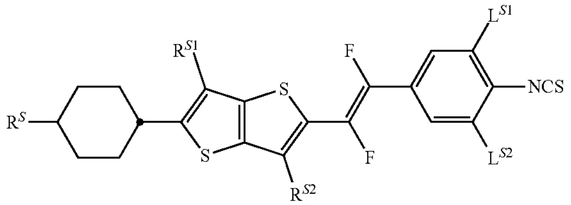

XI-19

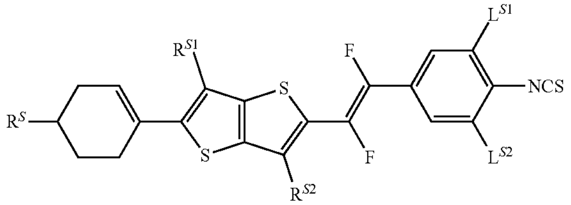

XI-20

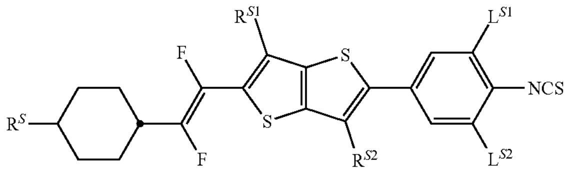

XI-21

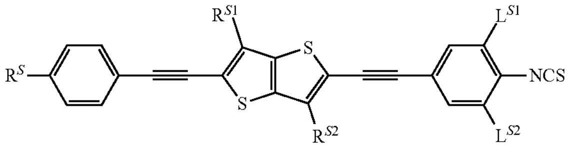

XI-22

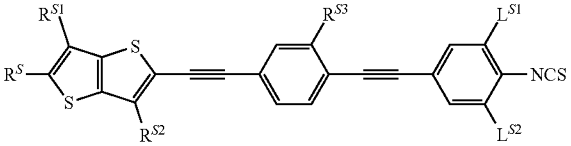

XI-23

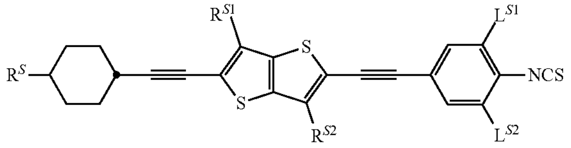

XI-24

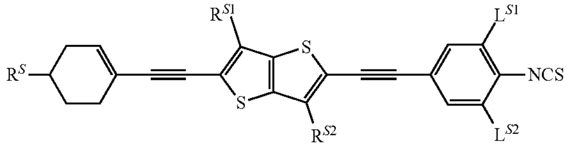

in which the occurring groups have the meanings given above for formula XI and preferably $R^S$ denotes alkyl or alkenyl having 2 to 6 C atoms, in which one or more $CH_2$-groups may be replaced by

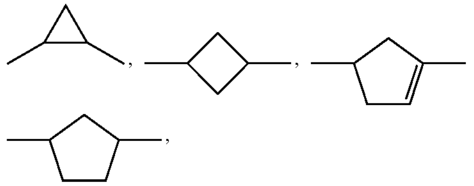 or $R^{S1}$ and $R^{S2}$ identically or differently, denote H or alkyl having 1 to 6 C atoms, preferably H, $R^{S3}$ denotes H, F or alkyl, having up to 6 C atoms, or cyclopropyl, preferably H, F or ethyl, very preferably H, $L^{S1}$ and $L^{S2}$ identically or differently, denote H or F, preferably F.

Preferably, the medium comprises one or more compounds of formula XII

XII

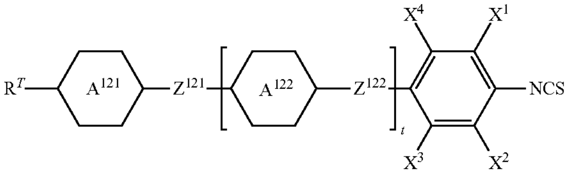

in which $R^{12}$ denotes H, alkyl or alkoxy having 1 to 12 C atoms, or alkenyl, alkenyloxy or alkoxyalkyl having 2 to 12 C atoms, in which one or more $CH_2$-groups may be replaced by, or

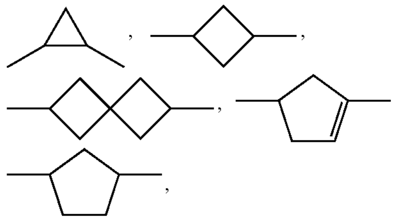 or or denotes a group $R^P$, $R^P$ denotes halogen, CN, NCS, $R^F$, $R^F$—O— or $R^F$—S—, wherein $R^F$ denotes fluorinated alkyl or fluorinated alkenyl having up to 9 C atoms, $Z^{121}$, $Z^{122}$ identically or differently, denote —CH═CH—, —CF═CF—, —CH═CF—, —CF═CH—, —C≡C— or a single bond, preferably —C≡C— or a single bond, $X^1$, $X^2$, $X^3$ and $X^4$ identically or differently, denote Cl or F, preferably F, t is 0 or 1, and

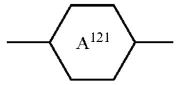 and 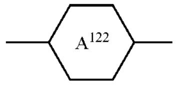

denote a radical selected from the following groups:

a) the group consisting of 1,4-phenylene, 1,4-naphthylene, and 2,6-naphthylene, in which one or two CH groups may be replaced by N and in which one or more H atoms may be replaced by L, wherein tetrafluoro-1,4-phenylene is excluded, b) the group consisting of trans-1,4-cyclohexylene, 1,4-cyclohexenylene, bicyclo[1.1.1]pentane-1,3-diyl, 4,4'-bicyclohexylene, bicyclo[2.2.2]octane-1,4-diyl, spiro[3.3]heptane-2,6-diyl, in which one or more non-adjacent $CH_2$ groups may be replaced by —O— and/or —S— and in which one or more H atoms may be replaced by F, c) the group consisting of thiophene-2,5-diyl, thieno[3,2-b]thiophene-2,5-diyl, selenophene-2,5-diyl, each of which may also be mono- or polysubstituted by L, L on each occurrence, identically or differently, denotes F, C, CN, SCN, $SF_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms.

The compounds of formula XII are preferably selected from the compounds of the sub-formulae XII-1 to XII-11:

XII-1

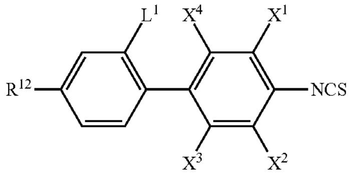

XII-2

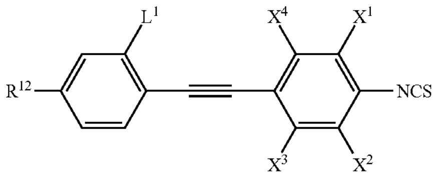

XII-3

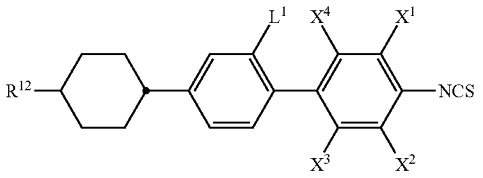

XII-4

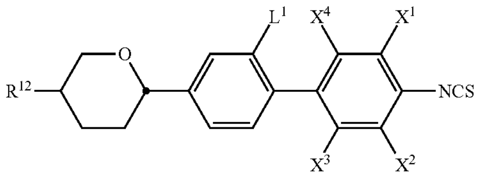

XII-5

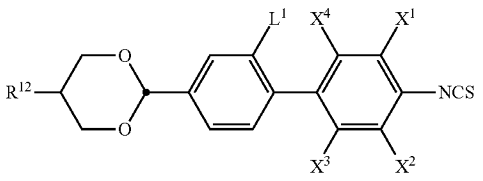

-continued

XII-6

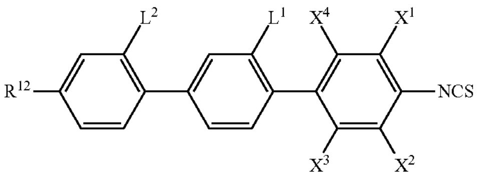

XII-7

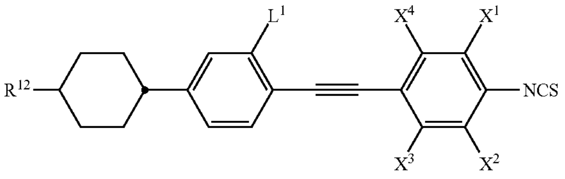

XII-8

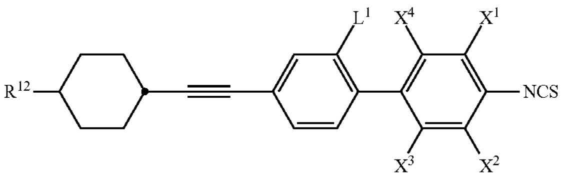

XII-9

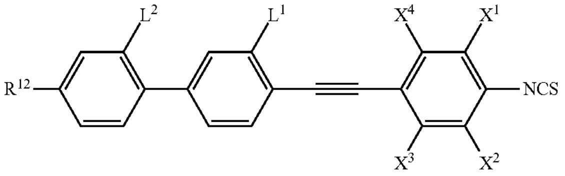

XII-10

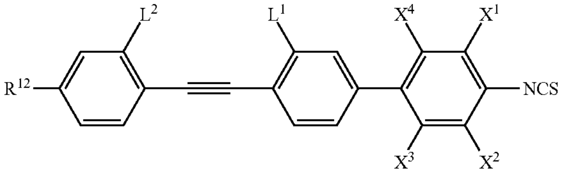

XII-11

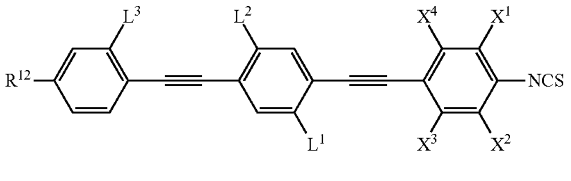

in which $L^1$, $L^2$ and $L^3$ identically or differently, denote H, F, Cl, methyl, ethyl, n-propyl, isopropyl, cyclopropyl, cyclobutyl, cyclopentyl or cyclopentenyl, and $R^{12}$, $X^1$, $X^2$, $X^3$ and $X^4$ have the meanings given above.

Very preferably, the medium comprises a compound of formula XII-3, in which the occurring groups have the meanings given above and particularly preferably $L^1$ denotes H, $X^1$, $X^2$, $X^3$ and $X^4$ denote F and $R^{12}$ denotes alkyl having 1 to 7 C atoms.

The medium according to the invention preferably comprises one or more compounds of the formula XIII

XIII

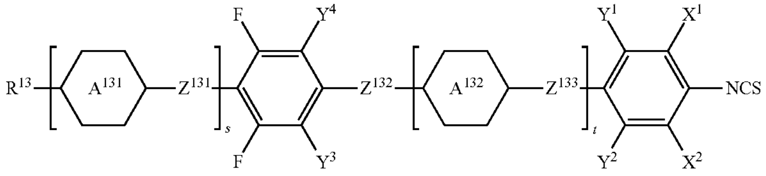

in which $R^{13}$ denotes H, alkyl or alkoxy having 1 to 12 C atoms, or alkenyl, alkenyloxy or alkoxyalkyl having 2 to 12 C atoms, in which one or more $CH_2$-groups may be replaced by

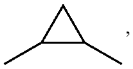, 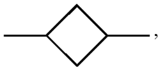,

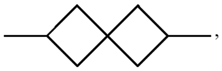, 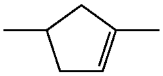 or

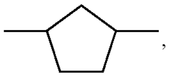, or a group R, $R^P$ denotes halogen, CN, NCS, $R^F$, $R^F$—O— or $R^F$—S—, wherein $R^F$ denotes fluorinated alkyl or fluorinated alkenyl having up to 9 C atoms, $Z^{131}$, $Z^{132}$, $Z^{133}$ identically or differently, denote —CH═CH—, —CF═CF—, —CH═CF—, —CF═CH—, —C≡C— or a single bond, preferably —C≡C— or a single bond, $X^1$, $X^2$ identically or differently, denote H, Cl, F, $CH_3$ or $C_2H_5$, preferably H or F, $Y^1$, $Y^2$, $Y^3$, $Y^4$, identically or differently, denote H, F, Cl, or straight chain or branched or cyclic alkyl, alkenyl, alkoxy or alkenyloxy, each having up to 12 C atoms, where at least one of $Y^1$, $Y^2$, $Y^3$ and $Y^4$ is different from F, s is 0, 1 or 2, preferably 0 or 1, t is 0, 1 or 2, preferably 0 or 1, and s+t is 0, 1 or 2, preferably 0 or 1,

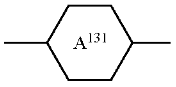 and 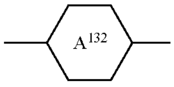

denote a radical selected from the following groups:

a) the group consisting of 1,4-phenylene, 1,4-naphthylene, and 2,6-naphthylene, in which one or two CH groups may be replaced by N and in which one or more H atoms may be replaced by L, b) the group consisting of trans-1,4-cyclohexylene, 1,4-cyclohexenylene, bicyclo[1.1.1]pentane-1,3-diyl, 4,4'-bicyclohexylene, bicyclo[2.2.2]octane-1,4-diyl, spiro[3.3]heptane-2,6-diyl, in which one or more non-adjacent $CH_2$ groups may be replaced by —O— and/or —S— and in which one or more H atoms may be replaced by F, c) the group consisting of thiophene-2,5-diyl, thieno[3,2-b]thiophene-2,5-diyl, selenophene-2,5-diyl, each of which may also be mono- or polysubstituted by L, L on each occurrence, identically or differently, denotes F, Cl, CN, SCN, $SF_5$ or straight-chain or branched, in each case optionally fluorinated, alkyl, alkoxy, alkylcarbonyl, alkoxycarbonyl, alkylcarbonyloxy or alkoxycarbonyloxy having 1 to 12 C atoms.

In a preferred embodiment of the present invention, the compounds of formula XIII are selected from the compounds of the formulae XIII-1 to XIII-20, very preferably from the compounds of the formulae XIII-1 to XIII-13:

XIII-1

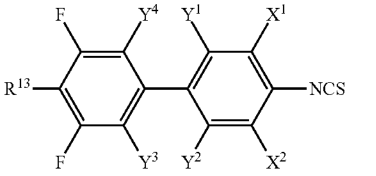

XIII-2

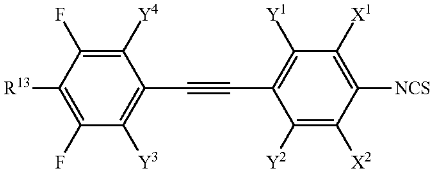

XIII-3

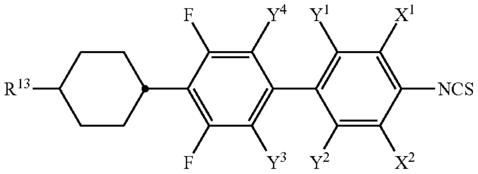

XIII-4

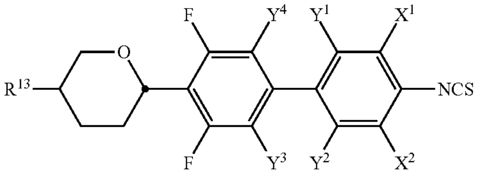

XIII-5

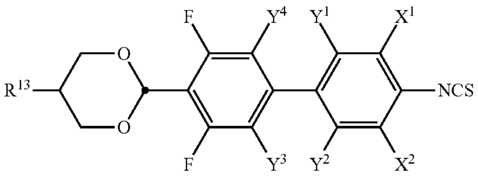

-continued

XIII-6

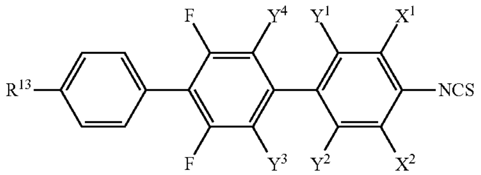

XIII-7

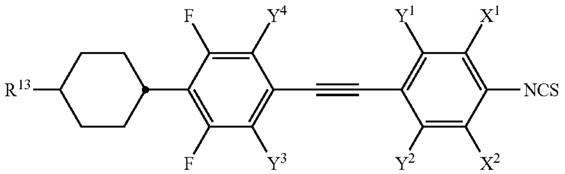

XIII-8

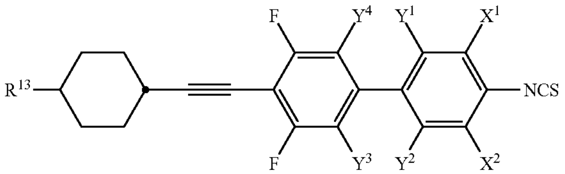

XIII-9

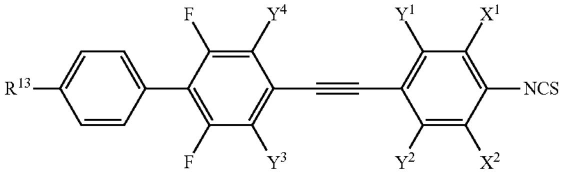

XIII-10

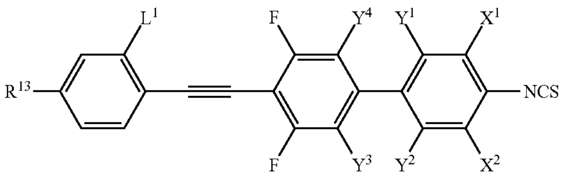

XIII-11

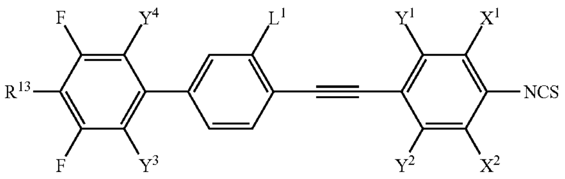

XIII-12

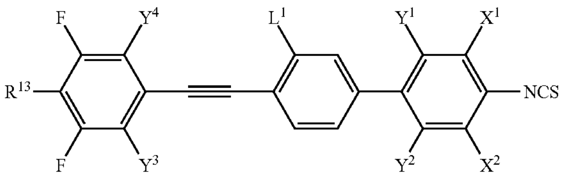

XIII-13

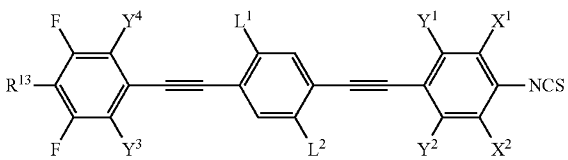

-continued

XIII-14

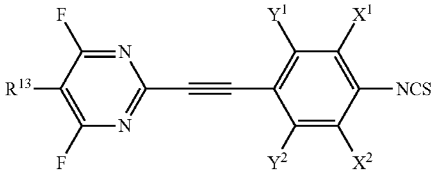

XIII-15

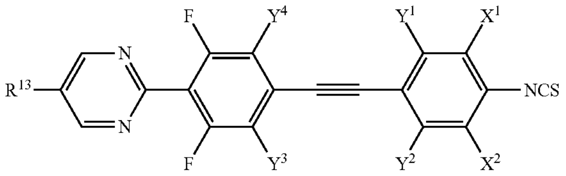

XIII-16

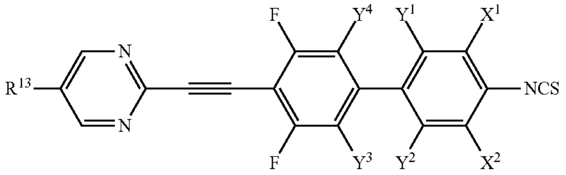

XIII-17

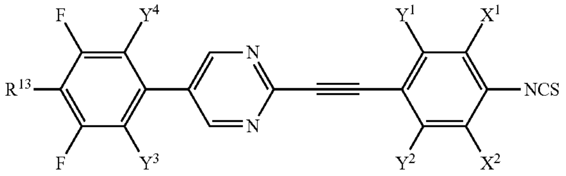

XIII-18

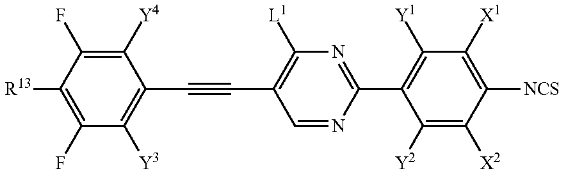

XIII-19

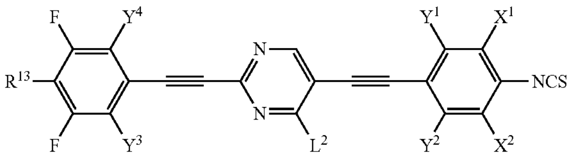

XIII-20

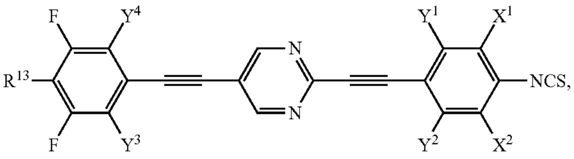

in which the occurring groups have the meanings indicated above for formula XIII and its sub-formulae and preferably $R^{13}$ denotes alkyl having 1 to 7 C atoms, $Y^1$, $Y^2$, $Y^3$, and $Y^4$, identically or differently, denote H, F, Cl, methyl, ethyl, n-propyl, isopropyl, cyclopropyl, cyclobutyl, cyclopentyl or cyclopentenyl, and more preferably $Y^1$ and $Y^2$ independently denote H or F, in particular H, and $Y^3$ and $Y^4$ very preferably denote H, and $L^1$ and $L^2$, identically or differently, very preferably denote H, F, methyl or ethyl, in particular H.

Preferably, the medium according to the invention comprises one or more compounds of formula T

T

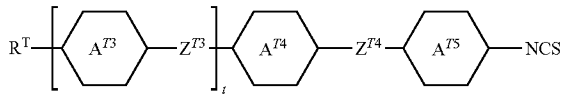

in which $R^T$ denotes halogen, CN, NCS, $R^F$, $R^F$—O— or $R^F$—S—, wherein $R^F$ denotes fluorinated alkyl or fluorinated alkenyl having up to 12 C atoms,

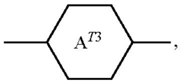, 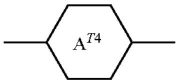 and

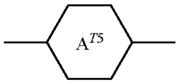

on each occurrence, independently of one another, denote

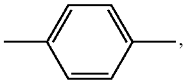, 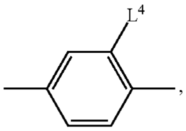,

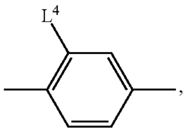, 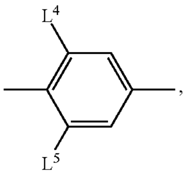,

-continued

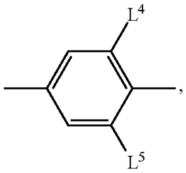, 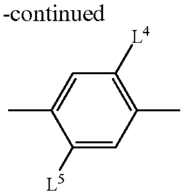 or

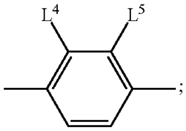;

$L^4$ and $L^5$ identically or differently, denote F, Cl or straight-chain or branched or cyclic alkyl or alkenyl each having up to 12 C atoms;

$Z^{T3}$, $Z^{T4}$ identically or differently, denote —CH═CH—, —CF═CF—, —CH═CF—, —CF═CH—, —C≡C— or a single bond, and t is 0 or 1.

In a preferred embodiment, the liquid crystalline media according to the invention comprise one or more compounds selected from the group of compounds of the formulae T-1a to T-3b below:

T-1a

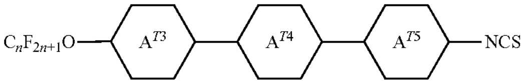

T-1b

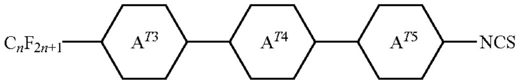

T-2a

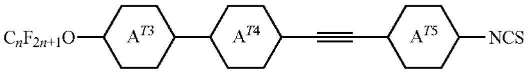

T-2b

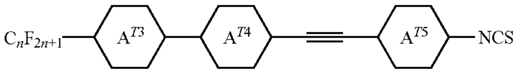

T-3a

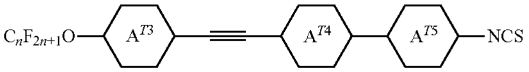

T-3b

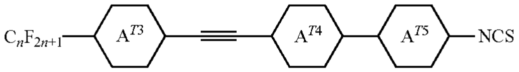

T-4a

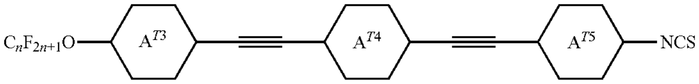

T-4b

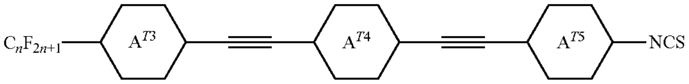

in which

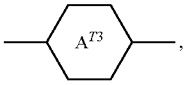, 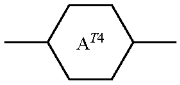 and

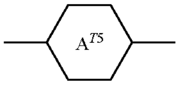

have the meanings given above and n is 1, 2, 3, 4, 5, 6 or 7, preferably 1, 2, 3 or 4, particularly preferably 1.

In a particularly preferred embodiment of the present invention the media comprise one or more compounds selected from the compounds of the formulae T-1a and T-2a.

Preferred compounds of formula T-1a are selected from the group of compounds of the following sub-formulae:

T-1a-1

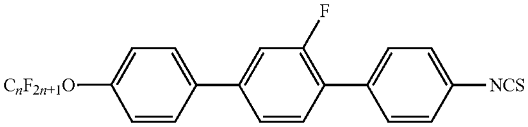

T-1a-2

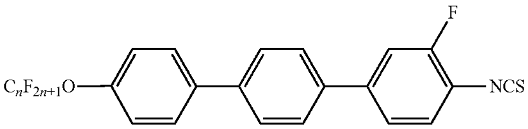

T-1a-3

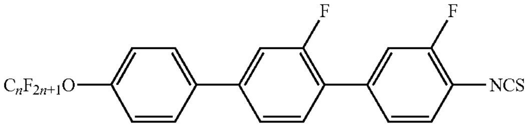

T-1a-4

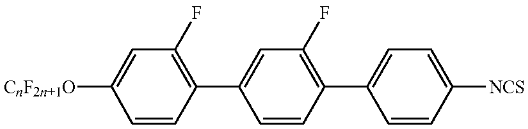

T-1a-5

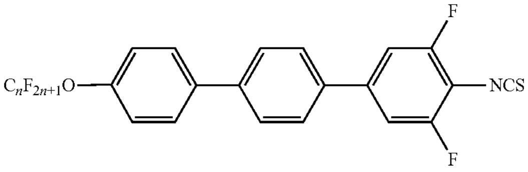

T-1a-6

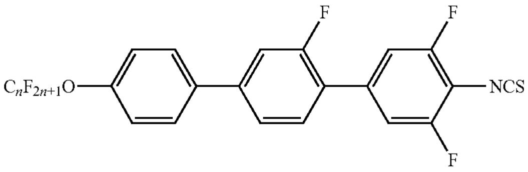

in which n is 1, 2, 3 or 4, preferably 1.

Preferred compounds of formula T-2a are selected from the group of compounds of the following sub-formulae:

T-2a-1

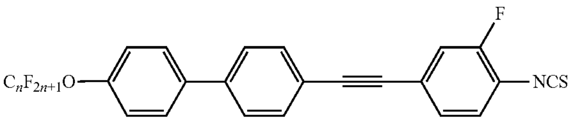

T-2a-2

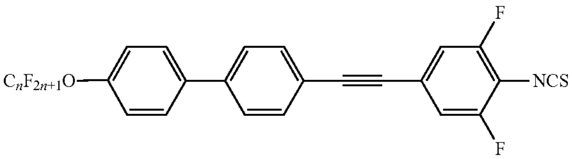

-continued

T-2a-3

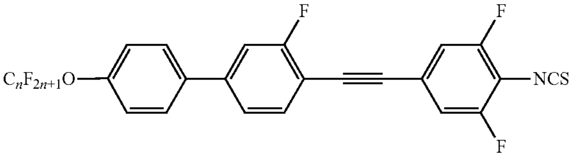

T-2a-4

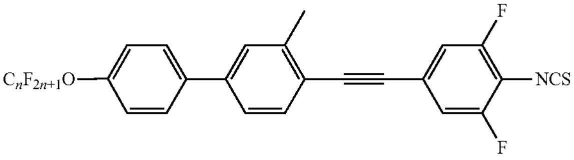

T-2a-5

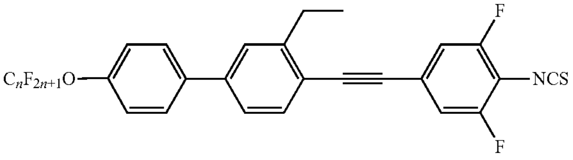

T-2a-6

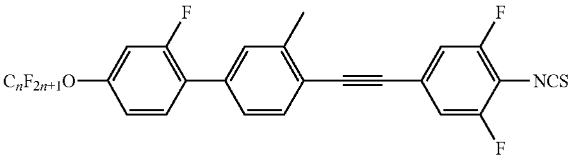

in which n is 1, 2, 3 or 4, preferably 1.

Very preferably, the medium according to the invention comprises one or more compounds of formula T-1a-5.

In an embodiment, the medium according to the invention comprises one or more compounds of formula I, II, III, IV, V, VI, VII, VIII, IX, X in which the radical $R^1$, $R^2$, $R^3$, $R^{41}$, $R^{42}$, $R^{51}$, $R^{52}$, $R^{61}$, $R^{62}$, $R^{71}$, $R^{72}$, $R^{81}$, $R^{82}$, $R^{91}$, $R^{92}$, $R^{101}$, $R^{102}$ and $R^S$, respectively, is a cyclic alkyl group.

Very preferred compounds comprising a cyclic alkyl group are selected from the compounds of the formulae Cy-1 to Cy-14

Cy-1

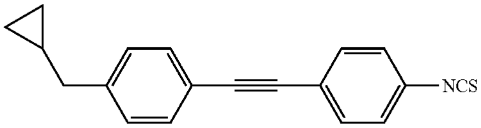

Cy-2

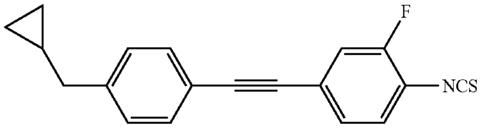

Cy-3

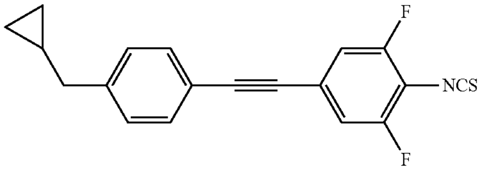

-continued

Cy-4

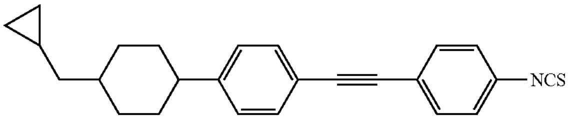

Cy-5

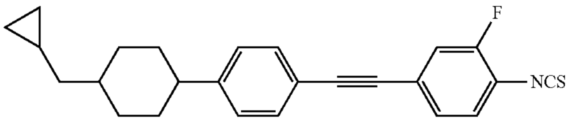

Cy-6

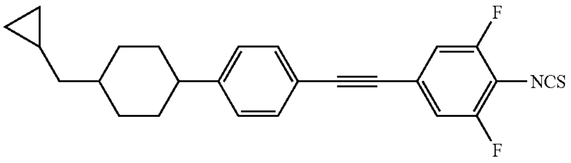

Cy-7

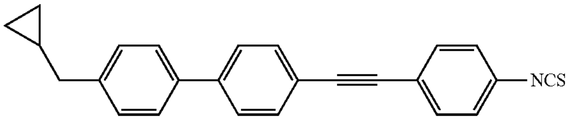

Cy-8

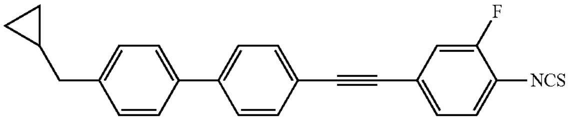

Cy-9

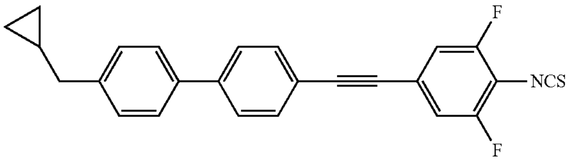

Cy-10

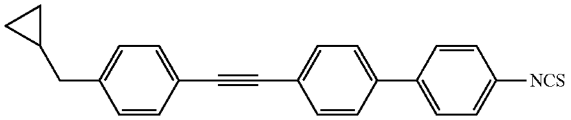

Cy-11

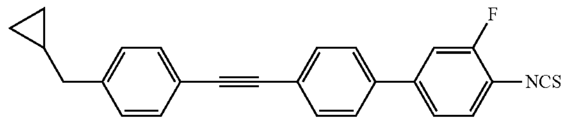

Cy-12

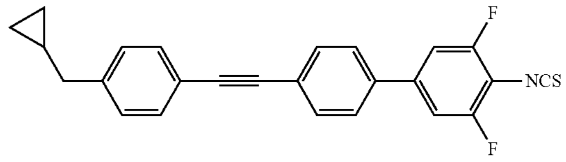

-continued

Cy-13

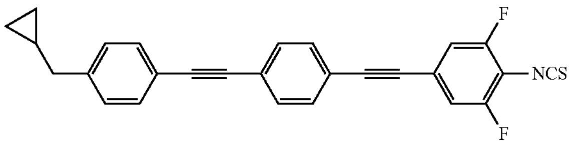

Cy-14

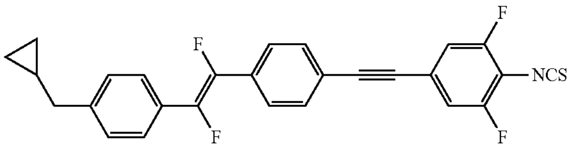

The media according to the present invention comprise one or more chiral dopants. Preferably these chiral dopants have an absolute value of the helical twisting power (HTP) in the range of from 1 $\mu m^{-1}$ to 150 $\mu m^{-1}$, preferably in the range of from 10 $m^{-1}$ to 100 $m^{-1}$. In case the media comprise two or more chiral dopants, these may have opposite signs of their HTP-values. This condition is preferred for some specific embodiments, as it allows to compensate the chirality of the respective compounds to some degree and, thus, may be used to compensate various temperature dependent properties of the resulting media in the devices. Generally, however, it is preferred that most, preferably all of the chiral compounds present in the media according to the present invention have the same sign of their HTP-values.

Preferably the chiral dopants present in the media according to the instant application are mesogenic compounds and most preferably they exhibit a mesophase on their own.

In a preferred embodiment of the present invention, the medium comprises two or more chiral compounds which all have the same algebraic sign of the HTP.

The temperature dependence of the HTP of the individual compounds may be high or low. The temperature dependence of the pitch of the medium can be compensated by mixing compounds having different temperature dependencies of the HTP in corresponding ratios.

For the optically active component, a multitude of chiral dopants, some of which are commercially available, is available to the person skilled in the art, such as, for example, cholesteryl nonanoate, R- and S-811, R- and S-1011, R- and S-2011, R- and S-3011, R- and S-4011, or CB15 (all Merck KGaA, Darmstadt).

Particularly suitable dopants are compounds which contain one or more chiral groups and one or more mesogenic groups, or one or more aromatic or alicyclic groups which form a mesogenic group with the chiral group.

Suitable chiral groups are, for example, chiral branched hydrocarbon radicals, chiral ethane diols, binaphthols or dioxolanes, furthermore mono- or polyvalent chiral groups selected from the group consisting of sugar derivatives, sugar alcohols, sugar acids, lactic acids, chiral substituted glycols, steroid derivatives, terpene derivatives, amino acids or sequences of a few, preferably 1-5, amino acids.

Preferred chiral groups are sugar derivatives, such as glucose, mannose, galactose, fructose, arabinose and dextrose; sugar alcohols, such as, for example, sorbitol, mannitol, iditol, galactitol or anhydro derivatives thereof, in particular dianhydrohexitols, such as dianhydrosorbide (1,4:3,6-dianhydro-D-sorbide, isosorbide), dianhydromannitol (isosorbitol) or dianhydroiditol (isoiditol); sugar acids, such as, for example, gluconic acid, gulonic acid and ketogulonic acid; chiral substituted glycol radicals, such as, for example, mono- or oligoethylene or propylene glycols, in which one or more $CH_2$ groups are substituted by alkyl or alkoxy; amino acids, such as, for example, alanine, valine, phenylglycine or phenylalanine, or sequences of from 1 to 5 of these amino acids; steroid derivatives, such as, for example, cholesteryl or cholic acid radicals; terpene derivatives, such as, for example, menthyl, neomenthyl, campheyl, pineyl, terpineyl, isolongifolyl, fenchyl, carreyl, myrthenyl, nopyl, geraniyl, linaloyl, neryl, citronellyl or dihydrocitronellyl.

The media according to the present invention preferably comprise chiral dopants which are selected from the group of known chiral dopants. Suitable chiral groups and mesogenic chiral compounds are described, for example, in DE 34 25 503, DE 35 34 777, DE 35 34 778, DE 35 34 779 and DE 35 34 780, DE 43 42 280, EP 01 038 941 and DE 195 41 820. Examples are also compounds listed in Table F below.

Chiral compounds preferably used according to the present invention are selected from the group consisting of the formulae shown below.

Particular preference is given to chiral dopants selected from the group consisting of compounds of the following formulae A-1 to A-III and A-Ch:

$R^{a21}$ and $R^{a22}$, independently of one another, denote alkyl having 1 to 15 C atoms, in which, in addition, one or more non-adjacent $CH_2$ groups may each be replaced, independently of one another, by —C($R^z$)═C($R^z$)—, —C≡C—, —O—, —S—, —CO—, —CO—O—, —O—CO— or —O—CO—O— in such a way that 0 and/or S atoms are not linked directly to one another, and in which, in addition, one or more H atoms may be replaced by F, C, Br, I or CN, preferably both are alkyl, more preferably n-alkyl, $R^{a31}$, $R^{a32}$ and $R^{b32}$, independently of one another, denote straight-chain or branched alkyl having 1 to 15 C atoms, in which, in addition, one or more non-adjacent $CH_2$ groups may each be replaced, independently of one another, by —C($R^z$)═C($R^z$)—, —C≡C—, —O—, —S—, —CO—, —CO—O—, —O—CO— or —O—CO—O— in such a way that 0 and/or S atoms are not linked directly to one another, and in which, in addition, one or more H atoms may be replaced by F, Cl, Br, I or CN, preferably alkyl, more preferably n-alkyl, with the proviso that $R^{a32}$ is different from $R^{b32}$;

A-I

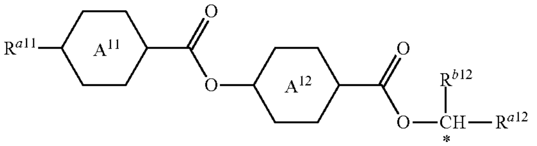

A-II

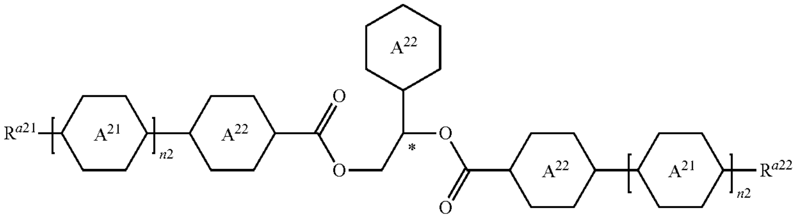

A-III

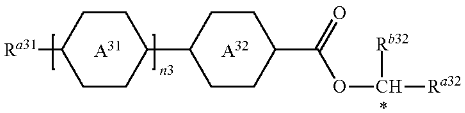

A-Ch

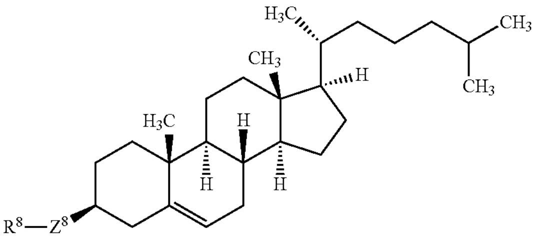

in which $R^{a11}$, $R^{a12}$ and $R^{b12}$, independently of one another, denote alkyl having 1 to 15 C atoms, in which, in addition, one or more non-adjacent $CH_2$ groups may each be replaced, independently of one another, by —C($R^z$)═C($R^z$)—, —C≡C—, —O—, —S—, —CO—, —CO—O—, —O—CO— or —O—CO—O— in such a way that 0 and/or S atoms are not linked directly to one another, and in which, in addition, one or more H atoms may each be replaced by F, Cl, Br, I or CN, preferably alkyl, more preferably n-alkyl, with the proviso that $R^{a12}$ is different from $R^{b12}$, $R^z$ denotes H, $CH_3$, F, Cl, or CN, preferably H or F, $R^8$ has one of the meanings of $R^{a11}$ given above, preferably alkyl, more preferably n-alkyl having 1 to 15 C atoms, $Z^8$ denotes-C(O)O—, $CH_2O$, $CF_20$ or a single bond, preferably —C(O)O—, $A^{11}$ is defined as $A^{12}$ below, or alternatively denotes

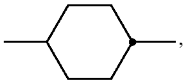,
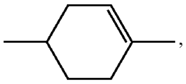,

-continued

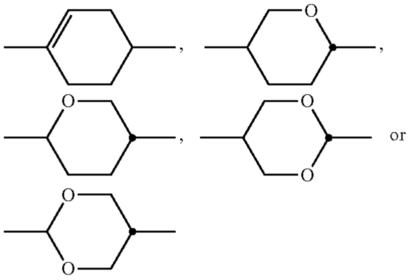

A$^{12}$ denotes

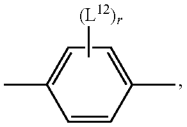

preferably

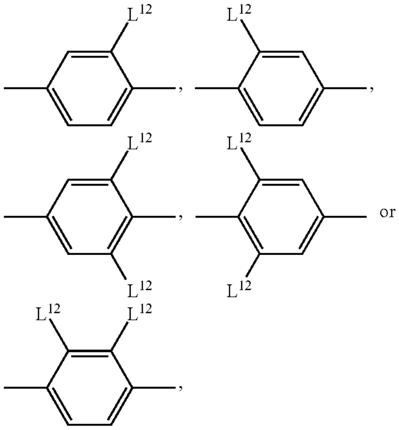

in which $L^{12}$ on each occurrence, independently of one another, denotes halogen, CN, or alkyl, alkenyl, alkoxy or alkenyloxy having up to 12 C atoms and in which one or more H atoms are optionally replaced with halogen, preferably methyl, ethyl, Cl or F, particularly preferably F, $A^{21}$ denotes

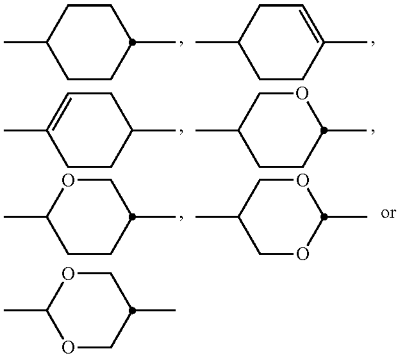

$A^{22}$ has the meanings given for $A^{12}$ $A^{31}$ has the meanings given for $A^{11}$, or alternatively denotes

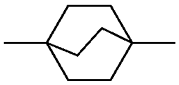

$A^{32}$ has the meanings given for $A^{12}$.

n2 on each occurrence, identically or differently, is 0, 1 or 2, and n3 is 1, 2 or 3, and r is 0, 1, 2, 3 or 4.

Particular preference is given to dopants selected from the group consisting of the compounds of the following formulae:

A-I-1

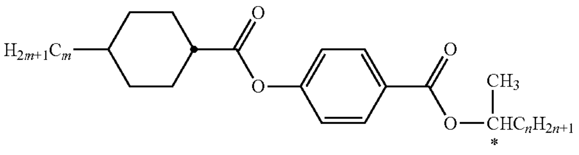

A-II-1

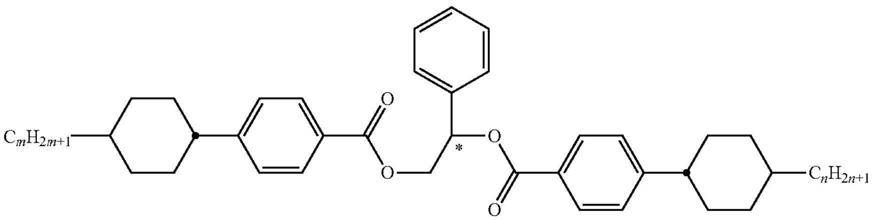

-continued

A-III-1

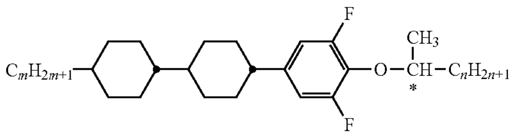

A-III-2

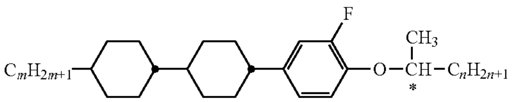

A-III-3

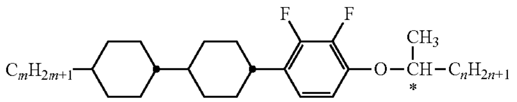

A-III-4

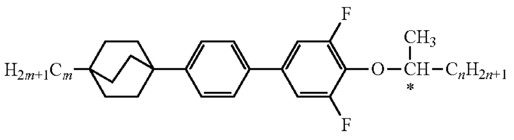

A-III-5

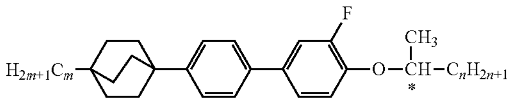

A-III-6

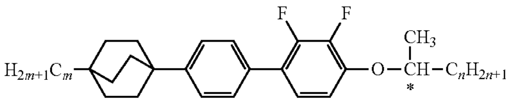

A-III-7

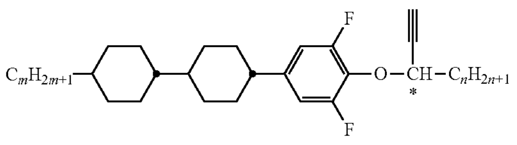

A-III-8

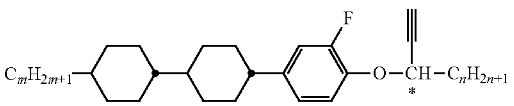

A-III-9

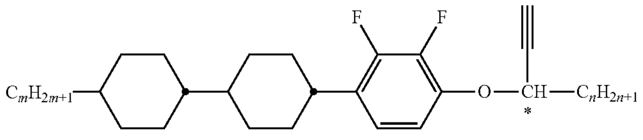

in which m is, on each occurrence, identically or differently, an integer from 1 to 9 and n is, on each occurrence, identically or differently, an integer from 2 to 9.

Particularly preferred compounds of formula A are compounds of formula A-III.

Further preferred dopants are derivatives of the isosorbide, isomannitol or isoiditol of the following formula A-IV:

A-IV

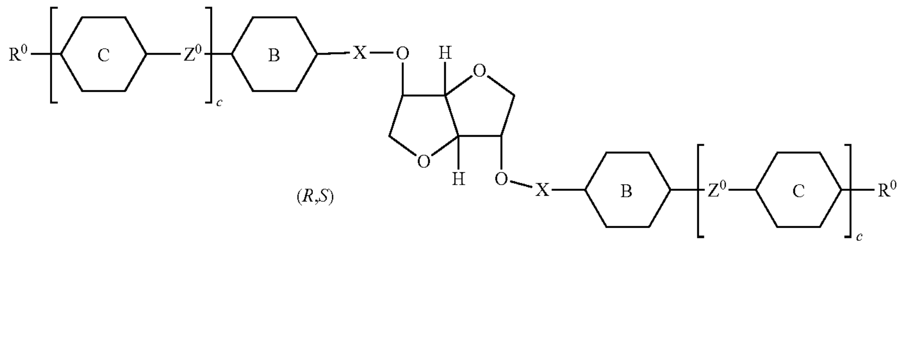

in which the group is
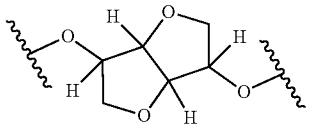 [SMILES: *OC1COC2C(O*)COC12]
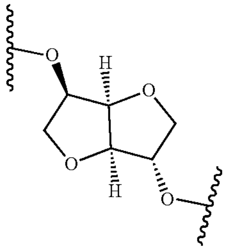 [SMILES: *O[C@H]1CO[C@H]2[C@@H]1OC[C@H]2O*]
(dianhydrosorbitol),
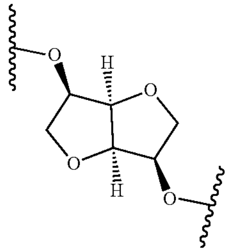 [SMILES: *O[C@@H]1CO[C@H]2[C@@H]1OC[C@H]2O*]
(dianhydromannitol), or
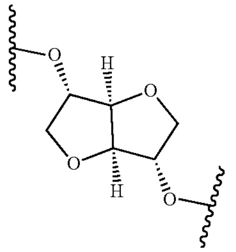 [SMILES: *O[C@H]1CO[C@H]2[C@@H]1OC[C@@H]2O*]
(dianhydroiditol),
preferably dianhydrosorbitol,
and chiral ethane diols, such as, for example, diphenylethanediol (hydrobenzoin), in particular mesogenic hydrobenzoin derivatives of the following formula A-V:
A-V
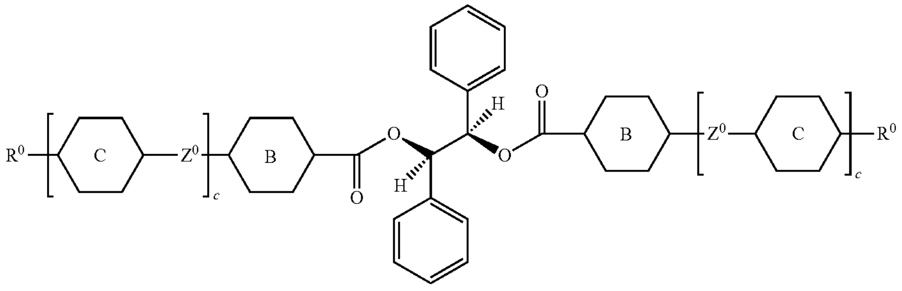

including the (S,S) enantiomers, which are not shown, in which

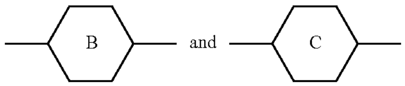

are each, independently of one another, 1,4-phenylene, which may also be mono-, di- or trisubstituted by L, or 1,4-cyclohexylene, L is H, F, Cl, CN or optionally halogenated alkyl, alkoxy, alkylcarbonyl, alkoxycarbonyl or alkoxycarbonyloxy having 1-7 carbon atoms, c is 0 or 1, X is $CH_2$ or —C(O)—, $Z^0$ is —COO—, —OCO—, —$CH_2CH_2$— or a single bond, and $R^0$ is alkyl, alkoxy, alkylcarbonyl, alkoxycarbonyl or alkylcarbonyloxy having 1-12 carbon atoms.

Examples of compounds of formula IV are:

A-IV-1

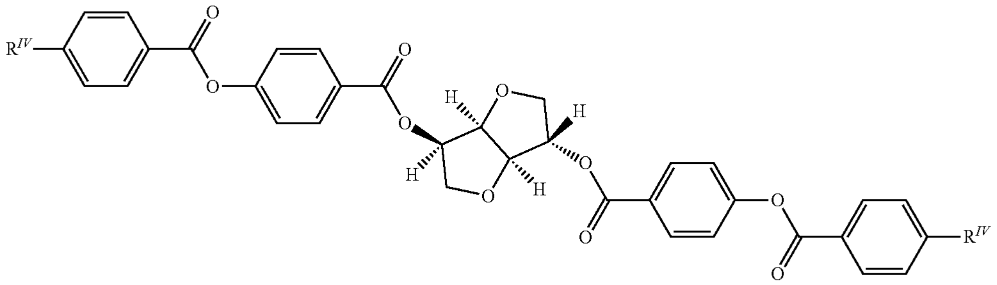

A-IV-2

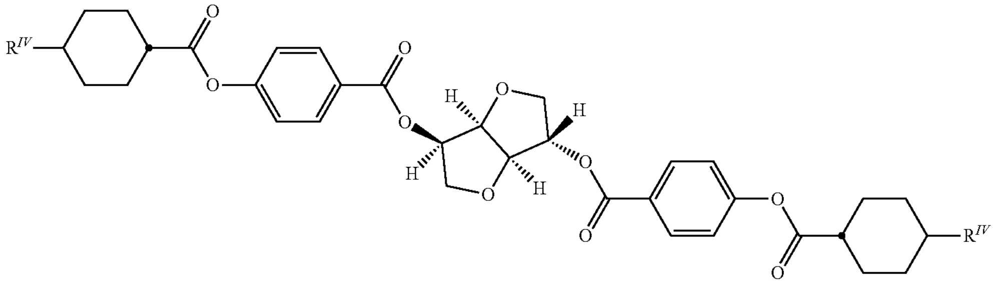

A-IV-3

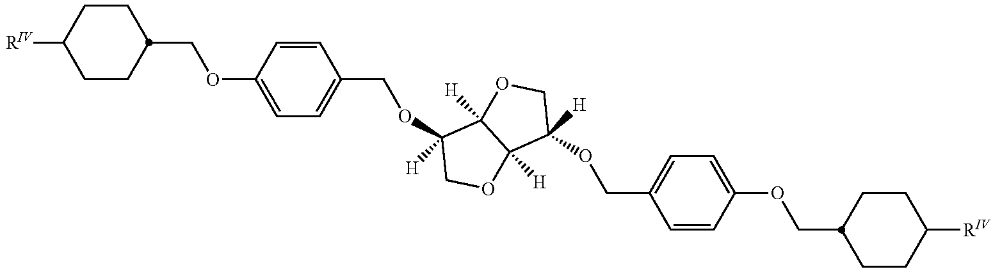

A-IV-4

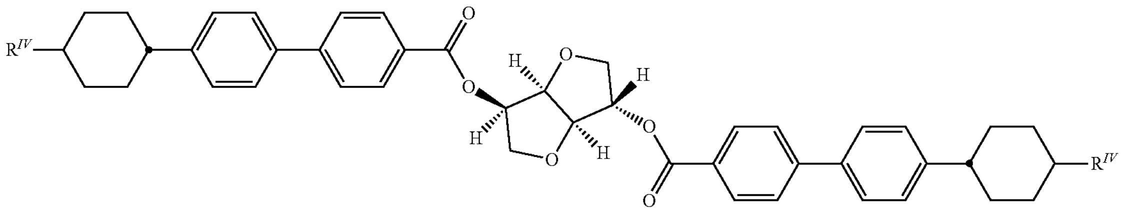

A-IV-5

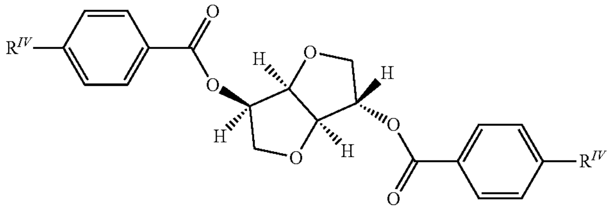

-continued

A-IV-6

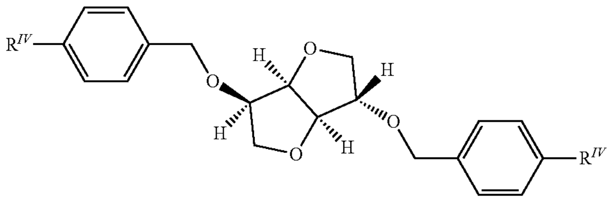

A-IV-7

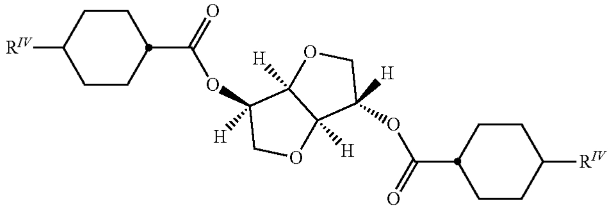

A-IV-8

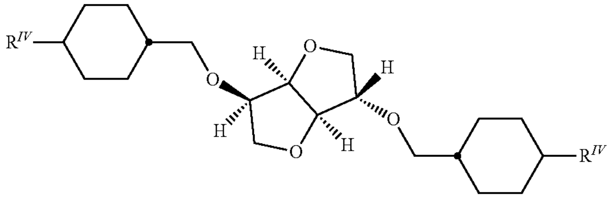

The compounds of the formula A-IV are described in WO 98/00428. The compounds of the formula A-V are described in GB-A-2,328,207.

Very particularly preferred dopants are chiral binaphthyl derivatives, as described in WO 02/94805, chiral binaphthol acetal derivatives, as described in WO 02/34739, chiral TADDOL derivatives, as described in WO 02/06265, and chiral dopants having at least one fluorinated bridging group and a terminal or central chiral group, as described in WO 02/06196 and WO 02/06195.

Particular preference is given to chiral compounds of the formula A-VI

A-VI

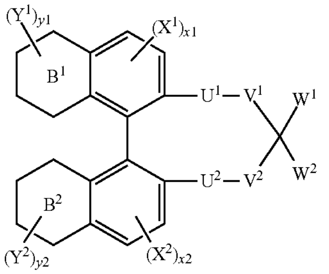

in which $X^1$, $X^2$, $Y^1$ and $Y^2$ are each, independently of one another, F, Cl, Br, I, CN, SCN, $SF_5$, straight-chain or branched alkyl having from 1 to 25 carbon atoms, which is unsubstituted or monosubstituted or polysubstituted by F, C, Br, I or CN and in which, in addition, one or more non-adjacent $CH_2$ groups may each, independently of one another, be replaced by —O—, —S—, —NH—, $NR^x$—, —CO—, —COO—, —OCO—, —OCOO—, —S—CO—, —CO—S—, —CH═CH— or —C≡C— in such a way that 0 and/or S atoms are not bonded directly to one another, a polymerisable group or cycloalkyl or aryl having up to 20 carbon atoms, which may optionally be monosubstituted or polysubstituted by halogen, preferably F, or by a polymerisable group, $x^1$ and $x^2$ are each, independently of one another, 0, 1 or 2, $y^1$ and $y^2$ are each, independently of one another, 0, 1, 2, 3 or 4, $B^1$ and $B^2$ are each, independently of one another, an aromatic or partially or fully saturated aliphatic six-membered ring in which one or more CH groups may each be replaced by N and one or more non-adjacent $CH_2$ groups may each be replaced by 0 or S, $W^1$ and $W^2$ are each, independently of one another, —$Z^1$-$A^1$-($Z^2$-$A^2$)m-R, and one of the two is alternatively $R^1$ or $A^3$, but both are not simultaneously H, or

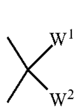

is

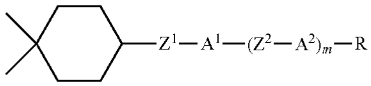

or

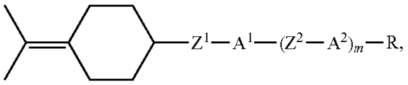

$U^1$ and $U^2$ are each, independently of one another, $CH_2$, O, S, CO or CS, $V^1$ and $V^2$ are each, independently of one another, $(CH_2)_n$, in which one or two non-adjacent $CH_2$ groups may each be replaced by 0 or S, or a single bond,n is 1, 2 or 3, $Z^1$ and $Z^2$ are each, independently of one another, —O—, —S—, —CO—, —COO—, —OCO—, —O—COO—, —CO—$NR^x$—, —$NR^x$—CO—, —O—$CH_2$—, —$CH_2$—O—, —S—$CH_2$—, —$CH_2$—S—, —$CF_2$—O—, —O—$CF_2$—, —$CF_2$—S—, —S—$CF_2$—, —$CH_2$—$CH_2$—, —$CF_2$—$CH_2$—, —$CH_2$—$CF_2$—, —$CF_2$—$CF_2$—, —CH═N—, —N═CH—, —N═N—, —CH═CH—, —CF═CH—, —CH═CF—, —CF═CF—, —C═C—, a combination of two of these groups, where no two 0 and/or S and/or N atoms are bonded directly to one another, preferably —CH═CH—COO—, or —COO—CH═CH—, or a single bond, $R^x$ denotes alkyl having 1 to 6 C atoms, $A^1$, $A^2$ and $A^3$ are each, independently of one another, 1,4-phenylene, in which one or two non-adjacent CH groups may each be replaced by N, 1,4-cyclohexylene, in which one or two non-adjacent $CH_2$ groups may each be replaced by 0 or S, 1,3-dioxolane-4,5-diyl, 1,4-cyclohexenylene, 1,4-bicyclo[2.2.2]octylene, piperi-dine-1,4-diyl, naphthalene-2,6-diyl, decahydronaphthalene-2,6-diyl or 1,2,3,4-tetrahydronaphthalene-2,6-diyl, where each of these groups may be monosubstituted or polysubstituted by L, and in addition $A^1$ can be a single bond, L is a halogen atom, preferably F, CN, $NO_2$, alkyl, alkoxy, alkylcarbonyl, alkoxycarbonyl or alkoxycarbonyloxy having 1-7 carbon atoms, in which one or more H atoms may each be replaced by F or Cl, m is in each case, independently, 0, 1, 2 or 3, and R and $R^1$ are each, independently of one another, H, F, Cl, Br, I, CN, SCN, $SF_5$, straight-chain or branched alkyl having from 1 or 3 to 25 carbon atoms respectively, which may optionally be monosubstituted or polysubstituted by F, C, Br, I or CN, and in which one or more non-adjacent $CH_2$ groups may each be replaced by —O—, —S—, —NH—, —$NR^0$—, —CO—, —COO—, —OCO—, —O—COO—, —S—CO—, —CO—S—, —CH═CH— or —C≡C—, where no two 0 and/or S atoms are bonded directly to one another, or a polymerisable group.

Particular preference is given to chiral binaphthyl derivatives of the formula A-VI-1

A-VI-1

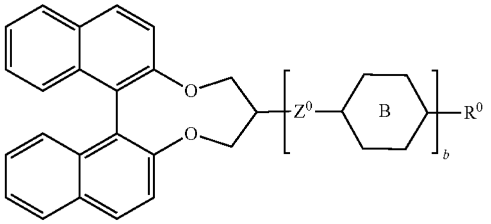

in which ring B, $R^0$ and $Z^0$ are as defined for the formulae A-IV and A-V, and b is 0, 1, or 2, in particular those selected from the following formulae A-VI-1a to A-VI-1c:

A-VI-1a

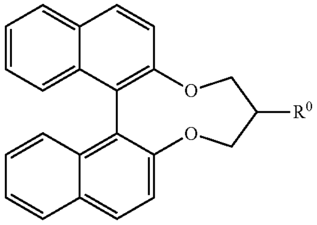

-continued

A-VI-1b

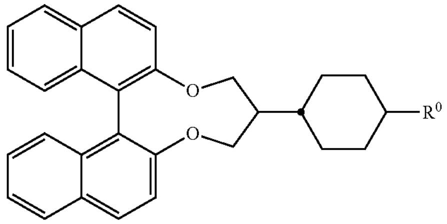

A-VI-1c

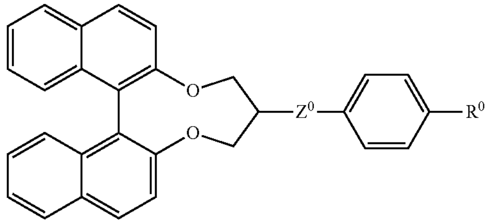

in which ring B, $R^0$ and $Z^0$ are as defined for the formula A-VI-1, and $R^0$ as defined for formula A-IV or H or alkyl having from 1 to 4 carbon atoms, and b is 0, 1 or 2, and $Z^0$ is, in particular, —OC(O)— or a single bond.

The concentration of the one or more chiral dopant(s), in the LC medium is preferably in the range from 0.001% to 20%, preferably from 0.05% to 5%, more preferably from 0.1% to 2%, and, most preferably from 0.5% to 1.5%. These preferred concentration ranges apply in particular to the chiral dopant S-4011 or R-4011 (both from Merck KGaA) and for chiral dopants having the same or a similar HTP. For Chiral dopants having either a higher or a lower absolute value of the HTP compared to S-4011 these preferred concentrations have to be decreased, respectively increased proportionally according to the ratio of their HTP values relatively to that of S-4011.

The pitch p of the LC media or host mixtures according to the invention is preferably in the range of from 5 to 50 μm, more preferably from 8 to 30 m and particularly preferably from 10 to 20 μm.

Preferably, the media according to the invention, comprise a stabiliser selected from the group of compounds of the formulae ST-1 to ST-18.

ST-1
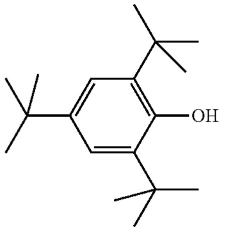
ST-2
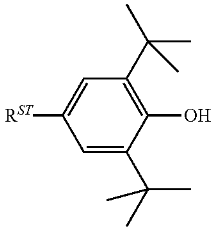
ST-3
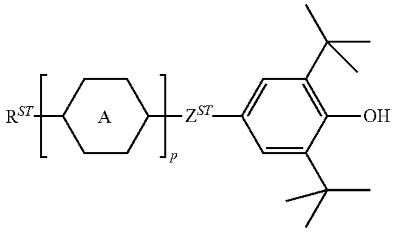
ST-4
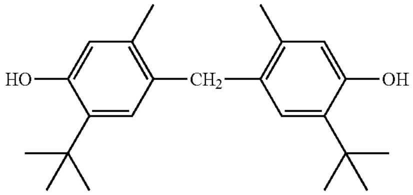
ST-5
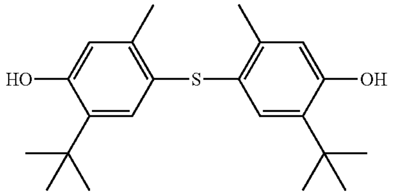
ST-6
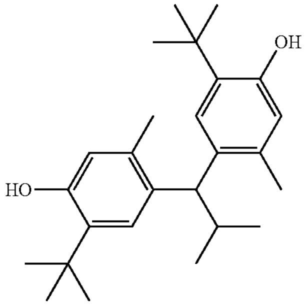
ST-7
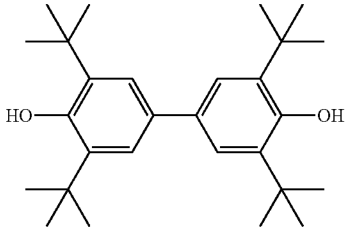
ST-8
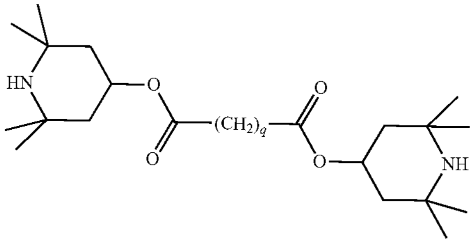
ST-9
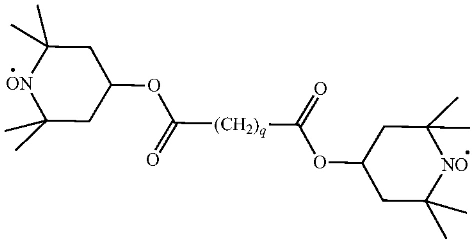
ST-10
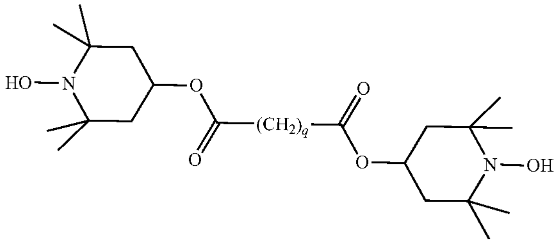
ST-11
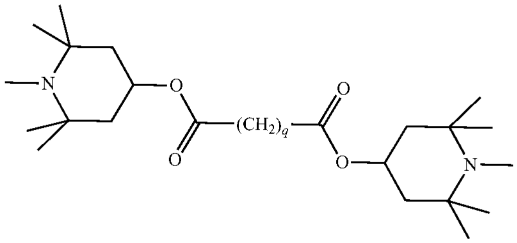

-continued
ST-12
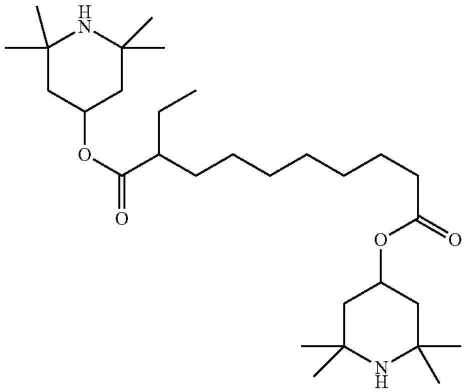
ST-13
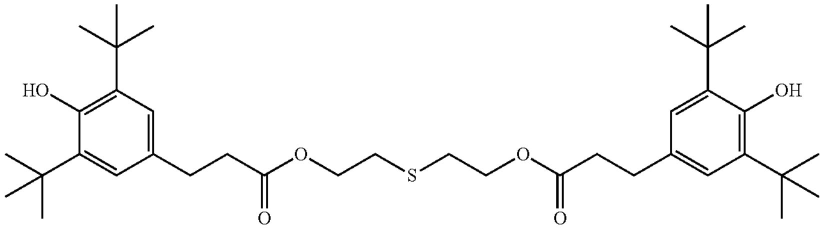
ST-14
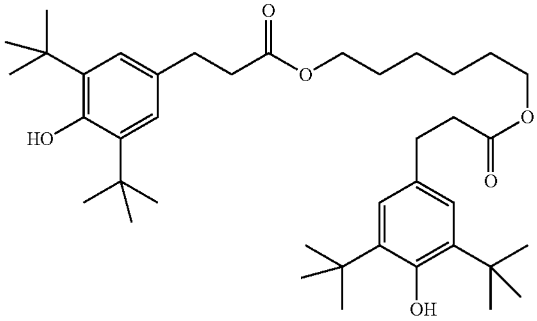
ST-15
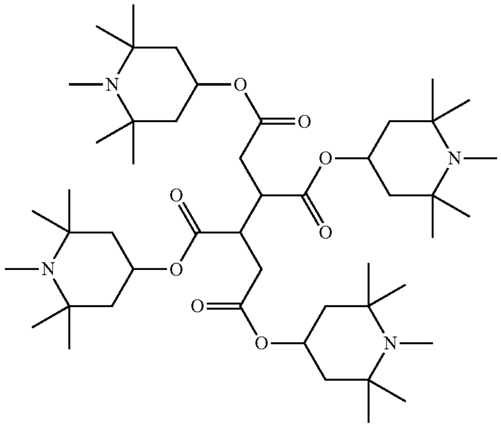
ST-16
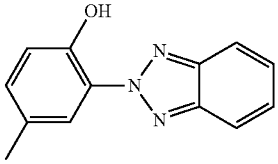

-continued

ST-17

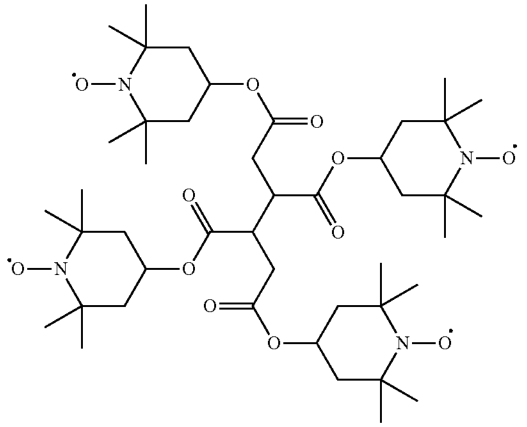

ST-18

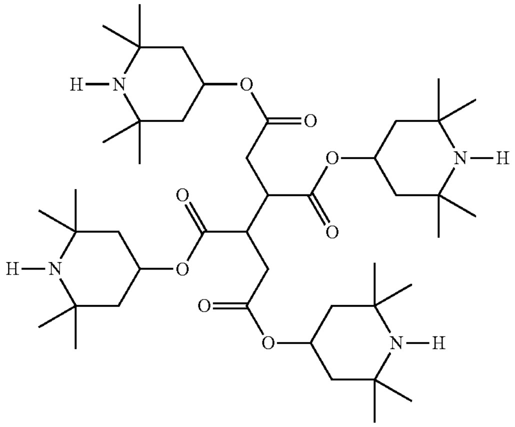

in which $R^{ST}$ denotes H, an alkyl or alkoxy radical having 1 to 15 C atoms, where, in addition, one or more $CH_2$ groups in these radicals may each be replaced, independently of one another, by —C≡C—, —$CF_2O$—, —$OCF_2$—, —CH═CH—,

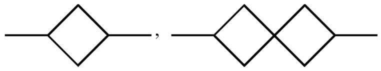

—O—, —CO—O—, —O—CO— in such a way that O atoms are not linked directly to one another, and in which, in addition, one or more H atoms may be replaced by halogen,

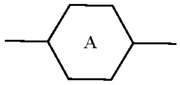

denotes

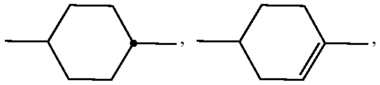

-continued

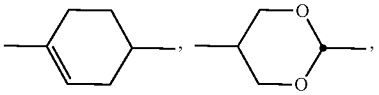

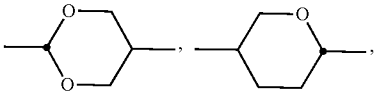

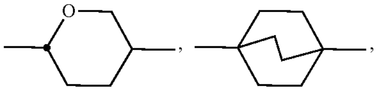

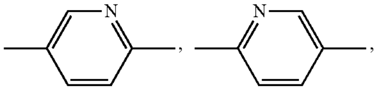

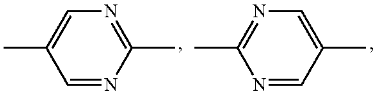

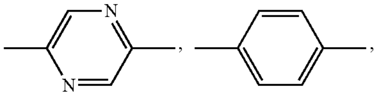

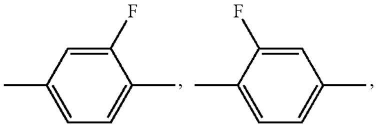

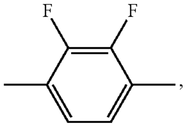, 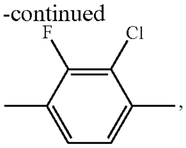,

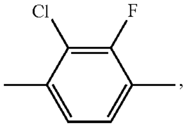, 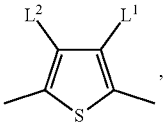,

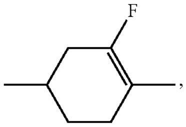, 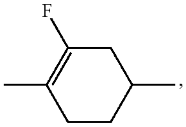,

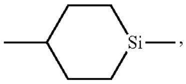, 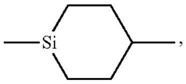,

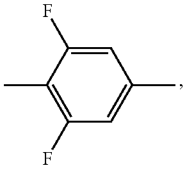, 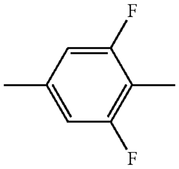,

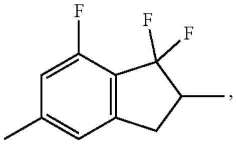, 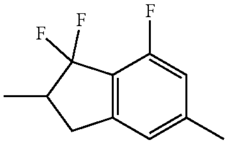,

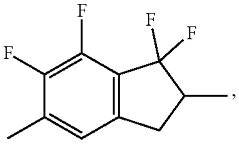, 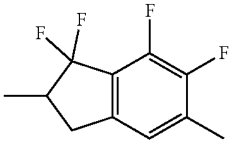,

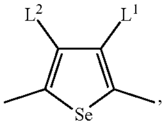, 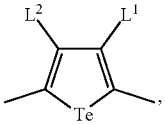,

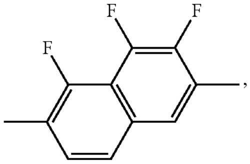, 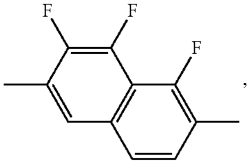,

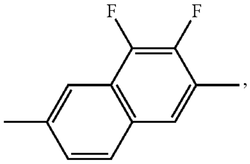, 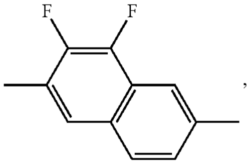,

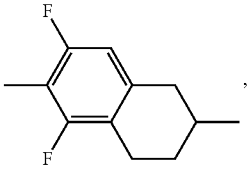, 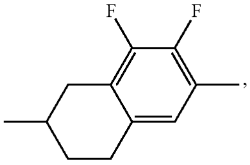,

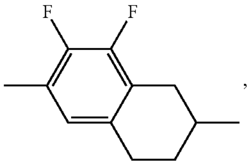, 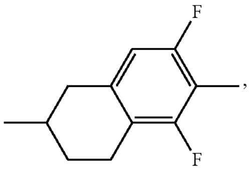,

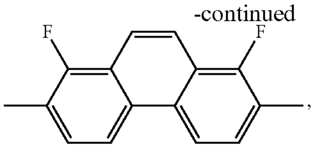,

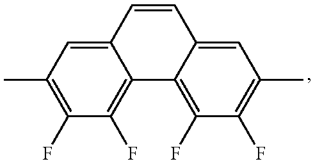,

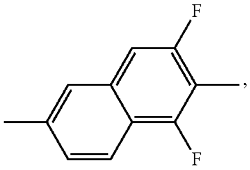,

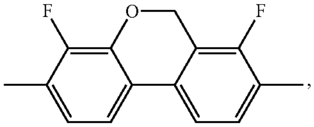,

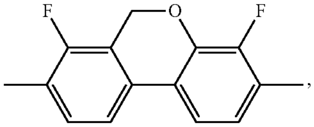,

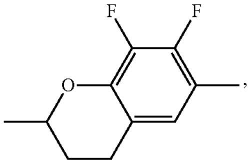, 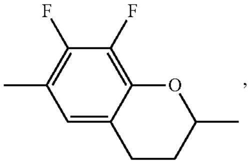,

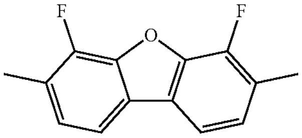

$Z^{ST}$ each, independently of one another, denote —CO—O—, —O—CO—, $—CF_2O—$, $—OCF_2—$, $—CH_2O—$, $—OCH_2—$, $—CH_2—$, $—CH_2CH_2—$, $—(CH_2)_4—$, $—CH{=}CH—CH_2O—$, $—C_2F_4—$, $—CH_2CF_2—$, $—CF_2CH_2—$, —CF═CF—, —CH═CF—, —CF═CH—, —CH═CH—, —C≡C— or a single bond, $L^1$ and $L^2$ each, independently of one another, denote F, Cl, $CF_3$ or $CHF_2$, p denotes 1 or 2, q denotes 1, 2, 3, 4, 5, 6, 7, 8, 9 or 10.

Of the compounds of the formula ST, special preference is given to the compounds of the formulae

ST-1

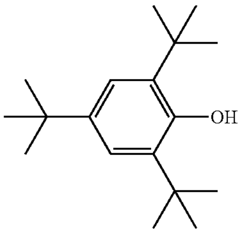

-continued
ST-2a
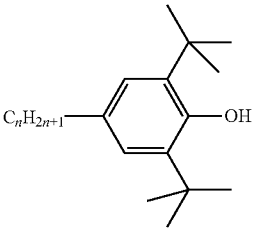
in which n=1, 2, 3, 4, 5, 6 or 7, preferably n=1 or 7
ST-3a
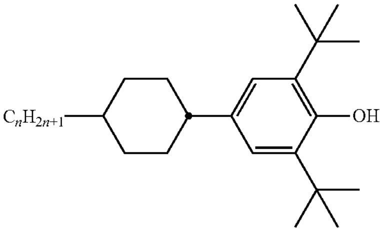
in which n=1, 2, 3, 4, 5, 6 or 7, preferably n=3
ST-3b
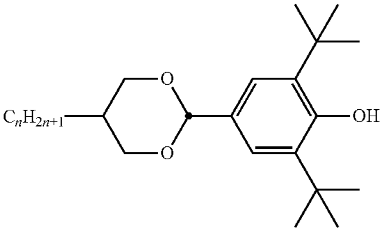
in which n=1, 2, 3, 4, 5, 6 or 7, preferably n=3
ST-8-1
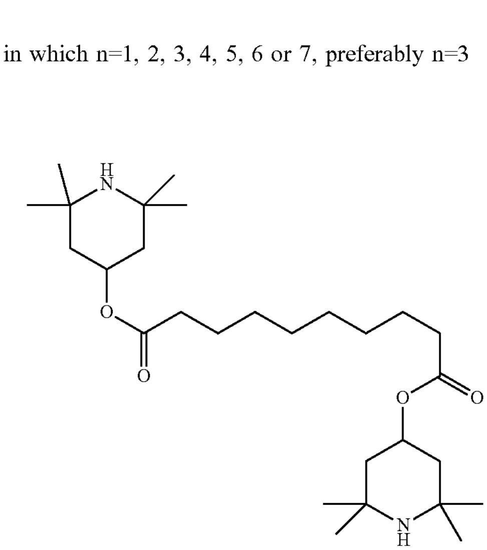
-continued
ST-9-1
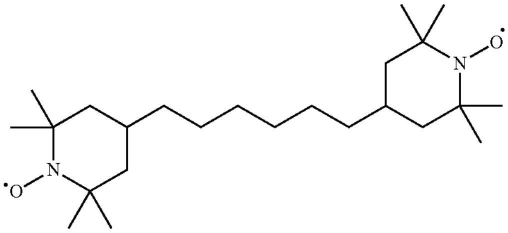
ST-12
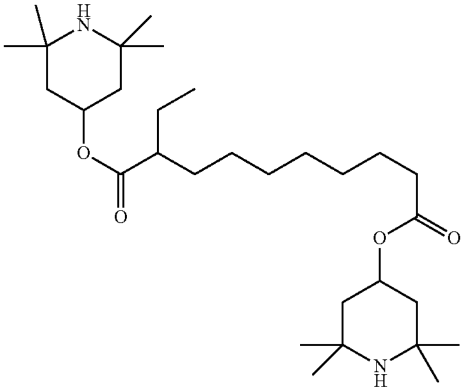
ST-16
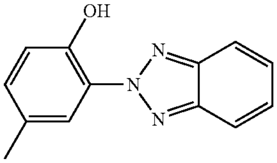
ST-17
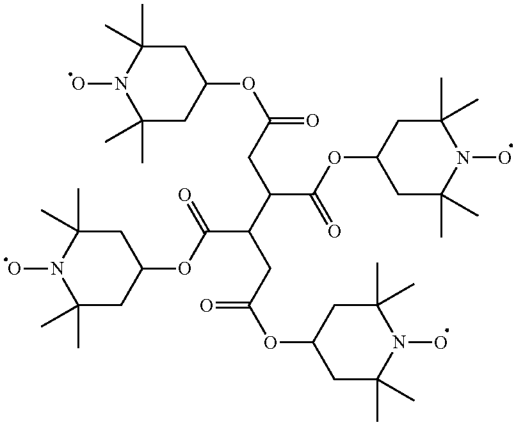

-continued

ST-18

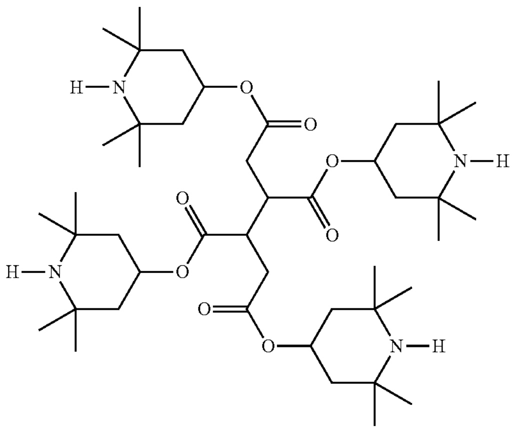

In the compounds of the formulae ST-3a and ST-3b, n preferably denotes 3. In the compounds of the formula ST-2a, n preferably denotes 7.

Very particularly preferred mixtures according to the invention comprise one or more stabilisers from the group of the compounds of the formulae ST-2a-1, ST-3a-1, ST-3b-1, ST-8-1, ST-9-1 and ST-12:

ST-2a-1

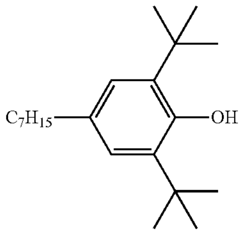

ST-3a-1

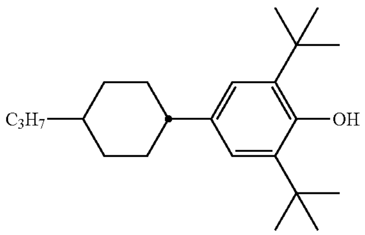

ST-3b-1

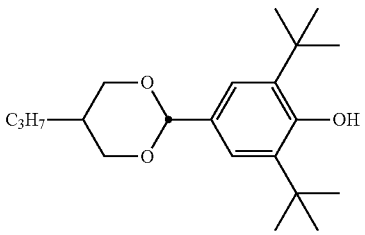

-continued

ST-8-1

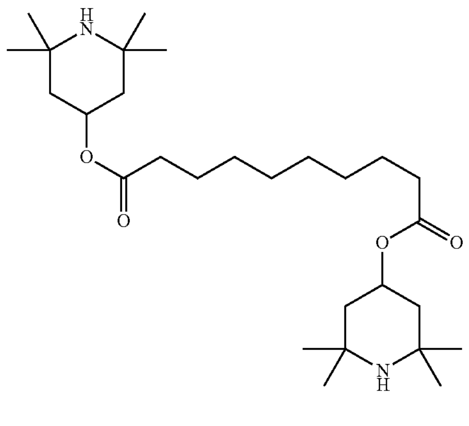

ST-9-1

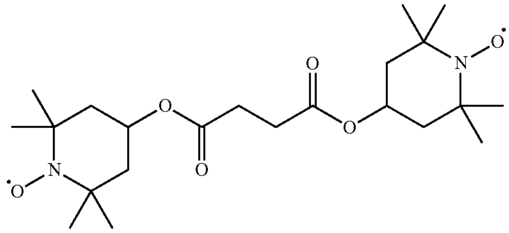

ST-12

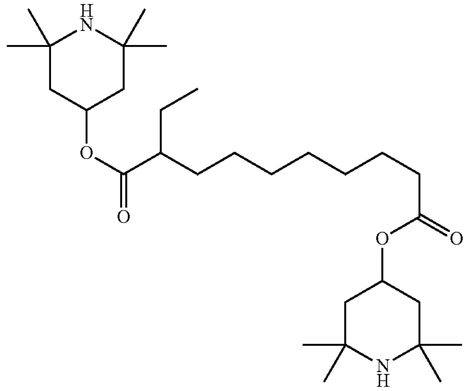

The compounds of the formulae ST-1 to ST-18 are preferably each present in the liquid-crystal mixtures according to the invention in amounts of 0.005-0.5%, based on the mixture.

If the mixtures according to the invention comprise two or more compounds from the group of the compounds of the formulae ST-1 to ST-18, the concentration correspondingly increases to 0.01-1% in the case of two compounds, based on the mixtures.

However, the total proportion of the compounds of the formulae ST-1 to ST-18, based on the mixture according to the invention, should not exceed 2%.

Other mesogenic compounds which are not explicitly mentioned above can optionally and advantageously also be used in the media in accordance with the present invention. Such compounds are known to the person skilled in the art.

In a preferred embodiment of the present invention, the total concentration of compounds of formula UI in the liquid-crystalline medium is 5% or 6% or more, preferably 7% or more, very preferably 8% or more and particularly preferably 10% or 12% or more.

In a preferred embodiment of the present invention, the total concentration of compounds of formula UII in the liquid-crystalline medium is 5% or more, preferably 6% or more, very preferably 8% or more and particularly preferably 10% or more.

In a preferred embodiment of the present invention, the liquid-crystalline media preferably comprise in total 2% to 45%, preferably 5% to 40%, more preferably 6% to 30% and particularly preferably 8% to 25% of compounds of formula UI.

In a preferred embodiment of the present invention, the liquid-crystalline media preferably comprise in total 2% to 40%, preferably 5% to 30% and particularly preferably 8% to 25% of compounds of formula UII.

In a preferred embodiment of the present invention, the liquid-crystalline media preferably comprise in total 10% to 60%, preferably 12 to 55%, more preferably 15% to 50% and particularly preferably 20% to 45% of compounds of formula UI and UII.

In a preferred embodiment of the present invention, the liquid-crystalline media comprise in total 5% to 35%, preferably 6% to 30% and particularly preferably 7% to 25% of one or more compounds of formula T, preferably selected from the formulae T-1a and T-2a, very preferably from T-1a-5 and T-2a-2.

In a preferred embodiment, the medium comprises one or more compounds of formula I, preferably of formula 1-2 or 1-3, in a total concentration in the range of from 1% to 30%, more preferably from 2% to 25%, very preferably 3% to 20% and particularly preferably from 5% to 15%.

In a preferred embodiment of the present invention the medium comprises one or more compounds of formula II, preferably of formula II-1, in a total concentration of 2% to 20%, more preferably 3% to 15%, particularly preferably 5% to 10%.

In a preferred embodiment of the present invention the medium comprises one or more compounds of formula IIA-1 in a total concentration of 5% to 25%, more preferably 8% to 20%, particularly preferably 12% to 17%.

In a preferred embodiment of the present invention the medium comprises one or more compounds of formula II-1 in an total concentration of 30% or less, more preferably 25% or less, particularly preferably 20% or less.

In a preferred embodiment of the present invention the medium comprises one or more compounds of formula III, preferably III-1 and/or III-2, more preferably III-1f and/or III-1b, and/or III-1 h in a total concentration of 15% to 60% or 65% or 70%, more preferably 18% to 55%, particularly preferably 20% to 50%.

In a preferred embodiment of the present invention the medium comprises one or more compounds of formula XII in a total concentration of 5% to 30%, more preferably 8% to 25%, particularly preferably 10% to 20%.

In a preferred embodiment, the medium comprises one or more compounds of the formulae UI and/or UII and one or more compounds selected from the group consisting of the formulae I, II and/or IIA, Ill, XII, T, preferably in a total concentration of 90% or more, more preferably 95%, 96% or 97% or more, very preferably 98% or more and in particular 99% or more.

In a preferred embodiment, the medium comprises one or more compounds of the formulae UI and/or UII and one or more compounds selected from the group consisting of the formulae I, II and/or IIA, III, XII, T in a total concentration in the range of from 40% to 90% and 10% or more of one or more compounds of the formula IV.

In a preferred embodiment, the medium comprises one or more compounds of the formulae UI and UII and one or more compounds selected from the group consisting of the formulae I, II and/or IIA, Ill, XII and T in a total concentration in the range of from 40% to 70% and 30% or more of one or more compounds of the formula IV.

In a preferred embodiment, the medium comprises one or more compounds of the formulae UI and/or UII and one or more compounds selected from the group consisting of the formulae I, II and/or IIA, III, XII, T in a total concentration in the range of from 40% to 60% and 40% or more of one or more compounds of the formula IV.

Further preferred embodiments of the present invention, taken alone or in combination with one another, are as follows, wherein some compounds are abbreviated using the acronyms as described in Tables A and B and given in Table C below:

- The medium comprises one, two, three, four or more compounds of formula III-1, preferably selected from the compounds of the formulae III-1b, III-1f and III-1 h; more preferably of III-1b and III-1 h;
- The medium comprises a compound of formula III-1b, preferably in a total concentration in the range of from 5% to 35%, more preferably 10% to 30%, in particular 15% to 25%;
- The medium comprises a compound of formula III-1h, preferably in a total concentration in the range of from 5% to 35%, more preferably 7% to 30%, in particular 10% to 25%;
- The medium comprises the compound PPU-TO-S and/or PPTU-TO-S and/or PTPU-TO-S and/or PP(1)TO-n-S;
- The medium comprises one or more compounds of formula I-2d, preferably the compounds PGU-2-S and/or PGU-3-S and/or PGU-4-S, and/or CPU-2-S and/or CPU-3-S and/or CPU-4-S;
- The medium comprises one or more compounds of formula II-1b, preferably the compounds PTU-4-S and/or PTU-5-S;
- The medium comprises one or more compounds of formula PPTU-n-S and/or PTPU-n-S in an total concentration in the range of from 15 to 25%;
- The medium comprises one or more compounds of formula PPTU-n-S and/or PTPU-n-S and/or PGTU-n-S in a total concentration in the range of from 15 to 30%, in which n is 1, 2, 3, 4, 5, or 6;
- The medium comprises one or more compounds of formula ST-3, preferably ST-3a and/or ST-3b, particularly preferably ST-3b-1, in a total concentration in the range of from 0.01 to 1%, preferably from 0.05 to 0.5%, particularly from 0.10 to 0.15%.

The liquid-crystal media in accordance with the present invention preferably have a clearing point of 90° C. or more, more preferably 100° C. or more, more preferably 110° C. or more, more preferably 120° C. or more, more preferably 130° C. or more, particularly preferably 140° C. or more and very particularly preferably 150° C. or more.

The liquid-crystal media in accordance with the present invention preferably have a clearing point of 160° C. or less, more preferably 140° C. or less, particularly preferably 120° C. or less, and very particularly preferably 100° C. or less.

The nematic phase of the media according to the invention preferably extends at least from 0° C. or less to 90° C. or more. It is advantageous for the media according to the invention to exhibit even broader nematic phase ranges, preferably at least from −10° C. or less to 120° C. or more, very preferably at least from −20° C. or less to 140° C. or more and in particular at least from −30° C. or less to 150° C. or more, very particularly preferably at least from −40° C. or less to 170° C. or more.

The Δε of the liquid-crystal medium according to the present invention, at 1 kHz and 20° C., is preferably 5 or more, more preferably 7 or more and very preferably 8 or more.

The birefringence (Δn) of the liquid-crystal media according to the present invention, at 589 nm ($Na^D$) and 20° C., is preferably 0.280 or more, more preferably 0.300 or more, even more preferably 0.320 or more, very preferably 0.330 or more and in particular 0.350 or more.

The λn of the liquid-crystal media according to the present invention, at 589 nm ($Na^D$) and 20° C., is preferably in the range from 0.200 to 0.900, more preferably in the range from 0.250 to 0.800, even more preferably in the range from 0.300 to 0.700 and very particularly preferably in the range from 0.350 to 0.600.

In a preferred embodiment of the present application, the Δn of the liquid-crystal media in accordance with the present invention is preferably 0.50 or more, more preferably 0.55 or more.

The compounds of the formulae I to Ill in each case include dielectrically positive compounds having a dielectric anisotropy of greater than 3, dielectrically neutral compounds having a dielectric anisotropy of less than 3 and greater than −1.5 and dielectrically negative compounds having a dielectric anisotropy of -1.5 or less.

The compounds of the formulae UI, UII, I, II and III are preferably dielectrically positive.

In the present application, the expression dielectrically positive describes compounds or components where $\Delta\varepsilon>3.0$, dielectrically neutral describes those where $-1.5\leq\Delta\varepsilon\leq3.0$ and dielectrically negative describes those where $\Delta\varepsilon<-1.5$. Δε is determined at a frequency of 1 kHz and at 20° C. The dielectric anisotropy of the respective compound is determined from the results of a solution of 10% of the respective individual compound in a nematic host mixture. If the solubility of the respective compound in the host mixture is less than 10%, the concentration is reduced to 5%. The capacitances of the test mixtures are determined both in a cell having homeotropic alignment and in a cell having homogeneous alignment. The cell thickness of both types of cells is approximately 20 μm. The voltage applied is a rectangular wave having a frequency of 1 kHz and an effective value of typically 0.5 V to 1.0 V, but it is always selected to be below the capacitive threshold of the respective test mixture.

Δε is defined as $(\varepsilon_{\|}-\varepsilon_{\perp})$, while $\varepsilon_{ave.}$ is $(\varepsilon_{\|}+2\,\varepsilon_{\perp})/3$.

The host mixture used for the determination of physical constants of pure compounds by extrapolation is ZLI-4792 from Merck KGaA, Germany. The absolute values of the dielectric constants, the birefringence (Δn) and the rotational viscosity ($\gamma_1$) of the compounds are determined from the change in the respective values of the host mixture on addition of the compounds. The concentration in the host is 10% or in case of insufficient solubility 5%. The values are extrapolated to a concentration of 100% of the added compounds.

In the examples, the phase sequences of pure compounds are given using the following abbreviations:

K: crystalline, N:nematic, SmA:smectic A, SmB:smectic B, I:isotropic.

Components having a nematic phase at the measurement temperature of 20° C. are measured as such, all others are treated like compounds.

The expression threshold voltage in the present application refers to the optical threshold and is quoted for 10% relative contrast ($V_{10}$), and the expression saturation voltage refers to the optical saturation and is quoted for 90% relative contrast ($V_{90}$), in both cases unless expressly stated otherwise. The capacitive threshold voltage ($V_0$), also called the Freedericks threshold ($V_{Fr}$), is only used if expressly mentioned.

The parameter ranges indicated in this application all include the limit values, unless expressly stated otherwise.

The different upper and lower limit values indicated for various ranges of properties in combination with one another give rise to additional preferred ranges.

Throughout this application, the following conditions and definitions apply, unless expressly stated otherwise. All concentrations are quoted in percent by weight and relate to the respective mixture as a whole, all temperatures are quoted in degrees Celsius and all temperature differences are quoted in differential degrees. All physical properties are determined in accordance with "Merck Liquid Crystals, Physical Properties of Liquid Crystals", Status November 1997, Merck KGaA, Germany, and are quoted for a temperature of 20° C., unless expressly stated otherwise. The optical anisotropy (Δn) is determined at a wavelength of 589.3 nm. The dielectric anisotropy (Δε) is determined at a frequency of 1 kHz. The threshold voltages, as well as all other electro-optical properties, are determined using test cells produced at Merck KGaA, Germany. The test cells for the determination of Δε have a cell thickness of approximately 20 μm. The electrode is a circular ITO electrode having an area of 1.13 $cm^2$ and a guard ring. The orientation layers are SE-1211 from Nissan Chemicals, Japan, for homeotropic orientation ($\varepsilon_{\|}$) and polyimide AL-1054 from Japan Synthetic Rubber, Japan, for homogeneous orientation ($\varepsilon_{\perp}$). The capacitances are determined using a Solatron 1260 frequency response analyser using a sine wave with a voltage of 0.3 $V_{rms}$. The light used in the electro-optical measurements is white light. A set-up using a commercially available DMS instrument from Autronic-Melchers, Germany, is used here. The charac-teristic voltages have been determined under perpendicular observation. The threshold ($V_{10}$), mid-grey ($V_{50}$) and saturation ($V_{90}$) voltages have been determined for 10%, 50% and 90% relative contrast, respectively.

The liquid-crystalline media are investigated with respect to their properties in the microwave frequency range as described in A. Penirschke et al. "Cavity Perturbation Method for Characterization of Liquid Crystals up to 35 GHz", $34^{th}$ European Microwave Conference—Amsterdam, pp. 545-548. Compare in this respect also A. Gaebler et al. "Direct Simulation of Material Permittivities . . . ", 12MTC 2009—International Instrumentation and Measurement Technology Conference, Singapore, 2009 (IEEE), pp. 463-467, and DE 10 2004 029 429 A, in which a measurement method is likewise described in detail.

The liquid crystal is introduced into a polytetrafluoroethylene (PTFE) or quartz capillary. The capillary has an inner diameter of 0.5 mm and an outer diameter of 0.78 mm. The effective length is 2.0 cm. The filled capillary is introduced into the centre of the cylindrical cavity with a resonance frequency of 19 GHz. This cavity has a length of 11.5 mm and a radius of 6 mm. The input signal (source) is then applied, and the frequency depending response of the cavity is recorded using a commercial vector network analyser (N5227A PNA Microwave Network Analyzer, Keysight Technologies Inc. USA. For other frequencies, the dimensions of the cavity are adapted correspondingly.

The change in the resonance frequency and the Q factor between the measurement with the capillary filled with the liquid crystal and the measurement without the capillary filled with the liquid crystal is used to determine the dielectric constant and the loss angle at the corresponding target frequency by means of equations 10 and 11 in the above-mentioned publication A. Penirschke et al., 34th European Microwave Conference—Amsterdam, pp. 545-548, as described therein.

The values for the components of the properties perpendicular and parallel to the director of the liquid crystal are obtained by alignment of the liquid crystal in a magnetic field. To this end, the magnetic field of a permanent magnet is used. The strength of the magnetic field is 0.35 tesla.

Preferred components are phase shifters, varactors, wireless and radio wave antenna arrays, matching circuit adaptive filters and others.

In the present application, the term compounds is taken to mean both one compound and a plurality of compounds, unless expressly stated otherwise.

All mixtures according to the invention are nematic. The liquid-crystal media according to the invention preferably have nematic phases in preferred ranges given above. The expression have a nematic phase here means on the one hand that no smectic phase and no crystallisation are observed at low temperatures at the corresponding temperature and on the other hand that no clearing occurs on heating from the nematic phase. At high temperatures, the clearing point is measured in capillaries by conventional methods. The investigation at low temperatures is carried out in a flow viscometer at the corresponding temperature and checked by storage of bulk samples: The storage stability in the bulk (LTS) of the media according to the invention at a given temperature T is determined by visual inspection. 2 g of the media of interest are filled into a closed glass vessel (bottle) of appropriate size placed in a refrigerator at a predetermined temperature. The bottles are checked at defined time intervals for the occurrence of smectic phases or crystallisation. For every material and at each temperature two bottles are stored. If crystallisation or the appearance of a smectic phase is observed in at least one of the two correspondent bottles the test is terminated and the time of the last inspection before the one at which the occurrence of a higher ordered phase is observed is recorded as the respective storage stability. The test is finally terminated after 1000 h, i.e. an LTS value of 1000 h means that the mixture is stable at the given temperature for at least 1000 h.

The liquid crystals employed preferably have a positive dielectric anisotropy. This is preferably 2 or more, preferably 4 or more, particularly preferably 6 or more and very particularly preferably 10 or more.

Furthermore, the liquid-crystal media according to the invention are characterised by high anisotropy values in the microwave range. The birefringence at about 19 GHz is, for example, preferably 0.14 or more, particularly preferably 0.15 or more, particularly preferably 0.20 or more, particularly preferably 0.25 or more and very particularly preferably 0.30 or more. In addition, the birefringence is preferably 0.80 or less.

The dielectric anisotropy in the microwave range is defined as $$\Delta\varepsilon_r=(\varepsilon_{r,\parallel}-\varepsilon_{r,\perp}).$$

The tunability (t) is defined as $$\tau=(\Delta\varepsilon_r/\varepsilon_{r,\parallel}).$$

The material quality (i) is defined as $$\tau=(\tau/\tan\delta_{\varepsilon r,max.}),\text{ where}$$

the maximum dielectric loss is $$\tan\delta_{\varepsilon r,max.}=\max.\{\tan\delta_{\varepsilon r,\perp};\tan\delta_{\varepsilon r,\parallel}\}.$$

The tunability ti of the medium according to the invention, measured at 20° C. and 19 GHz is 0.250 or more, preferably 0.300 or more, 0.310 or more, 0.320 or more, 0.330 or more, or 0.340 or more, very preferably 0.345 or more and in particular 0.350 or more.

The material quality (i) of the preferred liquid-crystal materials is 6 or more, preferably 8 or more, preferably 10 or more, preferably 15 or more, preferably 17 or more, preferably 20 or more, particularly preferably 25 or more and very particularly preferably 30 or more.

In the corresponding components, the preferred liquid-crystal materials have phase shifter qualities of 15°/dB or more, preferably 20°/dB or more, preferably 30°/dB or more, preferably 40°/dB or more, preferably 50°/dB or more, particularly preferably 80°/dB or more and very particularly preferably 100°/dB or more.

In some embodiments, however, liquid crystals having a negative value of the dielectric anisotropy can also advantageously be used.

The liquid crystals employed are either individual substances or mixtures. They preferably have a nematic phase.

The liquid-crystal media in accordance with the present invention may comprise further additives and chiral dopants in the usual concentrations. The total concentration of these further constituents is in the range from 0% to 10%, preferably 0.1% to 6%, based on the mixture as a whole. The concentrations of the individual compounds used are each preferably in the range from 0.1% to 3%. The concentration of these and similar additives is not taken into consideration when quoting the values and concentration ranges of the liquid-crystal components and liquid-crystal compounds of the liquid-crystal media in this application.

Preferably the media according to the present invention comprise one or more chiral compounds as chiral dopants in order to adjust their cholesteric pitch. Their total concentration in the media according to the instant invention is preferably in the range 0.05% to 15%, more preferably from 1% to 10% and most preferably from 2% to 6%.

Optionally the media according to the present invention may comprise further liquid crystal compounds in order to adjust the physical properties. Such compounds are known to the skilled person. Their concentration in the media according to the instant invention is preferably 0% to 30%, more preferably 0.1% to 20% and most preferably 1% to 15%.

The response times are given as rise time ($\tau_{on}$) for the time for the change of the relative tuning, respectively of the relative contrast for the electro-optical response, from 0% to 90% ($t_{90}$-$t_0$), i.e. including the delay time ($t_{10}$-$t_0$), as decay time ($\tau_{off}$) for the time for the change of the relative tuning, respectively of the relative contrast for the electro-optical response, from 100% back to 10% ($t_{100}$-$t_{10}$) and as the total response time ($\tau_{total}=\tau_{on}+\tau_{off}$), respectively.

The liquid-crystal media according to the invention consist of a plurality of compounds, preferably 3 to 30, more preferably 4 to 20 and very preferably 4 to 16 compounds. These compounds are mixed in a conventional manner. In general, the desired amount of the compound used in the smaller amount is dissolved in the compound used in the larger amount. If the temperature is above the clearing point of the compound used in the higher concentration, it is particularly easy to observe completion of the dissolution process. It is, however, also possible to prepare the media in other conventional ways, for example using so-called premixes, which can be, for example, homologous or eutectic mixtures of compounds, or using so-called "multi bottle" systems, the constituents of which are themselves ready-to-use mixtures.

All temperatures, such as, for example, the melting point T(C,N) or T(C,S), the transition from the smectic (S) to the nematic (N) phase T(S,N) and the clearing point T(N,I) of the liquid crystals, are quoted in degrees Celsius. All temperature differences are quoted in differential degrees.

In the present invention and especially in the following examples, the structures of the mesogenic compounds are indicated by means of abbreviations, also referred to as acronyms. In these acronyms, the chemical formulae are abbreviated as follows using Tables A to C below. All groups $C_nH_{2n+1}$, $C_mH_{2m+1}$ and $C_mH_{21+1}$, and $C_nH_{2n-1}$, $C_mH_{2m-1}$ and $C_1H_{21-1}$ denote straight-chain alkyl or akylene, respectively, in each case having n, m or I C atoms, wherein n and m, independently are 1, 2, 3, 4, 5, 6 or 7 and I is 1, 2 or 3. Table A lists the codes used for the ring elements of the core structures of the compounds, while Table B shows the linking groups and end groups. Table C shows illustrative structures of compounds with their respective abbreviations.

TABLE A

| Ring elements | |
|---|---|
| C | 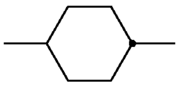 |
| D | 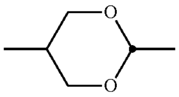 |
| DI | 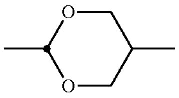 |
| A | 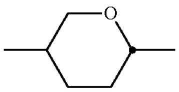 |
| AI | 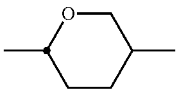 |
| G | 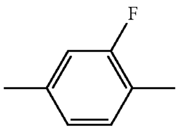 |
| GI | 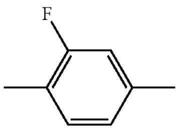 |
| G(Cl) | 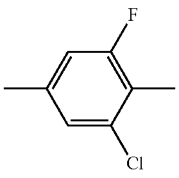 |

TABLE A-continued

| Ring elements | |
|---|---|
| P(Cl,Cl) | 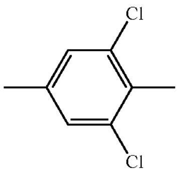 |
| GI(Cl) | 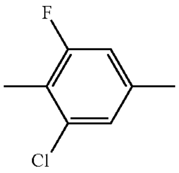 |
| P(Cl,Cl)I | 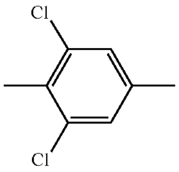 |
| U | 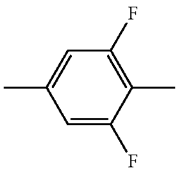 |
| UI | 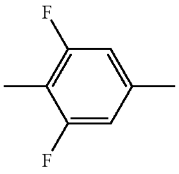 |
| U(F,F) | 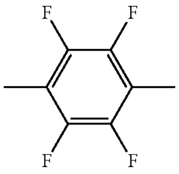 |
| Y | 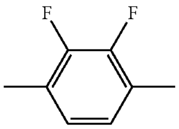 |
| M | 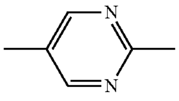 |
| MI | 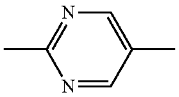 |
| N | 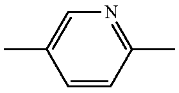 |

TABLE A-continued
| Ring elements | |
|---|---|
| NI | 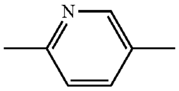 |
| Np | 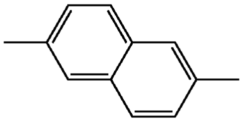 |
| N3f | 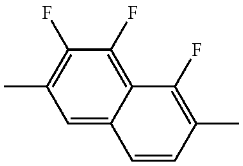 |
| N3fl | 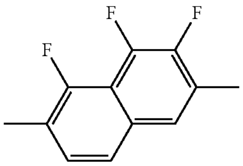 |
| tH | 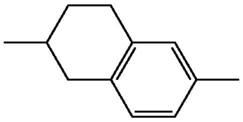 |
| tHI | 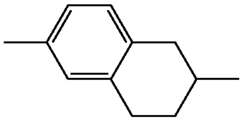 |
| tH2f | 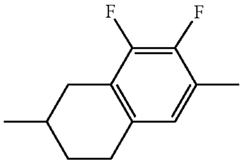 |
| tH2fl | 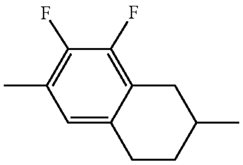 |
| dH | 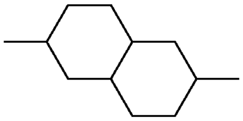 |
| K | 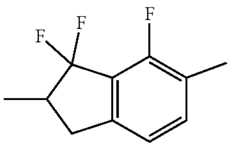 |
TABLE A-continued
| Ring elements | |
|---|---|
| KI | 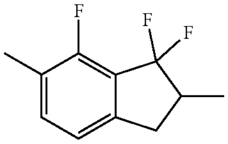 |
| L | 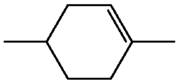 |
| LI | 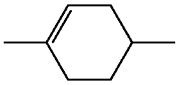 |
| F | 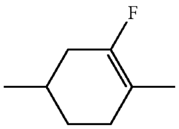 |
| FI | 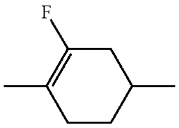 |
| P | 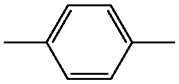 |
| P(n,m) | 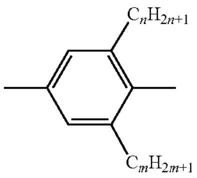 |
| P(o) | 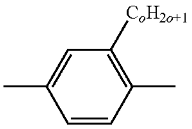 |
| PI(o) | 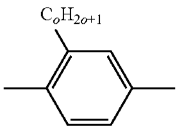 |
| P(i3) | 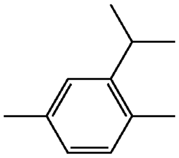 |
| PI(ic3) | 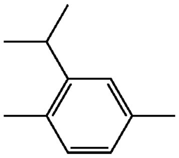 |

TABLE A-continued
| Ring elements | |
|---|---|
| P(t4) | 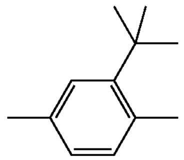 |
| PI(t4) | 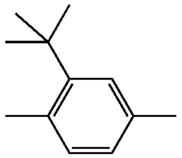 |
| P(c3) | 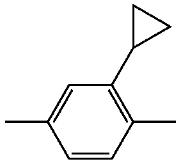 |
| PI(c3) | 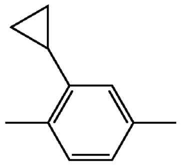 |
| P(c4) | 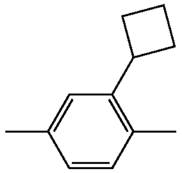 |
| PI(c4) | 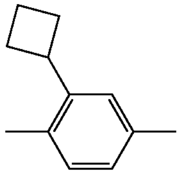 |
| P(c5) | 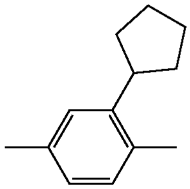 |
| PI(c5) | 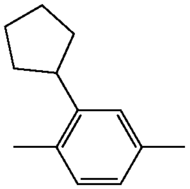 |
TABLE A-continued
| Ring elements | |
|---|---|
| P(e5) | 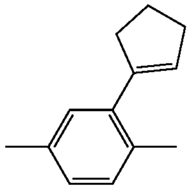 |
| PI(e5) | 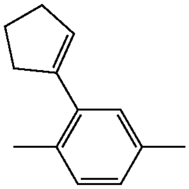 |
| P(c6) | 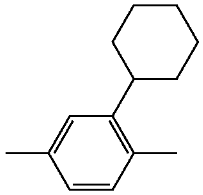 |
| PI(c6) | 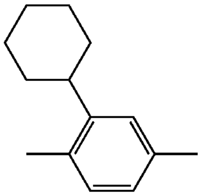 |
| P(e6) | 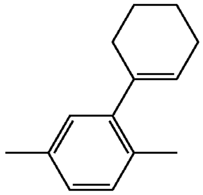 |
| PI(e6) | 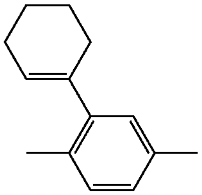 |
| GI(o) | 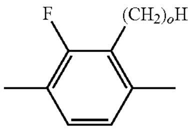 in which o = 1, 2, 3, 4, 5 or 6 |
| G(o) | 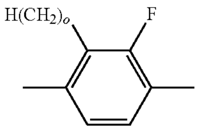 in which o = 1, 2, 3, 4, 5 or 6 |

TABLE A-continued
| Ring elements | |
|---|---|
| GI(i3) | 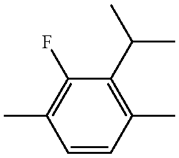 |
| G(i3) | 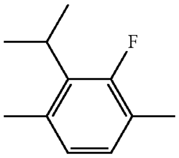 |
| GI(t4) | 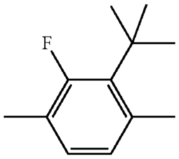 |
| G(t4) | 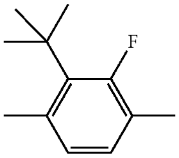 |
| GI(c3) | 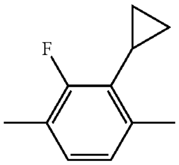 |
| G(c3) | 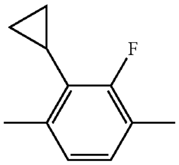 |
| GI(c4) | 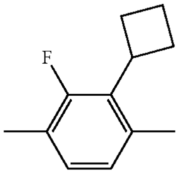 |
| G(c4) | 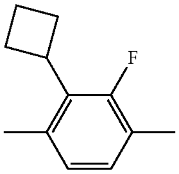 |
| GI(c5) | 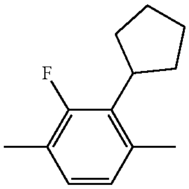 |
TABLE A-continued
| Ring elements | |
|---|---|
| G(c5) | 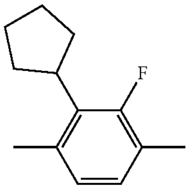 |
| GI(e5) | 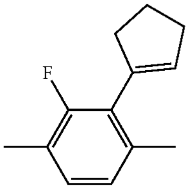 |
| G(e5) | 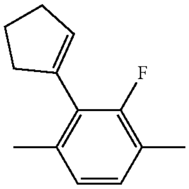 |
| GI(c6) | 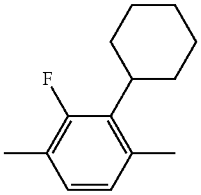 |
| G(c6) | 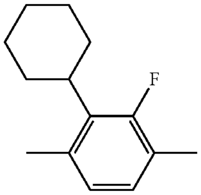 |
| GI(e6) | 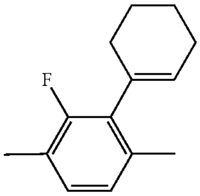 |
| G(e6) | 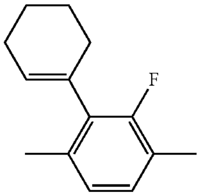 |

TABLE A-continued

| Ring elements | |
|---|---|
| Np(1,4) | 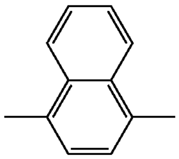 |
| Th | 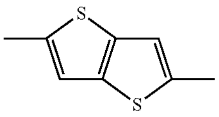 |

TABLE B

| Linking groups | | | |
|---|---|---|---|
| E | $-CH_2CH_2-$ | Z | -CO-O- |
| V | -CH=CH- | ZI | -O-CO- |
| X | -CF=CH- | O | $-CH_2-O-$ |
| XI | -CH=CF- | OI | -O-CH2- |
| B | -CF=CF- | Q | $-CF_2-O-$ |
| T | -C≡C- | QI | $-O-CF_2-$ |
| W | $-CF_2CF_2-$ | | |

TABLE B

End groups

| Left-hand side | | Right-hand side: Used alone | |
|---|---|---|---|
| —n— | $C_nH_{2n+1}$— | —n | —$C_nH_{2n+1}$ |
| —nO— | $C_nH_{2n+1}$—O— | —On | —O—$C_nH_{2n+1}$ |
| —V— | $CH_2$=CH— | —V | —CH=$CH_2$ |
| —nV— | $C_nH_{2n+1}$—CH=CH— | —nV | —$C_nH_{2n}$—CH=$CH_2$ |
| —Vn— | $CH_2$=CH—$C_nH_{2n+1}$— | —Vn | —CH=CH—$C_nH_{2n+1}$ |
| —nVm— | $C_nH_{2n+1}$—CH=CH—$C_mH_{2m}$— | —nVm | —$C_nH_{2n}$—CH=CH—$C_mH_{2m+1}$ |
| —N— | N≡C— | —N | —C≡N |
| —S— | S=C=N— | —S | —N=C=S |
| —F— | F— | —F | —F |
| —CL— | Cl— | —CL | —Cl |
| —M— | $CFH_2$— | —M | —$CFH_2$ |
| —D— | $CF_2H$— | —D | —$CF_2H$ |
| —T— | $CF_3$— | —T | —$CF_3$ |
| —MO— | $CFH_2O$— | —OM | —$OCFH_2$ |
| —DO— | $CF_2HO$— | —OD | —$OCF_2H$ |
| —TO— | $CF_3O$— | —OT | —$OCF_3$ |
| —FXO— | $CF_2$=CH—O— | —OXF | —O—CH=$CF_2$ |
| —A— | H—C≡C— | —A | —C≡C—H |
| —nA— | $C_nH_{2n+1}$—C≡C— | —An | —C≡C—$C_nH_{2n+1}$ |
| —NA— | N≡C—C≡C— | —AN | —C≡C—C≡N |
| —(cn)— | 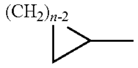 | —(cn) | 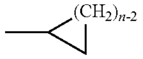 |
| —(cn)m— | 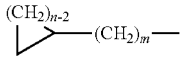 | —m(cn) | 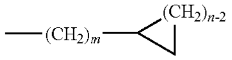 |

Used in Combination with Others

| | | | |
|---|---|---|---|
| -...A...- | -C≡C- | -...A... | -C≡C- |
| -...V...- | -CH=CH- | -...V... | -CH=CH- |
| -...Z...- | -CO-O- | -...Z... | -CO-O- |
| -...ZI...- | -O-CO- | -...ZI... | -O-CO- |
| -...K...- | -CO- | -...K... | -CO- |
| -...W...- | -CF=CF- | -...W... | -CF=CF- |

in which n and m each denote integers, and the three dots " . . . " are placeholders for other abbreviations from this table.

Branched lateral groups are numbered starting from the position next to the ring (1) where the longest chain is selected, the smaller number indicating the length of the branch and the superscript number in brackets indicates the position of the branch, for example:

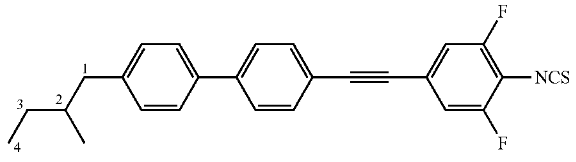

PPTU-4(1[2])-S

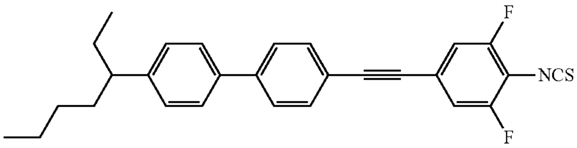

PPTU-5(2[1])-S

The following table shows illustrative structures together with their respective abbreviations. These are shown in order to illustrate the meaning of the rules for the abbreviations. They furthermore represent compounds which are preferably used.

TABLE C

| Illustrative structures |
|---|
| The following illustrative structures are examples as well as compounds, which are preferably additionally used in the media: |
| 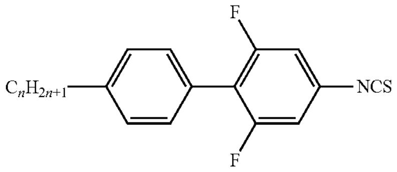 |
| PUI-n-S |
| 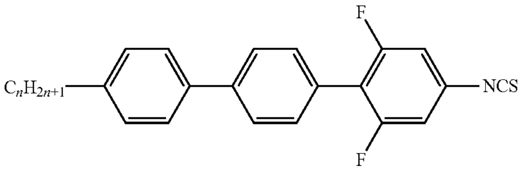 |
| PPUI-n-S |
| 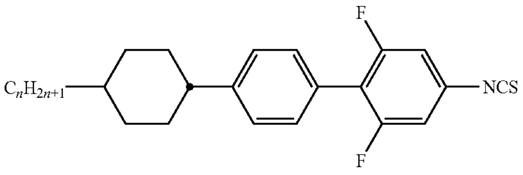 |
| CPUI-n-S |
| 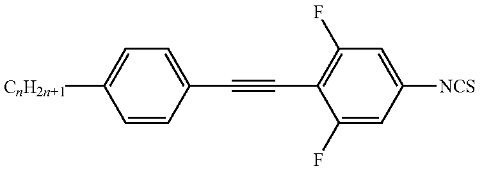 |
| PTUI-n-S |

TABLE C-continued
| Illustrative structures |
| --- |
| The following illustrative structures are examples as well as compounds, which are preferably additionally used in the media: |
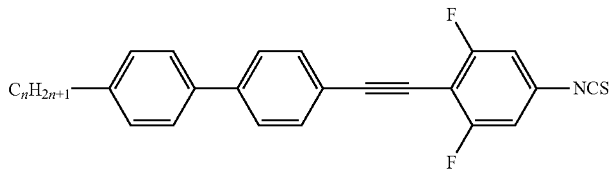
PPTUI-n-S
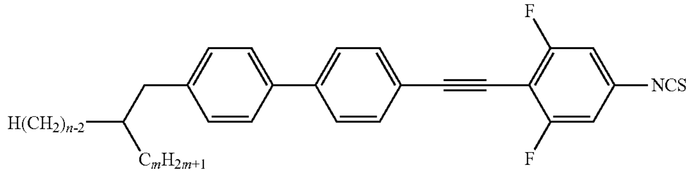
PPTUI-n(m[2])-S
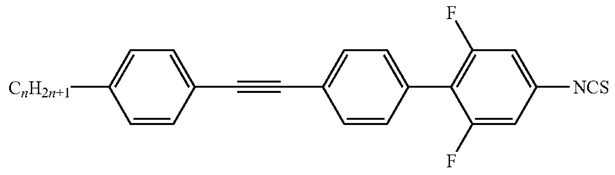
PTPUI-n-S
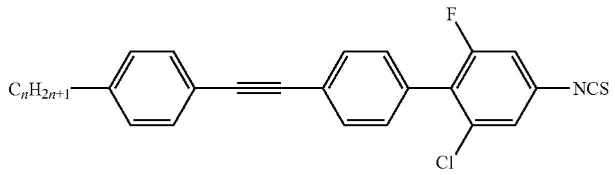
PTPG(Cl)I-n-S
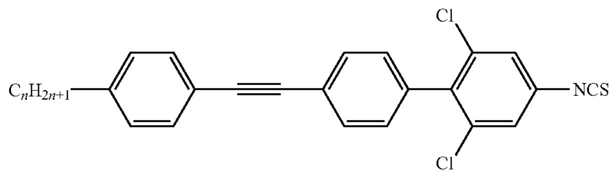
PTPP(Cl,Cl)I-n-S
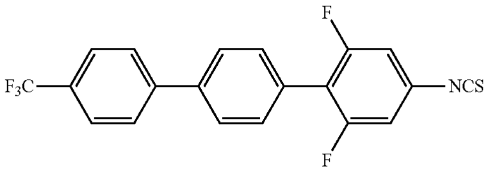
PPUI-T-S TABLE C-continued
| Illustrative structures |
| --- |
| The following illustrative structures are examples as well as compounds, which are preferably additionally used in the media: |
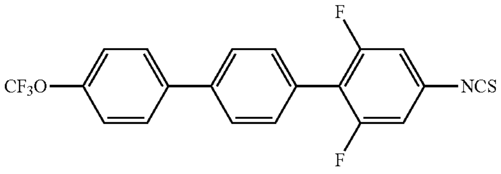
PPUI-TO-S
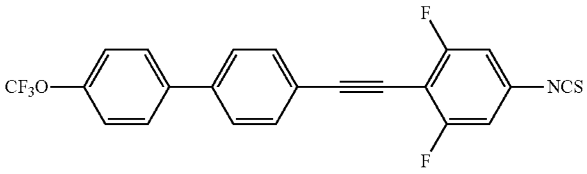
PPTUI-TO-S
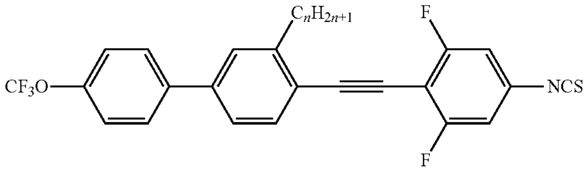
PP(n)TUI-TO-S
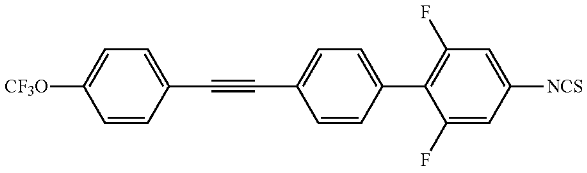
PTPUI-TO-S
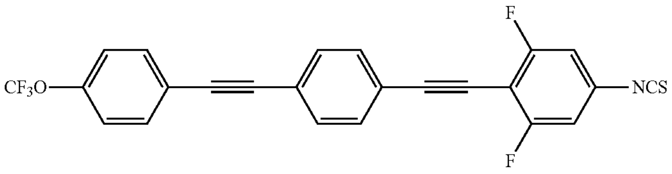
PTPTUI-TO-S
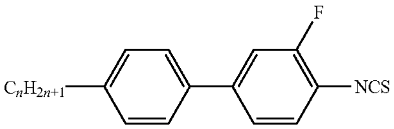
PG-n-S
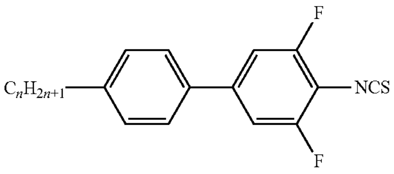
PU-n-S TABLE C-continued
| Illustrative structures |
| --- |
| The following illustrative structures are examples as well as compounds, which are preferably additionally used in the media: |
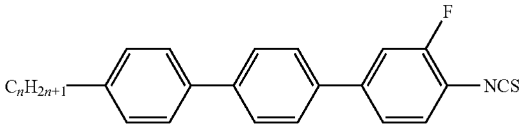
PPG-n-S
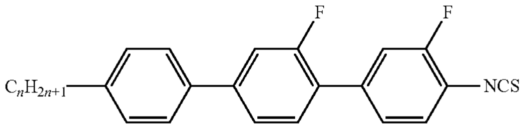
PGG-n-S
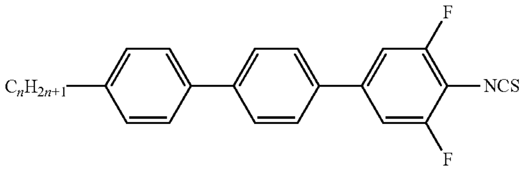
PPU-n-S
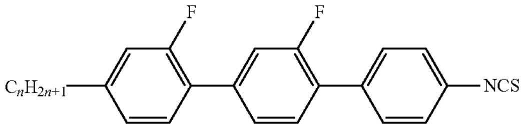
GGP-n-S
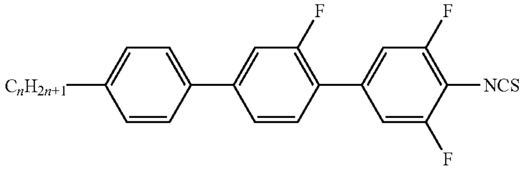
PGU-n-S
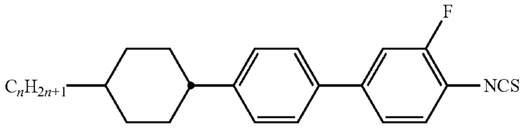
CPG-n-S
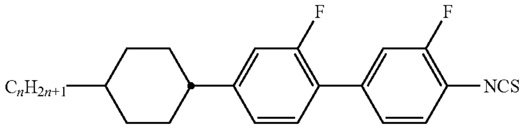
CGG-n-S TABLE C-continued
| Illustrative structures |
| --- |
| The following illustrative structures are examples as well as compounds, which are preferably additionally used in the media: |
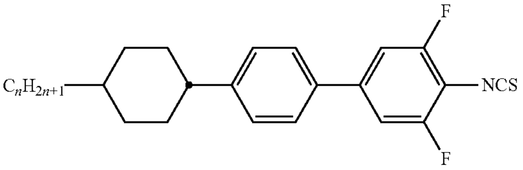
CPU-n-S
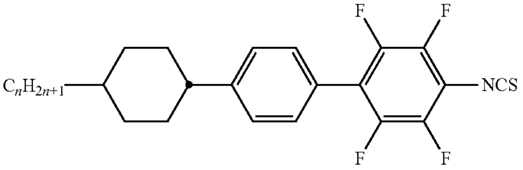
CPU(F,F)-n-S
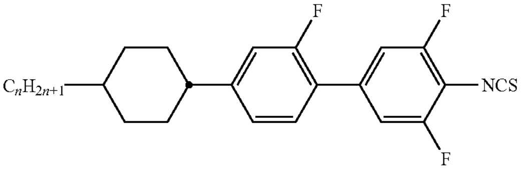
CGU-n-S
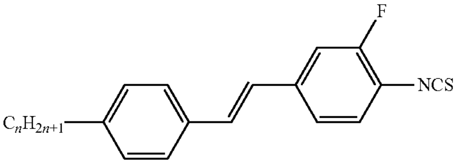
PVG-n-S
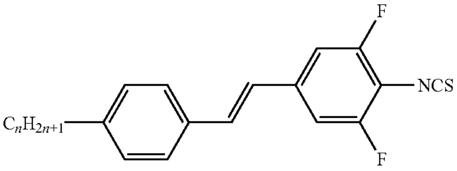
PVU-n-S
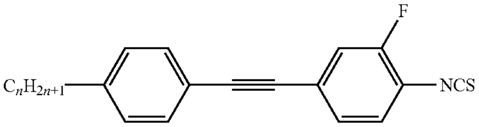
PTG-n-S
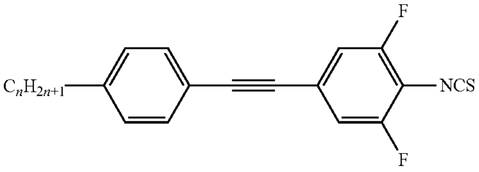
PTU-n-S TABLE C-continued
| Illustrative structures |
| --- |
| The following illustrative structures are examples as well as compounds, which are preferably additionally used in the media: |
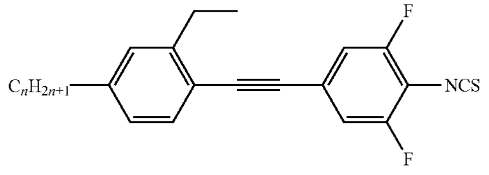
P(2)TU-n-S
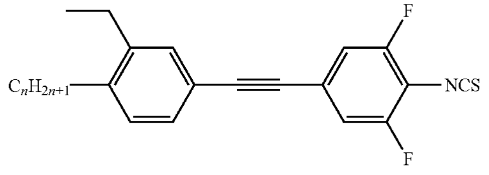
PI(2)TU-n-S
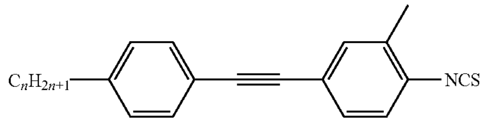
PTP(1)-n-S
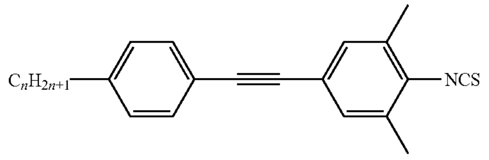
PTP(1,1)-n-S
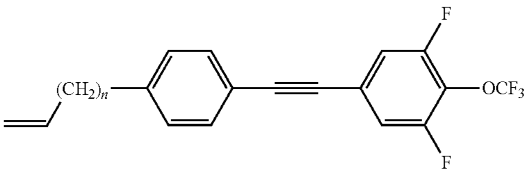
PTU-Vn-OT
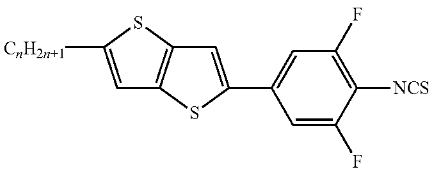
ThU-n-S
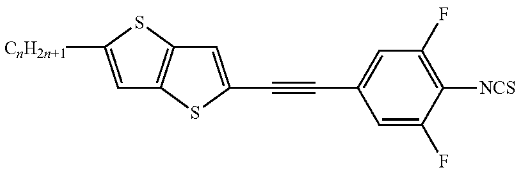
ThTU-n-S TABLE C-continued
| Illustrative structures |
| --- |
| The following illustrative structures are examples as well as compounds, which are preferably additionally used in the media: |
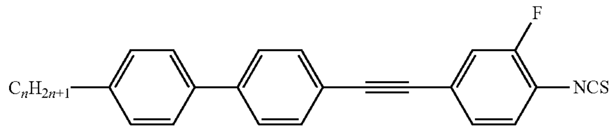
PPTG-n-S
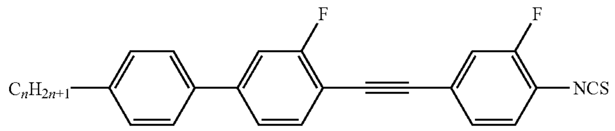
PGTG-n-S
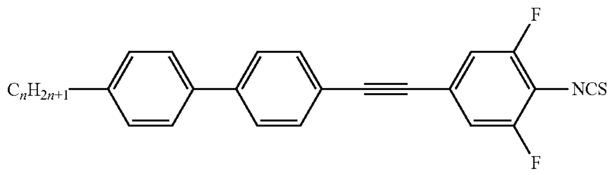
PPTU-n-S
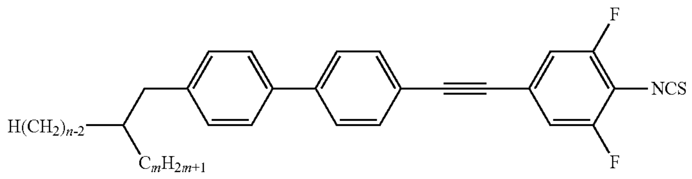
PPTU-n(m[2])-S
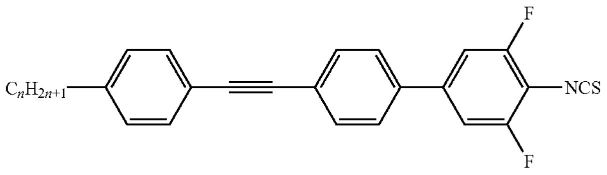
PTPU-n-S
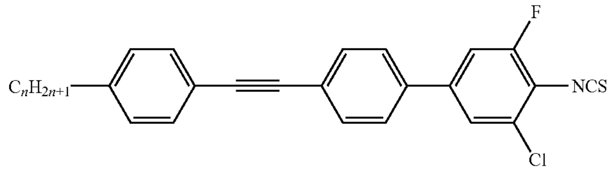
PTPG(Cl)-n-S
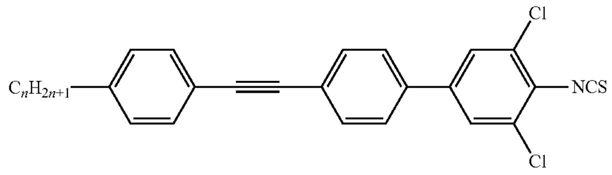
PTPP(Cl,Cl)-n-S TABLE C-continued
| Illustrative structures |
|---|
| The following illustrative structures are examples as well as compounds, which are preferably additionally used in the media: |
| 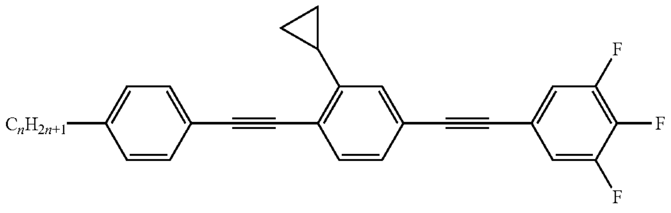 |
| PTPI(c3)TU-n-F |
| 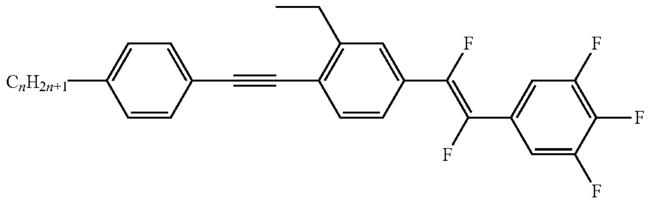 |
| PTPI(2)WU-n-F |
| 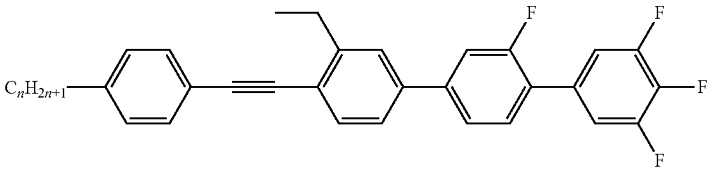 |
| PTPI(2)GU-n-F |
| 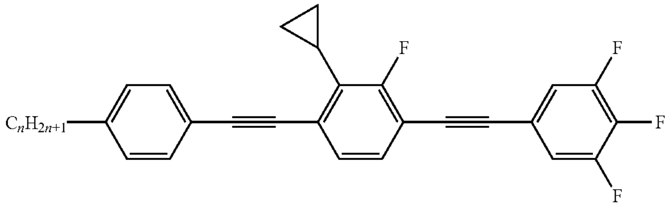 |
| PTG(c3)TU-n-F |
| 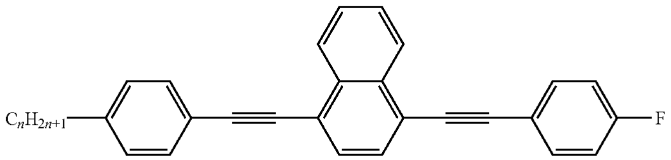 |
| PTN(1,4)TP-n-F |
| 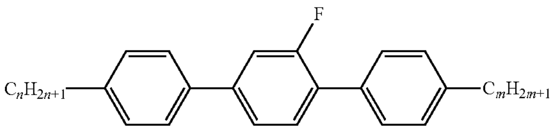 |
| PGP-n-m |

TABLE C-continued
| Illustrative structures |
|---|
| The following illustrative structures are examples as well as compounds, which are preferably additionally used in the media: |
| 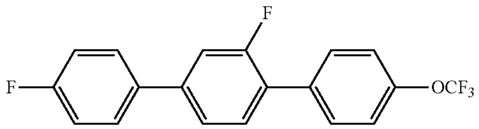 [SMILES: Fc1ccc(-c2ccc(-c3ccc(OC(F)(F)F)cc3)c(F)c2)cc1] |
| PGP-F-OT |
| 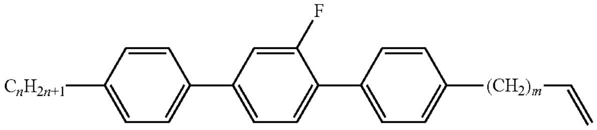 |
| PGP-n-mV |
| 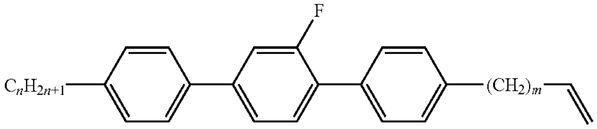 |
| PGP-n-mVI |
| 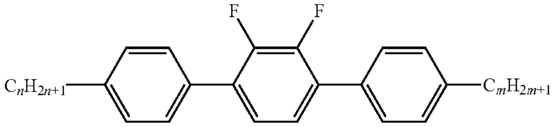 |
| PYP-n-m |
| 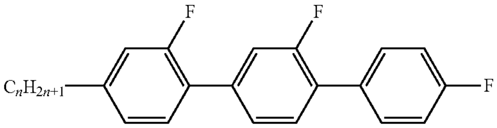 |
| GGP-n-F |
| 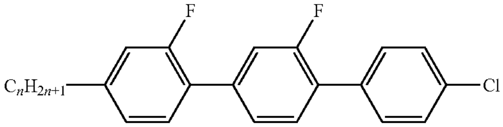 |
| GGP-n-CL |
| 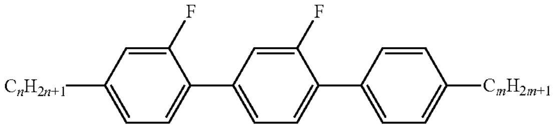 |
| GGP-n-m |
| 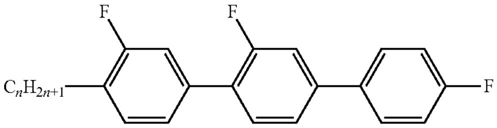 |
| PGIGI-n-F |

TABLE C-continued
| Illustrative structures |
|---|
| The following illustrative structures are examples as well as compounds, which are preferably additionally used in the media: |
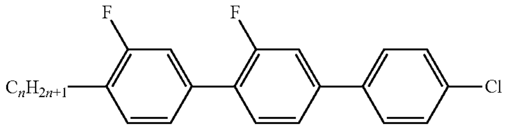
PGIGI-n-CL
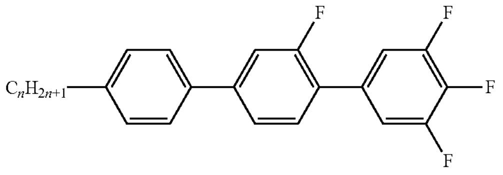
PGU-n-F
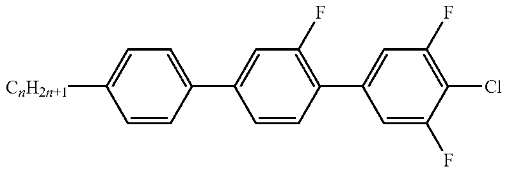
PGU-n-CL
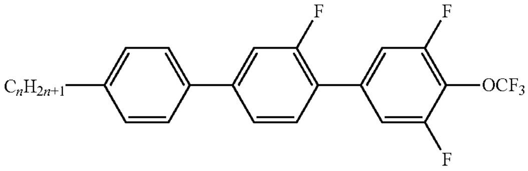
PGU-n-OT
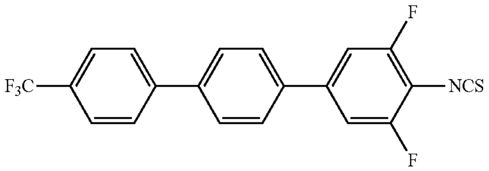
PPU-T-S
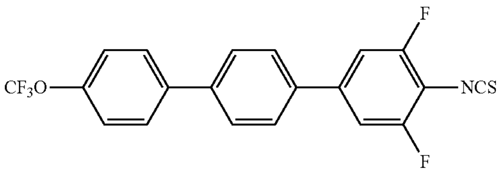
PPU-TO-S
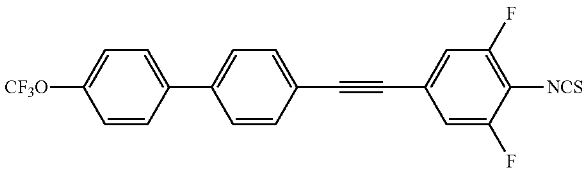
PPTU-TO-S TABLE C-continued
| Illustrative structures |
|---|
| The following illustrative structures are examples as well as compounds, which are preferably additionally used in the media: |
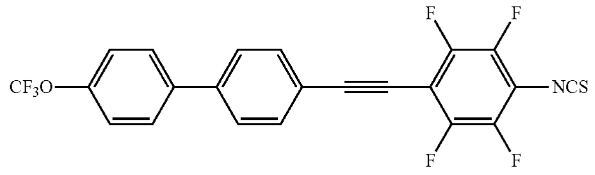
PPTU(F,F)-TO-S
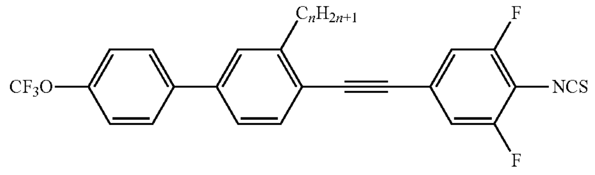
PP(n)TU-TO-S
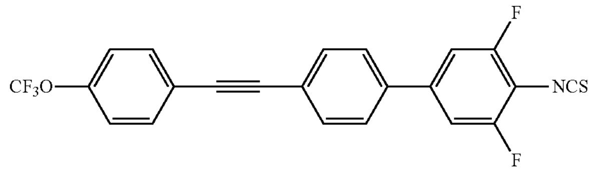
PTPU-TO-S
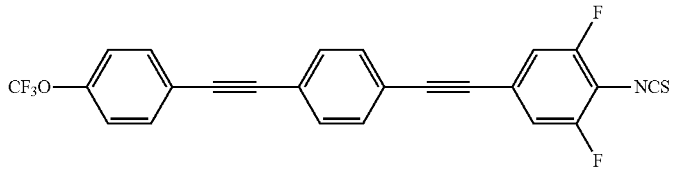
PTPTU-TO-S
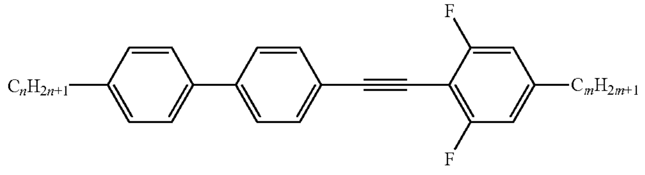
PPTUI-n-m
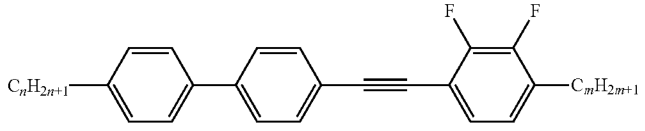
PPTY-n-m
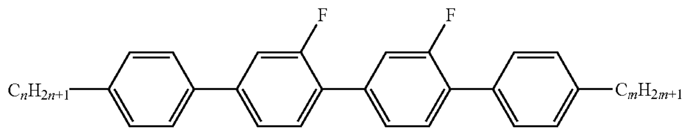
PGGP-n-m TABLE C-continued
| Illustrative structures |
| --- |
| The following illustrative structures are examples as well as compounds, which are preferably additionally used in the media: |
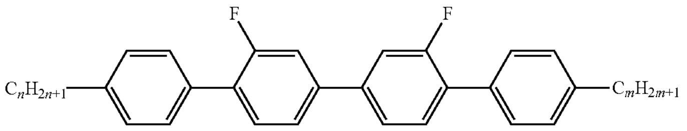
PGIGP-n-m
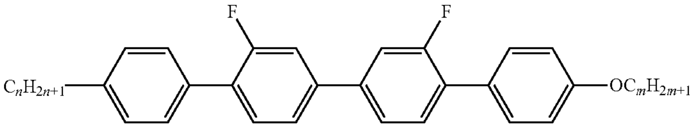
PGIGP-n-Om
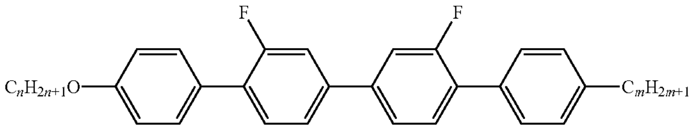
PGIGP-nO-m
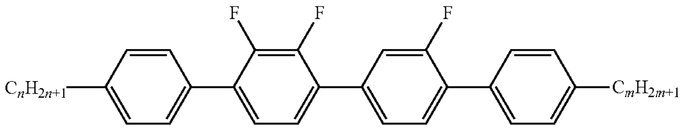
PYGP-n-m
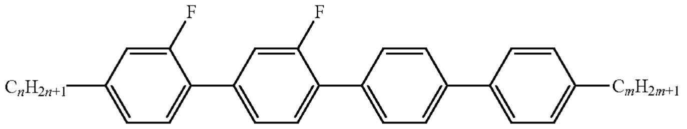
GGPP-n-m
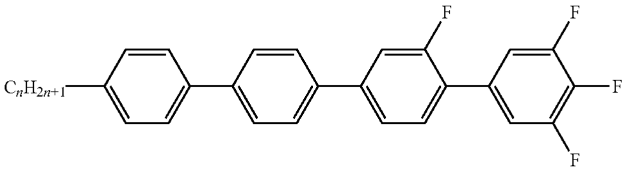
PPGU-n-F
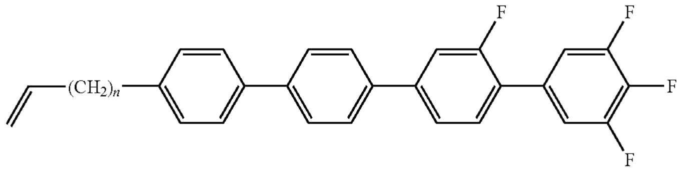
PPGU-Vn-F
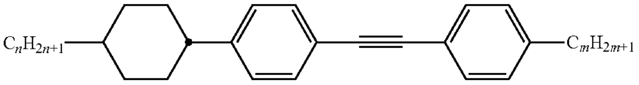
CPTP-n-m TABLE C-continued
| Illustrative structures |
|---|
| The following illustrative structures are examples as well as compounds, which are preferably additionally used in the media: |
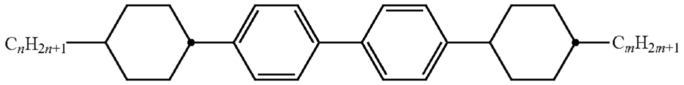
CPPC-n-m
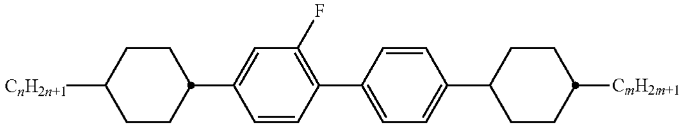
CGPC-n-m
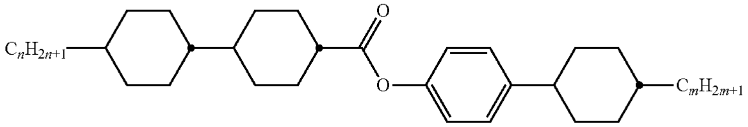
CCZPC-n-m
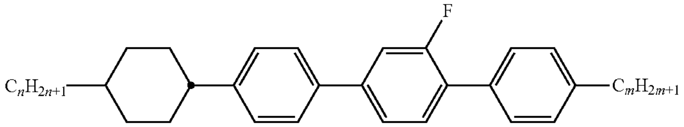
CPGP-n-m
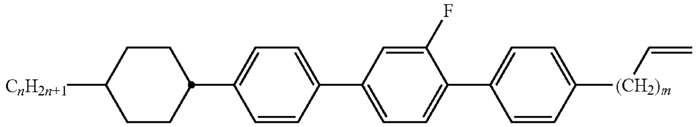
CPGP-n-mV
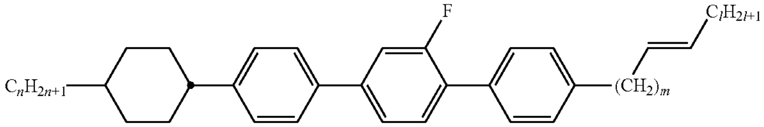
CPGP-n-mVI
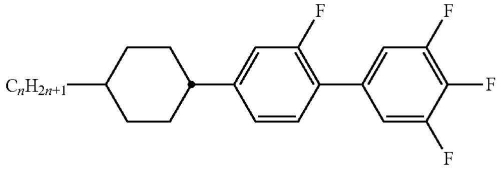
CGU-n-F
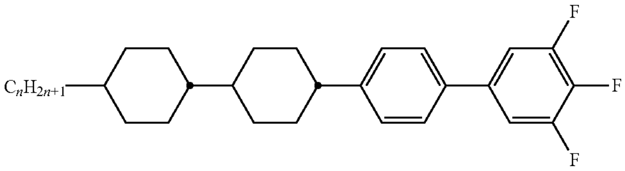
CCPU-n-F TABLE C-continued
| Illustrative structures |
| --- |
| The following illustrative structures are examples as well as compounds, which are preferably additionally used in the media: |
| 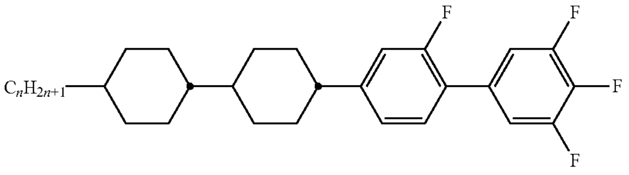 |
| CCGU-n-F |
| 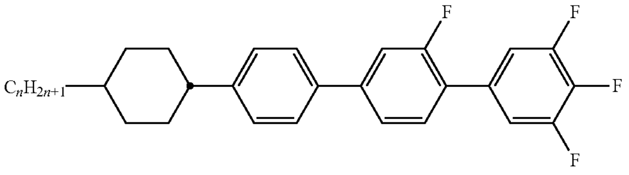 |
| CPGU-n-F |
| 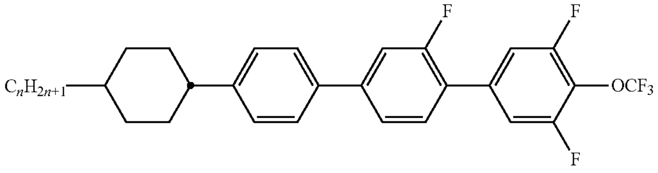 |
| CPGU-n-OT |
| 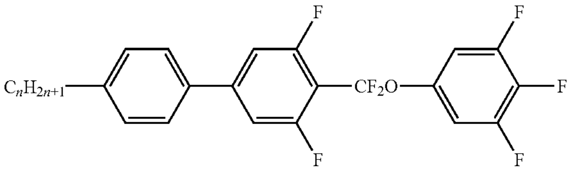 |
| PUQU-n-F |
| 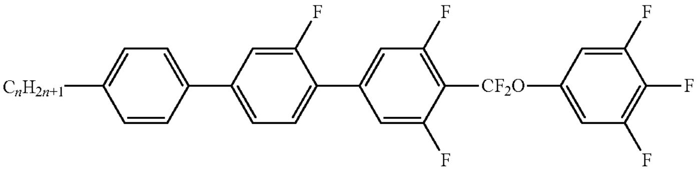 |
| PGUQU-n-F |
| 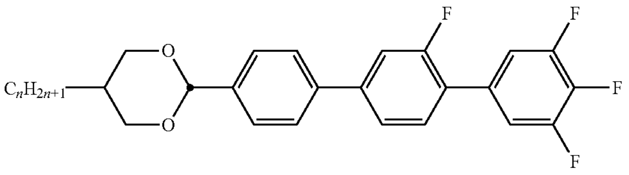 |
| DPGU-n-F |
| 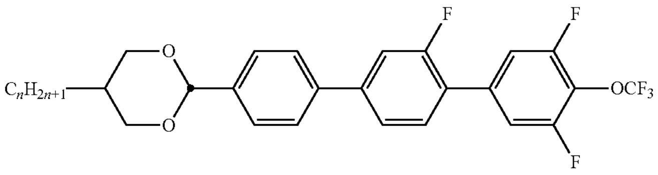 |
| DPGU-n-OT |

TABLE C-continued

| Illustrative structures |
| --- |
| The following illustrative structures are examples as well as compounds, which are preferably additionally used in the media: |
| 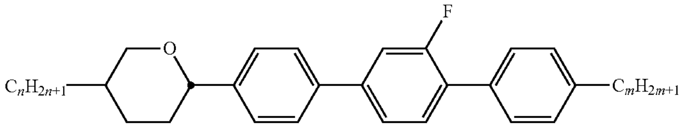<br>APGP-n-m |

in which m and n, identically or differently, are 1, 2, 3, 4, 5, 6 or 7.

Preferably, the medium according to the invention comprises one or more compounds selected from the compounds of Table C.

The following table, Table D, shows illustrative compounds which can be used as alternative stabilisers in the mesogenic media in accordance with the present invention.

The total concentration of these and similar compounds in the media is preferably 5% or less.

TABLE D

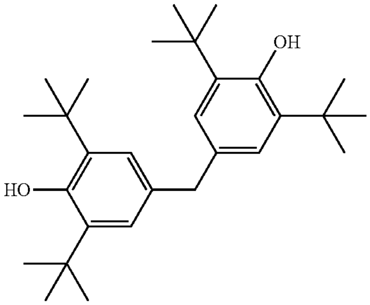 [SMILES: CC(C)(C)c1cc(Cc2cc(C(C)(C)C)c(O)c(C(C)(C)C)c2)cc(C(C)(C)C)c1O]

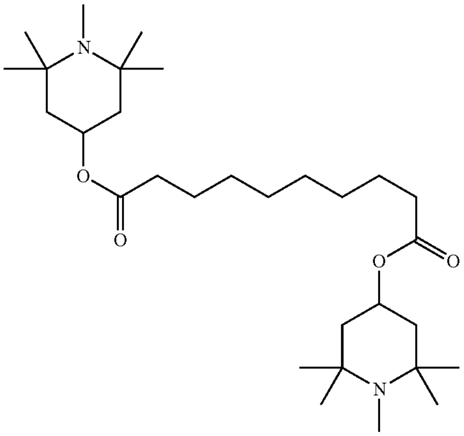

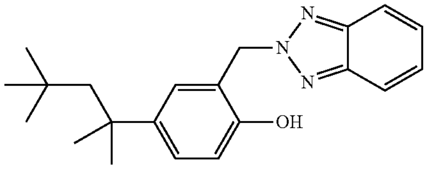 [SMILES: CC(C)(C)CC(C)(C)c1ccc(O)c(Cn2nc3ccccc3n2)c1]

TABLE D-continued
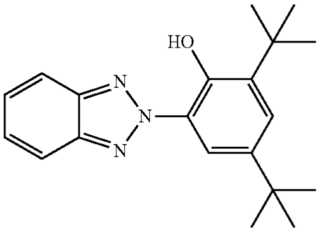 [SMILES: CC(C)(C)c1cc(-n2nc3ccccc3n2)c(O)c(C(C)(C)C)c1]
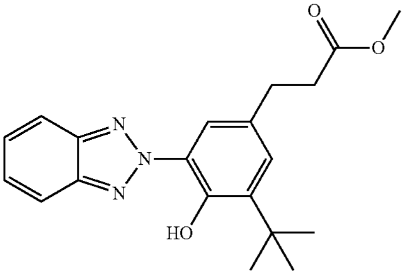 [SMILES: COC(=O)CCc1cc(-n2nc3ccccc3n2)c(O)c(C(C)(C)C)c1]
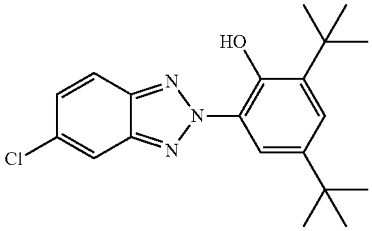 [SMILES: CC(C)(C)c1cc(-n2nc3ccc(Cl)cc3n2)c(O)c(C(C)(C)C)c1]
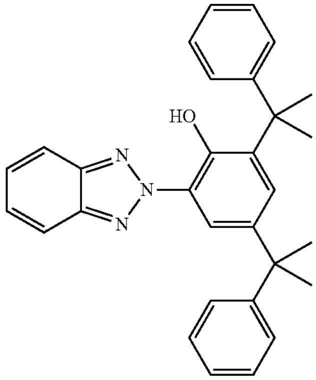 [SMILES: CC(C)(c1ccccc1)c1cc(-n2nc3ccccc3n2)c(O)c(C(C)(C)c2ccccc2)c1]
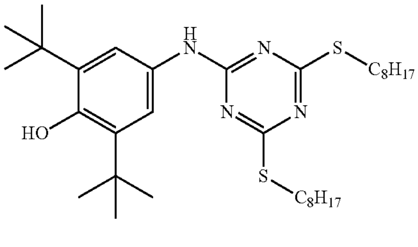

TABLE D-continued
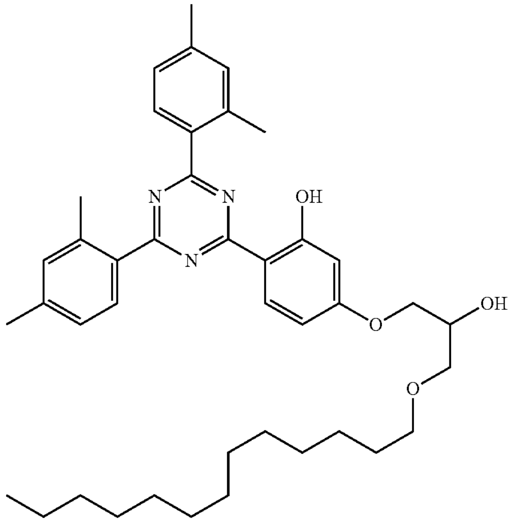 [SMILES: CCCCCCCCCCCCCOCC(O)COc1ccc(-c2nc(-c3ccc(C)cc3C)nc(-c3ccc(C)cc3C)n2)c(O)c1]
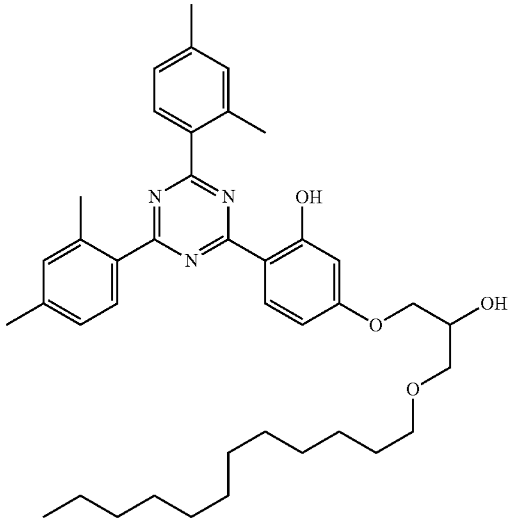 [SMILES: CCCCCCCCCCCCOCC(O)COc1ccc(-c2nc(-c3ccc(C)cc3C)nc(-c3ccc(C)cc3C)n2)c(O)c1]
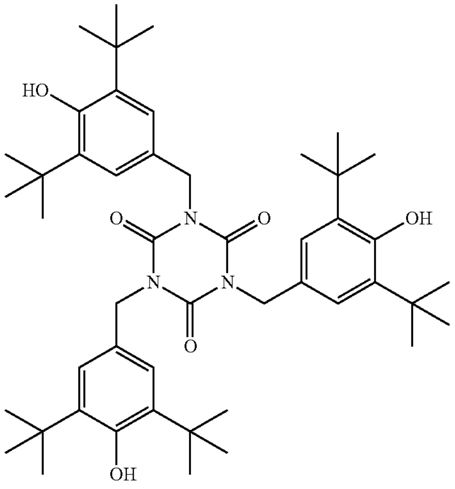 [SMILES: CC(C)(C)c1cc(Cn2c(=O)n(Cc3cc(C(C)(C)C)c(O)c(C(C)(C)C)c3)c(=O)n(Cc3cc(C(C)(C)C)c(O)c(C(C)(C)C)c3)c2=O)cc(C(C)(C)C)c1O]

TABLE D-continued
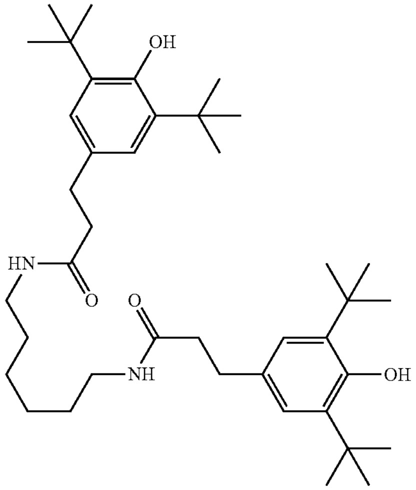 [SMILES: CC(C)(C)c1cc(CCC(=O)NCCCCCCNC(=O)CCc2cc(C(C)(C)C)c(O)c(C(C)(C)C)c2)cc(C(C)(C)C)c1O]
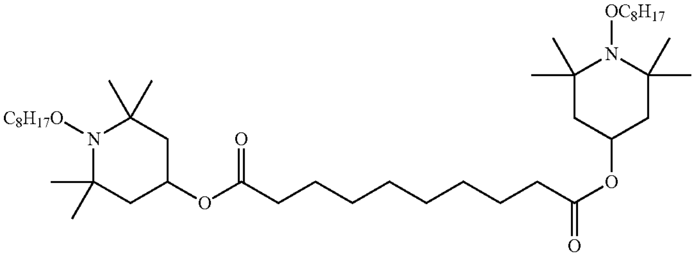
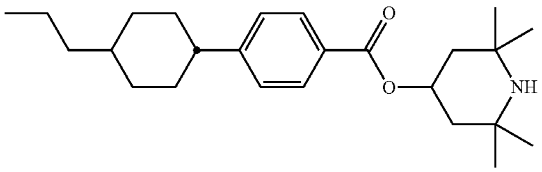
In a preferred embodiment of the present invention, the mesogenic media comprise one or more compounds selected from the group of the compounds from Table D. The following table, Table E, shows illustrative compounds which can preferably be used as chiral dopants in the mesogenic media in accordance with the present invention.
TABLE E
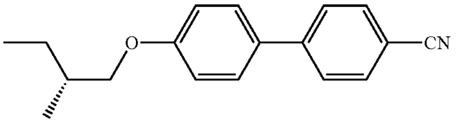 [SMILES: CC[C@@H](C)COc1ccc(-c2ccc(C#N)cc2)cc1]
C 15
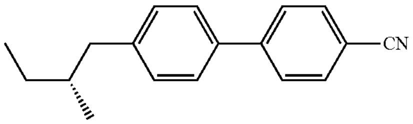 [SMILES: CC[C@@H](C)Cc1ccc(-c2ccc(C#N)cc2)cc1]
CB 15
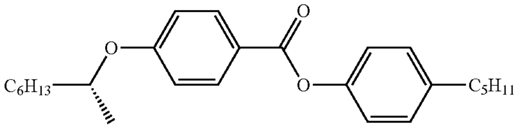
CM 21

TABLE E-continued
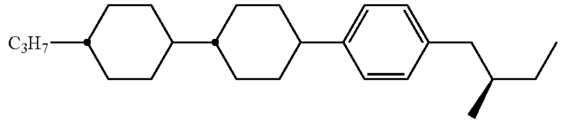
CM 44
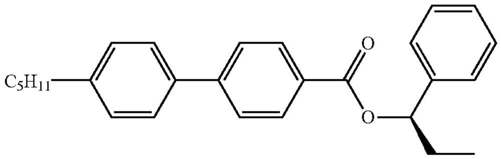
CM 45
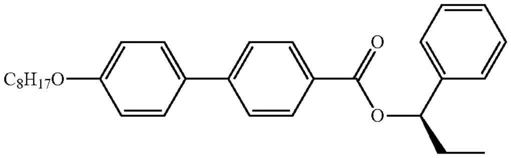
CM 47
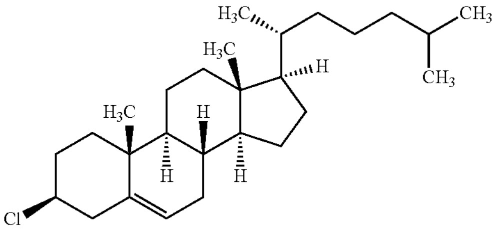
CC
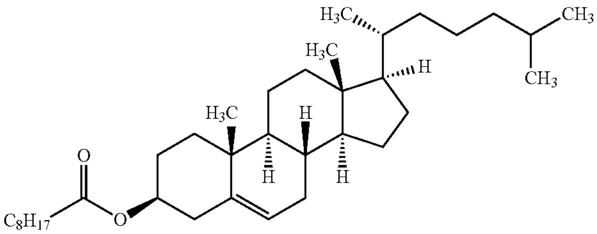
CN
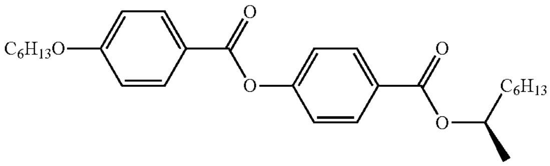
R/S-811

TABLE E-continued

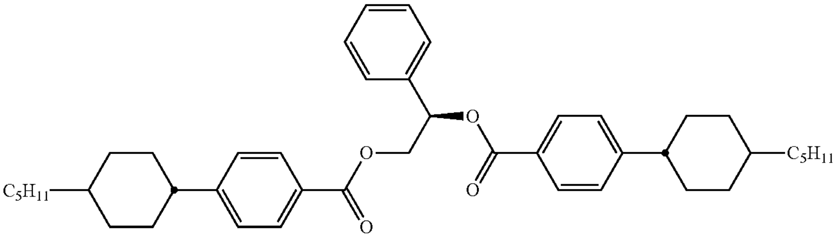

R/S-1011

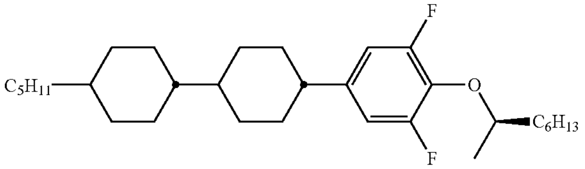

R/S-2011

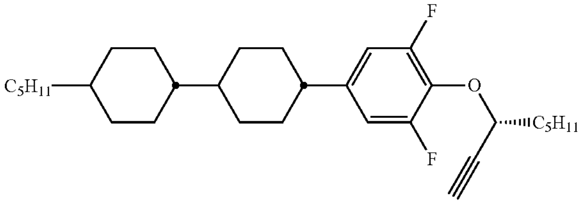

R/S-3011

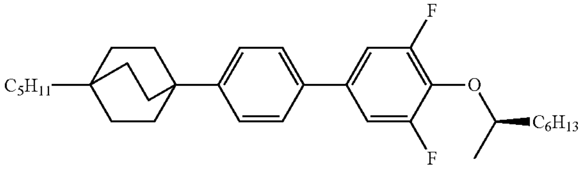

R/S-4011

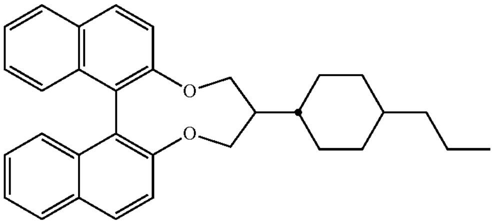

R/S-5011

In a preferred embodiment of the present invention, the mesogenic media comprise one or more compounds selected from the group of the compounds of Table E.

The mesogenic media in accordance with the present application preferably comprise two or more, preferably four or more, compounds selected from the group consisting of the compounds from the above tables.

Unless indicated otherwise, parts or percent data denote parts by weight or percent by weight.

Above and below:

$V_o$ denotes threshold voltage, capacitive [V] at 20° C., $n_e$ denotes extraordinary refractive index at 20° C. and 589 nm, $n_o$ denotes ordinary refractive index at 20° C. and 589 nm, $\Delta n$ denotes optical anisotropy at 20° C. and 589 nm, $\varepsilon_\perp$ denotes dielectric permittivity perpendicular to the director at 20° C. and 1 kHz, $\varepsilon_\parallel$ denotes dielectric permittivity parallel to the director at 20° C. and 1 kHz, $\Delta\varepsilon$ denotes dielectric anisotropy at 20° C. and 1 kHz, cl.p., T(N,I) denotes clearing point [° C.], $\gamma_1$ denotes rotational viscosity measured at 20° C. [mPa·s], $K_1$ denotes elastic constant, "splay" deformation at 20° C. [pN], $K_2$ denotes elastic constant, "twist" deformation at 20° C. [pN], $K_3$ denotes elastic constant, "bend" deformation at 20° C. [pN], $K_{avg.}$ denotes average elastic constant defined as $K_{avg.}=\frac{1}{3}(1.5\cdot K_1+K_3)$ LTS denotes low-temperature stability (nematic phase), determined in test cells or in the bulk, as specified.

Unless explicitly noted otherwise, all values indicated in the present application for temperatures, such as, for example, the melting point T(C,N), the transition from the smectic (S) to the nematic (N) phase T(S,N) and the clearing point T(N,I) or cl.p., are indicated in degrees Celsius (° C.). M.p. denotes melting point. Furthermore, Tg=glass state, C=crystalline state, N=nematic phase, S=smectic phase and I=isotropic phase. The numbers between these symbols represent the transition temperatures.

The term “threshold voltage” for the present invention relates to the capacitive threshold ($V_0$), also called the Freedericksz threshold, unless explicitly indicated otherwise. In the examples, as is generally usual, the optical threshold can also be indicated for 10% relative contrast ($V_{10}$).

The display used for measurement of the capacitive threshold voltage consists of two plane-parallel glass outer plates at a separation of 20 μm, which each have on the insides an electrode layer and an unrubbed polyimide alignment layer on top, which cause a homeotropic edge alignment of the liquid-crystal molecules.

The so-called “HTP” denotes the helical twisting power of an optically active or chiral substance in an LC medium (in μm). Unless indicated otherwise, the HTP is measured in the commercially available nematic LC host mixture MLD-6260 (Merck KGaA) at a temperature of 20° C.

The Clearing point is measured using the Mettler Thermosystem FP900. The optical anisotropy (Δn) is measured using an Abbe Refractometer H005 (Natrium-spectral lamp Na10 at 589 nm, 20° C.). The dielectric anisotropy (Δε) is measured using an LCR-Meter E4980A/Agilent (G005) at 20° C. (E-parallel-cells with JALS 2096-R[1]). The turn on voltage ($V_0$) is measured using an LCR-Meter E4980A/Agilent (G005) at 20° C. (ε-parallel-cells with JALS 2096-R1). The rotational viscosity (71) is measured using a TOYO LCM-2 (0002) at 20° C. (gamma 1 negative cells with JALS-2096-R 1). The elastic constant ($K_1$, splay) is measured using an LCR-Meter E4980A/Agilent (G005) at 20° C. (E parallel-cells with JALS 2096-R1). $K_3$: The elastic constant ($K_3$, bend) is measured using an LCR-Meter E4980A/Agilent (G005) at 20° C. (E-parallel-cells with JALS 2096-R1).

Unless explicitly noted otherwise, all concentrations in the present application are indicated in percent by weight and relate to the corresponding mixture as a whole, comprising all solid or liquid-crystalline components, without solvents. All physical properties are determined in accordance with “Merck Liquid Crystals, Physical Properties of Liquid Crystals”, Status November 1997, Merck KGaA, Germany, and apply for a temperature of 20° C., unless explicitly indicated otherwise.

EXAMPLES

The following examples illustrate the present invention without limiting it in any way. It is clear to the person skilled in the art from the physical properties what properties can be achieved and in what ranges they can be modified. In particular, the combination of the various properties which can preferably be achieved is thus well defined for the person skilled in the art.

Synthesis Examples

Abbreviations dist. distilled

DABCO 1,4-Diazabicyclo[2.2.2]octane

THE Tetrahydrofuran

MTB ether Methyl-tert-butyl ether dist. distilled

XPhos 2-Dicyclohexylphosphino-2',4',6'-triisopropylbiphenyl

XPhos Pd G2 Chloro(2-dicyclohexylphosphino-2',4',6'-triisopropyl-1,1'-biphenyl)[2-(2'-amino-1,1'-biphenyl) palladium (II)

Synthesis Example 1: 2-[4-(4-Butylcyclohexyl)phenyl]-1,3-difluoro-5-isothiocyanato-benzene

Step 1.1: 4-[4-(4-Butylcyclohexyl)phenyl]-3,5-difluoro-aniline

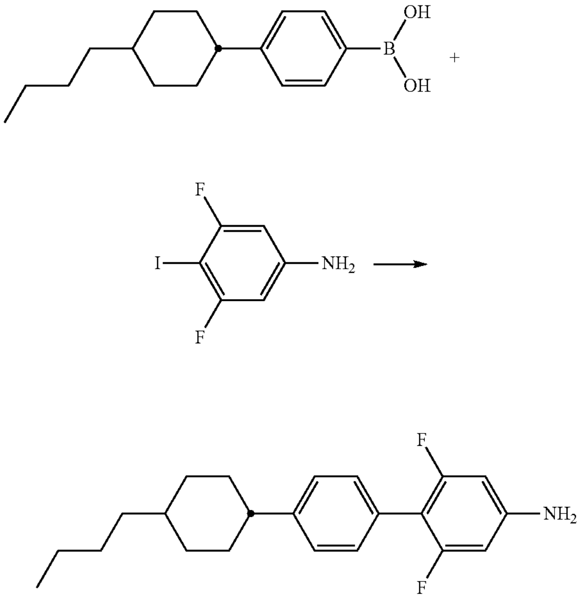

Bis(dibenzylidene-acetone)palladium(0) (20 mg, 0.04 mmol) and tris-(o-tolyl)phosphine (50 mg, 0.2 mmol) are added to a mixture of [4-(4-butylcyclohexyl)phenyl]boronic acid (CAS 516510-90-0) (4.5 g, 17 mmol) and 3,5-difluoro-4-iodo-aniline (4.3 g, 17 mmol) in acetone (50 ml) under argon atmosphere at 50° C. Aqueous sodium hydroxide (2 N) (17.0 ml, 34 mmol) is slowly added at reflux temperature, and the reaction mixture is heated at reflux temperature overnight. Then it is allowed to cool to room temperature and is quenched with dist. water and hydrochloric acid (2 N) and diluted with MTB ether. The aqueous phase is separated and extracted with MTB ether. The combined organic layers are washed with brine, dried (sodium sulfate) and concentrated in vacuo. The residue is purified by silica gel chromatography (eluent 1-chlorobutane) to give 4-[4-(4-butylcyclohexyl)phenyl]-3,5-difluoro-aniline as a yellow solid.

Step 1.2: 2-[4-(4-Butylcyclohexyl)phenyl]-1,3-difluoro-5-isothiocyanato-benzene

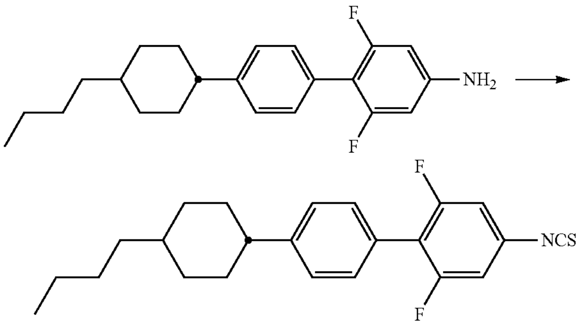

Thiophosgene (1.3 ml, 16 mmol) is slowly added to a solution of 4-[4-(4-butylcyclohexyl)phenyl]-3,5-difluoro-aniline (4.8 g, 12 mmol) and DABCO (4.0 g, 36 mmol) in dichloromethane (60 ml) at 0° C. under argon atmosphere. The reaction mixture is stirred at room temperature overnight. Then it is quenched with dist. water and brine. The aqueous phase is separated and extracted with dichloromethane. The combined organic phases are washed with brine, dried (sodium sulfate), filtered and concentrated in vacuo. The residue is purified by silica gel chromatography (eluent heptane) and crystallization (heptane) to give colorless crystals of 2-[4-(4-butylcyclohexyl)phenyl]-1,3-difluoro-5-isothiocyanato-benzene.

Phase sequence K 91 N 160 I.

$\Delta\varepsilon$=3.01

$\Delta n$=0.2455

$\gamma_1$=525 m Pas

Synthesis Example 2: 2-[4-(4-Butylphenyl)phenyl]-1,3-difluoro-5-isothiocyanato-benzene Step 2.1: 4-[4-(4-Butylphenyl)phenyl]-3,5-difluoro-aniline

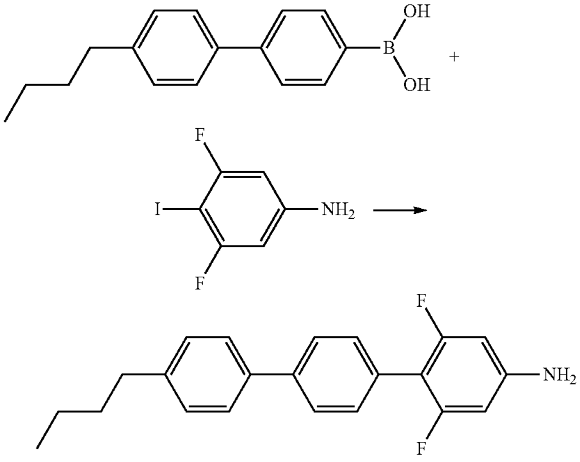

Bis(dibenzylidene-acetone)palladium(0) (20 mg, 0.04 mmol) and tris-(o-tolyl)phosphine (50 mg, 0.2 mmol) are added to a mixture of [4-(4-butylphenyl)phenyl]boronic acid (CAS 145413-17-8; 4.5 g, 17 mmol) and 3,5-difluoro-4-iodo-aniline (4.3 g, 17 mmol) in acetone (50 ml) under argon atmosphere at 50° C. Aqueous sodium hydroxide (2 N) (18.0 ml, 36 mmol) is slowly added at reflux temperature, and the reaction mixture is heated at reflux temperature overnight. Then it is allowed to cool to room temperature and quenched with dist. water and hydrochloric acid (2 N) and diluted with MTB ether. The aqueous phase is separated and extracted with MTB ether. The combined organic phases are washed with brine, dried (sodium sulfate) and concentrated in vacuo. The residue is purified by silica gel chromatography (eluent 1-chlorobutane) to give 4-[4-(4-butylphenyl)phenyl]-3,5-difluoro-aniline as a yellow solid.

Step 2.2: 2-[4-(4-Butylphenyl)phenyl]-1,3-difluoro-5-isothiocyanato-benzene

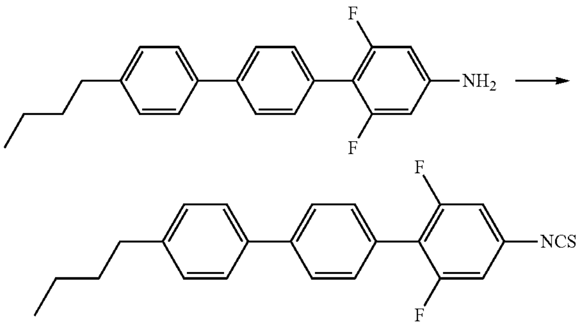

Thiophosgene (1.3 ml, 16 mmol) is slowly added to a solution of 4-[4-(4-butylphenyl)phenyl]-3,5-difluoro-aniline (4.7 g, 14 mmol) and DABCO (4.0 g, 36 mmol) in dichloromethane (60 ml) at 0° C. under argon atmosphere. The reaction mixture is stirred at room temperature overnight. Then it is quenched with dist. water and brine. The aqueous phase is separated and extracted with dichloromethane. The combined organic phases are washed with brine, dried (sodium sulfate), filtered and concentrated in vacuo. The residue is purified by silica gel chromatography (eluent heptane) and crystallization (heptane) to give colorless crystals of 2-[4-(4-butylphenyl)phenyl]-1,3-difluoro-5-isothiocyanato-benzene.

Phase sequence K 114 SmA (98) N 139 I.

$\Delta\varepsilon$=3.92

$\Delta n$=0.3414

$\gamma_1$=430 mPas

Synthesis Example 3: 2-[2-(4-Butylphenyl)ethynyl]-1,3-difluoro-5-isothiocyanato-benzene Step 3.1: 4-[2-(4-Butylphenyl)ethynyl]-3,5-difluoro-aniline

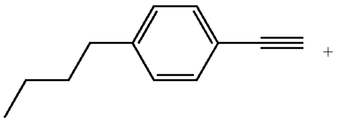

-continued

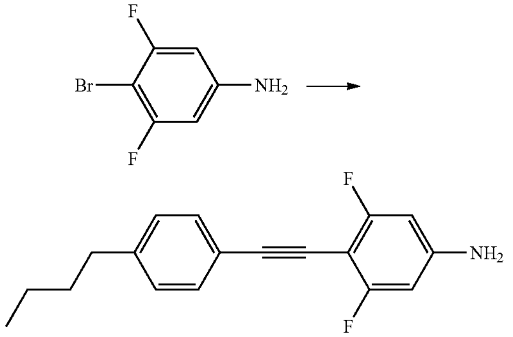

XPhos Pd G2 (40 mg, 0.05 mmol), XPhos (25 mg, 0.05 mmol) and copper(I) iodide (5 mg, 0.03 mmol) are added to a mixture of 1-butyl-4-ethynylbenzene (4.0 g, 25 mmol) and 3,5-difluoro-4-iodo-aniline (6.3 g, 25 mmol) in diisopropylamine (60 ml) and THE (60 ml) under argon atmosphere slightly below the boiling point. The reaction mixture is heated at reflux temperature overnight. Then it is allowed to cool to room temperature, and the precipitate is filtered off and washed with THF. The filtrate is concentrated in vacuo. The residue is purified by silica gel chromatography (eluent 1-chlorobutane) to give 4-[2-(4-butylphenyl)ethynyl]-3,5-difluoro-aniline (3) as a brown oil.

Step 3.2: 2-[2-(4-Butylphenyl)ethynyl]-1,3-difluoro-5-isothiocyanato-benzene

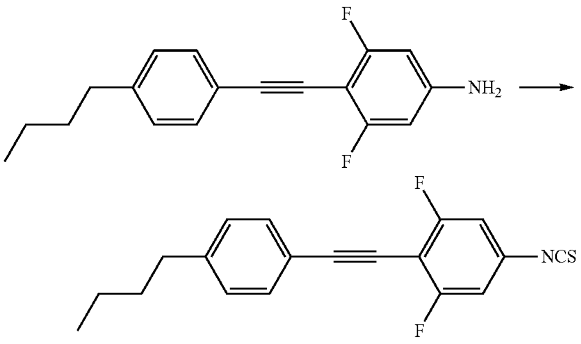

Thiophosgene (1.9 ml, 24 mmol) is slowly added to a solution of 4-[2-(4-butylphenyl)ethynyl]-3,5-difluoro-aniline (6.1 g, 20 mmol) and DABCO (6.0 g, 53 mmol) in dichloromethane (100 ml) at 0° C. under argon atmosphere, and the reaction mixture is stirred at room temperature for 1 h. Then it is quenched with dist. water and brine. The aqueous phase is separated and extracted with dichloromethane. The combined organic phases are washed with brine, dried (sodium sulfate), filtered and concentrated in vacuo. The residue is purified by silica gel chromatography (eluent heptane) and crystallization (heptane) to give colorless crystals of 2-[2-(4-butylphenyl)ethynyl]-1,3-difluoro-5-isothiocyanato-benzene.

Phase sequence: K 44 N (29) I.

$\Delta\varepsilon$=3.70

$\Delta n$=0.3690

$\gamma_1$=53 m Pas

Synthesis Example 4:1,3-Difluoro-5-isothiocyanato-2-[4-[4-(trifluoromethoxy)-phenyl]phenyl]benzene Step 4.1: 3,5-Difluoro-4-[4-[4-(trifluoromethoxy) phenyl]phenyl]aniline

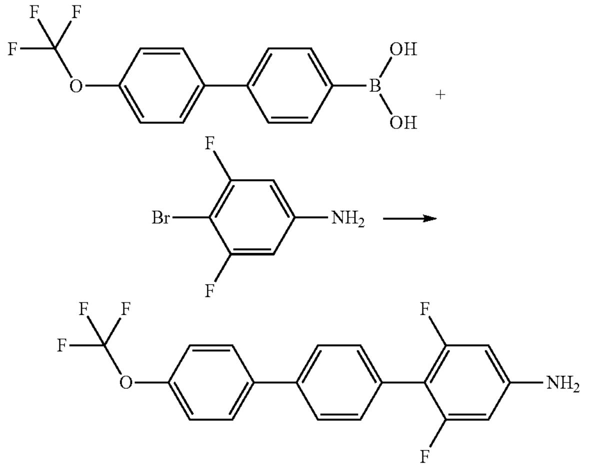

Bis(dibenzylidene-acetone)palladium(0) (20 mg, 0.04 mmol) and tris-(o-tolyl)phosphine (45 mg, 0.1 mmol) are added to a mixture of [4-(4-(trifluoromethoxy)phenyl]phenyl]-boronic acid (CAS 501944-50-9) (4.0 g, 14 mmol) and 4-bromo-3,5-difluoro-aniline (3.0 g, 14 mmol) in acetone (40 ml) at 50° C. under argon atmosphere. Aqueous sodium hydroxide (2 N) (15 ml, 30 mmol) is slowly added at reflux temperature, and the reaction mixture is heated at reflux temperature overnight. Then it is allowed to cool to room temperature and quenched with dist. water and diluted with MTB ether. The aqueous phase is separated and extracted with MTB ether. The combined organic phases are washed with brine, dried (sodium sulfate) and concentrated in vacuo. The residue is purified by silica gel chromatography (eluent 1-chlorobutane) to give 3,5-difluoro-4-[4-[4-(trifluoromethoxy)phenyl]phenyl]aniline as a yellow solid.

Step 4.2: 1,3-Difluoro-5-isothiocyanato-2-[4-[4-(trifluoromethoxy)phenyl]phenyl]-benzene

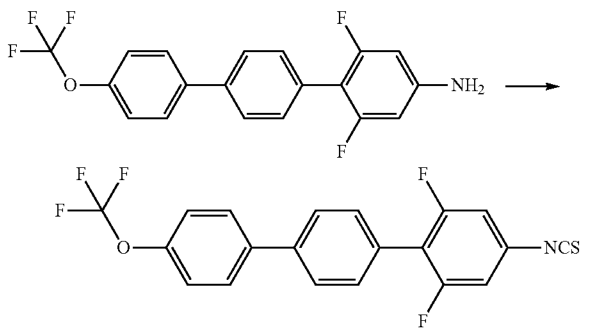

Thiophosgene (1.0 ml, 13 mmol) is slowly added to a solution of 3,5-difluoro-4-[4-[4-(trifluoromethoxy)phenyl]phenyl]aniline (3.9 g, 11 mmol) and DABCO (3.0 g, 27 mmol) in dichloromethane (50 ml) at 0° C. under argon atmosphere. The reaction mixture is stirred at room temperature overnight. Then it is quenched with dist. water and brine. The aqueous phase is separated and extracted with dichloromethane. The combined organic phases are washed with brine, dried (sodium sulfate), filtered and concentrated in vacuo. The residue is purified by silica gel chromatography (eluent heptane) and crystallization (heptane) to give white crystals of 1,3-difluoro-5-isothiocyanato-2-[4-[4-(trifluoromethoxy)phenyl]phenyl]benzene.

Phase sequence K 135 N (128) I.

Δε=3.47

Δn=0.3212

In analogy to Synthesis Examples 1 to 4 the following compounds are obtained:

| No. | Compound | physical properties |
|---|---|---|
| 5 | 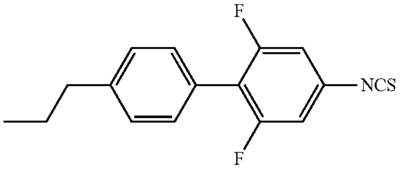 | |
| 6 | 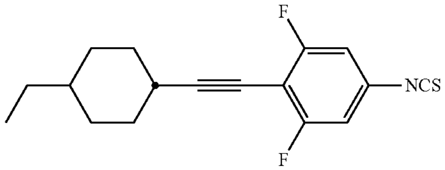 | |
| 7 | 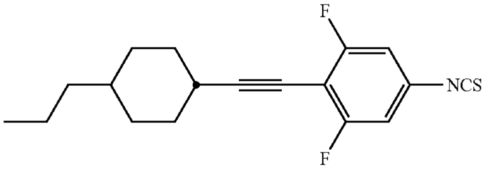 | |
| 8 | 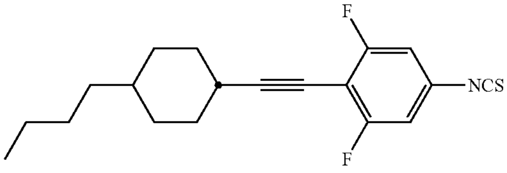 | |
| 9 | 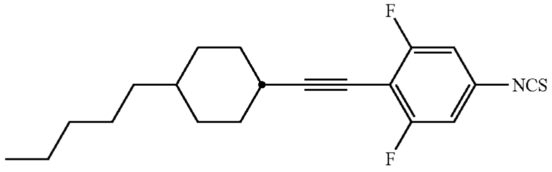 | |
| 10 | 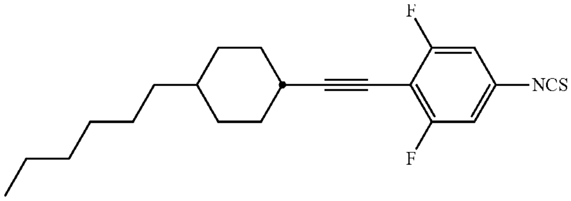 | |
| 11 | 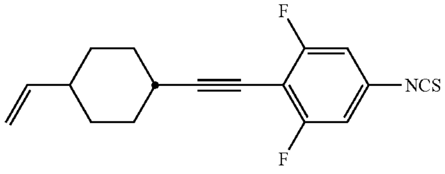 | |

-continued
| No. | Compound | physical properties |
|---|---|---|
| 12 | 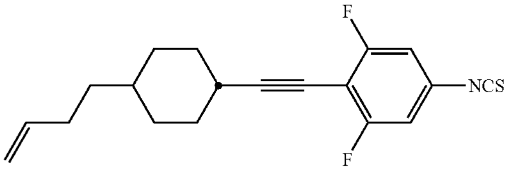 | |
| 13 | 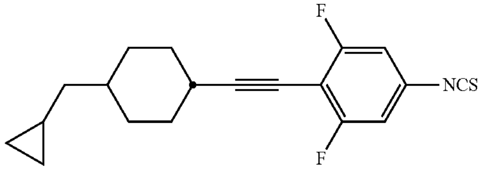 | |
| 14 | 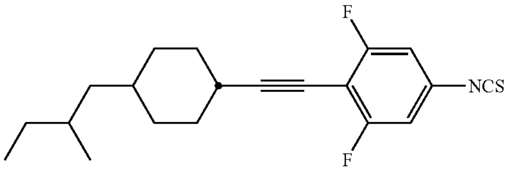 | |
| 15 | 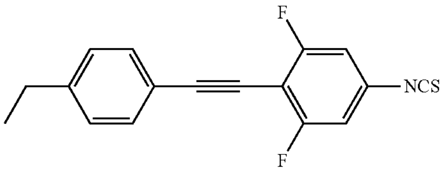 | K 59 I<br>$\Delta\varepsilon$ = 4.32<br>$\Delta n$ = 0.3956<br>$\gamma_1$ = 37 mPas |
| 16 | 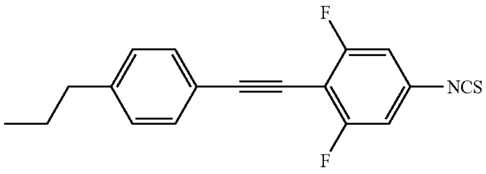 | K 75 I<br>$\Delta\varepsilon$ = 2.52<br>$\Delta n$ = 0.4026<br>$\gamma_1$ = 51 mPas |
| 17 | 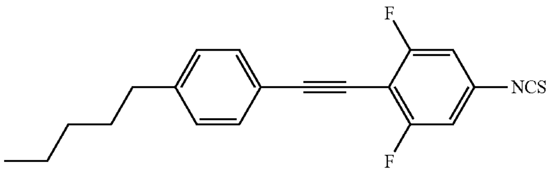 | K 82 I<br>$\Delta\varepsilon$ = 3.72<br>$\Delta n$ = 0.3732<br>$\gamma_1$ = 58 mPas |
| 18 | 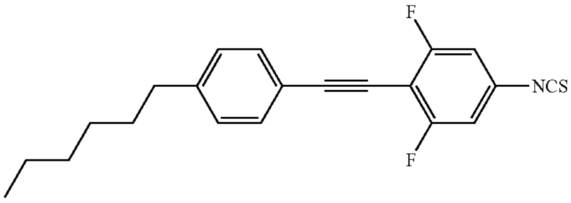 | K 63 N (36) I<br>$\Delta\varepsilon$ = 3.12<br>$\Delta n$ = 0.3489<br>$\gamma_1$ = 61 mPas |
| 19 | 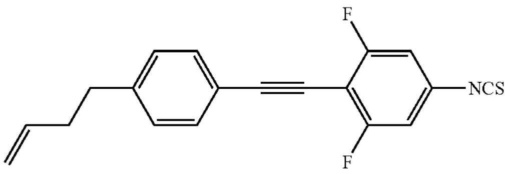 | |

-continued
| No. | Compound | physical properties |
|---|---|---|
| 20 | 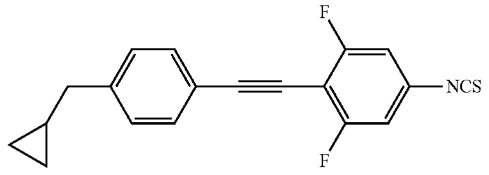 | |
| 21 | 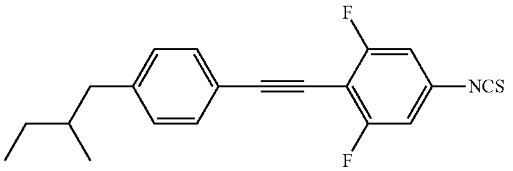 | |
| 22 | 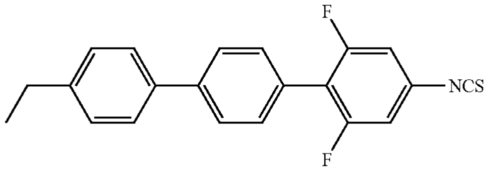 | |
| 23 | 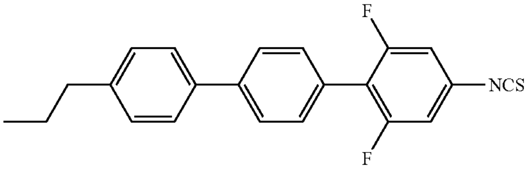 | |
| 24 | 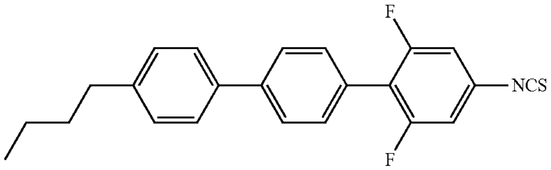 | |
| 25 | 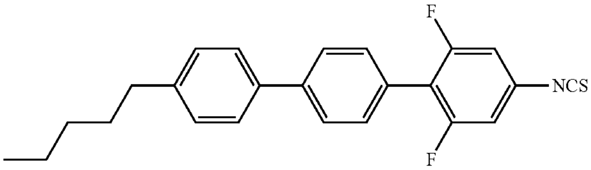 | |
| 26 | 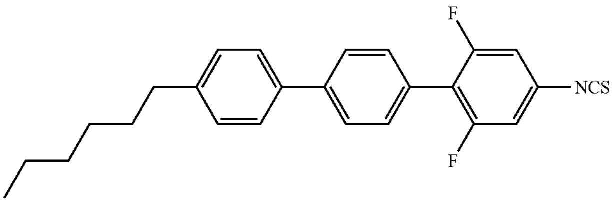 | |
| 27 | 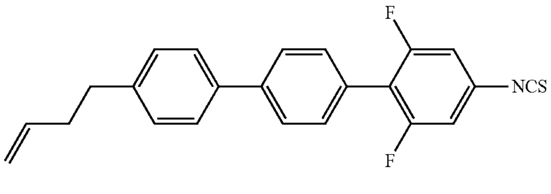 | |

-continued
| No. | Compound | physical properties |
|---|---|---|
| 28 | 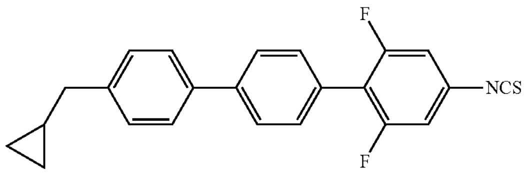 | |
| 29 | 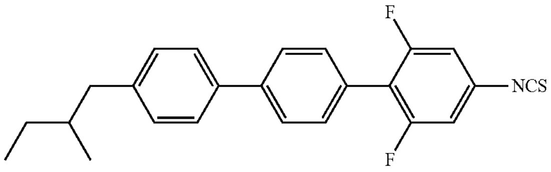 | |
| 30 | 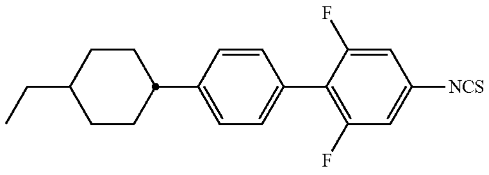 | |
| 31 | 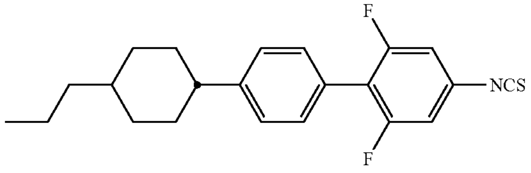 | K 116 N 163.2 I<br>Δε = 3.12<br>Δn = 0.2646<br>$\gamma_1$ = 493 mPas |
| 32 | 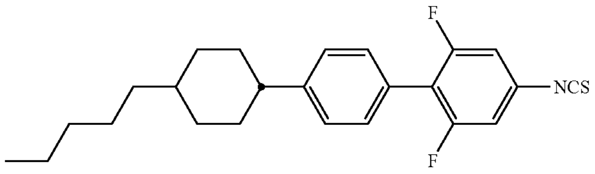 | K 94 N 163.9 I<br>Δε = 3.32<br>Δn = 0.2460<br>$\gamma_1$ = 678 mPas |
| 33 | 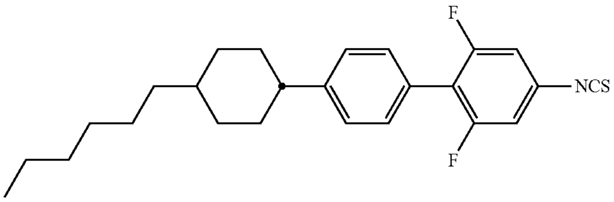 | |
| 34 | 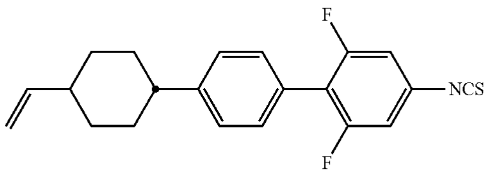 | |
| 35 | 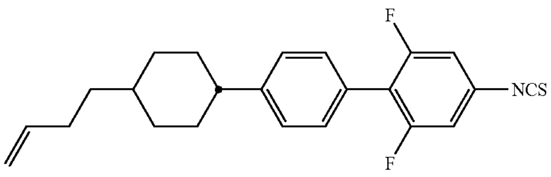 | |

-continued
| No. | Compound | physical properties |
|---|---|---|
| 36 | 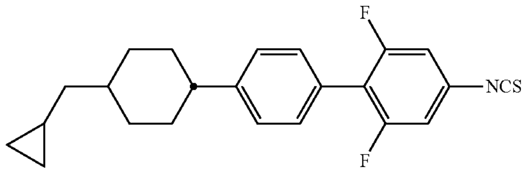 | |
| 37 | 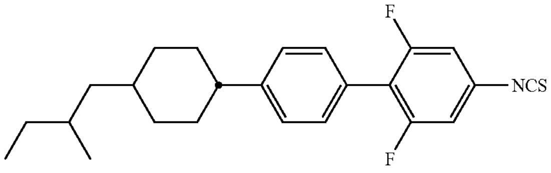 | |
| 38 | 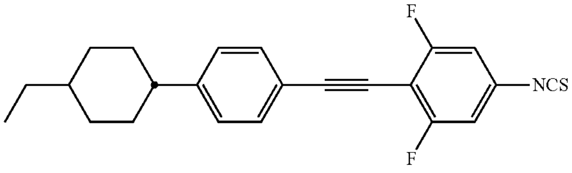 | |
| 39 | 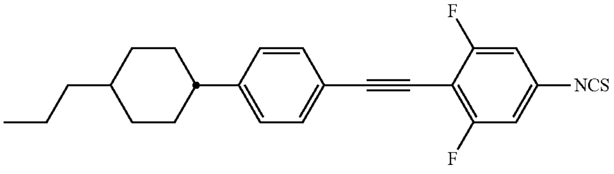 | |
| 40 | 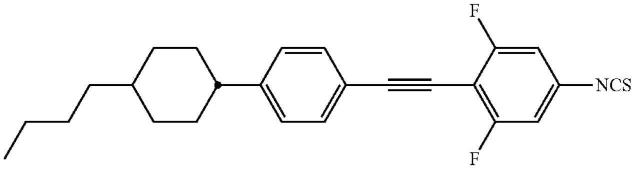 | |
| 41 | 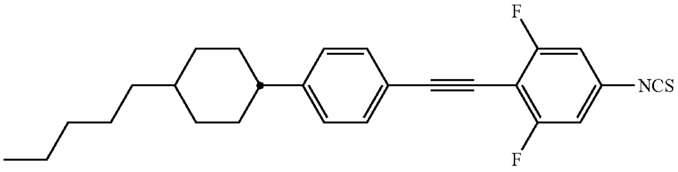 | |
| 42 | 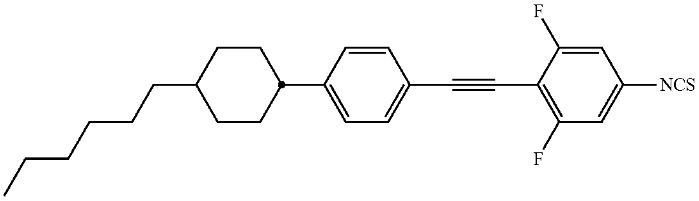 | |
| 43 | 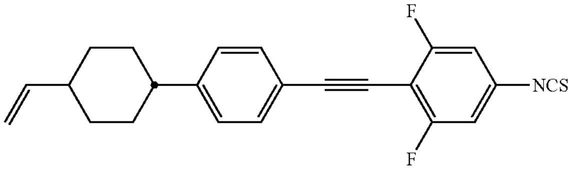 | |

-continued
| No. | Compound | physical properties |
|---|---|---|
| 44 | 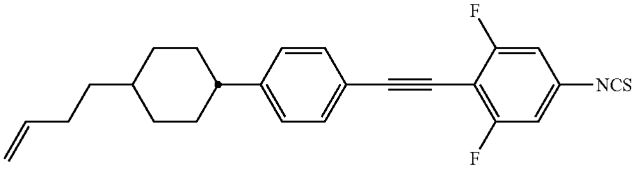 | |
| 45 | 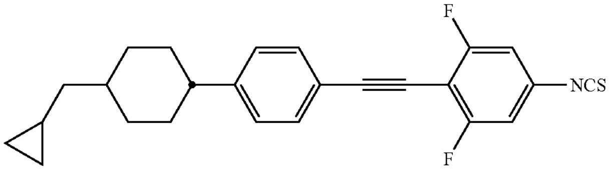 | |
| 46 | 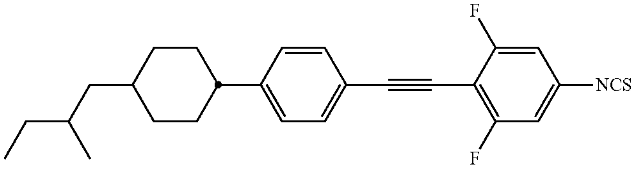 | |
| 47 | 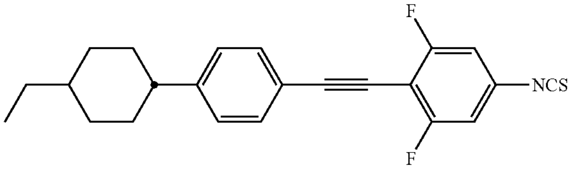 | |
| 48 | 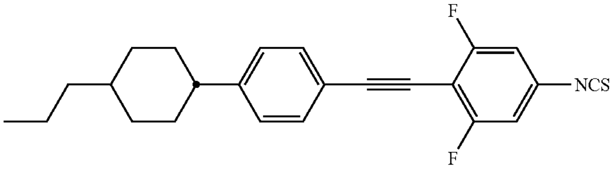 | |
| 49 | 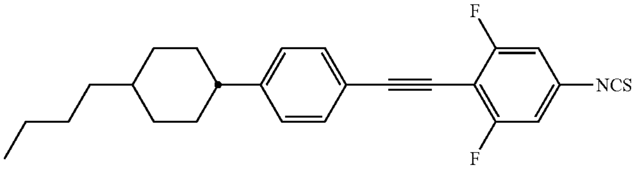 | |
| 50 | 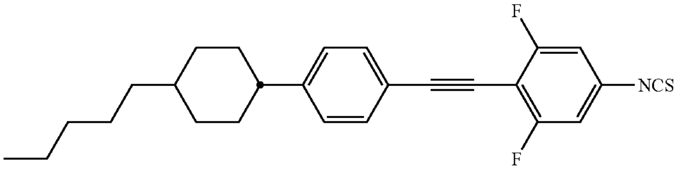 | |
| 51 | 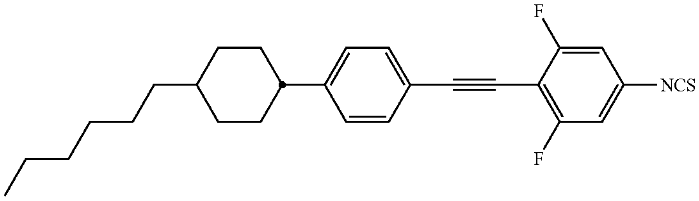 | |

-continued
| No. | Compound | physical properties |
|---|---|---|
| 52 | 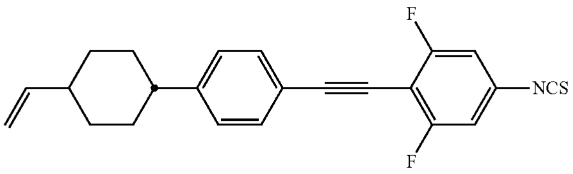 | |
| 53 | 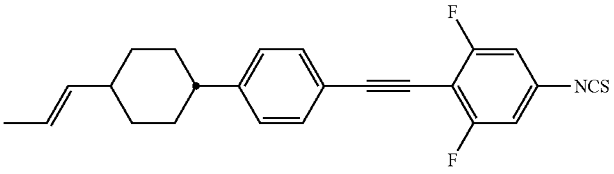 | |
| 54 | 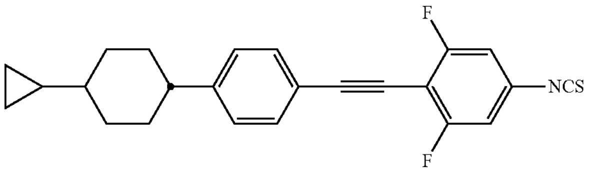 | |
| 55 | 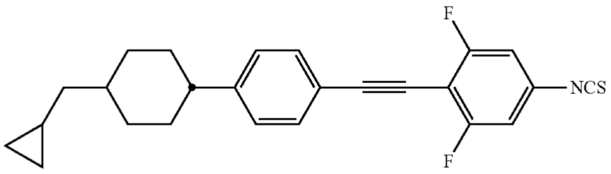 | |
| 56 | 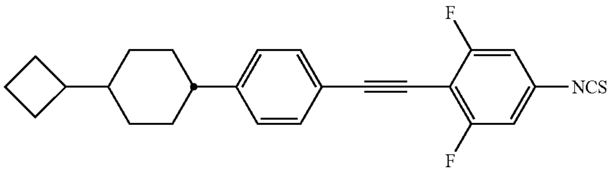 | |
| 57 | 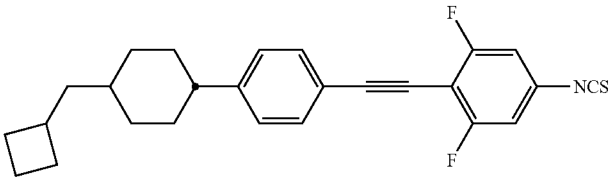 | |
| 58 | 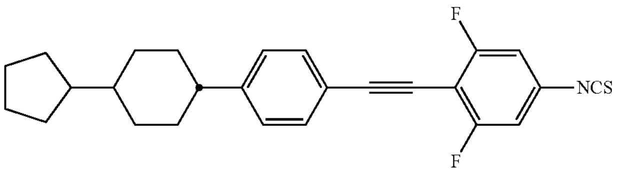 | |
| 59 | 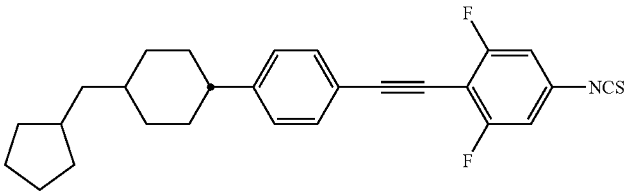 | |

-continued
| No. | Compound | physical properties |
|---|---|---|
| 60 | 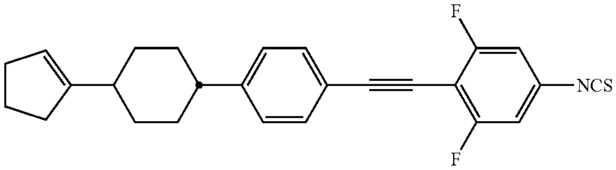 | |
| 61 | 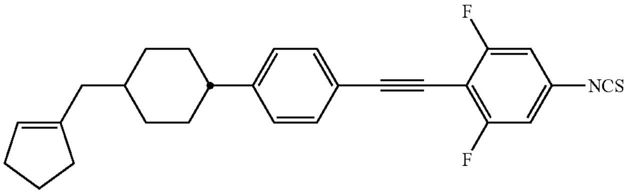 | |
| 62 | 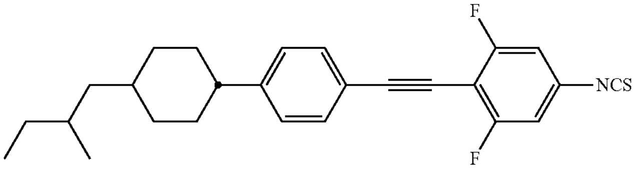 | |
| 63 | 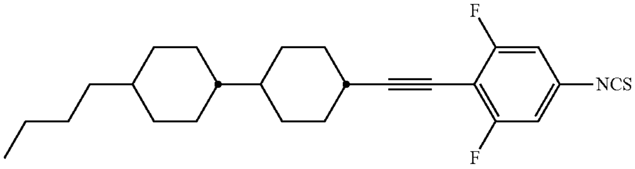 | |
| 64 | 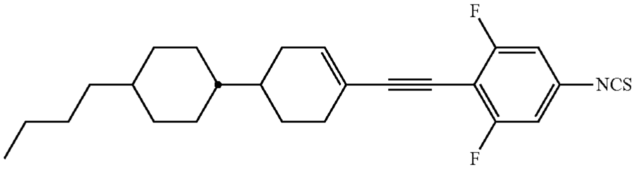 | |
| 65 | 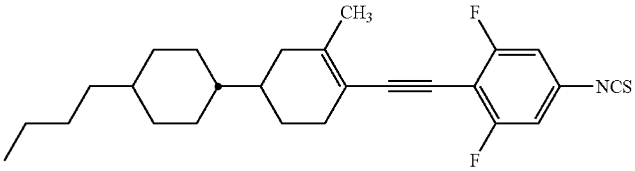 | |
Preferred compounds of formula UII are prepared as follows
Synthesis of Reference Example 1: 2-[4-[2-(4-Butylphenyl)ethynyl]phenyl]-1,3-difluoro-5-isothiocyanato-benzene
Step 1.1: 2-[4-[2-(4-Butylphenyl)ethynyl]phenyl]-4,4,5,5-tetramethyl-1,3,2-dioxaborolane
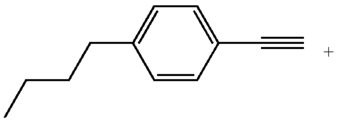
-continued
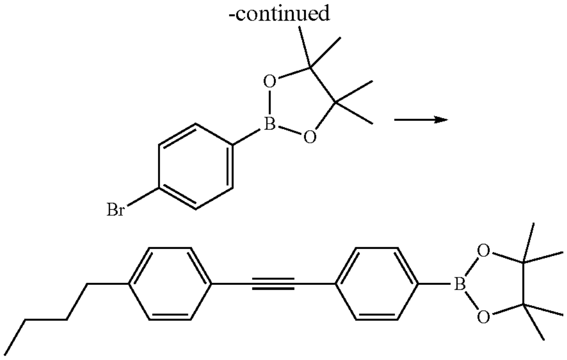
XPhos Pd G2 (170 mg, 0.2 mmol), XPhos (100 mg, 0.2 mmol) and copper(I) iodide (20 mg, 0.1 mmol) are added to a mixture of 1-butyl-4-ethynylbenzene (18.0 g, 0.1 mol) and 2-(4-bromophenyl)-4,4,5,5-tetramethyl-1,3,2-dioxaborolane (30.0 g, 0.1 mol) in diisopropylamine (250 ml) and THE (27 ml) under argon atmosphere at 55° C. The reaction mixture is heated at reflux temperature overnight. Then it is allowed to cool to room temperature, filtered and concentrated in vacuo. The residue is dissolved in toluene, washed with dist. water, dried (sodium sulfate), filtered and concentrated in vacuo. The crude product is purified by silica gel chromatography (eluent toluene) and crystallization (heptane) to give 2-[4-[2-(4-butylphenyl)ethynyl]phenyl]-4,4,5,5-tetramethyl-1,3,2-dioxaborolane as yellow crystals.

Step 1.2: 4-[4-[2-(4-Butylphenyl)ethynyl]phenyl]-3,5-difluoro-aniline

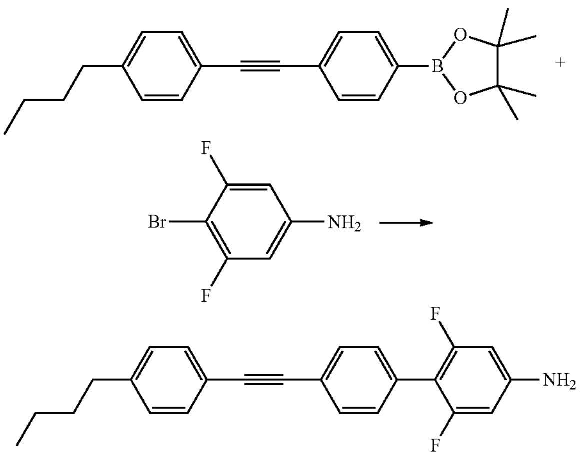

Bis(di-tert-butyl(4-dimethylaminophenyl)phosphine)dichloropalladium(II) (7 mg, 0.01 mmol) is added to a mixture of 2-[4-[2-(4-butylphenyl)ethynyl]phenyl]-4,4,5,5-tetramethyl-1,3,2-dioxaborolane (3.5 g, 10 mmol) and 4-bromo-3,5-difluoro-aniline (2.0 g, 10 mmol) in ethylene glycol (20 ml) and THE (20 ml) at 60° C. under argon atmosphere. Aqueous sodium hydroxide (2 N) (7.5 ml, 15 mmol) is slowly added at reflux temperature, and the reaction mixture is heated at reflux temperature overnight.

Then it is allowed to cool to room temperature and quenched with acetic acid (0.9 ml, 16 mmol) and dist. water. MTB ether is added, and the aqueous phase is separated and extracted with MTB ether. The combined organic phases are washed with brine, dried (sodium sulfate), filtered and concentrated in vacuo. The residue is purified by silica gel chromatography (eluent dichloromethane) to give 4-[4-[2-(4-butylphenyl)ethynyl]phenyl]-3,5-difluoro-aniline as a yellow solid.

Step 1.3: 2-[4-[2-(4-Butylphenyl)ethynyl]phenyl]-1,3-difluoro-5-isothiocyanato-benzene

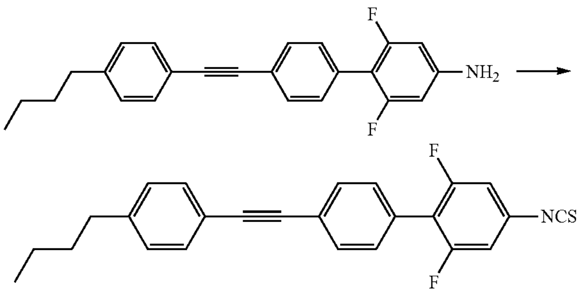

Thiophosgene (0.7 ml, 9 mmol) is slowly added to a solution of 4-[4-[2-(4-butylphenyl)ethynyl]phenyl]-3,5-difluoro-aniline (2.9 g, 8 mmol) and DABCO (2.3 g, 21 mmol) in dichloromethane (40 ml) at 0° C. under argon atmosphere. The reaction mixture is stirred at room temperature for 1 h. Then it is quenched with dist. water and brine. The aqueous phase is separated and extracted with dichloromethane. The combined organic phases are washed with brine, dried (sodium sulfate), filtered and concentrated in vacuo. The residue is purified by silica gel chromatography (eluent heptane) and crystallization (heptane) to give colorless crystals of 2-[4-[2-(4-butylphenyl)ethynyl]phenyl]-1,3-difluoro-5-isothiocyanato-benzene.

Phase sequence K 120 N 178 I.

$\Delta\varepsilon$=4.92

$\Delta n$=0.4369

$\gamma_1$=697 m Pas

In analogy to Reference Example 1, the following compounds are obtained:

2

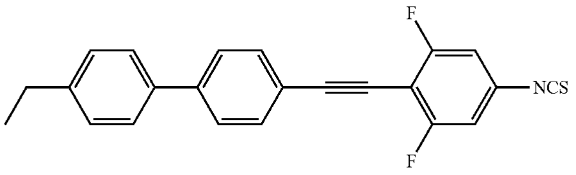

3

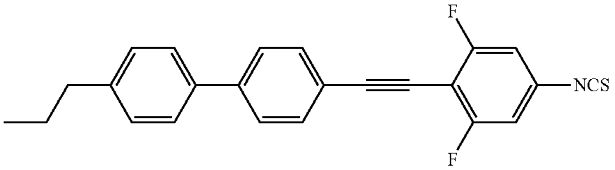

-continued
| | | |
|---|---|---|
| 4 | 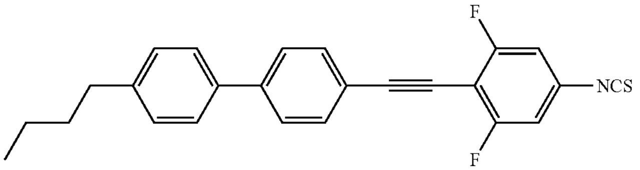 | K 82 SmA 138<br>N 227.1 I<br>Δε = 6.32<br>Δn = 0.5069<br>$\gamma_1$ = 385 mPas |
| 5 | 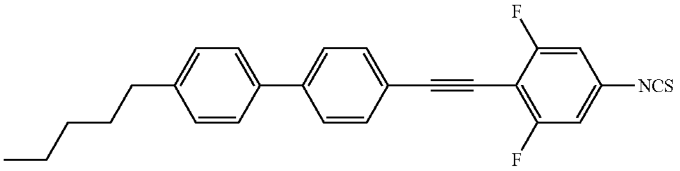 | K 85 SmA<br>155.5 N 222.8 I<br>Δε = 4.52<br>Δn = 0.4939 |
| 6 | 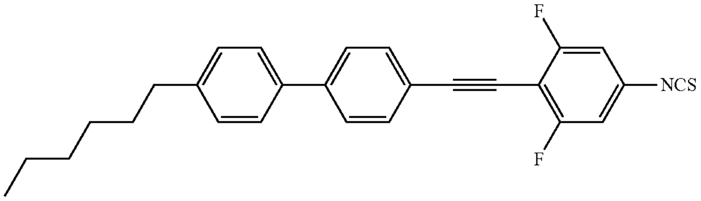 | |
| 7 | 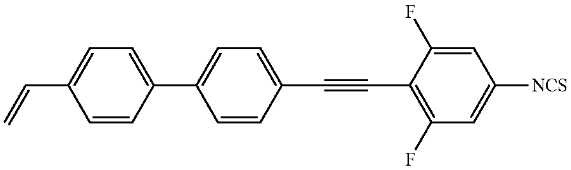 | |
| 8 | 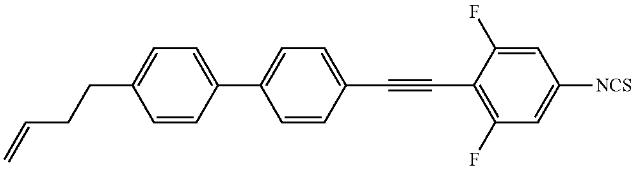 | |
| 9 | 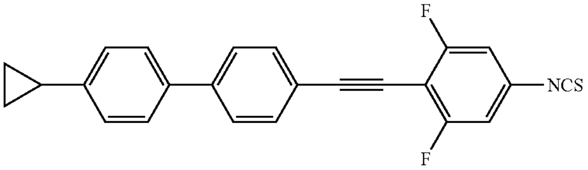 | |
| 10 | 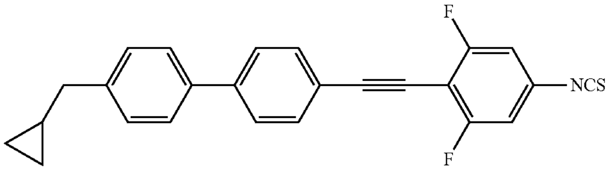 | |
| 11 | 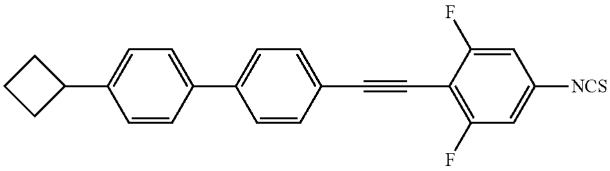 | |

-continued
12
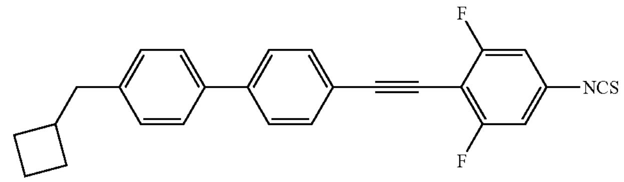
13
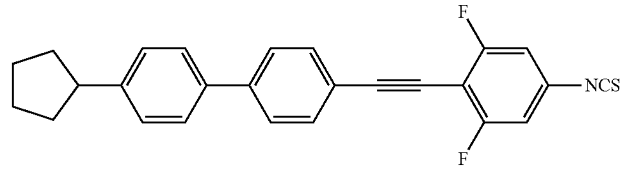
14
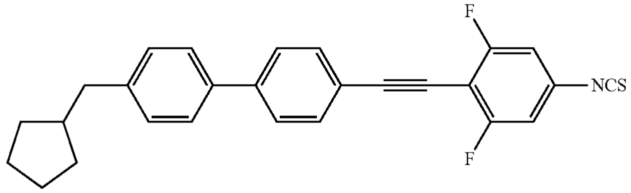
15
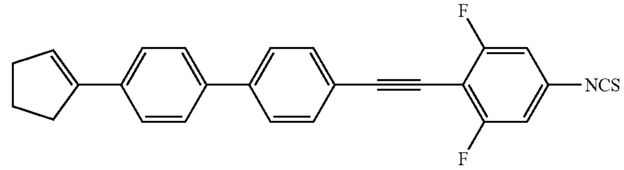
16
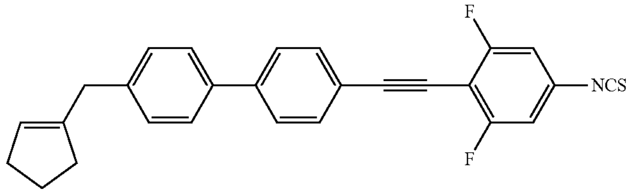
17
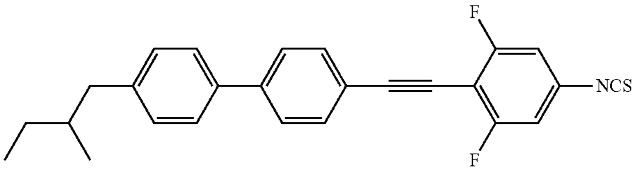
K 79 SmX 98 N 191.3 I
Δε = 4.04
Δn = 0.4487
18
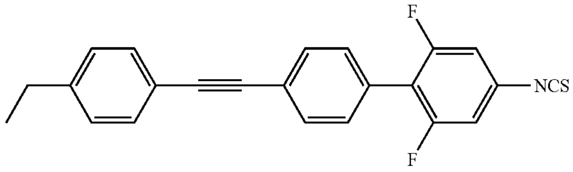
19
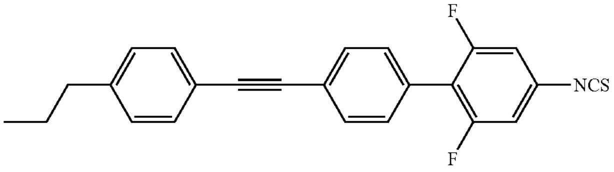

-continued
20
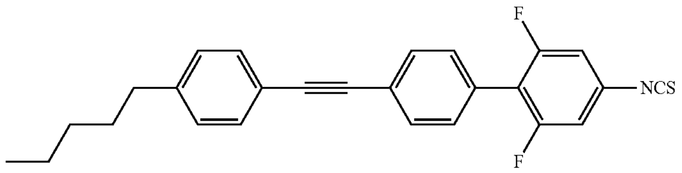
21
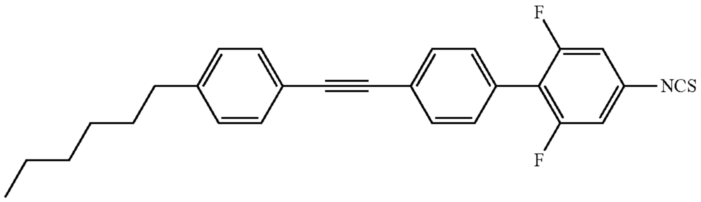
22
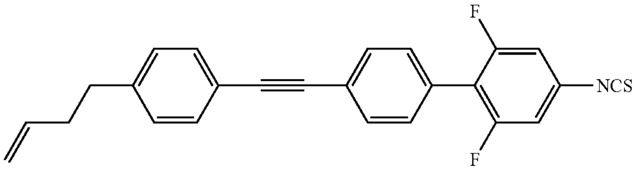
23
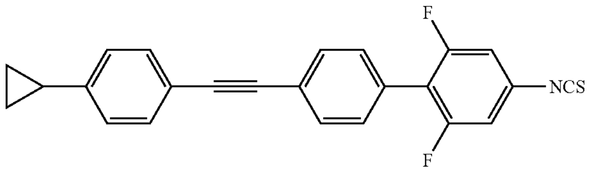
24
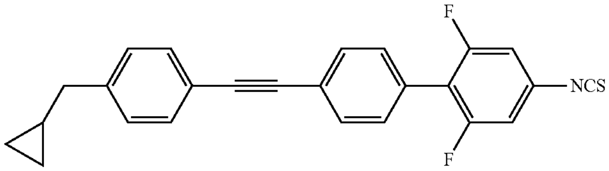
25
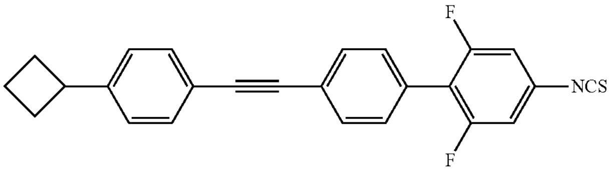
26
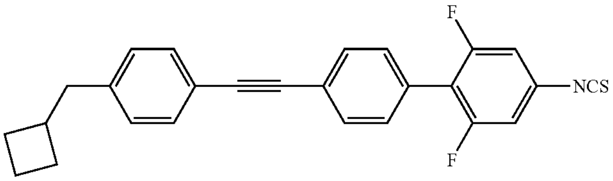
27
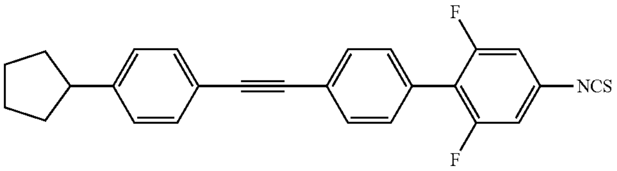

-continued

28

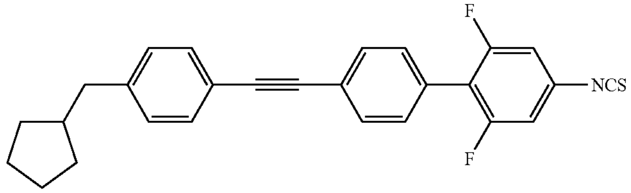

29

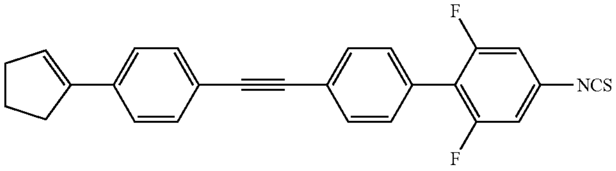

30

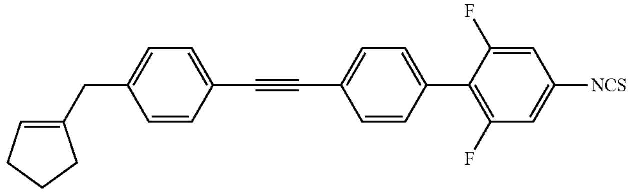

31

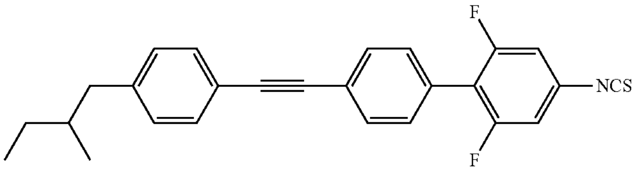

32

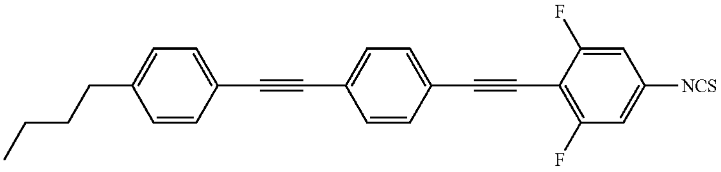

33

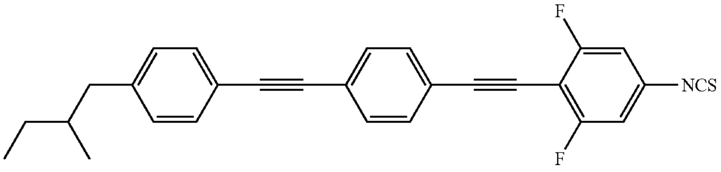

Mixture Examples

Comparative examples C1, C2 and Mixture Examples M1 to M13 are prepared and investigated as described below.

Comparative Example C1

| | | | |
|---|---|---|---|
| PPTU-4-S | 6.0 | T(N,I) [° C.]: | 159 |
| PPTU-5-S | 15.0 | $\Delta\varepsilon$ [1 kHz, 20° C.]: | 15.1 |
| PPU-TO-S | 16.0 | $\varepsilon_{\parallel}$ [1 kHz, 20° C.]: | 18.7 |
| CPTU-5-S | 25.0 | $\varepsilon_{\perp}$ [1 kHz, 20° C.]: | 3.6 |
| PTU-3-S | 10.0 | $\gamma_1$ [mPa s, 20° C.]: | 505 |
| PTU-5-S | 10.0 | $K_1$ [pN, 20° C.]: | 17.7 |
| CPU(F,F)-3-S | 18.0 | $K_3$ [pN, 20° C.]: | 24.7 |
| Σ | 100.0 | $K_3/K_1$ [pN, 20° C.]: | 1.39 |
| | | $V_0$ [V, 20° C.]: | 1.14 |
| | | LTS bulk [h, −40° C.]: | 936 |

-continued

| | |
|---|---|
| τ [20° C., 19 GHz]: | 0.326 |
| $\varepsilon_{r,\parallel}$ [20° C., 19 GHz]: | 3.57 |
| $\varepsilon_{r,\perp}$ [20° C., 19 GHz]: | 2.40 |
| tan $\delta_{\varepsilon\ r,\parallel}$ [20° C., 19 GHz]: | 0.0050 |
| tan $\delta_{\varepsilon\ r,\perp}$ [20° C., 19 GHz]: | 0.0083 |
| η [20° C., 19 GHz]: | 39.3 |

| | | | |
|---|---|---|---|
| PPTU-4-S | 6.0 | T(N,I) [° C.]: | 159.5 |
| PPTU-5-S | 12.0 | $\Delta\varepsilon$ [1 kHz, 20° C.]: | 12.4 |
| PPU-TO-S | 8.0 | $\varepsilon_{\parallel}$ [1 kHz, 20° C.]: | 15.7 |
| CPTU-5-S | 25.0 | $\varepsilon_{\perp}$ [1 kHz, 20° C.]: | 3.3 |
| PTU-5-S | 7.0 | $\gamma_1$ [mPa s, 20° C.]: | 435 |
| CPU(F,F)-3-S | 18.0 | $K_1$ [pN, 20° C.]: | 18.9 |

-continued

| | | | |
|---|---|---|---|
| PTPUI-4-S | 4.0 | $K_3$ [pN, 20° C.]: | 21.5 |
| PPTUI-4-S | 6.0 | $K_3/K_1$ [pN, 20° C.]: | 1.14 |
| PTUI-4-S | 14.0 | $V_0$ [V, 20° C.]: | 1.33 |
| Σ | 100.0 | τ [20° C., 19 GHz]: | 0.334 |
| | | $\varepsilon_{r,\parallel}$ [20° C., 19 GHz]: | 3.60 |
| | | $\varepsilon_{r,\perp}$ [20° C., 19 GHz]: | 2.40 |
| | | tan $\delta_{\varepsilon\ r,\parallel}$ [20° C., 19 GHz]: | 0.0049 |
| | | tan $\delta_{\varepsilon\ r,\perp}$ [20° C., 19 GHz]: | 0.0071 |
| | | η [20° C., 19 GHz]: | 47.4 |

Mixture Example M1 differs from Comparative Example C in that it additionally comprises the compounds PTPUI-4-S, PPTUI-4-S and PTUI-4-S. As a result, the medium M1 shows an improved figure-of-merit η due to a higher tunability τi and lower loss tan $\delta_{\varepsilon r,\perp}$.

Comparative Mixture C2

| | | | |
|---|---|---|---|
| PPTU-4-S | 10.0 | T(N,I) [° C.]: | 131 |
| PPTU-5-S | 20.0 | Δε [1 kHz, 20° C.]: | 10.4 |
| CPTU-5-S | 10.0 | $\varepsilon_\parallel$ [1 kHz, 20° C.]: | 13.5 |
| PTU-5-S | 10.0 | $\varepsilon_\perp$ [1 kHz, 20° C.]: | 3.2 |
| PTP(2)TP-6-3 | 50.0 | $K_1$ [pN, 20° C.]: | 22.0 |
| Σ | 100.0 | $K_3$ [pN, 20° C.]: | 28.9 |
| | | $K_3/K_1$ [pN, 20° C.]: | 1.32 |
| | | $V_0$ [V, 20° C.]: | 1.54 |
| | | τ [20° C., 19 GHz]: | 0.309 |
| | | $\varepsilon_{r,\parallel}$ [20° C., 19 GHz]: | 3.49 |
| | | $\varepsilon_{r,\perp}$ [20° C., 19 GHz]: | 2.41 |
| | | tan $\delta_{\varepsilon\ r,\parallel}$ [20° C., 19 GHz]: | 0.0038 |
| | | tan $\delta_{\varepsilon\ r,\perp}$ [20° C., 19 GHz]: | 0.0073 |
| | | η [20° C., 19 GHz]: | 42.3 |

Mixture Example M2

| | | | |
|---|---|---|---|
| PPTU-4-S | 10.0 | T(N,I) [° C.]: | 129.5 |
| PPTU-5-S | 20.0 | Δε [1 kHz, 20° C.]: | 8.7 |
| CPTU-5-S | 10.0 | $\varepsilon_\parallel$ [1 kHz, 20° C.]: | 11.7 |
| PTUI-4-S | 10.0 | $\varepsilon_\perp$ [1 kHz, 20° C.]: | 3.0 |
| PTP(2)TP-6-3 | 50.0 | $K_1$ [pN, 20° C.]: | 19.5 |
| Σ | 100.0 | $K_3$ [pN, 20° C.]: | 21.4 |
| | | $K_3/K_1$ [pN, 20° C.]: | 1.10 |
| | | $V_0$ [V, 20° C.]: | 1.58 |
| | | τ [20° C., 19 GHz]: | 0.310 |
| | | $\varepsilon_{r,\parallel}$ [20° C., 19 GHz]: | 3.49 |
| | | $\varepsilon_{r,\perp}$ [20° C., 19 GHz]: | 2.41 |
| | | tan $\delta_{\varepsilon\ r,\parallel}$ [20° C., 19 GHz]: | 0.0037 |
| | | tan $\delta_{\varepsilon\ r,\perp}$ [20° C., 19 GHz]: | 0.0067 |
| | | η [20° C., 19 GHz]: | 46.2 |

Mixture Example M2 differs from Comparative Example C2 in that it additionally comprises the compounds PTUI-4-S. As a result, the medium M2 shows an improved figure-of-merit η due to a lower loss tan $\delta_{\varepsilon\ r,\perp}$.

Mixture Example M3

| | | | |
|---|---|---|---|
| CPTU-5-S | 23.5 | T(N,I) [° C.]: | 173.5 |
| CPU(F,F)-3-S | 19.0 | τ [20° C., 19 GHz]: | 0.299 |
| CPUI-4-S | 12.5 | $\varepsilon_{r,\parallel}$ [20° C., 19 GHz]: | 3.46 |

-continued

| | | | |
|---|---|---|---|
| PTUI-4-S | 10.0 | $\varepsilon_{r,\perp}$ [20° C., 19 GHz]: | 2.43 |
| UIPTU-5-S | 15.0 | tan $\delta_{\varepsilon\ r,\parallel}$ [20° C., 19 GHz]: | 0.0043 |
| PPTUI-4-S | 20.0 | tan $\delta_{\varepsilon\ r,\perp}$ [20° C., 19 GHz]: | 0.0048 |
| Σ | 99.00 | η [20° C., 19 GHz]: | 62.9 |

Mixture Example M4

| | | | |
|---|---|---|---|
| PPTU-4-S | 10.0 | T(N,I) [° C.]: | 166.5 |
| PPTU-5-S | 20.0 | Δε [1 kHz, 20° C.]: | 17.7 |
| CPTU-5-S | 20.0 | $\varepsilon_\parallel$ [1 kHz, 20° C.]: | 21.3 |
| PGTU-4-S | 10.0 | $\varepsilon_\perp$ [1 kHz, 20° C.]: | 3.6 |
| PGU-3-S | 10.0 | $\gamma_1$ [mPa s, 20° C.]: | 451 |
| PPTU-TO-S | 10.0 | $K_1$ [pN, 20° C.]: | 23.3 |
| PTUI-4-S | 20.0 | $K_3$ [pN, 20° C.]: | 22.8 |
| Σ | 100.0 | $K_3/K_1$ [pN, 20° C.]: | 0.98 |
| | | $V_0$ [V, 20° C.]: | 1.21 |
| | | τ [20° C., 19 GHz]: | 0.354 |
| | | $\varepsilon_{r,\parallel}$ [20° C., 19 GHz]: | 3.79 |
| | | $\varepsilon_{r,\perp}$ [20° C., 19 GHz]: | 2.45 |
| | | tan $\delta_{\varepsilon\ r,\parallel}$ [20° C., 19 GHz]: | 0.0054 |
| | | tan $\delta_{\varepsilon\ r,\perp}$ [20° C., 19 GHz]: | 0.0095 |
| | | η [20° C., 19 GHz]: | 37.4 |

Mixture Example M5

| | | | |
|---|---|---|---|
| PPTU-4-S | 6.0 | T(N,I) [° C.]: | 159 |
| PPTU-5-S | 10.0 | Δε [1 kHz, 20° C.]: | 14.4 |
| PGTU-4-S | 6.0 | $\varepsilon_\parallel$ [1 kHz, 20° C.]: | 17.9 |
| PGU-3-S | 12.0 | $\varepsilon_\perp$ [1 kHz, 20° C.]: | 3.6 |
| PPU-TO-S | 23.0 | $\gamma_1$ [mPa s, 20° C.]: | 430 |
| CPTU-5-S | 22.0 | $K_1$ [pN, 20° C.]: | 19.0 |
| PTUI-4-S | 21.0 | $K_3$ [pN, 20° C.]: | 22.9 |
| Σ | 100.0 | $K_3/K_1$ [pN, 20° C.]: | 1.21 |
| | | $V_0$ [V, 20° C.]: | 1.21 |
| | | LTS bulk [h, −30° C.]: | 1000 |
| | | $\varepsilon_{r,\parallel}$ [20° C., 19 GHz]: | 3.72 |
| | | tan $\delta_{\varepsilon\ r,\parallel}$ [20° C., 19 GHz]: | 0.0062 |
| | | $\varepsilon_{r,\perp}$ [20° C., 19 GHz]: | 2.46 |
| | | tan $\delta_{\varepsilon\ r,\perp}$ [20° C., 19 GHz]: | 0.0100 |
| | | τ [20° C., 19 GHz]: | 0.339 |
| | | η [20° C., 19 GHz]: | 34.0 |

Mixture Example M6

| | | | |
|---|---|---|---|
| PPTU-4-S | 6.0 | T(N,I) [° C.]: | 160.5 |
| PPTU-5-S | 12.0 | Δε [1 kHz, 20° C.]: | 16.6 |
| PGTU-4-S | 6.0 | $\varepsilon_\parallel$ [1 kHz, 20° C.]: | 20.1 |
| PGU-3-S | 10.0 | $\varepsilon_\perp$ [1 kHz, 20° C.]: | 3.6 |
| CPTU-5-S | 10.0 | $\gamma_1$ [mPa s, 20° C.]: | 568 |
| PPU-TO-S | 10.0 | $K_1$ [pN, 20° C.]: | 22.7 |
| PTUI-4-S | 16.0 | $K_3$ [pN, 20° C.]: | 24.4 |
| CPU(F,F)-3-S | 10.0 | $K_3/K_1$ [pN, 20° C.]: | 1.08 |
| PPTU-4($1^2$)-S | 20.0 | $V_0$ [V, 20° C.]: | 1.24 |
| Σ | 100.0 | $\varepsilon_{r,\parallel}$ [20° C., 19 GHz]: | 3.73 |
| | | tan $\delta_{\varepsilon\ r,\parallel}$ [20° C., 19 GHz]: | 0.0050 |
| | | $\varepsilon_{r,\perp}$ [20° C., 19 GHz]: | 2.45 |
| | | tan $\delta_{\varepsilon\ r,\perp}$ [20° C., 19 GHz]: | 0.0082 |
| | | τ [20° C., 19 GHz]: | 0.344 |
| | | η [20° C., 19 GHz]: | 41.9 |

Mixture Example M7

| | | | |
|---|---|---|---|
| PPTU-4-S | 6.0 | T(N,I) [° C.]: | 159.5 |
| PPTU-5-S | 10.0 | $\Delta\varepsilon$ [1 kHz, 20° C.]: | 14.7 |
| PGTU-4-S | 6.0 | $\varepsilon_{\|\|}$ [1 kHz, 20° C.]: | 18.3 |
| PGU-3-S | 12.0 | $\varepsilon_{\perp}$ [1 kHz, 20° C.]: | 3.6 |
| PPU-TO-S | 23.0 | $\gamma_1$ [mPa s, 20° C.]: | 415 |
| CPTU-5-S | 22.0 | $K_1$ [pN, 20° C.]: | 18.9 |
| PTUI-2-S | 11.0 | $K_3$ [pN, 20° C.]: | 23.6 |
| PTUI-4-S | 10.0 | $K_3/K_1$ [pN, 20° C.]: | 1.25 |
| Σ | 100.0 | $V_0$ [V, 20° C.]: | 1.20 |
| | | LTS bulk [h, −30° C.]: | 1000 |
| | | $\varepsilon_{r,\|\|}$ [20° C., 19 GHz]: | 3.72 |
| | | tan $\delta_{\varepsilon\ r,\|\|}$ [20° C., 19 GHz]: | 0.0062 |
| | | $\varepsilon_{r,\perp}$ [20° C., 19 GHz]: | 2.44 |
| | | tan $\delta_{\varepsilon\ r,\perp}$ [20° C., 19 GHz]: | 0.0099 |
| | | $\tau$ [20° C., 19 GHz]: | 0.344 |
| | | $\eta$ [20° C., 19 GHz]: | 34.9 |

Mixture Example M8

| | | | |
|---|---|---|---|
| PPTU-4-S | 6.0 | T(N,I) [° C.]: | 145.5 |
| PPTU-5-S | 12.0 | $\Delta\varepsilon$ [1 kHz, 20° C.]: | 14.2 |
| PGTU-4-S | 6.0 | $\varepsilon_{\|\|}$ [1 kHz, 20° C.]: | 17.9 |
| PGU-3-S | 16.0 | $\varepsilon_{\perp}$ [1 kHz, 20° C.]: | 3.6 |
| PPU-TO-S | 26.0 | $\gamma_1$ [mPa s, 20° C.]: | 364 |
| CPTU-5-S | 8.0 | $K_1$ [pN, 20° C.]: | 18.8 |
| PTUI-2-S | 13.0 | $K_3$ [pN, 20° C.]: | 20.9 |
| PTUI-4-S | 13.0 | $K_3/K_1$ [pN, 20° C.]: | 1.11 |
| Σ | 100.0 | $V_0$ [V, 20° C.]: | 1.21 |
| | | $\varepsilon_{r,\|\|}$ [20° C., 19 GHz]: | 3.77 |
| | | tan $\delta_{\varepsilon\ r,\|\|}$ [20° C., 19 GHz]: | 0.0067 |
| | | $\varepsilon_{r,\perp}$ [20° C., 19 GHz]: | 2.46 |
| | | tan $\delta_{\varepsilon\ r,\perp}$ [20° C., 19 GHz]: | 0.0106 |
| | | $\tau$ [20° C., 19 GHz]: | 0.348 |
| | | $\eta$ [20° C., 19 GHz]: | 32.8 |

Mixture Example M9

| | | | |
|---|---|---|---|
| PPTU-4-S | 6.0 | T(N,I) [° C.]: | 154.5 |
| PPTU-5-S | 12.0 | $\Delta\varepsilon$ [1 kHz, 20° C.]: | 14.8 |
| PGTU-4-S | 6.0 | $\varepsilon_{\|\|}$ [1 kHz, 20° C.]: | 18.4 |
| PGU-3-S | 16.0 | $\varepsilon_{\perp}$ [1 kHz, 20° C.]: | 3.7 |
| PPU-TO-S | 26.0 | $\gamma_1$ [mPa s, 20° C.]: | 400 |
| CPTU-5-S | 12.0 | $K_1$ [pN, 20° C.]: | 19.1 |
| PTUI-2-S | 12.0 | $K_3$ [pN, 20° C.]: | 23.0 |
| PTUI-4-S | 10.0 | $K_3/K_1$ [pN, 20° C.]: | 1.20 |
| Σ | 100.0 | $V_0$ [V, 20° C.]: | 1.20 |
| | | $\varepsilon_{r,\|\|}$ [20° C., 19 GHz]: | 3.82 |
| | | tan $\delta_{\varepsilon\ r,\|\|}$ [20° C., 19 GHz]: | 0.0065 |
| | | $\varepsilon_{r,\perp}$ [20° C., 19 GHz]: | 2.52 |
| | | tan $\delta_{\varepsilon\ r,\perp}$ [20° C., 19 GHz]: | 0.0106 |
| | | $\tau$ [20° C., 19 GHz]: | 0.341 |
| | | $\eta$ [20° C., 19 GHz]: | 32.2 |

Mixture Example M10

-continued

| | | | |
|---|---|---|---|
| PPTU-4-S | 6.0 | T(N,I) [° C.]: | 160 |
| PPTU-5-S | 15.0 | $\Delta\varepsilon$ [1 kHz, 20° C.]: | 14.3 |
| PGU-3-S | 12.0 | $\varepsilon_{\|\|}$ [1 kHz, 20° C.]: | 17.8 |
| PPU-TO-S | 23.0 | $\varepsilon_{\perp}$ [1 kHz, 20° C.]: | 3.5 |
| CPTU-5-S | 23.0 | $\gamma_1$ [mPa s, 20° C.]: | 427 |
| PTUI-2-S | 11.0 | $K_1$ [pN, 20° C.]: | 19.3 |
| PTUI-4-S | 10.0 | $K_3$ [pN, 20° C.]: | 24.2 |
| Σ | 100.0 | $K_3/K_1$ [pN, 20° C.]: | 1.26 |
| | | $V_0$ [V, 20° C.]: | 1.23 |
| | | $\varepsilon_{r,\|\|}$ [20° C., 19 GHz]: | 3.75 |
| | | tan $\delta_{\varepsilon\ r,\|\|}$ [20° C., 19 GHz]: | 0.0060 |
| | | $\varepsilon_{r,\perp}$ [20° C., 19 GHz]: | 2.47 |
| | | tan $\delta_{\varepsilon\ r,\perp}$ [20° C., 19 GHz]: | 0.0095 |
| | | $\tau$ [20° C., 19 GHz]: | 0.341 |
| | | $\eta$ [20° C., 19 GHz]: | 36.1 |

Mixture Example M11

| | | | |
|---|---|---|---|
| PGU-3-S | 6.0 | T(N,I) [° C.]: | 154 |
| PPTU-4-S | 6.0 | $\Delta\varepsilon$ [1 kHz, 20° C.]: | 12.3 |
| PPTU-5-S | 12.0 | $\varepsilon_{\|\|}$ [1 kHz, 20° C.]: | 15.6 |
| PPU-TO-S | 22.0 | $\varepsilon_{\perp}$ [1 kHz, 20° C.]: | 3.4 |
| CPTU-5-S | 23.0 | $\gamma_1$ [mPa s, 20° C.]: | 403 |
| CPU(F,F)-3-S | 7.0 | $K_1$ [pN, 20° C.]: | 18.2 |
| PTUI-2-S | 12.0 | $K_3$ [pN, 20° C.]: | 23.1 |
| PTUI-4-S | 12.0 | $K_3/K_1$ [pN, 20° C.]: | 1.27 |
| Σ | 100.0 | $V_0$ [V, 20° C.]: | 1.29 |
| | | $\varepsilon_{r,\|\|}$ [20° C., 19 GHz]: | 3.70 |
| | | tan $\delta_{\varepsilon\ r,\|\|}$ [20° C., 19 GHz]: | 0.0059 |
| | | $\varepsilon_{r,\perp}$ [20° C., 19 GHz]: | 2.45 |
| | | tan $\delta_{\varepsilon\ r,\perp}$ [20° C., 19 GHz]: | 0.0086 |
| | | $\tau$ [20° C., 19 GHz]: | 0.338 |
| | | $\eta$ [20° C., 19 GHz]: | 39.3 |

Mixture Example M12

| | | | |
|---|---|---|---|
| PPTU-4-S | 6.0 | T(N,I) [° C.]: | 160 |
| PPTU-5-S | 15.0 | $\Delta\varepsilon$ [1 kHz, 20° C.]: | 11.7 |
| PPU-TO-S | 15.0 | $\varepsilon_{\|\|}$ [1 kHz, 20° C.]: | 15.0 |
| CPTU-5-S | 25.0 | $\varepsilon_{\perp}$ [1 kHz, 20° C.]: | 3.3 |
| CPU(F,F)-3-S | 18.0 | $\gamma_1$ [mPa s, 20° C.]: | 442 |
| PTUI-2-S | 10.0 | $K_1$ [pN, 20° C.]: | 18.7 |
| PTUI-4-S | 11.0 | $K_3$ [pN, 20° C.]: | 23.4 |
| Σ | 100.0 | $K_3/K_1$ [pN, 20° C.]: | 1.25 |
| | | $V_0$ [V, 20° C.]: | 1.33 |
| | | LTS bulk [h, −30° C.]: | 816 |
| | | $\varepsilon_{r,\|\|}$ [20° C., 19 GHz]: | 3.64 |
| | | tan $\delta_{\varepsilon\ r,\|\|}$ [20° C., 19 GHz]: | 0.0052 |
| | | $\varepsilon_{r,\perp}$ [20° C., 19 GHz]: | 2.43 |
| | | tan $\delta_{\varepsilon\ r,\perp}$ [20° C., 19 GHz]: | 0.0073 |
| | | $\tau$ [20° C., 19 GHz]: | 0.333 |
| | | $\eta$ [20° C., 19 GHz]: | 45.9 |

Mixture Example M13

| | | | |
|---|---|---|---|
| PPTU-4-S | 6.0 | T(N,I) [° C.]: | 156 |
| PPTU-5-S | 15.0 | $\Delta\varepsilon$ [1 kHz, 20° C.]: | 11.8 |
| PPU-TO-S | 12.0 | $\varepsilon_{\|\|}$ [1 kHz, 20° C.]: | 15.1 |
| CPTU-5-S | 25.0 | $\varepsilon_{\perp}$ [1 kHz, 20° C.]: | 3.3 |
| CPU(F,F)-3-S | 18.0 | $\gamma_1$ [mPa s, 20° C.]: | 409 |
| PTUI-2-S | 12.0 | $K_1$ [pN, 20° C.]: | 18.3 |
| PTUI-4-S | 12.0 | $K_3$ [pN, 20° C.]: | 23.2 |
| Σ | 100.0 | $K_3/K_1$ [pN, 20° C.]: | 1.26 |
| | | $V_0$ [V, 20° C.]: | 1.31 |
| | | LTS bulk [h, −30° C.]: | 1000 |
| | | $\varepsilon_{r,\|\|}$ [20° C., 19 GHz]: | 3.65 |

-continued

| | |
|---|---|
| tan $\delta_{\varepsilon\ r,\parallel}$ [20° C., 19 GHz]: | 0.0052 |
| $\varepsilon_{r,\perp}$ [20° C., 19 GHz]: | 2.44 |
| tan $\delta_{\varepsilon\ r,\perp}$ [20° C., 19 GHz]: | 0.0073 |
| $\tau$ [20° C., 19 GHz]: | 0.332 |
| $\eta$ [20° C., 19 GHz]: | 45.8 |

The invention claimed is:

1. A liquid crystal medium comprising one or more compounds of formula UI-1-3

UI-1-3

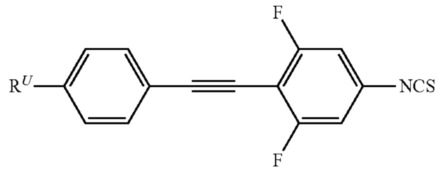

in which $R^U$ denotes H, straight-chain non-fluorinated alkyl having 1 to 12 C atoms, or branched non-fluorinated alkyl having 3 to 12 C atoms, or non-fluorinated alkenyl having 2 to 12 C atoms, in which one or more $CH_2$-groups may be replaced by

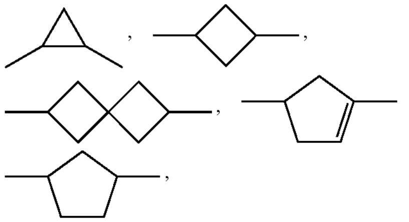

or and in which one or more non-adjacent $CH_2$-groups may be replaced by O, or denotes a group R", $R^P$ denotes halogen, CN, NCS, fluorinated alkyl, $R^F$—O- or $R^F$—S—, $R^F$ denotes fluorinated alkyl having 1 to 9 C atoms or fluorinated alkenyl having 2 to 9 C atoms;

and one or more compounds of formula UII

UII

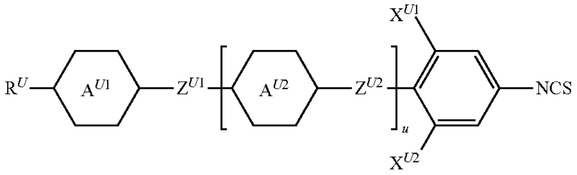

in which $R^U$ denotes H, a straight-chain alkyl having 1 to 12 C atoms or branched alkyl having 3 to 12 C atoms or alkenyl having 2 to 12 C atoms, in which one or more $CH_2$-groups may be replaced by

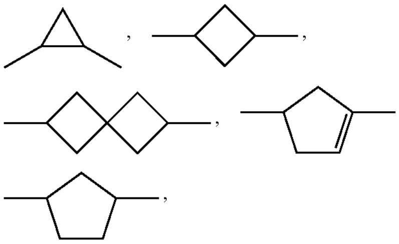

or and in which one or more non-adjacent $CH_2$-groups may be replaced by O, or denotes a group $R^P$, $R^P$ denotes halogen, CN, NCS, $R^F$—, $R^F$—O- or $R^F$—S—, $R^F$ denotes fluorinated alkyl having 1 to 9 C atoms or fluorinated alkenyl having 2 to 9 C atoms, $Z^{U1}$, $Z^{U2}$ identically or differently, denote —CH═CH—, —CF═CF—, —CH═CF—, —CF═CH—, —C≡C—, —C≡C—C≡C- or a single bond, $X^{U1}$, $X^{U2}$, identically or differently, denote Cl or F,

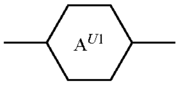

and

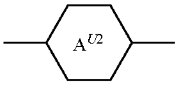

each independently denote:

a) 1,4-phenylene, 1,4-naphthylene or 2,6-naphthylene, in which one or two CH groups may be replaced by N and in which one or more H atoms may be replaced by L, b) trans-1,4-cyclohexylene, 1,4-cyclohexenylene, tetralin-2,6-diyl, tetralin-5,8-diyl, decalin-2,6-diyl, bicyclo[1.1.1]pentane-1,3-diyl, 4,4'-bicyclohexylene, bicyclo[2.2.2]octane-1,4-diyl or spiro [3.3]heptane-2,6-diyl, in which one or two CH groups may be replaced by N, one or more non-adjacent $CH_2$ groups may be replaced by —O— and/or —S— and in which one or more H atoms may be replaced by L, or c) thiophene-2,5-diyl, thieno [3,2-b]thiophene-2,5-diyl or selenophene-2,5-diyl, each of which may also be mono- or polysubstituted by L, L on each occurrence, identically or differently, denotes F, Cl, CN, SCN, $SF_5$ or a straight-chain, in each case optionally fluorinated, alkyl, alkoxy, alkylcarbonyl, alkoxycarbonyl, alkylcarbonyloxy or alkoxycarbonyloxy each having 1 to 12 C atoms, or branched, in each case optionally fluorinated, alkyl, alkoxy, alkylcarbonyl, alkoxycarbonyl, alkylcarbonyloxy or alkoxycarbonyloxy each having 3 to 12 C atoms, and atoms, and u is 0, 1 or 2, from which the compounds of formula UI-1-3 are excluded, and one or more compounds selected from the group of compounds of formulae UI-1, UI-2 and UI-3

UI-1

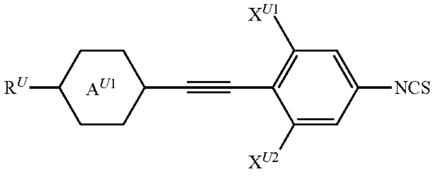

from which compounds of formulae UI-1, the compounds of formula UI-1-3 are excluded

UI-2

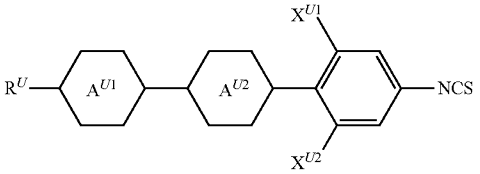

UI-3

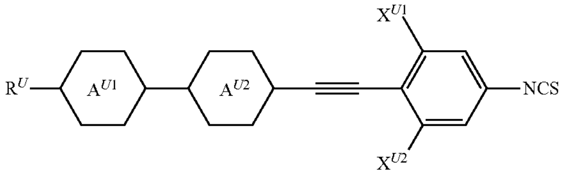

in which $R^U$ denotes H, straight-chain non-fluorinated alkyl having 1 to 12 C atoms, or branched non-fluorinated alkyl having 3 to 12 C atoms, or non-fluorinated alkenyl having 2 to 12 C atoms, in which one or more $CH_2$-groups may be replaced by

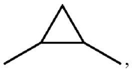,
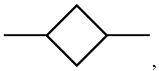,
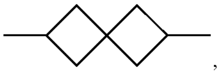,
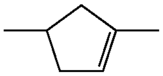 or 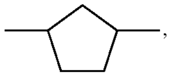, and in which one or more non-adjacent $CH_2$-groups may be replaced by O, or denotes a group $R^P$, $R^P$ denotes halogen, CN, NCS, fluorinated alkyl, $R^F$—O- or $R^F$—S—, $R^F$ denotes fluorinated alkyl having 1 to 9 C atoms or fluorinated alkenyl having 2 to 9 C atoms;

$X^{U1}$, $X^{U2}$ identically or differently, denote Cl or F,

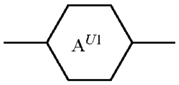 and 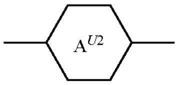

each independently denote:

a) 1,4-phenylene, 1,4-naphthylene or 2,6-naphthylene, in which one or two CH groups may be replaced by N and in which one or more H atoms may be replaced by L, b) trans-1,4-cyclohexylene, 1,4-cyclohexenylene, tetralin-2,6-diyl, tetralin-5,8-diyl, decalin-2,6-diyl, bicyclo [1.1.1]pentane-1,3-diyl, 4,4'-bicyclohexylene, bicyclo [2.2.2]octane-1,4-diyl or spiro [3.3]heptane-2,6-diyl, in which one or two CH groups may be replaced by N, one or more non-adjacent $CH_2$ groups may be replaced by —O— and/or —S— and in which one or more H atoms may be replaced by L, or c) thiophene-2,5-diyl, thieno [3,2-b]thiophene-2,5-diyl or selenophene-2,5-diyl, each of which may also be mono- or polysubstituted by L, L on each occurrence, identically or differently, denotes F, Cl, CN, SCN, $SF_5$ or a straight-chain, in each case optionally fluorinated, alkyl, alkoxy, alkylcarbonyl, alkoxycarbonyl, alkylcarbonyloxy or alkoxycarbonyloxy each having 1 to 12 C atoms, or a branched, in each case optionally fluorinated, alkyl, alkoxy, alkylcarbonyl, alkoxycarbonyl, alkylcarbonyloxy or alkoxycarbonyloxy each having 3 to 12 C atoms;

with the proviso that in formula UI-3 at least one of

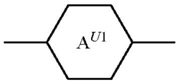

and

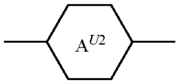

denotes trans-1,4-cyclohexylene, 1,4-cyclohexenylene, tetralin-2,6-diyl, tetralin-5,8-diyl, decalin-2,6-diyl, bicyclo [1.1.1]pentane-1,3-diyl, 4,4'-bicyclohexylene, bicyclo [2.2.2]octane-1,4-diyl, and spiro [3.3]heptane-2,6-diyl, in which one or two CH groups may be replaced by N, one or more non-adjacent $CH_2$ groups may be replaced by —O— and/or —S— and in which one or more H atoms may be replaced by L, wherein L, on each occurrence, identically or differently, denotes F, Cl, CN, SCN, $SF_5$ or a straight-chain, in each case optionally fluorinated, alkyl, alkoxy, alkylcarbonyl, alkoxycarbonyl, alkylcarbonyloxy or alkoxycarbonyloxy each having 1 to 12 C atoms or a branched, in each case optionally fluorinated, alkyl, alkoxy, alkylcarbonyl, alkoxycarbonyl, alkyl-carbonyloxy or alkoxycarbonyloxy each having 1 to 12 C atoms, wherein the medium contains the one or more compounds selected from the group of compounds of formulae UI-1, UI-2 and UI-3, the one or more compounds of formula UI-1-3 and the one or more compounds of formula UII in a total concentration of 15% to 50%;

and one or more compounds of formula III-1b:

III-1b

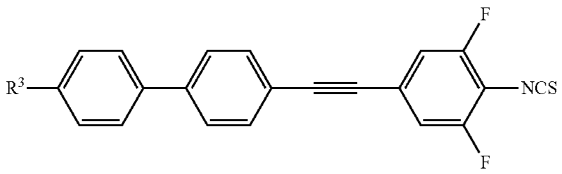

$R^3$ denotes H, unfluorinated alkyl or unfluorinated alkoxy having 1 to 17 C atoms, or unfluorinated alkenyl, unfluorinated alkenyloxy or unfluorinated alkoxyalkyl having 2 to 15 C atoms, in which one or more $CH_2$-groups may be replaced by

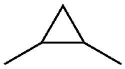, 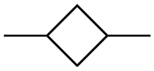, 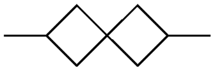,

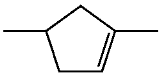 or 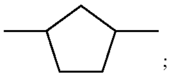;

and one or more compounds of formulae I, II and/or III, wherein from the compounds of formula III the compounds of formula III-1*b* are excluded:

I

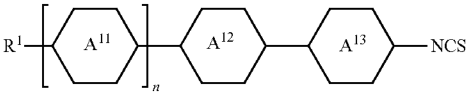

II

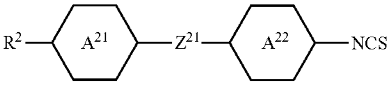

III

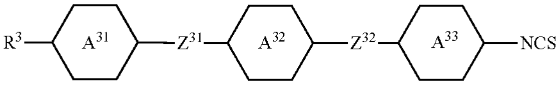

in which $R^1$ denotes H, unfluorinated alkyl or unfluorinated alkoxy having 1 to 17 C atoms, or unfluorinated alkenyl, unfluorinated alkenyloxy or unfluorinated alkoxyalkyl having 2 to 15 C atoms, in which one or more $CH_2$-groups may be replaced by

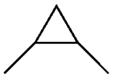, 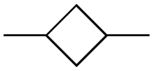, 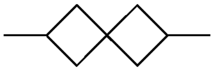,

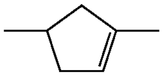 or 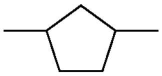, n is 0, 1 or 2,

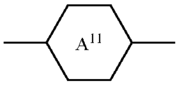 to 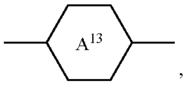, on each occurrence, independently of one another, denote

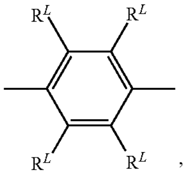, 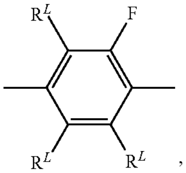,

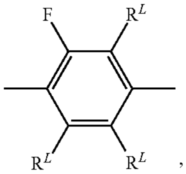, 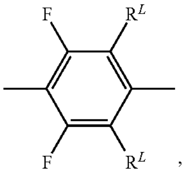,

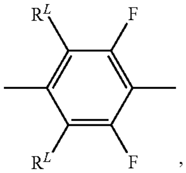, 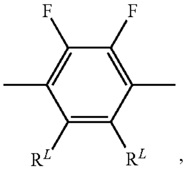,

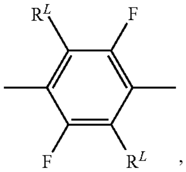, or 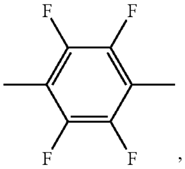, in which $R^L$, on each occurrence, identically or differently, denotes H or alkyl having 1 to 6 C atoms, or

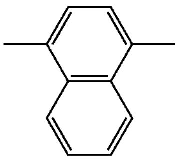 or 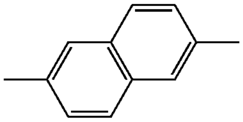

in which one or more H atoms may be replaced by alkyl having 1 to 6 C atoms or F,

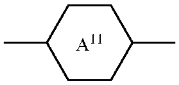

and wherein alternatively denotes

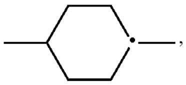, 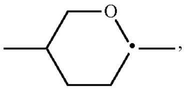,

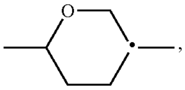, 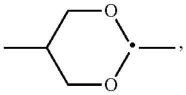,

-continued

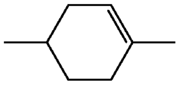 or 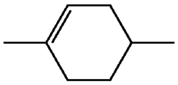, $R^2$ denotes H, unfluorinated alkyl or unfluorinated alkoxy having 1 to 17 C atoms, or unfluorinated alkenyl, unfluorinated alkenyloxy or unfluorinated alkoxyalkyl having 2 to 15 C atoms, in which one or more $CH_2$-groups may be replaced by

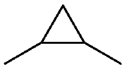, 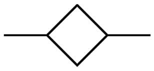, 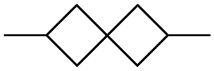,

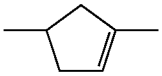 or 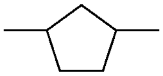, $Z^{21}$ denotes trans-CH═CH—, trans-CF═CF— or —C≡C—, and

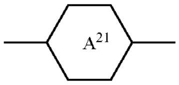 and 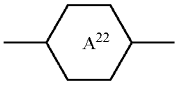, independently of one another, denote

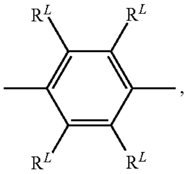, 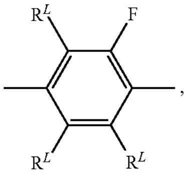,

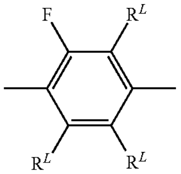, 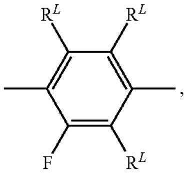,

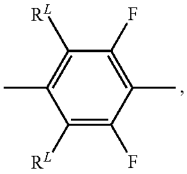, 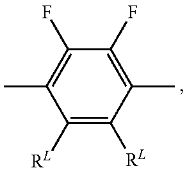,

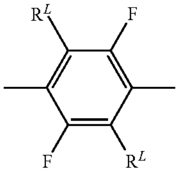 or 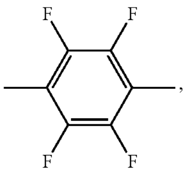, in which $R^L$, on each occurrence, identically or differently, denotes H or alkyl having 1 to 6 C atoms, or

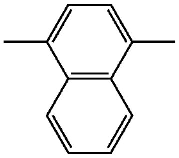 or 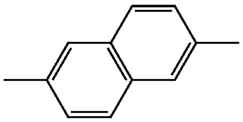

in which one or more H atoms may be replaced by alkyl having 1 to 6 C atoms or F, $R^3$ denotes H, unfluorinated alkyl or unfluorinated alkoxy having 1 to 17 C atoms, or unfluorinated alkenyl, unfluorinated alkenyloxy or unfluorinated alkoxyalkyl having 2 to 15 C atoms, in which one or more $CH_2$-groups may be replaced by

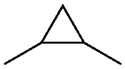, 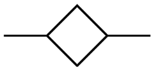, 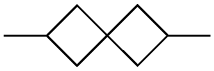,

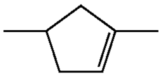 or 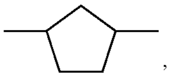, one of $Z^{31}$ and $Z^{32}$ denotes trans-CH═CH—, trans-CF═CF— or —C═C— and the other one, independently thereof, denotes —C≡C—, trans-CH═CH—, trans-CF═CF- or a single bond, and

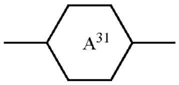 to 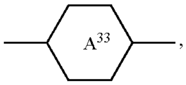, independently of one another, denote

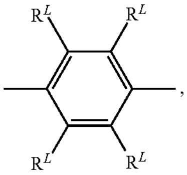, 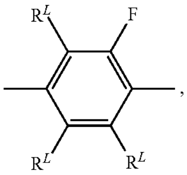,

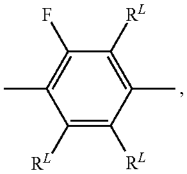, 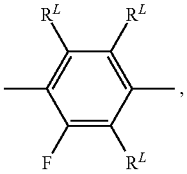,

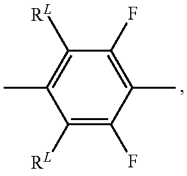, 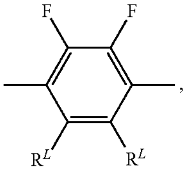,

-continued

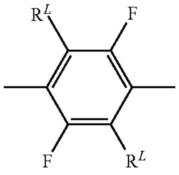
or
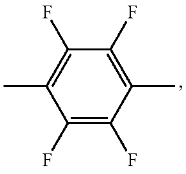
, in which $R^L$, on each occurrence, identically or differently, denotes H or alkyl having 1 to 6 C atoms, or

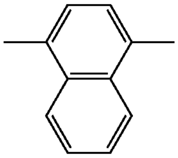
or
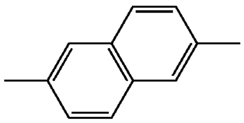

in which one or more H atoms may be replaced by alkyl having 1 to 6 C atoms or F, and wherein

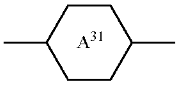

alternatively denotes

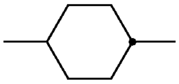
,
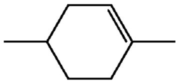
or
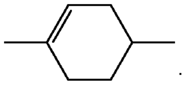
.

2. The medium according to claim 1, wherein the one or more compounds of formula UII are of formulae UII-1, UII-2 and/or UII-3

UII-1

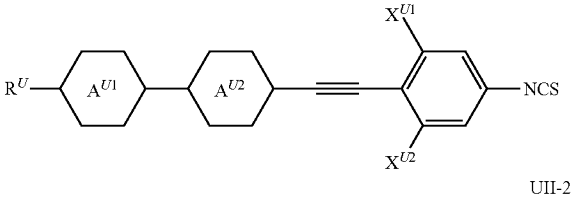

UII-2

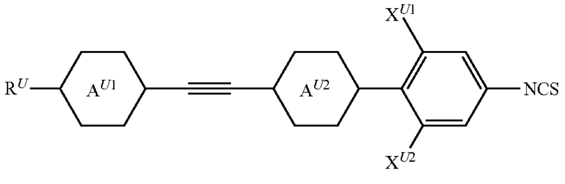

-continued

UII-3

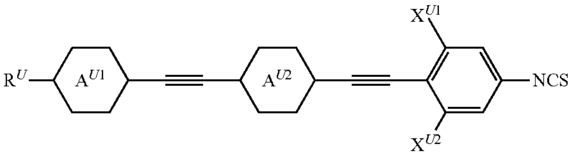

in which $R^U$, $X^{U1}$ and $X^{U2}$,

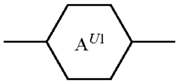
and
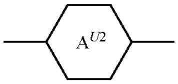

have the meanings given for formula UII.

3. The liquid crystal medium according to claim 1, wherein the medium comprises one or more compounds of formula III from which one or more compounds of formula III, the compounds of formula III-1*b* are excluded.

4. The liquid crystal medium according to claim 1, wherein the medium comprises one or more compounds of formula I, which are one or more compounds of formulae I-1 to I-5

I-1

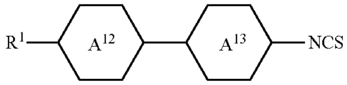

I-2

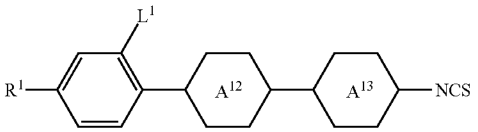

I-3

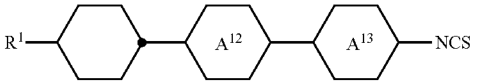

I-4

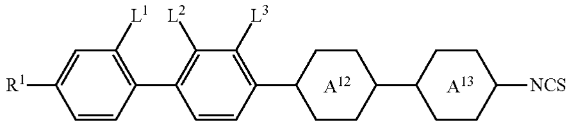

I-5

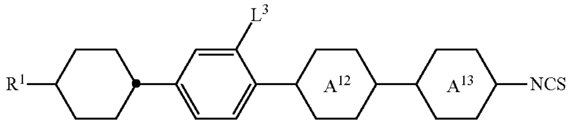

in which $L^1$, $L^2$ and $L^3$ on each occurrence, identically or differently, denote H or F, and $R^1$,

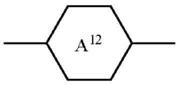
and
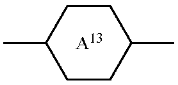

have the meanings given for formula I.

5. The liquid crystal medium according to claim 1, wherein the medium comprises one or more compounds of formula II, which are one or more compounds of formulae II-1 to II-3

II-1

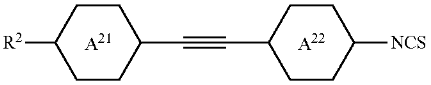

II-2

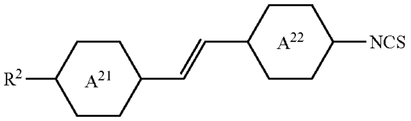

II-3

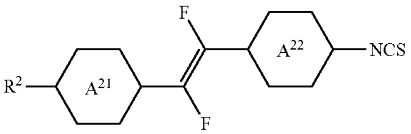

in which $R^2$,

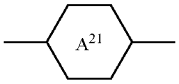 and 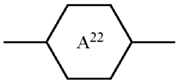

have the meanings given for formula II.

6. The liquid crystal medium according to claim 1, wherein the medium comprises one or more compounds of formula III, which are one or more compounds of formulae III-1 to III-6, from which one or more compounds of formula III-1, the compounds of formula III-1b are excluded

III-1

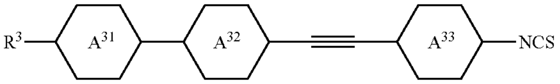

III-2

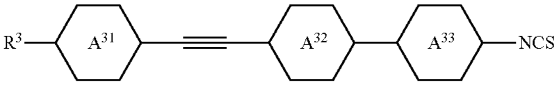

III-3

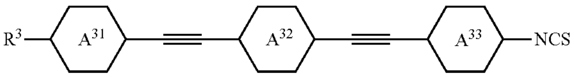

III-4

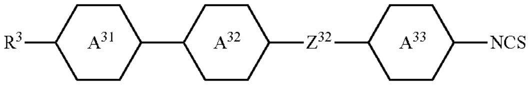

III-5

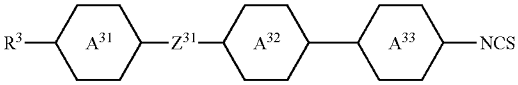

-continued

III-6

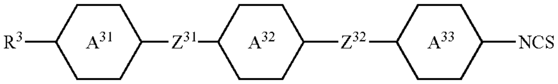

in which $Z^{31}$ and $Z^{32}$ independently of one another denote trans-CH═CH- or trans-CF═CF—, and in formula III-6 alternatively one of $Z^{31}$ and $Z^{32}$ may denote —C≡C—, $R^3$ denotes unfluorinated alkyl or alkoxy having 1 to 7 C atoms or unfluorinated alkenyl having 2 to 7 C atoms, and one of

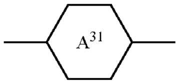 to 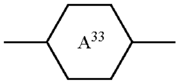

denotes

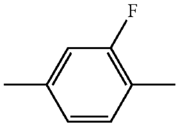, 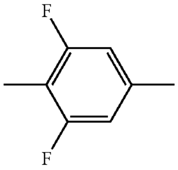,

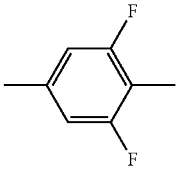, or 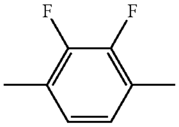, and the others, independently of one another, denote

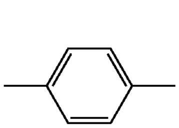, 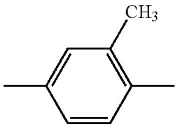,

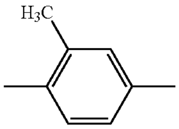, 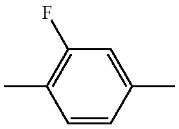,

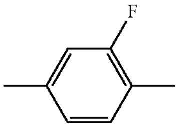, 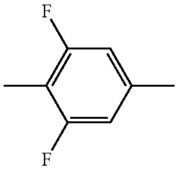,

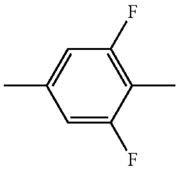, 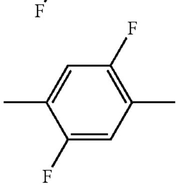 or

-continued

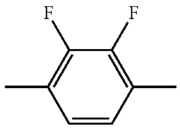, where

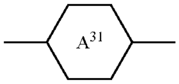

alternatively denotes

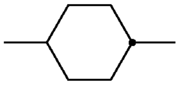.

7. The liquid crystal medium according to claim 1, wherein the medium further comprises one or more compounds of formula T

T

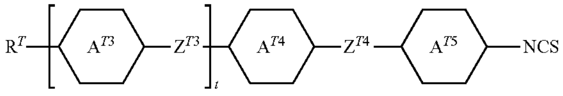

in which $R^T$ denotes halogen, CN, NCS, $R^F$, $R^F$—O- or $R^F$—S—, $R^F$ denotes fluorinated alkyl having 1 to 12 C atoms or fluorinated alkenyl having 2 to 12 C atoms,

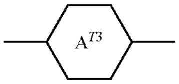, 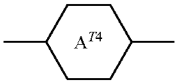 and 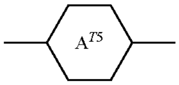

on each occurrence, independently of one another, denote

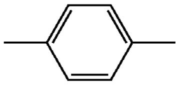, 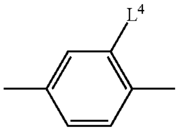, 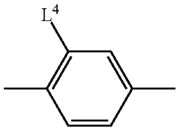, 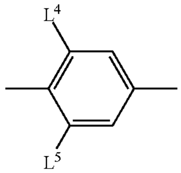,

-continued

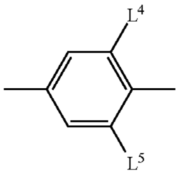, 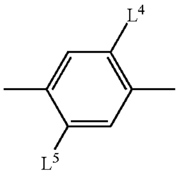 or 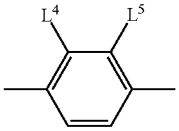;

$L^4$ and $L^5$ identically or differently, denote F, Cl or a straight-chain alkyl having 1 to 12 C atoms or a branched or cyclic alkyl having 3 to 12 C atoms or an alkenyl having 2 to 12 C atoms;

$Z^{T3}$, $Z^{T4}$ identically or differently, denote —CH═CH—, —CF═CF—, —CH═CF—, —CF═CH—, —C═C- or a single bond, and t is 0 or 1.

8. The liquid crystal medium according to claim 1, wherein the medium further comprises one or more compounds of formula U

U

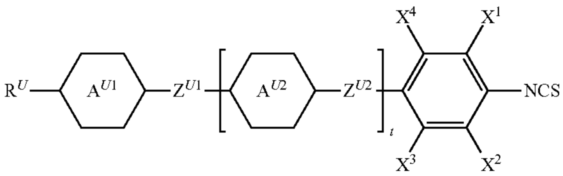

in which $R^U$ denotes H, alkyl or alkoxy having 1 to 12 C atoms, or alkenyl, alkenyloxy or alkoxyalkyl having 2 to 12 C atoms, in which one or more $CH_2$-groups may be replaced by

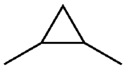, 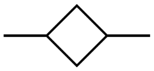, 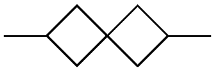, 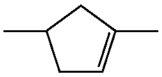 or 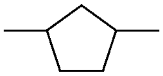, or denotes a group $R^P$, $R^P$ denotes halogen, CN, NCS, RE, $R^F$—O- or $R^F$—S—, $R^F$ denotes fluorinated alkyl having 1 to 9 C atoms or fluorinated alkenyl having 2 to 9 C atoms, $Z^{U1}$, $Z^{U2}$ identically or differently, denote —CH═CH—, —CF═CF—, —CH═CF—, —CF═CH—, —C≡C- or a single bond, $X^1$, $X^2$, $X^3$ and $X^4$ identically or differently, denote Cl or F, t is 0 or 1, and

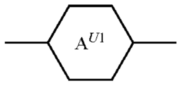

and

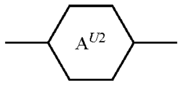

each independently denote:

a) 1,4-phenylene, 1,4-naphthylene, or 2,6-naphthylene, in which one or two CH groups may be replaced by N and in which one or more H atoms may be replaced by L, wherein tetrafluoro-1,4-phenylene is excluded, b) trans-1,4-cyclohexylene, 1,4-cyclohexenylene, bicyclo [1.1.1]pentane-1,3-diyl, 4,4'-bicyclohexylene, bicyclo [2.2.2]octane-1,4-diyl or spiro [3.3]-heptane-2,6-diyl, in which one or more non-adjacent $CH_2$ groups may be replaced by —O— and/or —S— and in which one or more H atoms may be replaced by F, or c) thiophene-2,5-diyl, thieno [3,2-b]thiophene-2,5-diyl or selenophene-2,5-diyl, each of which may also be mono- or polysubstituted by L, L on each occurrence, identically or differently, denotes F, Cl, CN, SCN, $SF_5$ or a straight-chain, in each case optionally fluorinated, alkyl, alkoxy, alkylcarbonyl, alkoxycarbonyl, alkylcarbonyloxy or alkoxycarbonyloxy having 1 to 12 C atoms or a branched, in each case optionally fluorinated, alkyl, alkoxy, alkylcarbonyl, alkoxycarbonyl, alkylcarbonyloxy or alkoxycarbonyloxy having 3 to 12 C atoms.

9. The liquid crystal medium according to claim 8, wherein the medium comprises one or more compounds of formula U, which are one or more compounds of formulae U-1 to U-11

U-1

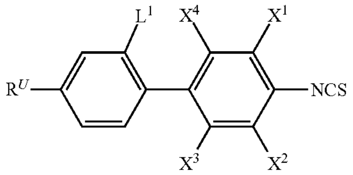

U-2

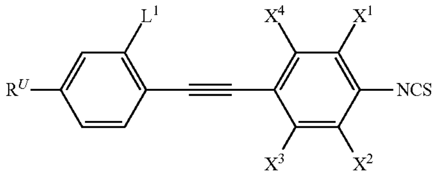

U-3

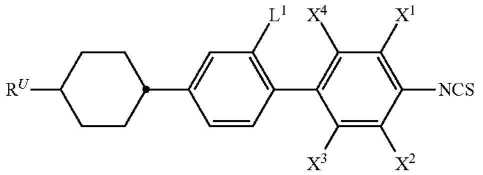

U-4

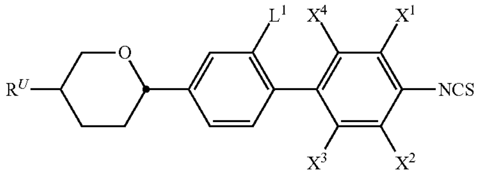

-continued

U-5

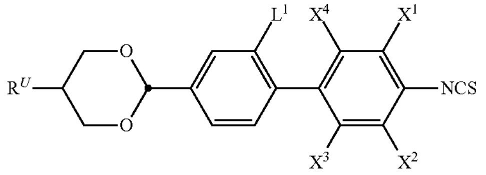

U-6

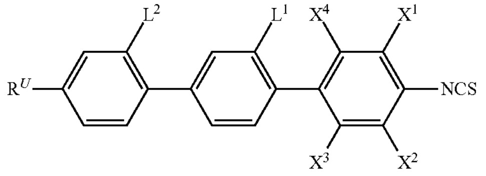

U-7

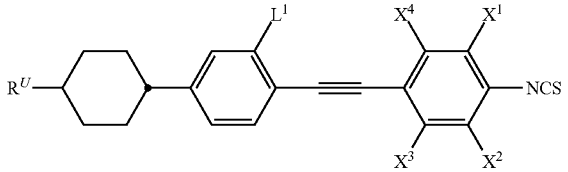

U-8

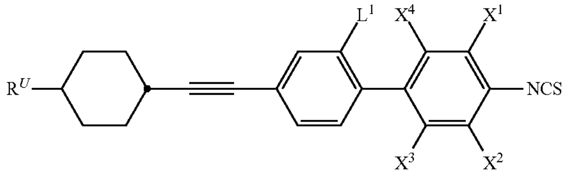

U-9

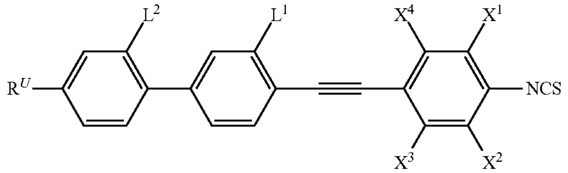

U-10

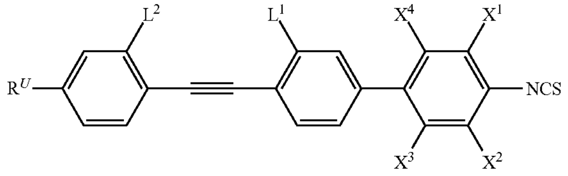

U-11

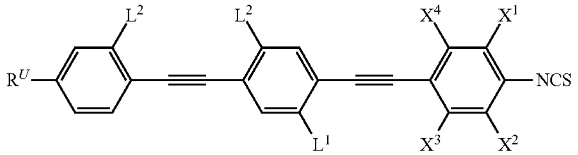

in which $L^1$, $L^2$ and $L^3$ identically or differently, denote H, F, Cl, methyl, ethyl, n-propyl, isopropyl, cyclopropyl, cyclobutyl, cyclopentyl or cyclopentenyl, and $R^U$, $X^1$, $X^2$, $X^3$ and $X^4$ have the meanings given for formula U.

10. A component for high-frequency technology, comprising the liquid crystal medium according to claim 1.

11. The component according to claim 10, wherein the component is a liquid-crystal based antenna element, a phase shifter, a tunable filter, a tunable metamaterial structure, a matching network or a varactor.

12. A microwave antenna array, comprising one or more components according to claim 10.

13. The medium according to claim 1, further comprising two or more compounds selected from the group of compounds of formulae UI-1, UI-2 and UI-3

UI-1

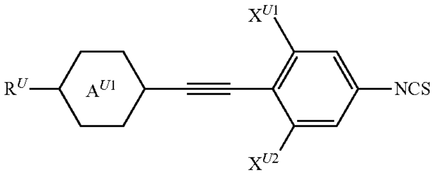

from which compounds of formulae UI-1, the compounds of formula UI-1-3 are excluded

UI-2

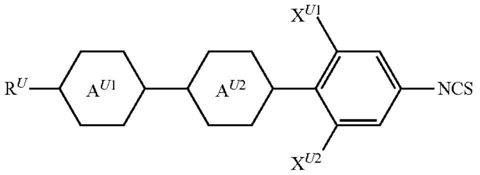

UI-3

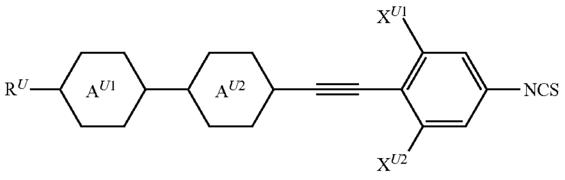

in which $R^U$ denotes H, straight-chain non-fluorinated alkyl having 1 to 12 C atoms, or branched non-fluorinated alkyl having 3 to 12 C atoms, or non-fluorinated alkenyl having 2 to 12 C atoms, in which one or more $CH_2$-groups may be replaced by

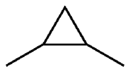, 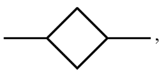,

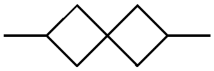, 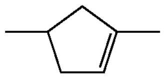 or

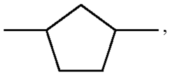, and in which one or more non-adjacent $CH_2$-groups may be replaced by O, or denotes a group $R^P$, $R^P$ denotes halogen, CN, NCS, fluorinated alkyl, $R^F$—O- or $R^F$—S—, $R^F$ denotes fluorinated alkyl having 1 to 9 C atoms or fluorinated alkenyl having 2 to 9 C atoms;

$X^{U1}$, $X^{U2}$ identically or differently, denote Cl or F,

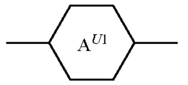 and 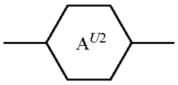

each independently denote:

a) 1,4-phenylene, 1,4-naphthylene or 2,6-naphthylene, in which one or two CH groups may be replaced by N and in which one or more H atoms may be replaced by L, b) trans-1,4-cyclohexylene, 1,4-cyclohexenylene, tetralin-2,6-diyl, tetralin-5,8-diyl, decalin-2,6-diyl, bicyclo [1.1.1]pentane-1,3-diyl, 4,4'-bicyclohexylene, bicyclo [2.2.2]octane-1,4-diyl or spiro [3.3]heptane-2,6-diyl, in which one or two CH groups may be replaced by N, one or more non-adjacent $CH_2$ groups may be replaced by —O— and/or —S— and in which one or more H atoms may be replaced by L, or c) thiophene-2,5-diyl, thieno [3,2-b]thiophene-2,5-diyl or selenophene-2,5-diyl, each of which may also be mono- or polysubstituted by L, L on each occurrence, identically or differently, denotes F, Cl, CN, SCN, $SF_5$ or a straight-chain, in each case optionally fluorinated, alkyl, alkoxy, alkylcarbonyl, alkoxycarbonyl, alkylcarbonyloxy or alkoxycarbonyloxy each having 1 to 12 C atoms, or a branched, in each case optionally fluorinated, alkyl, alkoxy, alkylcarbonyl, alkoxycarbonyl, alkylcarbonyloxy or alkoxycarbonyloxy each having 3 to 12 C atoms;

with the proviso that in formula UI-3 at least one of

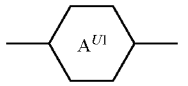 and 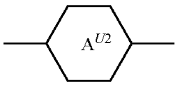

denotes trans-1,4-cyclohexylene, 1,4-cyclohexenylene, tetralin-2,6-diyl, tetralin-5,8-diyl, decalin-2,6-diyl, bicyclo [1.1.1]pentane-1,3-diyl, 4,4'-bicyclohexylene, bicyclo [2.2.2]octane-1,4-diyl, and spiro [3.3]heptane-2,6-diyl, in which one or two CH groups may be replaced by N, one or more non-adjacent $CH_2$ groups may be replaced by —O— and/or —S— and in which one or more H atoms may be replaced by L, wherein L, on each occurrence, identically or differently, denotes F, Cl, CN, SCN, $SF_5$ or a straight-chain, in each case optionally fluorinated, alkyl, alkoxy, alkylcarbonyl, alkoxycarbonyl, alkylcarbonyloxy or alkoxycarbonyloxy each having 1 to 12 C atoms or a branched, in each case optionally fluorinated, alkyl, alkoxy, alkylcarbonyl, alkoxycarbonyl, alkylcarbonyloxy or alkoxycarbonyloxy each having 1 to 12 C atoms.

14. The liquid crystal medium according to claim 6, wherein, in the one or more compounds of formulae III-4 to III-6, $Z^{31}$ and/or $Z^{32}$, which are present, denote trans-CH═CH—.

15. The medium according to claim 1, comprising one or more compounds selected from the following compounds

UI-1-1

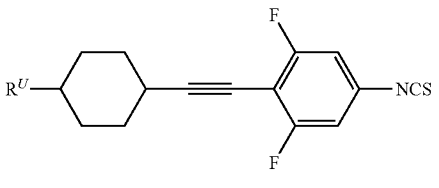

-continued

UI-1-2

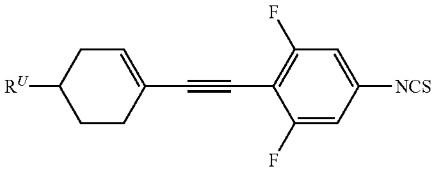

UI-2-1

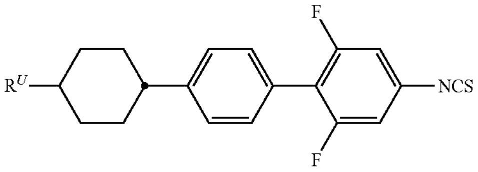

UI-2-2

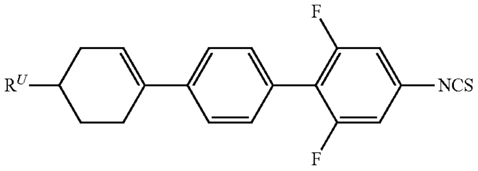

UI-3-1

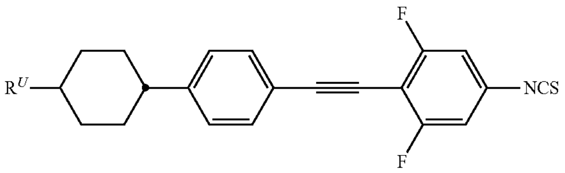

UI-3-2

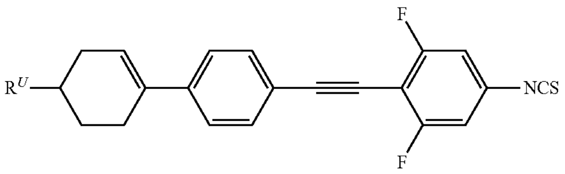

in which $R^U$ denotes H, straight-chain non-fluorinated alkyl having 1 to 12 C atoms, or branched non-fluorinated alkyl having 3 to 12 C atoms, or non-fluorinated alkenyl having 2 to 12 C atoms, in which one or more $CH_2$-groups may be replaced by

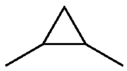,
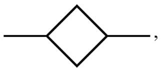,
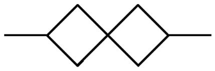,
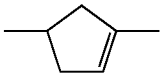 or
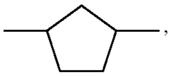, and in which one or more non-adjacent $CH_2$-groups may be replaced by O, or denotes a group $R^P$, $R^P$ denotes halogen, CN, NCS, fluorinated alkyl, $R^F$—O- or $R^F$—S—, $R^F$ denotes fluorinated alkyl having 1 to 9 C atoms or fluorinated alkenyl having 2 to 9 C atoms.

16. The medium according to claim 15, wherein $R^U$ denotes straight chain alkyl having 1 to 7 C atoms or branched alkyl having 3 to 7 C atoms.

17. The medium according to claim 15, wherein $R^U$ denotes methyl, ethyl, n-propyl, n-butyl, n-pentyl, n-hexyl or n-heptyl.

18. The medium according to claim 1, which comprises 8% to 25% of the one or more compounds of formula UI-1-3.

19. The medium according to claim 1, which comprises 10% to 21% of the one or more compounds of formula UI-1-3.

20. The medium according to claim 1, wherein the one or more compounds of formula UI-1-3 include the following compound

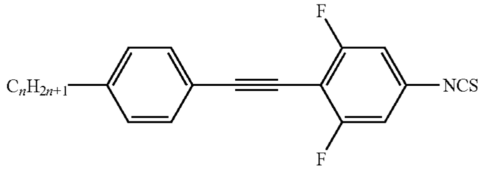

PTUI-n-S wherein n is 4.

* * * * *